US007625922B2

(12) United States Patent
Niculescu-Duvaz et al.

(10) Patent No.: US 7,625,922 B2
(45) Date of Patent: Dec. 1, 2009

(54) IMIDAZO[4,5-B]PYRIDIN-2-ONE AND OXAZOLO[4,5-B]PYRIDIN-2-ONE COMPOUNDS AND ANALOGS THEREOF AS THERAPEUTIC COMPOUNDS

(75) Inventors: Dan Niculescu-Duvaz, Sutton (GB); Caroline Joy Springer, Sutton (GB); Adrian Liam Gill, Macclesfield (GB); Richard David Taylor, Slough (GB); Richard Malcol Marais, London (GB); Harmen Dijkstra, Utrecht (NL); Catherine Gaulon, Le Mans Cedex (FR); Delphine Menard, Sutton (GB); Esteban Roman Vela, Granada (ES)

(73) Assignees: Cancer Research Technology Limited, London, Greater London (GB); The Institute of Cancer Research: Royal Cancer Hospital, London, Greater London (GB); Astex Therapeutics Limited, Cambridge, Cambridgeshire (GB)

( * ) Notice: Subject to any disclaimer, the term of this patent is extended or adjusted under 35 U.S.C. 154(b) by 152 days.

(21) Appl. No.: 11/665,640
(22) PCT Filed: Oct. 21, 2005
(86) PCT No.: PCT/GB2005/004081
§ 371 (c)(1), (2), (4) Date: Aug. 8, 2007
(87) PCT Pub. No.: WO2006/043090
PCT Pub. Date: Apr. 27, 2006

(65) Prior Publication Data
US 2007/0287838 A1 Dec. 13, 2007

Related U.S. Application Data

(60) Provisional application No. 60/620,658, filed on Oct. 22, 2004.

(30) Foreign Application Priority Data
Oct. 22, 2004 (GB) ................................. 0423554.5

(51) Int. Cl.
A01N 43/42 (2006.01)
A61K 31/44 (2006.01)
A01N 43/52 (2006.01)
C07D 239/70 (2006.01)
C07D 471/00 (2006.01)
C07D 487/00 (2006.01)
C07D 471/02 (2006.01)

(52) U.S. Cl. ........................ 514/300; 514/302; 514/303; 514/393; 544/253; 544/256; 544/255; 546/113; 546/115; 546/118

(58) Field of Classification Search ................. 544/255, 544/256, 253; 546/115, 118; 514/300, 302, 514/303, 393
See application file for complete search history.

(56) References Cited
U.S. PATENT DOCUMENTS
5,521,073 A 5/1996 Davis et al.
(Continued)

FOREIGN PATENT DOCUMENTS
JP 56-65863 6/1981
(Continued)

OTHER PUBLICATIONS
Itaya et al., Tetrahedron Letters (1998), 39(26), 4695-4696.*
(Continued)

Primary Examiner—D. Margaret Seaman
Assistant Examiner—Niloofar Rahmani
(74) Attorney, Agent, or Firm—Nixon & Vanderhye P.C.

(57) ABSTRACT

The present invention pertains to certain imidazo[4,5-b]pyridin-2-one and oxazolo[4,5-b]pyridin-2-one compounds and analogs thereof, which, inter alia, inhibit RAF (e.g., B-RAF) activity, inhibit cell proliferation, treat cancer, etc., and more particularly to compounds of the formula (I): wherein: J is independently —O— or —NR$^{N1}$—; R$^{N1}$, if present, is independently —H or a substituent; R$^{N2}$ is independently —H or a substituent; Y is independently —CH═ or —N═; Q is independently —(CH$_2$)$_j$—M—(CH$_2$)$_k$— wherein: j is independently 0, 1 or 2; k is independently 0, 1, or 2; j+k is 0, 1, or 2; M is independently —O—, —S—, —NH—, —NMe—, or —CH$_2$—; each of R$^{P1}$, R$^{P2}$, R$^{P3}$, and R$^{P4}$ is independently —H or a substituent; and additionally R$^{P1}$ and R$^{P2}$ taken together may be —CH═CH—CH═CH—; L is independently: a linker group formed by a chain of 2, 3, or 4 linker moieties; each linker moiety is independently —CH$_2$—, —NR$^N$—, —C(═X)—, or —S(═O)$_2$—; exactly one linker moiety is —NR$^N$—, or: exactly two linker moieties are —NR$^N$—; exactly one linker moiety is —C(═X)—, and no linker moiety is —S(═O)$_2$—; or: exactly one linker moiety is —S(═O)$_2$—, and no linker moiety is —C(═X)—; no two adjacent linker moieties are —NR$^N$—; X is independently ═O or ═S; each R$^N$ is independently —H or a substituent; A is independently: C$_{6-14}$carboaryl, C$_{5-14}$heteroaryl, C$_{3-12}$carbocyclic, C$_{3-12}$heterocyclic; and is independently unsubstituted or substituted; and pharmaceutically acceptable salts, solvates, amides, esters, ethers, N-oxides, chemically protected forms, and prodrugs thereof. The present invention also pertains to pharmaceutical compositions comprising such compounds, and the use of such compounds and compositions, both in vitro and in vivo, to inhibit RAF (e.g., B-RAF) activity, to inhibit receptor tyrosine kinase (RTK) activity, to inhibit cell proliferation, and in the treatment of diseases and conditions that are ameliorated by the inhibition of RAF, RTK, etc., proliferative conditions such as cancer (e.g., colorectal cancer, melanoma), etc.

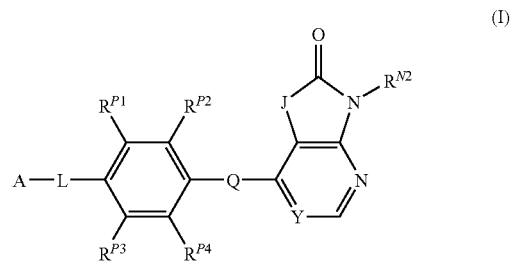

44 Claims, No Drawings

U.S. PATENT DOCUMENTS

| | | | |
|---|---|---|---|
| 5,877,020 | A | 3/1999 | Alitalo |
| 5,879,672 | A | 3/1999 | Davis et al. |
| 6,030,831 | A | 2/2000 | Godowski et al. |
| 6,258,809 | B1 | 7/2001 | Rajagopalan et al. |
| 6,492,529 | B1 | 12/2002 | Kapadia et al. |
| 2004/0082583 | A1 | 4/2004 | Cheung et al. |

FOREIGN PATENT DOCUMENTS

| | | |
|---|---|---|
| JP | 57-038777 | 3/1982 |
| WO | WO 99/16438 | 4/1999 |
| WO | WO 99/21859 | 5/1999 |
| WO | WO 01/36383 | 5/2001 |
| WO | WO 03/056036 | 7/2003 |
| WO | WO 2004/014300 | 2/2004 |

OTHER PUBLICATIONS

Adams, R.H., et al, 1999, "Roles of ephrinB ligands and EphB receptors in cardiovascular development: demarcation of arterial/venous domains, vascular morphogenesis, and sprouting angiogenesis", *Genes Dev.*, vol. 13, pp. 295-306.

Ananthanarayanan, C., et al, 1988, "Reaction of azidees in presence of aluminum chloride", *Indian Journal of Chemistry, Section B*, vol. 27B, pp. 156-157.

Angerer, L.M., et al, 1987, "Demonstration of tissue-specific gene expression by in situ hybridization", *Method in Enzymology*, vol. 152, pp. 649-661.

Auvray, P., et al, 1988, "Preparation and nucleophilic substitution of (E)-1-bromo-2-phenylsulfonyl-2-alkenes and 3-acetoxy-2-phenylsulfonyl-1-alkenes", *Tetrahedron*, vol. 44, pp. 6095-6106.

Avenoza, A., et al, 1995, "New efficient synthesis of 4-amino-3-arylphenols", *Synthesis*, pp. 671-674.

Ballesteros, P., et al, 1987, "Study of the catalytic properties of tris (2,6-dioxaheptyl) amine (TDA-1) in heteroaromatic nucleophilic substitution of chloropyridines and their N-oxides", *Tetrahedron*, vol. 43, pp. 2557-2564.

Bhatt, D.J., et al, 1980, "Preparation of N'-2-phenyl-4-quinolinoyl-$N^3$-aryl thioureas", *J. Instit. Chem.* (India), vol. 52, pp. 113-114.

Bianchi, M., et al, 1981, "Compounds with antiulcer and antisecretory activity", *Eur. J. Med. Chem.*, vol. 16, pp. 321-326.

Borthakur, N., et al, 1995, "New direct synthesis of thioamides from carboxylic acids", *Tetrahedron Letters*, vol. 36, pp. 6745-6746.

Broekhof, N., et al, 1981, "Novel applications of α-aminosubstituted diphenylphosphine oxides. The conversion of aldehydes into α-aminomethylketones", *Tetrahedron Letters*, vol. 22, pp. 2799-2802.

Brooks, P.C., et al, 1994, "Integrin $α_V β_3$ antagonists promote tumor regression by inducing apoptosis of angiogenic blood vessels", *Cell*, vol. 79, pp. 1157-1164.

Brose, M.S., et al, 2002, "*BRAF* and *RAS* mutations in human lung cancer and melanoma", *Cancer Research*, vol. 62, pp. 6997-7000.

Brückner, K., et al, 1997, "Tyrosine phosphorylation of transmembrane ligands for Eph receptors", *Science*, vol. 275, pp. 1640-1643.

Bruder, J.T., et al, 1992, "Serum-, TPA-, and Ras-induced expression from Ap-1/Ets-driven promotors requires Raf-1 kinase", *Genes & Development*, vol. 6, pp. 545-556.

Cantrell, D.A., 2003, "GTPases and T cell activation", *Immunological Reviews*, vol. 192, pp. 122-130.

Chan, A.C., et al, 1996, "Regulation of antigen receptor signal tgransdu8ction by protein tyrosine kinases", *Current Opin. Immunol.*, vol. 8, pp. 394-401.

Clare, B.W., et al, 2001, "Protease inhibitors: synthesis of a series of bacterial collagenase inhibitors of the sulfonyl amino acyl hydroxamate type", *J. Med. Chem.*, vol. 44, pp. 2253-2258.

Cohen, Y., et al, 2003, "Lack of BRAF mutation in primary uveal melanoma", *Invest. Ophthalmol. Vis. Sci.*, vol. 44, pp. 2876-2878.

Colville-Nash, P.R., et al, 1992, "Angiogenesis and rheumatoid arthritis: pathogenic and therapeutic implications", *Annals of the Rheum. Dis.*, vol. 51, pp. 919-925.

Comins, D.L., et al, 1994, "Grignard addition to 1-acyl salts of chiral 4-alkoxypyridines. A new enantioselective preparation of 2-alkyl-2,3-dihydro-4-pyridones", *Tetrahedron Letters*,. vol. 35, pp. 7343-7346.

Cooper, J.A., 1994, "Membrane-associated tyrosine kinases as molecular switches", *Sem. Cell Biology*, vol. 5, pp. 377-387.

Correia, J., 1978, "Reaction of phenylglyoxal with aniline under acidic conditions", *J. Org. Chem.*, vol. 43, pp. 3394-3396.

Courtneidge, S.A., et al, 1993, "The Src family of protein tyrosine kinases: regulation and functions", *Development 1993 Supplement*, pp. 57-64.

Cowley, S., et al, 1994, "Activation of MAP kinase kinase is necessary and sufficient for PC12 differentiation and for transformation of NIH 3T3 cells", *Cell*, vol. 77, pp. 841-852.

Davies, H., et al, 2002, "Mutations of the *BRAF* gene in human cancer", *Nature*, vol. 417, pp. 949-954.

Davis, S., et al, 1996, "Isolation of angiopoietin-1, a ligand for the TIE2 receptor, by secretion-trap expression cloning", *Cell*, vol. 87, pp. 1161-1169.

Denekamp, J., 1993, "Review article: angiogenesis, neovascular proliferation and vascular pathophysiology as targets for cancer therapy", *British Journal of Radiology*, vol. 66, pp. 181-196.

Dickson, B., et al, 1992, "Raf functions downstream of Ras1 in the sevenless signal transduction pathway", *Nature*, vol. 360, pp. 600-603.

DuBois, G.E., 1980, "Amination of aryl sufamate esters. A convenient general synthesis of aliphatic sulfamides", *Journal of Organic Chemistrty*, vol. 45, pp. 5373-5375.

Fidler, I.J., et al, 1994, "The implications of angiogenesis for the biology and therapy of cancer metastasis", *Cell*, vol. 79, pp. 185-188.

Folkman, J., et al, 1992, "Angiogensis", *Journal of Biol. Chem.*, vol. 267, pp. 10931-10934.

Folkman, J., 1992, "The role of angiogenesis in tumor growth", *Cancer Biology*, vol. 3, pp. 65-71.

Folkman, J., et al, 1995, "Angiogenesis in cancer, vascular, rheumatoid and other disease", *Nature Medicine*, vol. 1, pp. 27-31.

Folkman, J., 1997, "Angiogenesis and angiogenesis inhibition: an overview", *EXS*, vol. 79, pp. 1-8.

Fourrey, J-L.,1987, "Preparation of stable 1,4-dihydropyrazines", *J. Chem. Soc., Perkins. Transactions 1: Org. & Bio. Chem.*, vol. 8, pp. 1841-1843.

Friedlander, et al, 1995, "Definition of two angiogenic pathways by distinct $α_v$ integrins", *Science*, vol. 270, pp. 1500-1502.

Gale, et al, 1999, "Growth factors acting via endothelial cell-specific receptor tyrosine kinases: VEGFs, angiopoietins, and ephrins in vascular development", *Genes Dev.*, vol. 13, pp. 1055-1066.

Galons, H., et al, 1981, "Cyclisation indolique selon Bischler en presence d'acides de Lewis", *J. Heterocyclic Chemistry*, vol. 18, pp. 561-563 (in French, with partial English language translation).

Genot, E., et al, 2000, "Ras regulation and function in lymphocytes", *Curr. Opin. Immunol.*, vol. 12, pp. 289-294.

Giannotti, D., et al, 1991, "New dibenzothiadiazepine derivatives with antidepressant activities", *J. Med. Chem.*, vol. 34, pp. 1356-1362.

Giardina, G.A.M., et al, 1999, "Replacement of the quinoline system in 2-phenyl-4-quinolinecarboxamide NK-3 receptor antagonists", *II Farmaco*, vol. 54, pp. 364-374.

Glinka, R., et al, 1991, "Synthesis and structure of new hetercyclic systems containing the sulgamide group", *Pol. J. Chem.*, vol. 65, pp. 2053-2055.

Gorden, A., et al, 2003, "Analysis of *BRAF* and *N-RAS* mutations in metastatic malanoma tissues", *Cancer Reserch*, vol. 63, pp. 3955-3957.

Guarna, A., et al, 2002, "Synthesis of a new enantiopure bicyclic γ/δ-amino acid (BTKa) derived from tartaric acid and α-amino acetophenone", *Tetrahedron*, vol. 58, pp. 9865-9870.

Haesslein, J., et al, 2002, "Recent advances in cyclin-dependent kinas inhibition. Purine-based derivatives as anti-cancer agents. Roles and perspectives for the future", *Curr. Top. Med. Chem.*, vol. 2, pp. 1037-1050.

Hammond, M., et al, 2003, "Structure-activity relationships in a series of NPY Y5 antagonists: 2-amido-9-ethylcarbazoles, core-modified analogues and amide isosteres", *Bioorganic & Medicinal Chemistry Letters*, vol. 13, pp. 1989-1992.

Helbling, P.M., et al, 2000, "The receptor tyrosine kinase EphB4 and ephrin-B ligands restrict angiogenic growth of embryonic veins in *Xenopus laevis*", *Development*, vol. 127, pp. 269-278.

Hirayama, F., et al, 2002, "Design, synthesis and biological activity of YM-60828 derivatives: potent and orally-bioavailable factor Xa inhibitors based on naphthaoanilide and naphthalensulfonanilide templates", *Biorganic & Medicinal Chemistry*, vol. 10, pp. 2597-2610.

Holland, S.J., et al, 1996, "Bidirectional signalling through the EPH-family receptor Nuk and its transmembrane ligands", *Nature*, vol. 383, pp. 722-725.

Ingber, et al., 1990, "Synthetic analogues of fumagillin that inhibit angiogenesis and suppress tumour growth", *Nature*, vol. 348, pp. 555-557.

Ishii, A., et al, 1997, "First synthesis and reactivities of isolable dithiiranes and their 1-oxides", *Bull. chem. Soc. Jpn.*, vol. 70, pp. 509-523.

Itaya, T., et al, 1998, "Syntheses of the marine ascidian purine aplidiamine and its 9-beta-d-ribofuranoside", *Tetrahedron Letters*, vol. 39, pp. 4695-4696.

Janvier, P., et al, 2002, "Ammonium chloride-promoted four-component synthesis of pyrrolo[3-4-b]pyridin-5-one", *J. American Chemical Society*, vol. 124, pp. 2560-2567.

Johnson, C.R., et al, 1979, "Preparation and reactions of sulfonimidoyl chlorides", *Journal of Organic Chemistry*, vol. 44, pp. 2055-2061.

Jursic, B., 1988, "Synthetic application of micellar catalysis. Williamson's synthesis of ethers", *Tetrahedron*, vol. 44, pp. 6677-6680.

Kahlon, R., et al, 1992, "Angiogenesis in atherosclerosis", *Can. J. Cardiol.*, vol. 8, pp. 60-64.

Kolch, W., et al, 1991, "Raf-1 protein kinase is required for growth of induced NIH/3T3 cells", *Nature*, vol. 349, pp. 426-428.

Lemonnier, J., et al, 2001, "Role of N-cadherin and protein kinase C in osteoblast gene activation inducted by the S252W fibroblast growth factor receptor 2 mutation in apert craniosynostosis", *J. Bone & Min. Research*, vol. 16, pp. 832-845.

Liu, W., et al, 2004, "Effects of overexpression of ephrin-B2 on tumour growth in human colorectal cancer", *British Journal of Cancer*, vol. 90, pp. 1620-1626.

Lozinskii, M.O., et al, 2002, "Alkylthio derivatives of the aminoketene S,N-acetals of heterocyclic β-dicarbonyl compounds: one stage synthesis and properties", *Chemistry of Heterocyclic Compounds*, vol. 38, pp. 1077-1080.

Mansour, S.J., et al, 1994, "Transformation of mammalian cells by constitutively active MAP kinase kinase", *Science*, vol. 265, pp. 966-970.

Marais, R., et al, 1997, "Differential regulation of Rad-1, A-Raf, and B-Raf by oncogenic Ras and tyrosine kinases", *J. of Biol. Chem.*, vol. 272, pp. 4378-4383.

Mataloni, M., et al, 2003, "Synthesis of secondary amines by reduction of α-amidoalkylphenyl sulfones with sodium acetoxyborohbydride", *Synlett*, vol. 8, pp. 1129-1132.

McMahon, G., 2000, "VEGF receptor signaling in tumor angiogenesis", *The Oncologist*, vol. 5, pp. 3-10.

Messinger, P., et al, "Notiz zur synthese von α-amino- und α-amidosulfonen", *Archive Der Pharmazie*, 1974, vol. 307, pp. 653-655 (in German, with partial English language translation).

Meyers, G.A., et al, 1996, "FGFR2 Exon IIIa and IIIC mutations in Crouzon, Jackson-Weiss, and Pfeiffer syndromes: Evidence for Missense change, insertions and a deletion due to alternative RNA splicing", *Am. J. Hum. Genet.*, vol. 58, pp. 491-498.

Mineo, T.C., et al, 2004, "Prognostic impact of VEGF, CD31, CD34, and CD105 expression and tumour vessel invasion after radical surgery for IB-IIA non-small cell lung cancer", *J. Clin. Pathol.*, vol. 57, pp. 591-597.

Mohanta, P.K., et al, 2000, "1-(methyldithiocarbony)imidazole: a useful thiocarbonyl transfer reagent for synthesis of substituted thioureas", *Tetrahedron*, vol. 2000, pp. 629-637.

Moore, J.D., et al, 2003, "ROMP-generated oligomeric sulfonyl chlorides as versatile soluble scavenging agents", *Organic Letters*, vol. 5, pp. 105-107.

Mustonen, T., et al, 1995, "Endothelial receptor tyrosine kinases involved in angiogenesis", *J. Cell Biol.*, vol. 129, pp. 895-898.

Nakamoto, M., et al, 2002, "Diverse roles for the Eph family of receptor tyrosine kinases in carcinogenesis", *Micros. Res. and Tech.*, vol. 59, pp. 58-67.

O'Reilly, M.S., et al, 1994, "Angiostatin: A novel angiogenesis inhibitor that mediates the supression of metastases by a Lewis lung carcinolma", *Cell*, vol. 79, pp. 315-328.

Orre, M., et al, 1999, "VEGF, VEGFR-1, and VEGFR-2, microvessel density and endothelial cell proliferation in tumors of the ovary", *Int. J. Cancer*, vol. 84, pp. 101-108.

Ozawa, F., et al, 2001, "Growth factors and their receptors in pancreatic cancer", *Teratog. Carcinog. & Mutagen.*, vol. 21, pp. 27-44.

Pabst, B., et al, 1999, "Analysis of K-*ras* mutations in pancreatic tissue after fine needle aspirates", *Anticancer Research*, vol. 19, pp. 2481-2484.

Parlow, J.J., et al, 2003, "Synthesis and crystal structures of substituted benzenes and benzoquinones as tissue factor VIIa inhibitors", *J. Med. Chem.*, vol. 46, pp. 4297-4312.

Partanen, J., et al, 1992, "A novel endothelial cell surface receptor tyrosine kinase with extracellular epidermal growth factor homology domains", *Mol. Cell. Biol.*, vol. 12, pp. 1698-1707.

Partanen, J., et al, 1999, "Functions of Tie1 and Tie2 receptor tyrosine kinases in vascular development", *Current Topics in Microbiol. Immunol.*, vol. 237, pp. 159-172.

Paulson, R.F., et al, 1995, "Receptor tyrosine kinases and the regulation of hematopoiesis", *Semin. Immunol.*, vol. 7, pp. 267-277.

Peacock, D.J., et al, 1992, "Angiogenesis inhibition suppresses collagen artritis", *J. Exp. Med.*, vol. 175, pp. 1135-1138.

Peacock, D.J., et al, 1995, "A novel angiogenesis inhibitor suppresses rat adjuvant arthritis", *Cell. Immun.*, vol. 160, pp. 178-184.

Peters, K.G., 1998, "Vascular endothelial growth factor and the angiopoietins", Circ. Res., vol. 83, pp. 342-343.

Pinedo, H.M., et al, 2000, "Translational research: The role of VEGF in tumor angiogenesis", *The Oncologist*, vol. 5, pp. 1-2.

Plomp, A.S., et al, 1998, "Pfeiffer syndrome type 2: Further delineation and review of the literature", *Am. J. Med. Gen.*, vol. 75, pp. 245-251.

Powers, C.J., et al, 2000, "Fibroblast growth factors, their receptors and signaling", *Endocrine-Related Cancer*, vol. 7, pp. 165-197.

Prakash, 0., et al, 1992, *Indian Journal of Chemistry, Section B: Organic Chemistry Including Medicinal Chemistry*, vol. 31B, pp. 349-350.

Prix, L., et al, 2002, "Diagnostic biochip array for fast and sensitive detection of K-*ras* mutations in stool", *Clinical Chemistry*, vol. 48, pp. 428-435.

Rajagopalan, H., et al, 2002, "RAF/RAS oncogenes and mismatch-repair status", *Nature*, vol. 418, p. 934.

Ramadas, K., et al, 1997, "LAC sulfur assisted synthesis of symmetrical thioureas", *Synth. Comm.*, vol. 27, pp. 2255-2260.

Sarkis, G.Y., et al, 1985, "Synthesis and spectroscopic properties of some new N,N'- disubstituted thioureas of potential biological interest", *J. Heterocyclic Chemistry*, vol. 22, pp. 137-140.

Shaw, J.T., et al, 1980, "The preparation of 2,6-diaminopyrazine, 2,6-diazidopyrazine and some of their derivatives", *J. Het. Chem.*, vol. 17, pp. 11-16.

Shiina, I., et al, 2003, "A new method for the synthesis of carboxamides and peptides using 1,1'-carbonyldioxydi[2(1*H*)-pyridone] (CDOP) in the absence of basic promoters", *Tetrahedron Letters*, vol. 44, pp. 1952-1955.

Shin, D., et al, 2001, "Expression of EphrinB2 identifies a stable genetic difference between arterial and venous vascular smooth muscle as well as endothelial cells, and marks subsets of microvessels at sites of adult neovascularization", *Dev. Biol.*, vol. 230. pp. 139-150.

Singer, G., et al, 2003, "Mutations in BRAF and KRAS characterize the development of low-grade ovarian serous carcinoma", *J. Nat. Can. Inst.*, vol. 95, pp. 484-486.

Srinivas, K.V.N.S., et al, 2003, "A highly convenient, efficient, and selective process for preparation of esters and amides from carboxylic acids using $Fe^{3+}$-L-1- montmorillonite clay", *Journal of Organic Chemistry*, vol. 68, pp. 1165-1167.

Srivastava, P.K., et al, 1981, "Synthesis and antithyroid activity of some benzimidazolyl and benzenesulphonyl thiocarbamides", *Current Science*, vol. 50, pp. 305-307.

Suri, C., et al, 1996, "Requisite role of angiopoietin-1, a ligand for the TIE2 receptor, during embryonic angiogenesis", *Cell*, vol. 87, pp. 1171-1180.

Tang, X.X., et al, 1999, "High-level expression of EPHB6, EFNB2, and EFNB3 is associated with low tumor stage and high TrkA exp0ression in human neuroblastomas", *Clin. Can. Res.*, vol. 5, pp. 1491-1496.

Tang, X.X., et al, 1999, "Coexpression of transcripts encoding EPHB receptor protein tyrosine kinases and their Ephrin-B ligands in human small cell lung carincomal", *Clin. Can. Res.*, vol. 5, pp. 455-460.

Tanga, M.J., et al, 2003, "Synthesis of two potential food mutagens", *J. Heterocyclic. Chemistry*, vol. 40, pp. 569-573.

Taraboletti, G., et al, 1995, "Inhibition of angiogenesis and murine hemangioma growth by batimastat, a synthetic inhibitor of matrix metalloproteinases", *J. Nat. Can. Instit.*, vol. 87, pp. 293-298.

Temple, C., et al, 1989, "New anticancer agents: alterations of the carbamate group of ethyl (5-amino-1,2-dihydro-3-phenylpyrido[3,4-b]pyrazin-7-yl) carbamates", *J. Med. Chem.*, vol. 32, pp. 2363-2367.

Terao, Y., et al, 1977, "Synthesis of α-thio, α-sulfinyl, and a-sulfonyl-substituted nitrosamines", *Chem. Pharm. Bull.*, vol. 25(11), pp. 2964-2968.

Uchida, M., et al, 1985, "Studies on 2(1*H*)-quinolinone derivatives as gastric antiulcer active agents. 2-(4-chlorobenzoylamino)-3-[2(1*H*)-quinolinon-4-yl]propionic acid and related compounds", *Chem. Pharm. Bull.*, vol. 33(9), pp. 3775-3786.

Wan, P.T.C., et al, 2004, "Mechanism of activation of the RAF-ERK signaling pathway by oncogenic mutations of B-RAF", *Cell*, vol. 116, pp. 855-867.

Wang, H.U., et al, 1998, "Molecular distinction and angiogenic interaction between embryonic arteries and veins revealed by ephrin-B2 and its receptor Eph-B4", *Cell*, Vol. 93, pp. 741-753.

Wilks, a.F., 1990, "Structure and function of the protein tyrosine kinases", *Progress in Growth Factor Research*, vol. 2, pp. 97-111.

Yancopoulos, G.D., et al, 1998, "Vasculogenesis, angiogenesis, and growth factors: ephrins enter the fray at the border", *Cell*, vol. 93, pp. 661-664.

Yu, K., et al, 2000, "Loss of fibroblast growth factor receptor 2 ligand-binding specificity in Apert syndrome", *Proc. Natl. Acad. Sci. U.S.A.*, vol. 97, pp. 14536-14541.

Zejc, A., et al, 1990, "Synthesis and anticonvulsant properties of some arylsuccinate methylpyridylimides", *Pol. J. Pharmaceol. Pharm.*, vol. 42, pp. 69-77.

Zhou, Z-L., et al, 2001, "Synthesis and Sar of 5-, 6-, 7- and 8-aza analogues of 3-aryl-4-hydroxyguinolin-2(1*H*)-one as NMDA/glycine site antagonists", *Bioorganic & Medicinal Chemistry*, vol. 9, pp. 2061-2071.

UK Search Report for GB 0423554.5.

International Search Report (ISR) and Written Opinion of the International Searching Authority (WOISA) for PCT/GB2005/004081.

International Preliminary Report on Patentability (IPRP) for PCT/GB2005/004081.

* cited by examiner

IMIDAZO[4,5-B]PYRIDIN-2-ONE AND OXAZOLO[4,5-B]PYRIDIN-2-ONE COMPOUNDS AND ANALOGS THEREOF AS THERAPEUTIC COMPOUNDS

RELATED APPLICATION

This application is the U.S. national phase of International Application No. PCT/GB2005/004081 filed 21 Oct. 2005 which designated the U.S., and claims priority to GB 0423554.5 filed 22 Oct. 2004 and U.S. Provisional Application No. 60/620,658 filed 22 Oct. 2004, the entire contents of each of which are hereby incorporated by reference.

TECHNICAL FIELD

The present invention pertains generally to the field of therapeutic compounds for treating proliferative conditions, cancer, etc., and more specifically to certain imidazo[4,5-b]pyridin-2-one and oxazolo[4,5-b]pyridin-2-one compounds and analogs thereof which, inter alia, inhibit RAF (e.g., B-RAF) activity. The present invention also pertains to pharmaceutical compositions comprising such compounds, and the use of such compounds and compositions, both in vitro and in vivo, to inhibit RAF (e.g., BRAF) activity, to inhibit receptor tyrosine kinase (RTK) activity, to inhibit cell proliferation, and in the treatment of diseases and conditions that are ameliorated by the inhibition of RAF, RTK, etc., proliferative conditions such as cancer (e.g., colorectal cancer, melanoma), etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiments.

RAF, Proliferative Conditions, and Cancer

Mutations in genes that directly or indirectly control cell growth and differentiation are generally considered to be the main cause of cancer. Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation.

RAF is key downstream target for the ras GTPase and mediates the activation of the MAP kinase cascade consisting of raf-MEK-ERK. Activated ERK is a kinase that subsequently targets a number of proteins responsible for mediating, amongst other things, the growth, survival and transcriptional functions of the pathway. These include the transcription factors ELK1, C-JUN, the Ets family (including Ets 1, 2, and 7), and the FOS family. The ras-raf-MEK-ERK signal transduction pathway is activated in response to many cell stimuli including growth factors such as EGF, PDGF, KGF etc. Because the pathway is a major target for growth factor action, the activity of raf-MEK-ERK has been found to be upregulated in many factor dependent tumours. The observation that about 20% of all tumours have undergone an activating mutation in one of the ras proteins indicates that the pathway is more broadly important in tumorigenesis. There is growing evidence that activating mutations in other components of the pathway also occur in human tumours. This is true for RAF.

The RAF oncogene family includes three highly conserved genes termed A-RAF, B-RAF and C-RAF (also called Raf-1). RAF genes encode protein kinases that are thought to play important regulatory roles in signal transduction processes that regulate cell proliferation. RAF genes code for highly conserved serine-threonine-specific protein kinases, which are recruited to the plasma membrane following direct binding to the Ras small Guanine-nucleotide binding proteins and this is the initiating event in RAF activation. RAF proteins are part of a signal transduction pathway believed to consist of receptor tyrosine kinases, p21 Ras, RAF protein kinases, Mek1 (ERK activator or MAPKK) kinases and ERK (MAPK) kinases, which ultimately phosphorylate several cellular substrates, including transcription factors. Signaling through this pathway can mediate differentiation, proliferation or oncogenic transformation in different cellular contexts. Thus, RAF kinases are believed to play a fundamental role in the normal cellular signal transduction pathway, coupling a multitude of growth factors to their net effect, cellular proliferation. Because RAF proteins are direct downstream effectors of ras protein function, therapies directed against RAF kinases are believed to be useful in treatment of ras-dependent tumors.

The RAF kinases are differentially regulated and expressed; C-RAF is the most thoroughly characterized and is expressed in all organs and in all cell lines that have been examined. A-RAF and B-RAF also appear to be ubiquitous, but are most highly expressed in urogenital and brain tissues, respectively. Because B-RAF is highly expressed in neural tissues it was once thought to be limited to these tissues but it has since been found to be more widely expressed. Although all RAF proteins can bind to active Ras, B-raf is most strongly activated by oncogenic Ras, and may be the primary target of oncogenic Ras in transformed cells.

Recent evidence indicates that mutational activation of B-RAF is found in a number of different tumours including more than 65% of malignant melanomas, more than 10% of colorectal cancers (Davies, H., et al., 2002, *Nature*, Vol. 417, pp. 949-954; Rajagopalan, H. et al., 2002, *Nature*, Vol. 418, p. 934), ovarian cancers (Singer, G., et al., 2003, *J. Natl. Cancer Inst.*, Vol. 95, pp. 484-486) and papillary thyroid cancers (Brose, M., et al., 2002, *Cancer Res.*, Vol. 62, pp. 6997-7000;

Cohen, Y., et al., 2003, *Invest. Opthalmol. Vis. Sci.*, Vol. 44, pp. 2876-2878). A range of different B-RAF mutations have been identified in different tumours with the most common being a V600E mutation in the so-called activation loop of the kinase domain (Davies, H., et al., 2002, *Nature*, Vol. 417, pp. 949-954).

Other mutations of B-RAF found associated with human cancers may not necessarily activate B-RAF directly but do upregulate the activity of the ras-raf-MEK-ERK pathway by mechanisms which are not fully understood but may involve cross-talk with other RAF isoforms, such as A-RAF (Wan, P., et al., 2004, *Cell*, Vol. 116, pp. 855-867). In such cases, inhibition of RAF activity would remain a beneficial aim in cancer treatment.

In addition to link between B-RAF and certain cancers, there is a significant amount of evidence to indicate a more broad inhibition of RAF activity could be beneficial as an antitumour therapy. Blocking the pathway at the level of B-RAF would be effective at counteracting the upregulation of this pathway caused by tumourigenic ras mutations and also in tumours responding to growth factor action via this pathway. Genetic evidence in *Drosophila* and *C. elegans* indicates that RAF homologues are essential for ras dependent actions on differentiation (Dickson, B., et al., 1993, *Nature*, Vol. 360, pp. 600-603). Introduction of constitutively active MEK into NIH3T3 cells can have a transforming action whilst expression of dominant negative MEK proteins can suppress the tumourigenicity of ras transformed cell lines (Mansour, S. J., et al., 1994, *Science*, Vol. 265, pp. 966-970; Cowely, S., et al., 1994, *Cell*, Vol. 77, pp. 841-852). Expression of a dominant negative raf protein has also been found to inhibit ras dependent signalling as has suppression of raf expression using an antisense oligonucleotide construct (Koch, W., et al., 1991, *Nature*, Vol. 349, pp. 426-428; Bruder, T. T., et al., 1992, *Genes and Development*, Vol. 6, pp. 545-556).

This and other evidence suggests that inhibition of RAF (e.g., B-RAF) activity would be beneficial in the treatment of cancer, and that inhibition of RAF (e.g., B-RAF) activity could be particularly beneficial in those cancers containing a constitutively activated B-raf mutation.

The raf-MEK-ERK pathway functions downstream of many receptors and stimuli indicating a broad role in regulation of cell function. For this reason inhibitors of RAF may find utility in other disease conditions that are associated with upregulation of signalling via this pathway. The raf-MEK-ERK pathway is also an important component of the normal response of non-transformed cells to growth factor action. Therefore inhibitors of RAF may be of use in diseases where there is inappropriate or excessive proliferation of normal tissues. These include, but are not limited to glomerulonephritis and psoriasis. The cellular signalling pathway of which RAF is a part has also been implicated in inflammatory disorders characterized by T-cell proliferation (T-cell activation and growth), such as tissue graft rejection, endotoxin shock, and glomerular nephritis.

RAF (e.g., B-RAF) has been shown to be a valid therapeutic target in hyperproliferative disorders such as cancer. Activated versions of RAF (e.g., B-RAF) are able to transform mammalian cells, allowing them to take on the characteristics of cancer cells and the growth of these cells becomes dependent on the mutant RAF (e.g., B-RAF) protein. Inhibition of RAF (e.g., B-RAF) activity in human cancer cell lines that express the mutant forms of RAF (e.g., B-RAF) blocks their growth and ultimately induces their death.

Angiogenesis

Chronic proliferative diseases are often accompanied by profound angiogenesis, which can contribute to or maintain an inflammatory and/or proliferative state, or which leads to tissue destruction through the invasive proliferation of blood vessels. (Folkman, 1997, *EXS*, Vol. 79, pp. 1-81; Folkman, 1995, *Nature Medicine*, Vol. 1, pp. 27-31; Folkman and Shing, 1992, *J. Biol. Chem.*, Vol. 267, p. 10931.)

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, 1992, *Ann. Rhum. Dis.*, Vol. 51, p. 919). In diabetes (and in many different eye diseases), new vessels invade the macula or retina or other ocular structures, and may cause blindness (Brooks et al, 1994, *Cell*, Vol. 79, p. 1157). The process of atherosclerosis has been linked to angiogenesis (Kahlon et al., 1992, *Can. J. Cardiol.*, Vol. 8, p. 60). Tumor growth and metastasis have been found to be angiogenesis-dependent (Folkman, 1992, *Cancer Biol.*, Vol. 3, p. 65; Denekamp, 1993, *Br. J. Rad.*, Vol. 66, p. 181; Fidler and Ellis, 1994, *Cell*, Vol. 79, p. 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., 1994, *Cell*, Vol. 79, p. 315; Ingber et al., 1990, *Nature*, Vol. 348, p. 555), ocular diseases (Friedlander et al., 1995, *Science*, Vol. 270, p. 1500), arthritis (Peacock et al., 1992, *J. Exp. Med.*, Vol. 175, p. 1135; Peacock et al., 1995, *Cell. Immun.*, Vol. 160, p. 178) and hemangioma (Taraboletti et al., 1995, *J. Natl. Cancer Inst.*, Vol. 87, p. 293).

RTKs

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

FGFR

The fibroblast growth factor (FGF) family of signaling polypeptides regulates a diverse array of physiologic functions including mitogenesis, wound healing, cell differentiation and angiogenesis, and development. Both normal and malignant cell growth as well as proliferation are affected by changes in local concentration of these extracellular signaling molecules, which act as autocrine as well as paracrine factors. Autocrine FGF signaling may be particularly important in the progression of steroid hormone-dependent cancers and to a hormone independentstate (Powers et al., 2000, *Endocr. Relat. Cancer*, Vol. 7, pp. 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa et al., 2001, *Teratog. Carcinog. Mutagen.*, Vol. 21, pp. 2744).

The two prototypic members are acidic fibroblast growth factor (aFGF or FGF1) and basic fibroblast growth factors (bFGF or FGF2), and to date, at least twenty distinct FGF family members have been identified. The cellular response to FGFs is transmitted via four types of high affinity transmembrane tyrosine-kinase fibroblast growth factor receptors numbered 1 to 4 (FGFR-1 to FGFR-4). Upon ligand binding, the receptors dimerize and auto- or trans-phosphorylate specific cytoplasmic tyrosine residues to transmit an intracellular signal that ultimately reaches nuclear transcription factor effectors.

Disruption of the FGFR-1 pathway should affect tumor cell proliferation since this kinase is activated in many tumor types in addition to proliferating endothelial cells. The overexpression and activation of FGFR-1 in tumor-associated vasculature has suggested a role for these molecules in tumor angiogenesis.

FGFR-2 has high affinity for the acidic and/or basic fibroblast growth factors, as well as the keratinocyte growth factor ligands. FGFR-2 also propagates the potent osteogenic effects of FGFs during osteoblast growth and differentiation. Mutations in FGFR-2, leading to complex functional alterations, were shown to induce abnormal ossification of cranial sutures (craniosynostosis), implying a major role of FGFR signaling in intramembranous bone formation. For example, in Apert (AP) syndrome, characterized by premature cranial suture ossification, most cases are associated with point mutations engendering gain-of-function in FGFR-2 (Lemonnier et al., 2001, *J. Bone Miner. Res.*, Vol. 16, pp. 832-845).

Several severe abnormalities in human skeletal development, including Apert, Crouzon, Jackson-Weiss, Beare-Stevenson cutis gyrata, and Pfeiffer syndromes are associated with the occurrence of mutations in FGFR-2. Most, if not all, cases of Pfeiffer Syndrome (PS) are also caused by de novo mutation of the FGFR-2 gene (Meyers et al., 1996, *Am. J. Hum. Genet.*, Vol. 58, pp. 491-498; Plomp et al., 1998, *Am. J. Med. Genet.*, Vol. 75, 245-251), and it was recently shown that mutations in FGFR-2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of FGFR-2 (Yu et al., 2000, *Proc. Natl. Acad. Sci. U.S.A.*, Vol. 97, pp. 14536-14541).

Activating mutations of the FGFR-3 receptor tyrosine kinase such as chromosomal translocations or point mutations produce deregulated, constitutively active, FGFR-3 receptors which have been involved in multiple myeloma and in bladder and cervix carcinomas (Powers, C. J., et al., 2000, *Endocr. Rel. Cancer*, Vol. 7, p. 165). Accordingly, FGFR-3 inhibition would be useful in the treatment of multiple myeloma, bladder and cervix carcinomas.

VEGFR

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al., 2000, *The Oncologist*, Vol. 5 (90001), pp. 1-2). VEGFR(s) are protein tyrosine kinases (PTKs). PTKs catalyze the phosphorylation of specific tyrosyl residues in proteins involved in the regulation of cell growth and differentiation. (Wilks, A. F., 1990, *Progress in Growth Factor Research*, Vol. 2, pp. 97-111; Courtneidge, S. A., 1993, *Dev. Suppl.*, pp. 57-64; Cooper, J. A., 1994, *Semin. Cell Biol.*, Vol. 5(6), pp. 377-387; Paulson, R. F., 1995, *Semin. Immunol.*, Vol. 7(4), pp. 267-277; Chan, A. C., 1996, *Curr. Opin. Immunol.*, Vol. 8(3), pp. 394-401).

Three PTK receptors for VEGF have been identified: VEGFR-1 (Flt-1), VEGFR-2 (Flk-1 or KDR), and VEGFR-3 (Flt4). These receptors are involved in angiogenesis and participate in signal transduction (Mustonen, T., et al., 1995, *J. Cell Biol.*, Vol. 129, pp. 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G., 2000, *The Oncologist*, Vol. 5(90001), pp. 3-10).

Inhibition at the kinase domain binding site of VEGFR-2 would block phosphorylation of tyrosine residues and serve to disrupt initiation of angiogenesis.

TIE

Angiopoieten 1 (Ang1), a ligand for the endothelium-specific receptor tyrosine kinase TIE-2 is a novel angiogenic factor (Davis et al., 1996, *Cell*, Vol. 87, pp. 1161-1169; Partanen et al., 1992, *Mol. Cell. Biol.*, Vol. 12, pp. 1698-1707; U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of anEGF-like domain and an immunoglobulin (IG) like domain, which consists of extracellular folding units, stabilized by intra-chain disulfide bonds (Partanen et al., 1999, *Curr. Topics Microbiol. Immunol.*, Vol. 237, pp. 159-172). Unlike VEGF, which functions during the early stages of vascular development, Ang1 and its receptor TIE-2 function in the later stages of vascular development, i.e., during vascular remodelling (remodelling refers to formation of a vascular lumen) and maturation (Yancopoulos et al, 1998, *Cell*, Vol. 93, pp. 661-664; Peters, K. G., 1998, *Circ. Res.*, Vol. 83(3), pp. 342-343; Suri et al., 1996, *Cell*, Vol. 87, pp. 1171-1180).

Consequently, inhibition of TIE-2 would be expected to serve to disrupt remodelling and maturation of new vasculature initiated by angiogenesis thereby disrupting the angiogenic process.

Eph

The largest subfamily of receptor tyrosine kinases (RTKs), the Eph family, and their ligands (ephrins), play important roles in physiologic and pathologic vascular processes. Both the Ephs (receptors) and ephrins (ligands) are divided into two groups, A and B subfamilies (Eph Nomenclature Committee, 1997). The binding of ephrin ligands to Eph receptors is dependent on cell-cell interactions. The interactions of ephrins and Ephs have recently been shown to function via bi-directional signalling. The ephrins binding to Eph receptors initiate phosphorylation at specific tyrosine residues in the cytoplasmic domain of the Eph receptors. In response to Eph receptor binding, the ephrin ligand also undergoes tyrosine phosphorylation, so-called 'reverse' signalling (Holland, S. J., et al., 1996, *Nature*, Vol. 383, pp. 722-725; Bruckner et al., 1997, *Science*, Vol. 275, pp. 1640-1643).

Eph RTKs and their ephrin ligands play important roles in embryonic vascular development. Disruption of specific Eph receptors and ligands (including ephrin-B2) leads to defective vessel remodelling, organisation, and sprouting resulting in embryonic death (Wang, H. U., et al., 1998, *Cell*, Vol. 93, pp. 741-753; Adams, R. H., et al., 1999, *Genes Dev*, Vol. 13, pp. 295-306; Gale and Yancopoulos, 1999, *Genes Dev*, Vol. 13, pp. 1055-1066; Helbling, P. M., et al., 2000, *Development*, Vol. 127, pp. 269-278). Coordinated expression of the Eph/ephrin system determines the phenotype of embryonic vascular structures: ephrin-B2 is present on arterial endothelial cells (ECs), whereas EphB4 is present on venous ECs (Gale and Yancopoulos, 1999, *Genes Dev*, Vol. 13, pp. 1055-1066; Shin, D., et al., 2001, *Dev Biol*, Vol. 230, pp. 139-150). Recently, specific Ephs and ephrins have been implicated in tumour growth and angiogenesis.

The Ephs and ephrins have been found to be overexpressed in many human tumours. In particular, the role of EphB2 has been identified in small cell lung carcinoma (Tang, X. X., et al., 1999, *Clin Cancer Res*, Vol. 5, pp. 455-460), human neuroblastomas (Tang, X. X., et al., 1999, *Clin Cancer Res*, Vol. 5, pp. 1491-1496) and colorectal cancers (Liu, W., et al., 2004, *Brit. J. Canc.*, Vol. 90, pp. 1620-1626), and higher expression levels of Ephs and ephrins, including EphB2, have been found to correlate with more aggressive and metastatic tumours (Nakamoto, M. and Bergemann, A. D., 2002, *Microsc. Res Tech*, Vol. 59, pp. 587).

Consequently, inhibition of EphB2 would be expected to serve to disrupt angiogenesis, and in particular in certain tumours where over-expression occurs.

The inventors have discovered compounds that, e.g., inhibit RAF (e.g., B-RAF) activity and/or are useful in the treatment of, e.g., proliferative conditions, cancer, etc.

There is a recognized need for more and better treatments for proliferative conditions (e.g., cancer) which offer, for example, one or more the following benefits:

(a) improved activity;

(b) improved efficacy;

(c) improved specificity;

(d) reduced toxicity (e.g., cytotoxicity);

(e) complement the activity of other treatments (e.g., chemotherapeutic agents);

(f) reduced intensity of undesired side-effects;

(g) fewer undesired side-effects;

(h) simpler methods of administration (e.g., route, timing, compliance);

(i) reduction in required dosage amounts;

(j) reduction in required frequency of administration;

(k) increased ease of synthesis, purification, handling, storage, etc.;

(l) reduced cost of synthesis, purification, handling, storage, etc.

Thus, one aim of the present invention is the provision of active compounds that offer one or more of the above benefits.

SUMMARY OF THE INVENTION

One aspect of the invention pertains to active compounds, specifically, certain imidazo[4,5-b]pyridin-2-one and oxazolo[4,5-b]pyridin-2-one compounds and analogs thereof, as described herein.

Another aspect of the invention pertains to a composition comprising an active compound as described herein and a pharmaceutically acceptable carrier or diluent.

Another aspect of the present invention pertains to a method of inhibiting RAF (e.g., B-RAF) activity in a cell, in vitro or in vivo, comprising contacting the cell with an effective amount of an active compound, as described herein.

Another aspect of the present invention pertains to a method of inhibiting receptor tyrosine kinase (RTK) activity, such as FGFR, Tie, VEGFR and/or Eph activity, for example, FGFR-1, FGFR-2, FGFR-3, Tie2, VEGFR-2 and/or EphB2 activity, in a cell, in vitro or in vivo, comprising contacting the cell with an effective amount of an active compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting cells (or the cell) with an effective amount of an active compound, as described herein.

Another aspect of the present invention pertains to a method for the treatment comprising administering to a subject in need of treatment a therapeutically-effective amount of an active compound, as described herein, preferably in the form of a pharmaceutical composition.

Another aspect of the present invention pertains to an active compound as described herein for use in a method of treatment of the human or animal body by therapy.

Another aspect of the present invention pertains to use of an active compound, as described herein, in the manufacture of a medicament for use in treatment.

In one embodiment, the treatment is treatment of a disease or condition (e.g., cancer) that is characterised by the up-regulation and/or activation of RAF (e.g., B-RAF), and/or is ameliorated by the inhibition of RAF (e.g., B-RAF).

In one embodiment, the treatment is treatment of a disease or condition (e.g., cancer) that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of a disease or condition that is characterised by inappropriate, excessive, and/or undesirable angiogenesis.

In one embodiment, the treatment is treatment of a proliferative condition, e.g., cancer.

Another aspect of the present invention pertains to a kit comprising (a) an active compound, as described herein, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

One aspect of the present invention pertains to compounds which may be described as "imidazo[4,5-b]pyridin-2-one and oxazolo[4,5-b]pyridin-2-one compounds and analogs thereof", and their surprising and unexpected RAF (e.g., B-RAF) inhibitory, anti-proliferative, and anti-cancer properties.

Compounds

One aspect of the present invention pertains to compounds of the following formula:

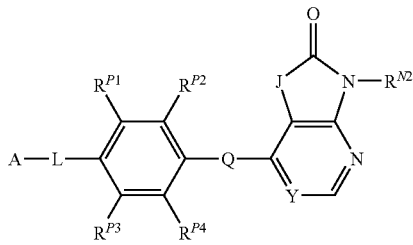

wherein:
J is independently —O— or —NR$^{N1}$—;
R$^{N1}$, if present, is independently —H or a group selected from:
  aliphatic saturated C$_{1-5}$alkyl,
  aliphatic C$_{2-5}$alkenyl,
  aliphatic C$_{2-4}$alkynyl,
  saturated C$_{3-6}$cycloalkyl,
  C$_{3-6}$cycloalkenyl;
  C$_6$carboaryl;
  C$_{5-6}$heteroaryl;
  C$_{5-6}$heterocyclic;
  and is independently unsubstituted or substituted;
R$^{N2}$ is independently —H or a group selected from:
  aliphatic saturated C$_{1-5}$alkyl,
  aliphatic C$_{2-5}$alkenyl,
  aliphatic C$_{2-5}$alkynyl,
  saturated C$_{3-6}$cycloalkyl,
  C$_{3-6}$cycloalkenyl;
  C$_6$carboaryl;
  C$_{5-6}$heteroaryl;
  C$_{5-6}$heterocyclic;
  and is independently unsubstituted or substituted;
Y is independently —CH= or —N=;
Q is independently —(CH$_2$)$_j$-M-(CH$_2$)$_k$— wherein:
  j is independently 0, 1 or 2;
  k is independently 0, 1, or 2;
  j+k is 0, 1, or 2;
  M is independently —O—, —S—, —NH—, —NMe—, or —CH$_2$—;
each of R$^{P1}$, R$^{P2}$, R$^{P3}$, and R$^{P4}$ is independently —H or a group selected from:
  aliphatic saturated C$_{1-5}$alkyl;
  aliphatic C$_{2-5}$alkenyl;
  aliphatic C$_{2-5}$alkynyl;
  saturated C$_{3-6}$cycloalkyl;
  C$_{3-6}$cycloalkenyl;
  aliphatic saturated C$_{1-5}$haloalkyl;
  —C(=O)OR$^1$,
    wherein R$^1$ is —H, C$_{5-12}$aryl-C$_{1-7}$alkyl, C$_{5-12}$aryl, C$_{3-12}$heterocyclyl, or C$_{1-7}$alkyl;
  —OR$^2$ and —SR$^2$,
    wherein R$^2$ is —H, C$_{5-12}$aryl-C$_{1-7}$alkyl, C$_{5-12}$aryl, C$_{3-12}$heterocyclyl, or C$_{1-7}$alkyl;
  —C(=O)NR$^3$R$^4$,
    wherein each of R$^3$ and R$^4$ is independently —H; or C$_{5-12}$aryl-C$_{1-7}$alkyl, C$_{5-12}$aryl, C$_{3-12}$heterocyclyl, or C$_{1-7}$alkyl; or R$^3$ and R$^4$ taken together with the nitrogen atom to which they are attached form a ring having from 3 to 7 ring atoms;
  —NR$^5$R$^6$,
    wherein each of R$^5$ and R$^6$ is independently —H; or C$_{5-12}$aryl-C$_{1-7}$alkyl, C$_{5-12}$aryl, C$_{3-12}$heterocyclyl, or C$_{1-7}$alkyl; or R$^5$ and R$^6$ taken together with the nitrogen atom to which they are attached form a ring having from 3 to 7 ring atoms;
  —NR$^7$C(=O)R$^8$,
    wherein:
      R$^7$ is —H or C$_{1-3}$alkyl;
      R$^8$ is C$_{5-12}$aryl-C$_{1-7}$alkyl, C$_{5-12}$aryl, C$_{3-12}$heterocyclyl, or C$_{1-7}$alkyl;
  —S(=O)R$^9$ or —S(=O)$_2$R$^9$,
    wherein R$^9$ is C$_{1-7}$alkyl, C$_{5-12}$aryl, or C$_{5-12}$aryl-C$_{1-7}$alkyl;
  —F, —Cl, —Br, or —I;
  —CN;
  and additionally R$^{P1}$ and R$^{P2}$ taken together may be —CH=CH—CH=CH—;
  wherein each C$_{1-5}$alkyl, C$_{2-5}$alkenyl, C$_{2-5}$alkynyl, C$_{3-6}$cycloalkyl, C$_{3-6}$cycloalkenyl, C$_{5-12}$aryl-C$_{1-7}$alkyl, C$_{5-12}$aryl, C$_{3-12}$heterocyclyl, and C$_{1-7}$alkyl is independently unsubstituted or substituted;
L is independently:
  a linker group formed by a chain of 2, 3, or 4 linker moieties;
  each linker moiety is independently —CH$_2$—, —NR$^N$—, —C(=X)—, or —S(=O)$_2$—;
  exactly one linker moiety is —NR$^N$—, or:
  exactly two linker moieties are —NR$^N$—;
  exactly one linker moiety is —C(=X)—, and no linker moiety is —S(=O)$_2$—; or:
  exactly one linker moiety is —S(=O)$_2$—, and no linker moiety is —C(=X)—;

no two adjacent linker moieties are —NR$^N$—;

X is independently =O or =S;

each R$^N$ is independently —H, saturated aliphatic C$_{1-3}$alkyl, or aliphatic C$_{2-3}$alkenyl;

A is independently:
- C$_{6-14}$carboaryl,
- C$_{5-14}$heteroaryl,
- C$_{3-12}$carbocyclic,
- C$_{3-12}$heterocyclic;

and is independently unsubstituted or substituted;

and pharmaceutically acceptable salts, solvates, amides, esters, ethers, N-oxides, chemically protected forms, and prodrugs thereof.

The Group Y

The group Y is independently —CH= or —N=.

In one embodiment, Y is independently —CH=.

In one embodiment, Y is independently —N=.

The Group J

The group J is independently —O— or —NR$^{N1}$—.

In one embodiment, J is independently —O—.

In one embodiment, J is independently —NR$^{N1}$—.

The Bicyclic Aryl-One Group

In one embodiment, the bicyclic aryl-one group is selected from:

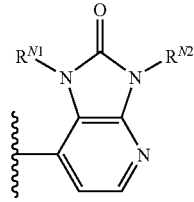 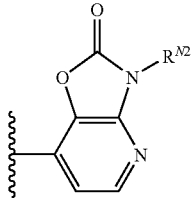

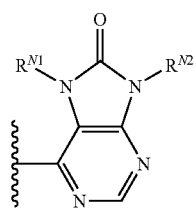 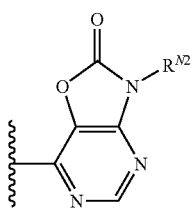

For example:

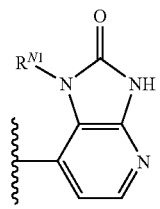 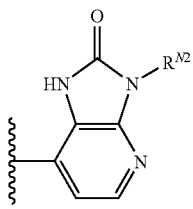

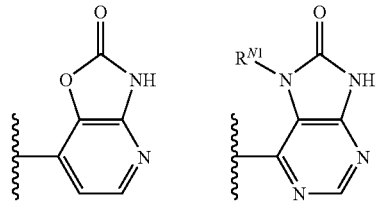

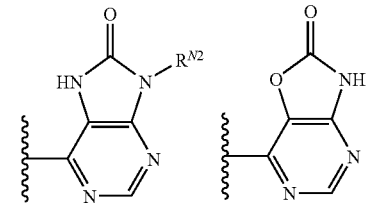

For example:

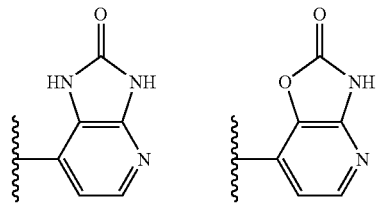

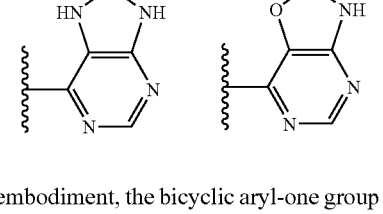

In one embodiment, the bicyclic aryl-one group is selected from:

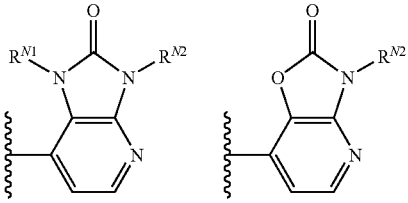

For example:

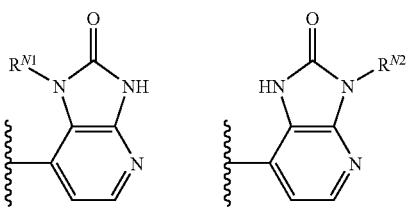

-continued

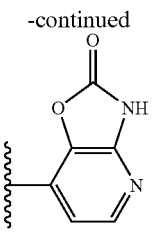

For example:

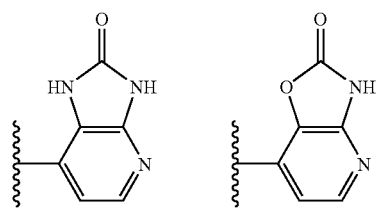

In one embodiment, the bicyclic aryl-one group is (a "1-(optionally substituted)-2-oxo-2,3-dihydro-1H-imidazo[4,5-b]pyridin-7-yl" group):

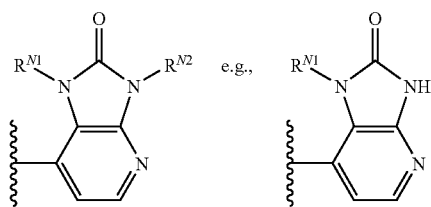

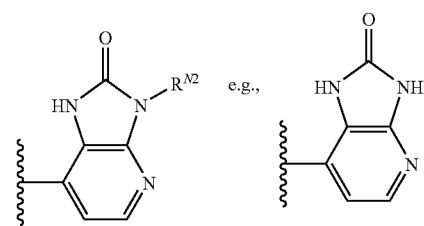

In one embodiment, the bicyclic aryl-one group is (a "2-oxo-2,3-dihydro-oxazolo[4,5-b]pyridin-7-yl" group):

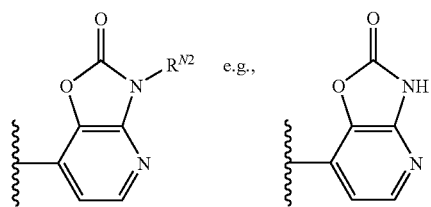

The Group $R^{N1}$

The group $R^{N1}$, if present, is independently —H or a group selected from:
   aliphatic saturated $C_{1-5}$alkyl;
      (e.g., —Me, —Et, —nPr, —iPr, —nBu, —iBu, —sBu, —tBu)
   aliphatic $C_{2-5}$alkenyl;
      (e.g., —CH=CH$_2$, —CH$_2$—CH=CH$_2$)
   aliphatic $C_{2-5}$alkynyl;
      (e.g., —C≡CH, —CH$_2$—C≡CH)
   saturated $C_{3-6}$cycloalkyl;
      (e.g., cyclopropyl, cyclobutyl, cyclopentyl, cyclohexyl)
   $C_{3-6}$cycloalkenyl;
      (e.g., cyclopropenyl, cyclobutenyl, cyclopentenyl, cyclohexenyl)
   $C_6$carboaryl;
      (e.g., phenyl)
   $C_{5-6}$heteroaryl;
      (e.g., pyridinyl, pyrazinyl, pyrimidinyl, pyridazinyl, furanyl, thiophenyl, pyrrolyl, imidazolyl, pyrazolyl, oxazolyl, thiazolyl, thiadiazole)
   $C_{5-6}$heterocyclic;
      (e.g., pyrrolidinyl, imidazolidinyl, pyrazolidinyl, piperidinyl, piperazinyl, tetrahydrofuranyl, tetrahydropyranyl, morpholinyl)
   and is independently unsubstituted or substituted.

In one embodiment, $R^{N1}$, if present, is independently —H or a group selected from:
   aliphatic saturated $C_{1-5}$alkyl;
      (e.g., —Me, —Et, —nPr, —iPr, —nBu, —iBu, —sBu, —tBu)
   aliphatic $C_{2-5}$alkenyl;
      (e.g., —CH=CH$_2$, —CH$_2$—CH=CH$_2$)
   and is independently unsubstituted or substituted.

In one embodiment, $R^{N1}$, if present, is independently —H or aliphatic saturated $C_{1-3}$alkyl.

In one embodiment, $R^{N1}$, if present, is independently —H or —Me.

In one embodiment, $R^{N1}$, if present, is independently —Me.

In one embodiment, $R^{N1}$, if present, is independently —H.

Substituents on the Group $R^{N1}$

The group $R^{N1}$, if present, is independently unsubstituted or substituted.

In one embodiment, $R^{N1}$, if present, is independently unsubstituted.

In one embodiment, $R^{N1}$, if present, is independently substituted.

In one embodiment, $R^{N1}$, if present, is independently unsubstituted or substituted with one or more (e.g., 1, 2, or 3) substituents.

In one embodiment, the substituents on $R^{N1}$, if present, are selected from the substituents described under the heading "Substituents on the Group A" below.

In one embodiment, the substituents are selected from: (3) amido or thioamido; (4) acyl; (8) hydroxy; (9) ether; (14) amino; (18) sulfonyl; (22) $C_{5-20}$aryl; (23) $C_{3-20}$heterocyclyl; as described under the heading "Substituents on the Group A" below.

For example, in one embodiment, the substituents are selected from:
(3)   —(C=O)NH$_2$,   —(C=O)NMe$_2$,   —(C=O)NEt$_2$, —(C=O)N(iPr)$_2$, —(C=O)N(CH$_2$CH$_2$OH)$_2$;
   —(C=O)-morpholino,   —(C=O)NHPh,   —(C=O)NHCH$_2$Ph;

(4) —C(=O)H, —(C=O)Me, —(C=O)Et, —(C=O)(tBu), —(C=O)-cHex, —(C=O)Ph; —(C=O)CH$_2$Ph;
(8) —OH;
(9) —OMe, —OEt, —O(iPr), —O(tBu), —OPh, —OCH$_2$Ph; —OCF$_3$, —OCH$_2$CF$_3$;
—OCH$_2$CH$_2$OH, —OCH$_2$CH$_2$OMe, —OCH$_2$CH$_2$OEt;
—OCH$_2$CH$_2$NH$_2$, —OCH$_2$CH$_2$NMe$_2$, —OCH$_2$CH$_2$N(iPr)$_2$;
—OPh—Me, —OPh—OH, —OPh—OMe, —OPh—F, —OPh—Cl, —OPh—Br, —OPh—I;
(14) —NH$_2$, —NHMe, —NHEt, —NH(iPr), —NMe$_2$, —NEt$_2$, —N(iPr)$_2$, —N(CH$_2$CH$_2$OH)$_2$;
—NHPh, —NHCH$_2$Ph; piperidino, piperazino, morpholino;
(18) —SO$_2$Me, —SO$_2$CF$_3$, —SO$_2$Et, —SO$_2$Ph, —SO$_2$PhMe, —SO$_2$CH$_2$Ph;
(22) —Ph, —Ph—Me, —Ph—OH, —Ph—OMe, —Ph—NH$_2$, —Ph—F, —Ph—Cl, —Ph—Br, —Ph—I;
pyridinyl, pyrazinyl, pyrimidinyl, pyridazinyl; furanyl, thiophenyl, pyrrolyl, imidazolyl, pyrazolyl, oxazolyl, thiazolyl, thiadiazolyl;
(23) pyrrolidinyl, imidazolidinyl, pyrazolidinyl, piperidinyl, piperazinyl, azepinyl, tetrahydrofuranyl, tetrahydropyranyl, morpholinyl, azetidinyl.

In one embodiment, the substituents are independently (optionally additionally) selected from those defined under the heading "Substituents on the Group A" below.

In one embodiment, the substituents are independently (optionally additionally) selected from those substituents exemplified under the heading "Some Preferred Embodiments."

Additional examples of R$^{N1}$ groups include —(CH$_2$)$_n$—R, wherein n is independently 1, 2, or 3, and R is independently —H or a substituent on R$^{N1}$, e.g., as described under the heading "Substituents on the Group R$^{N1}$" below.

Additional examples of R$^{N1}$ groups (here R$^{N1}$ is —(CH$_2$)$_n$—, n is independently 1, 2, or 3) substituted with (14) amino include the following (where R is, e.g., independently —H or C$_{1-3}$alkyl):

Additional examples of R$^{N1}$ groups (here R$^{N1}$ is —(CH$_2$)$_n$—, n is independently 1, 2, or 3) substituted with (23) C$_{3-20}$heterocyclyl include the following:

Additional examples of R$^{N1}$ groups (here R$^{N1}$ is —(CH$_2$)$_n$—, n is independently 1, 2, or 3) substituted with (9) ether include the following (where m is independently 0, 1, 2, or 3):

The Group R$^{N2}$

The group R$^{N2}$ is independently as defined for R$^{N1}$.

For example:

In one embodiment, R$^{N2}$ is independently —H or aliphatic saturated C$_{1-3}$alkyl.

In one embodiment, R$^{N2}$ is independently —H or —Me.

In one embodiment, R$^{N2}$ is independently —Me.

In one embodiment, R$^{N2}$ is independently —H, for example, as in:

The Group Q

The group Q is independently —(CH$_2$)$_j$-M-(CH$_2$)$_k$—, wherein:
j is independently 0, 1 or 2;
k is independently 0, 1, or 2;
j+k is 0, 1, or 2;
M is independently —O—, —S—, —NH—, —NMe—, or —CH$_2$—.

In one embodiment, M is independently —O—, —S—, —NH—, or —NMe—.
In one embodiment, M is independently —O— or —S—.
In one embodiment, M is independently —O—.
In one embodiment, M is independently —S—.
In one embodiment, j is independently 0 or 1.
In one embodiment, j is independently 0.
In one embodiment, k is independently 0 or 1.
In one embodiment, k is independently 0.
In one embodiment, j+k is independently 0, 1, or 2.
In one embodiment, j+k is independently 0 or 1.
In one embodiment, j+k is independently 0.
In one embodiment, j+k is independently 1.
In one embodiment, j+k is independently 2.
In one embodiment, j is 0 and k is 0.
In one embodiment, Q is independently —O—.
In one embodiment, Q is independently —S—.

The Groups R$^{P1}$, R$^{P2}$, R$^{P3}$, and R$^{P4}$

Each of R$^{P1}$, R$^{P2}$, R$^{P3}$, and R$^{P4}$ is independently —H or a group selected from:
aliphatic saturated C$_{1-5}$alkyl;
(e.g., —Me, —Et, —nPr, —iPr, —nBu, —iBu, —sBu, —tBu)

aliphatic $C_{2-5}$alkenyl;
(e.g., —CH=CH$_2$, —CH$_2$—CH=CH$_2$)
aliphatic $C_{2-5}$alkynyl;
(e.g., —C≡CH, —CH$_2$—C≡CH)
saturated $C_{3-6}$cycloalkyl;
(e.g., cyclopropyl, cyclobutyl, cyclopentyl, cyclohexyl)
$C_{3-6}$cycloalkenyl;
(e.g., cyclopropenyl, cyclobutenyl, cyclopentenyl, cyclohexenyl)
aliphatic saturated $C_{1-5}$haloalkyl;
(e.g., —CF$_3$, —CH$_2$CF$_3$, —CF$_2$CF$_3$)
—C(=O)OR$^1$,
wherein R$^1$ is —H, $C_{6-12}$aryl-$C_{1-7}$alkyl, $C_{5-12}$aryl, $C_{3-12}$heterocyclyl, or $C_{1-7}$alkyl;
(e.g., —C(=O)OH, —C(=O)OMe, —C(=O)OEt)
—OR$^2$ and —SR$^2$,
wherein R$^2$ is —H, $C_{6-12}$aryl-$C_{1-7}$alkyl, $C_{3-12}$aryl, $C_{3-12}$heterocyclyl, or $C_{1-7}$alkyl;
(e.g., —OH, —OMe, —OEt; —SH, —SMe, SEt)
—C(=O)NR$^3$R$^4$,
wherein each of R$^3$ and R$^4$ is independently —H; or $C_{5-12}$aryl-$C_{1-7}$alkyl, $C_{5-12}$aryl, $C_{3-12}$heterocyclyl, or $C_{1-7}$alkyl; or R$^3$ and R$^4$ taken together with the nitrogen atom to which they are attached form a ring having from 3 to 7 ring atoms;
(e.g., —C(=O)NH$_2$, —C(=O)NHMe, —C(=O)NHEt, —C(=O)NMe$_2$,
—C(=O)morpholino, —C(=O)piperidino, —C(=O)piperizino)
—NR$^5$R$^6$,
wherein each of R$^5$ and R$^6$ is independently —H; or $C_{5-12}$aryl-$C_{1-7}$alkyl, $C_{5-12}$aryl, $C_{3-12}$heterocyclyl, or $C_{1-7}$alkyl; or R$^5$ and R$^6$ taken together with the nitrogen atom to which they are attached form a ring having from 3 to 7 ring atoms;
(e.g., —NH$_2$, —NHMe, —NMe$_2$, —NHEt, —NEt$_2$, morpholino, piperidino, piperazino)
—NR$^7$C(=O)R$^8$,
wherein:
R$^7$ is —H or $C_{1-3}$alkyl;
R$^8$ is $C_{5-12}$aryl-$C_{1-7}$alkyl, $C_{5-12}$aryl, $C_{3-12}$heterocyclyl, or $C_{1-7}$alkyl;
(e.g., —NHC(=O)Me, —NMeC(=O)Me, —NHC(=O)Et, —NMeC(=O)Et)
—S(=O)R$^9$ or —S(=O)$_2$R$^9$,
wherein R$^9$ is $C_{1-7}$alkyl, $C_{5-12}$aryl, or $C_{5-12}$aryl-$C_{1-7}$alkyl;
(e.g., —S(=O)Me, —S(=O)$_2$Me, —S(=O)$_2$Et, —S(=O)$_2$Et)
—F, —Cl, —Br, or —I;
—CN;
and additionally R$^{P1}$ and R$^{P2}$ taken together may be
—CH=CH—CH=CH—;
wherein each $C_{1-5}$alkyl, $C_{2-5}$alkenyl, $C_{2-5}$alkynyl, $C_{3-6}$cycloalkyl, $C_{3-6}$cycloalkenyl, $C_{5-12}$aryl-$C_{1-7}$alkyl, $C_{5-12}$aryl, $C_{3-12}$heterocyclyl, and $C_{1-7}$alkyl is independently unsubstituted or substituted.

In one embodiment, each of R$^{P1}$, R$^{P2}$, R$^{P3}$, and R$^{P4}$ is independently —H or a group selected from:
aliphatic saturated $C_{1-5}$alkyl;
(e.g., —Me, —Et, —nPr, —iPr, —nBu, —iBu, —sBu, —tBu)
aliphatic $C_{2-5}$alkenyl;
(e.g., —CH=CH$_2$, —CH$_2$—CH=CH$_2$)
aliphatic $C_{2-5}$alkynyl;
(e.g., —C≡CH, —CH$_2$C≡CH)
saturated $C_{3-6}$cycloalkyl;
(e.g., cyclopropyl, cyclobutyl, cyclopentyl, cyclohexyl)
$C_{3-6}$cycloalkenyl;
(e.g., cyclopropenyl, cyclobutenyl, cyclopentenyl, cyclohexenyl)
aliphatic saturated $C_{1-5}$haloalkyl;
(e.g., —CF$_3$, —CH$_2$CF$_3$, —CF$_2$CF$_3$)
—C(=O)OR$^1$,
wherein R$^1$ is —H, $C_{5-12}$aryl-$C_{1-7}$alkyl, $C_{5-12}$aryl, $C_{3-12}$heterocyclyl, or $C_{1-7}$alkyl;
(e.g., —C(=O)OH, —C(=O)OMe, —C(=O)OEt)
—OR$^2$,
wherein R$^2$ is —H, $C_{5-12}$aryl-$C_{1-7}$alkyl, $C_{5-12}$aryl, $C_{3-12}$heterocyclyl, or $C_{1-7}$alkyl;
(e.g., —OH, —OMe, —OEt)
—C(=O)NR$^3$R$^4$,
wherein each of R$^3$ and R$^4$ is independently —H; or $C_{5-12}$aryl-$C_{1-7}$alkyl, $C_{5-12}$aryl, $C_{3-12}$heterocyclyl, or $C_{1-7}$alkyl; or R$^3$ and R$^4$ taken together with the nitrogen atom to which they are attached form a ring having from 3 to 7 ring atoms;
(e.g., —C(=O)NH$_2$, —C(=O)NHMe, —C(=O)NHEt, —C(=O)NMe$_2$,
—C(=O)morpholino, —C(=O)piperidino, —C(=O)piperizino)
—NR$^5$R$^6$,
wherein each of R$^5$ and R$^6$ is independently —H; or $C_{5-12}$aryl-$C_{1-7}$alkyl, $C_{5-12}$aryl, $C_{3-12}$heterocyclyl, or $C_{1-7}$alkyl; or R$^5$ and R$^6$ taken together with the nitrogen atom to which they are attached form a ring having from 3 to 7 ring atoms;
(e.g., —NH$_2$, —NHMe, —NMe$_2$, —NHEt, —NEt$_2$, morpholino, piperidino, piperazino)
—NR$^7$C(=O)R$^8$,
wherein:
R$^7$ is —H or $C_{1-3}$alkyl;
R$^8$ is $C_{5-12}$aryl-$C_{1-7}$alkyl, $C_{5-12}$aryl, $C_{3-12}$heterocyclyl, or $C_{1-7}$alkyl;
(e.g., —NHC(=O)Me, —NMeC(=O)Me, —NHC(=O)Et, —NMeC(=O)Et)
—F, —Cl, —Br, or —I;
—CN;
and additionally R$^{P1}$ and R$^{P2}$ taken together may be
—CH=CH—CH=CH—;
wherein each $C_{1-5}$alkyl, $C_{2-5}$alkenyl, $C_{2-5}$alkynyl, $C_{3-6}$cycloalkyl, $C_{3-6}$cycloalkenyl, $C_{5-12}$aryl-$C_{1-7}$alkyl, $C_{5-12}$aryl, $C_{3-12}$heterocyclyl, and $C_{1-7}$alkyl is independently unsubstituted or substituted.

Examples of optional substituents on R$^{P1}$, R$^{P2}$, R$^{P3}$, and R$^{P4}$ include those described under the heading "Substituents on the Group R$^{N1}$" above, and/or under the heading "Substituents on the Group A" below.

When R$^{P1}$ and R$^{P2}$ together are —CH=CH—CH=CH—, then, together with the atoms they are attached to, they form a benzene ring fused to the central phenylene ring; together they form a naphthyl group. Thus, in one embodiment, the compounds are selected from compounds of the following formula, and pharmaceutically acceptable salts, solvates, amides, esters, ethers, N-oxides, chemically protected forms, and prodrugs thereof:

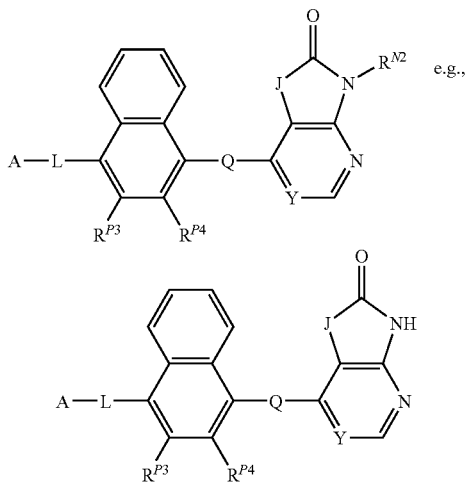

In one embodiment, $R^{P1}$ and $R^{P2}$ taken together are —CH═CH—CH═CH—; and each of $R^{P3}$ and $R^{P4}$ is independently —H.

In one embodiment, the alternative that $R^{P1}$ and $R^{P2}$ taken together are —CH═CH—CH═CH— is excluded.

In one embodiment, each of $R^{P1}$, $R^{P2}$, $R^{P3}$, and $R^{P4}$ is independently —H or a group selected from:
- —Me, —Et, —nPr, —iPr, —nBu, —iBu, —sBu, —tBu;
- —CH═CH$_2$, —CH$_2$—CH═CH$_2$;
- —C≡CH, —CH$_2$—C≡CH;
- cyclopropyl, cyclobutyl;
- cyclopropenyl, cyclobutenyl;
- —CF$_3$, —CH$_2$CF$_3$, —CF$_2$CF$_3$;
- —S(═O)Me, —S(═O)$_2$Me, —S(═O)$_2$Et, —S(═O)$_2$Et;
- —F, —Cl, —Br, or —I;
- —CN; and
- —SR$^2$, wherein R$^2$ is aliphatic saturated C$_{1-3}$alkyl.

In one embodiment, each of $R^{P1}$, $R^{P2}$, $R^{P3}$, and $R^{P4}$ is independently —H or a group selected from:
- —Me, —Et, —nPr, —iPr, —nBu, —iBu, —sBu, —tBu;
- —CH═CH$_2$, —CH$_2$—CH═CH$_2$;
- —C≡CH, —CH$_2$—C≡CH;
- cyclopropyl, cyclobutyl;
- cyclopropenyl, cyclobutenyl;
- —CF$_3$, —CH$_2$CF$_3$, —CF$_2$CF$_3$;
- —F, —Cl, —Br, or —I; and
- —CN.

In one embodiment, each of $R^{P1}$, $R^{P2}$, $R^{P3}$, and $R^{P4}$ is independently —H or a group selected from:
- aliphatic saturated C$_{1-3}$alkyl,
- aliphatic C$_{2-3}$alkenyl,
- aliphatic saturated C$_{1-5}$haloalkyl,
- —S(═O)R$^9$ and —S(═O)$_2$R$^9$, wherein R$^9$ is aliphatic saturated C$_{1-3}$alkyl;
- —F, —Cl, and
- —SR$^2$, wherein R$^2$ is aliphatic saturated C$_{1-3}$alkyl.

In one embodiment, each of $R^{P1}$, $R^{P2}$, $R^{P3}$, and $R^{P4}$ is independently —H or a group selected from:
- aliphatic saturated C$_{1-3}$alkyl,
- aliphatic C$_{2-3}$alkenyl,
- aliphatic saturated C$_{1-5}$haloalkyl, and
- —F, —Cl.

In one embodiment, each of $R^{P1}$, $R^{P2}$, $R^{P3}$, and $R^{P4}$ is independently —H or a group selected from:
- —Me, —Et, —nPr, —iPr;
- —CH═CH$_2$, —CH$_2$—CH═CH$_2$;
- —CF$_3$;
- —S(═O)Me, —S(═O)$_2$Me;
- —F, —Cl; and
- —SMe, —SEt.

In one embodiment, each of $R^{P1}$, $R^{P2}$, $R^{P3}$, and $R^{P4}$ is independently —H or a group selected from:
- —Me, —Et, —nPr, —iPr;
- —CH═CH$_2$, —CH$_2$—CH═CH$_2$;
- —CF$_3$; and
- —F, —Cl.

In one embodiment, each of $R^{P1}$, $R^{P2}$, $R^{P3}$, and $R^{P4}$ is independently —H, —Me, —S(═O)Me, —S(═O)$_2$Me, —F, —Cl, or —SMe.

In one embodiment, each of $R^{P1}$, $R^{P2}$, $R^{P3}$, and $R^{P4}$ is independently —H, —Me, —F, or —Cl.

In one embodiment, each of $R^{P1}$ and $R^{P2}$ is independently as defined above, and each of $R^{P3}$ and $R^{P4}$ is independently —H.

In one embodiment, each of $R^{P1}$ and $R^{P2}$ is independently as defined above, but is other than —H, and each of $R^{P3}$ and $R^{P4}$ is independently —H.

In one embodiment, exactly one of $R^{P1}$, $R^{P2}$, $R^{P3}$, and R$^4$ is independently as defined above, but is other than —H, and each of the remainder is independently —H.

In one embodiment, each of $R^{P1}$, $R^{P2}$, $R^{P3}$, and $R^{P4}$ is independently —H.

The Right-Hand Motif

In one embodiment, the right-hand motif is:

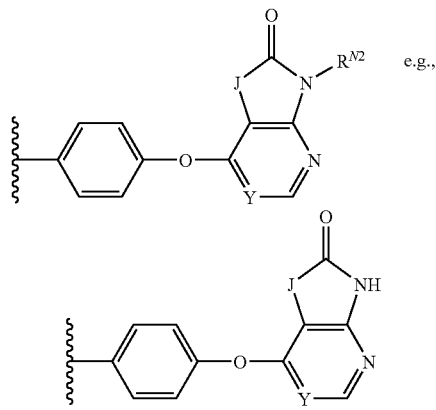

In one embodiment, the right-hand motif is:

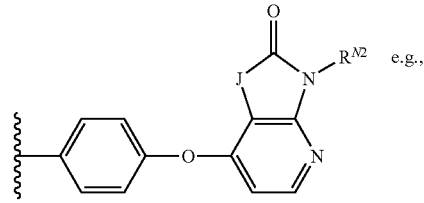

-continued

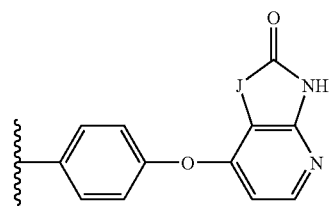

In one embodiment, the right-hand motif is:

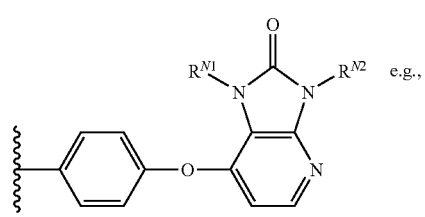

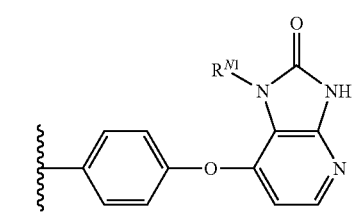

—F, —Cl.

In one embodiment, each of $R^{P1}$, $R^{P2}$, $R^{P3}$, and $R^{P4}$ is independently —H, —Me, —S(=O)Me, —S(—O)$_2$Me, —F, —Cl, or —SMe.

In one embodiment, each of $R^{P1}$, $R^{P2}$, $R^{P3}$, and $R^{P4}$ is independently -H, —Me, —F, or —Cl.

In one embodiment, each of $R^{P1}$ and $R^{P2}$ is independently as defined above, and each of $R^{P3}$ and $R^{P4}$ is independently —H.

In one embodiment, each of $R^{P1}$ and $R^{P2}$ is independently as defined above, but is other than —H, and each of $R^{P3}$ and $R^{P4}$ is independently —H.

In one embodiment, exactly one of $R^{P1}$, $R^{P2}$, $R^{P3}$, and $R^{P4}$ is independently as defined above, but is other than —H, and each of the remainder is independently —H.

In one embodiment, each of $R^{P1}$, $R^{P2}$, $R^{P3}$, and $R^{P4}$ is independently —H.

The Right-Hand Motif

In one embodiment, the right-hand motif is:

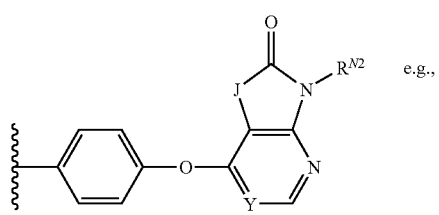

-continued

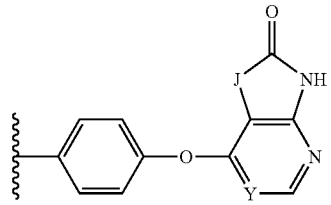

In one embodiment, the right-hand motif is:

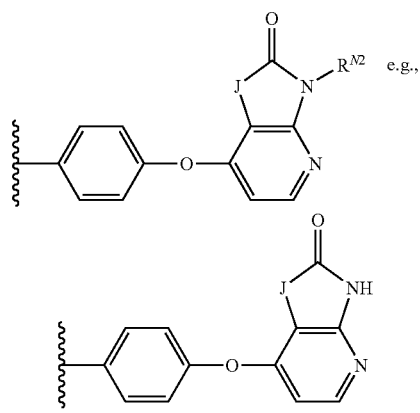

In one embodiment, the right-hand motif is:

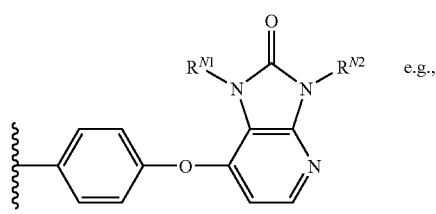

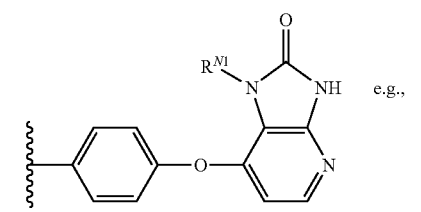

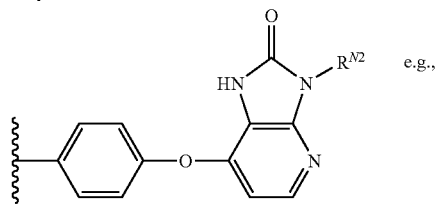

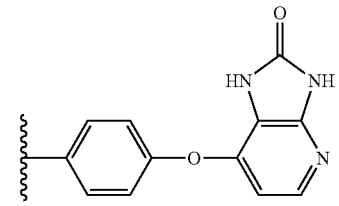

In one embodiment, the right-hand motif is:

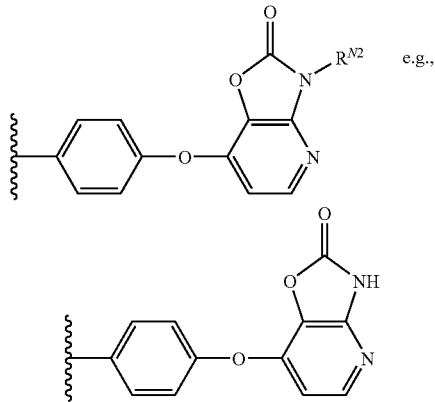

The Linker Group L

The linker group, L, is independently:
a linker group formed by a chain of 2, 3, or 4 linker moieties;
each linker moiety is independently —CH$_2$—, —NR$^N$—, —C(=X)—, or —S(=O)$_2$—;
exactly one linker moiety is —NR$^N$—, or:
exactly two linker moieties are —NR$^N$—;
exactly one linker moiety is —C(=X)—, and no linker moiety is —S(=O)$_2$—; or:
exactly one linker moiety is —S(=O)$_2$—, and no linker moiety is —C(=X)—;
no two adjacent linker moieties are —NR$^N$—.

In one embodiment, L, is independently:
a linker group formed by a chain of 2, 3, or 4 linker moieties;
each linker moiety is Independently —CH$_2$—, —NR$^N$—, or —C(=X)—;
exactly one linker moiety is —NR$^N$—, or:
exactly two linker moieties are —NR$^N$—;
exactly one linker moiety is —C(=X)—;
no two adjacent linker moieties are —NR$^N$—;

or:
a linker group formed by a chain of 2, 3, or 4 linker moieties;
each linker moiety is independently —CH$_2$—, —NR$^N$—, or —S(=O)$_2$—;
exactly one linker moiety is —NR$^N$—, or:
exactly two linker moieties are —NR$^N$—;
exactly one linker moiety is —S(=O)$_2$—;
no two adjacent linker moieties are —NR$^N$—.

The Linker Group L: Amides, Ureas, Etc.

In one embodiment, L is independently:
a linker group formed by a chain of 2, 3, or 4 linker moieties;
each linker moiety is independently —CH$_2$—, —NR$^N$—, or —C(=X)—;
exactly one linker moiety is —NR$^N$—, or:
exactly two linker moieties are —NR$^N$—;
exactly one linker moiety is —C(=X)—;
no two adjacent linker moieties are —NR$^N$—.

The phrase "no two adjacent linker moieties are —NR$^N$—" is intended to exclude possibilities such as —NR$^N$—NR$^N$—C(X)—.

In one embodiment, exactly one linker moiety is —NR$^N$—.
In one embodiment, exactly two linker moieties are —NR$^N$—.
In one embodiment, no linker moiety is —CH$_2$—.
In one embodiment, exactly one linker moiety is —CH$_2$—.
In one embodiment, exactly two linker moieties are —CH$_2$—.
In one embodiment, the linker group, L, includes a group —NR$^N$—C(=X)— or —C(=X)—NR$^N$— (as in, for example, —NR$^N$—C(=X), —NR$^N$—C(=X)—NR$^N$—, —NR$^N$—CH$_2$—C(=X)—NR$^N$—, etc.).
In one embodiment, the linker group, L, includes a group —NR$^N$—C(=X)—NR$^N$— (as in, for example, —NR$^N$—C(=X)—NR$^N$—, NR$^N$—C(X)—NR$^N$—CH$_2$—, etc.).
In one embodiment, the linker group, L, is formed by a chain of 2 or 3 linker moieties.
In one embodiment, the linker group, L, is formed by a chain of 3 or 4 linker moieties.
In one embodiment, the linker group, L, is formed by a chain of 2 linker moieties.
In one embodiment, the linker group, L, is formed by a chain of 3 linker moieties.
In one embodiment, the linker group, L, is formed by a chain of 4 linker moieties.

In one embodiment, the group A-L is independently selected from:

| | |
|---|---|
| A-NR$^N$—C(=X)—NR$^N$— | ("ureas/thioureas") |
| A-CH$_2$—NR$^N$—C(=X)—NR$^N$— | |
| A-NR$^N$—C(=X)—NR$^N$—CH$_2$— | |

In one embodiment, the group A-L is independently selected from:

| | |
|---|---|
| A-NR$^N$—C(=X)— | ("forward amides/thioamides") |
| A-CH$_2$—NR$^N$—C(=X)— | |
| A-NR$^N$—C(=X)—CH$_2$— | |
| A-CH$_2$—NR$^N$—C(=X)—CH$_2$— | |
| A-CH$_2$—CH$_2$—NR$^N$—C(=X)— | |
| A-NR$^N$—C(=X)—CH$_2$—CH$_2$— | |
| A-NR$^N$—C(=X)—CH$_2$—NR$^N$— | ("forward amides/thioamide amines") |
| A-NR$^N$—CH$_2$—NR$^N$—C(=X)— | |
| A-C(=X)—NR$^N$— | ("reverse amides/thioamides") |
| A-CH$_2$—C(=X)—NR$^N$— | |
| A-C(=X)—NR$^N$—CH$_2$— | |
| A-CH$_2$—C(=X)—NR$^N$—CH$_2$— | |
| A-CH$_2$—CH$_2$—C(=X)—NR$^N$— | |
| A-C(=X)—NR$^N$—CH$_2$—CH$_2$— | |
| A-NR$^N$—CH$_2$—C(=X)—NR$^N$— | ("reverse amides/thioamide amines") |
| A-C(=X)—NR$^N$—CH$_2$—NR$^N$— | |

In one embodiment, the group A-L is independently selected from:
A—C(=X)—CH$_2$—NR$^N$—
A—C(=X)—CH$_2$—NR$^N$—CH$_2$—
A—C(=X)—CH$_2$—CH$_2$NR$^N$—
A—CH$_2$—C(=X)—CH$_2$—NR$^N$—
A—NR$^N$—CH$_2$—C(=X)—
A—NR$^N$—CH$_2$—C(=X)—CH$_2$—
A—NR$^N$—CH$_2$—CH$_2$—C(=X)—
A—CH$_2$—NR$^N$—CH$_2$—C(=X)—

In one embodiment, the group A-L is independently selected from:

A—NR$^N$—C(=X)—NR$^N$—
A—CH$_2$—NR$^N$—C(=X)—NR$^N$—
A—NR$^N$—C(=X)—
A—C(=X)—NR$^N$—
A—NR$^N$—CH$_2$—C(=X)—NR$^N$—
A—CH$_2$—NR$^N$—C(=X)—

In one embodiment, the group A-L is independently selected from:

| | |
|---|---|
| A-NR$^N$—C(=X)—NR$^N$— | ("ureas/thioureas") |
| A-CH$_2$—NR$^N$—C(=X)—NR$^N$— | |
| A-NR$^N$—C(=X)—NR$^N$—CH$_2$— | |

In one embodiment, the group A-L is independently A—NR$^N$—C(=X)—NR$^N$—.

In one embodiment, X is =O ("ureas", "amides", etc.).

In one embodiment, X is =S ("thioureas", "thioamides", etc.).

In one embodiment, the group A-L is independently A—NR$^N$—C(=O)—NR$^N$—.

The Linker Group L: Sulfonamides etc.

In one embodiment, L is independently:
a linker group formed by a chain of 2, 3, or 4 linker moieties;
each linker moiety is independently —CH$_2$—, —NR$^N$—, or —S(=O)$_2$—;
exactly one linker moiety is —NR$^N$—, or:
exactly two linker moieties are —NR$^N$—;
exactly one linker moiety is —S(=O)$_2$—;
no two adjacent linker moieties are —NR$^N$—.

The phrase "no two adjacent linker moieties are —NR$^N$—" is intended to exclude possibilities such as —NR$^N$—NR$^N$—S(=O)$_2$—.

In one embodiment, exactly one linker moiety is —NR$^N$—N

In one embodiment, exactly two linker moieties are —NR$^N$—.

In one embodiment, no linker moiety is —CH$_2$—.
In one embodiment, exactly one linker moiety is —CH$_2$—.
In one embodiment, exactly two linker moieties are —CH$_2$—.

In one embodiment, the linker group, L, includes a group —NR$^N$—S(=O)$_2$— or —S(=O)$_2$—NR$^N$— (as in, for example, —NR$^N$—S(=O)$_2$—, —NR$^N$—S(=O)$_2$—NR$^N$—, —NR$^N$—CH$_2$—S(=O)$_2$—NR$^N$—, etc.).

In one embodiment, the linker group, L, includes a group —NR$^N$—S(=O)$_2$—NR$^N$— (as in, for example, —NR$^N$—S(=O)$_2$—NR$^N$—, —NR$^N$—S(=O)$_2$—NR$^N$—CH$_2$—, etc.).

In one embodiment, the linker group, L, is formed by a chain of 2 or 3 linker moieties.

In one embodiment, the linker group, L, is formed by a chain of 3 or 4 linker moieties.

In one embodiment, the linker group, L, is formed by a chain of 2 linker moieties.

In one embodiment, the linker group, L, is formed by a chain of 3 linker moieties.

In one embodiment, the linker group, L, is formed by a chain of 4 linker moieties.

In one embodiment, the group A-L is independently selected from:

| | |
|---|---|
| A-NR$^N$—S(=O)$_2$—NR$^N$— | ("sulfamides") |
| A-NR$^N$—S(=O)$_2$—NR$^N$—CH$_2$— | |
| A-CH$_2$—NR$^N$—S(=O)$_2$—NR$^N$— | |

In one embodiment, the group A-L is independently selected from:

| | |
|---|---|
| A-NR$^N$—S(=O)$_2$— | ("forward sulfonamides") |
| A-NR$^N$—S(=O)$_2$—CH$_2$— | |
| A-CH$_2$—NR$^N$—S(=O)$_2$— | |
| A-CH$_2$—NR$^N$—S(=O)$_2$—CH$_2$— | |
| A-CH$_2$—CH$_2$—NR$^N$—S(=O)$_2$— | |
| A-NR$^N$—S(=O)$_2$—CH$_2$—CH$_2$— | |
| A-NR$^N$—S(=O)$_2$—CH$_2$—NR$^N$— | ("forward sulfonamides amine") |
| A-NR$^N$—CH$_2$—NR$^N$—S(=O)$_2$— | |
| A-S(=O)$_2$—NR$^N$— | ("reverse sulfonamides") |
| A-S(=O)$_2$—NR$^N$—CH$_2$— | |
| A-CH$_2$—S(=O)$_2$—NR$^N$— | |
| A-CH$_2$—S(=O)$_2$—NR$^N$—CH$_2$— | |
| A-CH$_2$—CH$_2$—S(=O)$_2$—NR$^N$— | |
| A-S(=O)$_2$—NR$^N$—CH$_2$—CH$_2$— | |
| A-S(=O)$_2$—NR$^N$—CH$_2$—NR$^N$— | ("reverse sulfonamides amine") |
| A-NR$^N$—CH$_2$—S(=O)$_2$—NR$^N$— | |

In one embodiment, the group A-L is independently selected from:

A—NR$^N$—S(=O)$_2$—NR$^N$—
A—NR$^N$—S(=O)$_2$—
A—S(=O)$_2$—NR$^N$—
A—CH$_2$—NR$^N$—S(=O)$_2$—NR$^N$—
A—CH$_2$—NR$^N$—S(=O)$_2$—

The Groups R$^N$

Each of the groups R$^N$ is independently —H, saturated C$_{1-3}$alkyl, or C$_{2-3}$alkenyl.

In one embodiment, each of the groups R$^N$ is independently —H or saturated C$_{1-3}$alkyl.

In one embodiment, each of the groups R$^N$ is independently —H or —Me.

In one embodiment, each of the groups R$^N$ is independently —H.

For example:

In one embodiment, the group A-L is independently A—NH—C(=X)—NH—.

In one embodiment, the group A-L is independently A—NH—C(=O)—NH—.

Some Preferred Classes of Compounds

One particularly preferred class of compounds has the following motif:

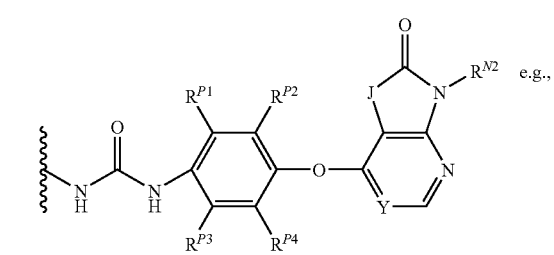

e.g.,

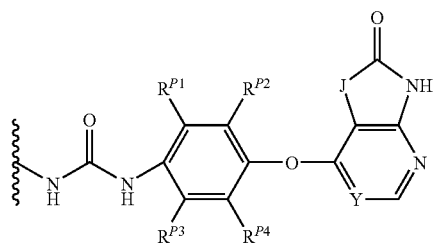
One particularly preferred class of compounds has the following motif:
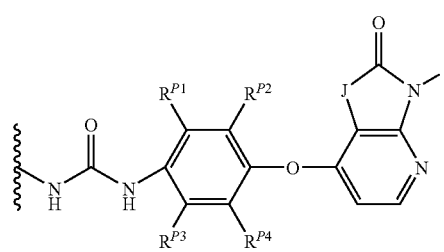
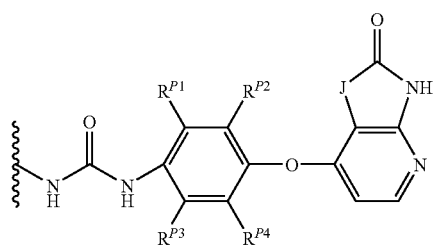
One particularly preferred class of compounds has the following motif:
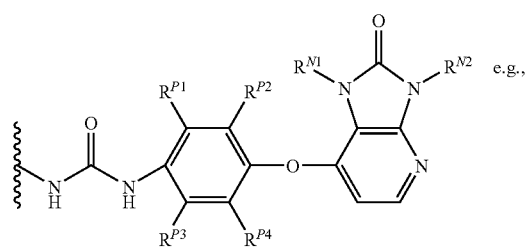
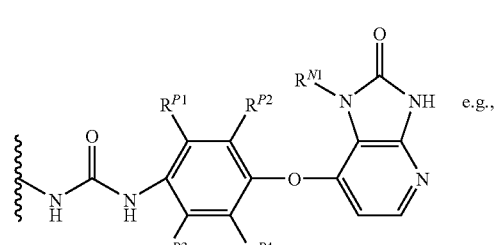
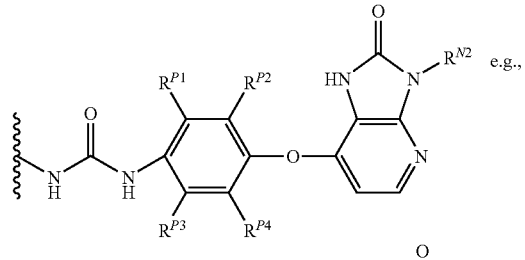
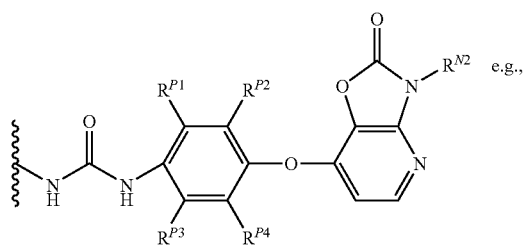
One particularly preferred class of compounds has the following motif:
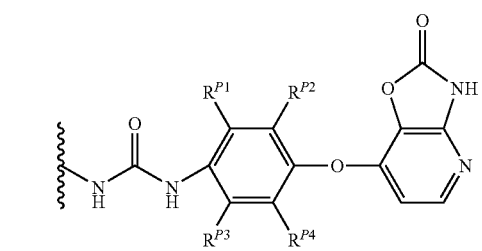
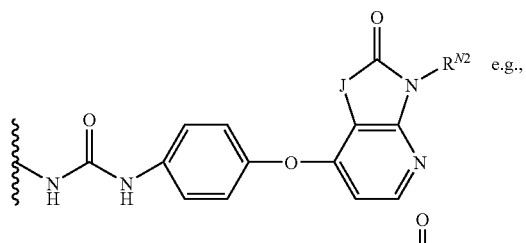
One particularly preferred class of compounds has the following motif:
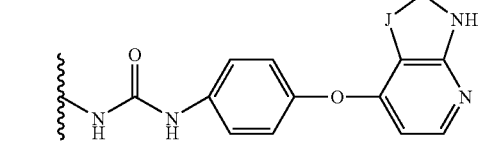

One particularly preferred class of compounds has the following motif:

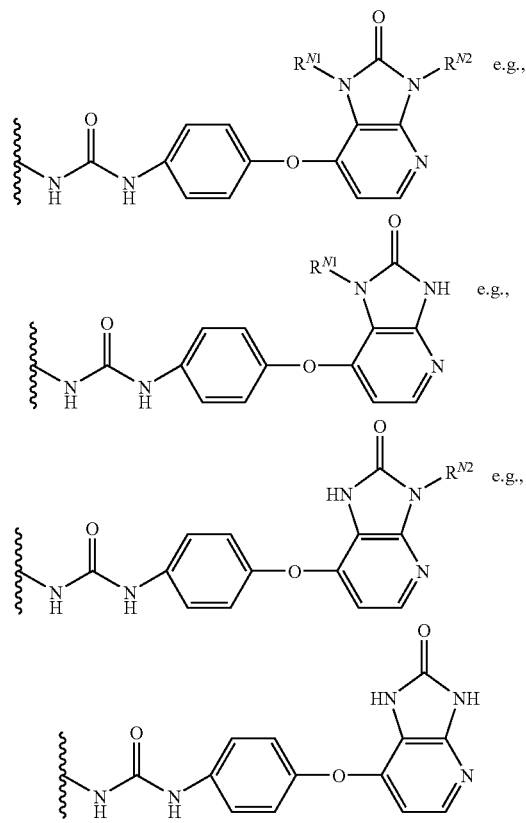

One particularly preferred class of compounds has the following motif:

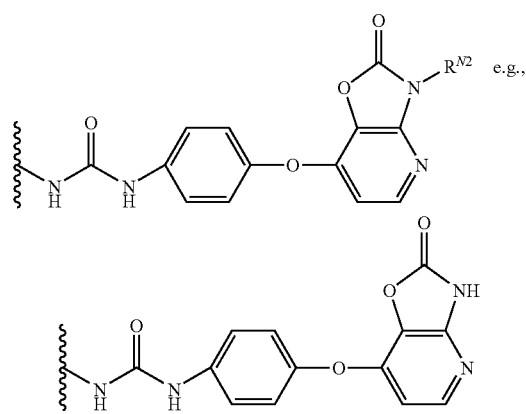

The Group A

The group A is independently:

$C_{6-14}$carboaryl, $C_{5-14}$heteroaryl, $C_{3-12}$ carbocyclic, $C_{3-12}$heterocyclic;

and is independently unsubstituted or substituted.

In one embodiment, A is independently $C_{6-14}$carboaryl or $C_{5-14}$heteroaryl, and is independently unsubstituted or substituted.

In one embodiment, A is independently $C_{6-12}$carboaryl or $C_{5-12}$heteroaryl, and is independently unsubstituted or substituted.

In one embodiment, A is independently $C_{6-10}$carboaryl or $C_{5-10}$heteroaryl, and is independently unsubstituted or substituted.

In one embodiment, A is independently monocyclic or bicyclic (e.g., "5-6" fused rings, "6-6" fused rings) $C_{6-10}$carboaryl or monocyclic or bicyclic $C_{5-10}$heteroaryl (e.g., having 1, 2, 3, 4, or 5 aromatic ring heteroatoms, e.g., selected from nitrogen and oxygen), and is independently unsubstituted or substituted.

In one embodiment, A is independently monocyclic $C_6$carboaryl or monocyclic $C_{5-6}$heteroaryl (e.g., having 1, 2, or 3 aromatic ring heteroatoms, e.g., selected from nitrogen and oxygen), and is independently unsubstituted or substituted.

In one embodiment, A is independently derived from: benzene (i.e., phenyl), naphthalene (i.e., naphthyl), fluorene, pyrrole, pyridine, furan, thiophene, oxazole, isoxazole, oxadiazole, thiazole, isothiazole, thiadiazole, imidazole, pyrazole, pyridazine, pyrimidine, pyrazine, tetrazole, benzofuran, chroman, indole, isoindole, 2,3-dihydro-1H-indole, benzimidazole, 1,3-dihydrobenzimidazole, benzoxazole, benzothiofuran, benzothiazole, benzothiadiazole, quinoline, isoquinoline, pyridopyridine, quinoxaline, 1,2,3,4-tetrahydroquinoxaline, 3,4-dihydro-2H-benzo[1,4]oxazine, benzodiazepine, carbazole, acridine; and is independently unsubstituted or substituted (including, e.g., 1,3-dihydrobenzimidazol-2-one; 1,3-dihydro-indol-2-one, etc.).

The phrase "derived from," as used in this context, pertains to groups that have the same ring atoms, in the same orientation/configuration, as the parent compound, and so include carbonyl-substituted, and other substituted derivatives. For example, 1-methyl-1H-pyrrolyl is derived from 'pyrrole'. In the simplest case, the phrase "is independently derived from . . . " may be replaced with "is independently a monovalent, monodentate moiety obtained by removing a hydrogen atom from a ring atom of . . . "

In one embodiment, A is independently derived from: benzene (i.e., phenyl), pyrrole (i.e., pyrolyl), pyridine, furan, thiophene, oxazole, isoxazole, thiadiazole, oxadiazole, thiazole, isothiazole, imidazole, pyrazole, pyridazine, pyrimidine, pyrazine, tetrazole; and is independently unsubstituted or substituted.

In one embodiment, A is independently derived from: benzene (i.e., phenyl), pyridine (i.e., pyridyl), thiadiazole (i.e., thiadiazolyl), thiazole (i.e., thiazolyl), pyrazole (i.e., pyrazolyl); and is independently unsubstituted or substituted.

In one embodiment, A is independently phenyl, and is independently unsubstituted or substituted.

In one embodiment, A is independently pyrazolyl, and is independently unsubstituted or substituted.

In one embodiment, A is independently $C_{3-12}$carbocyclic (e.g., saturated $C_{3-12}$cycloalkyl, $C_{3-12}$cycloalkenyl) or $C_{3-12}$heterocyclic, and is independently unsubstituted or substituted.

In one embodiment, A is independently $C_{5-10}$carbocyclic (e.g., saturated $C_{3-10}$cycloalkyl, $C_{3-10}$cycloalkenyl) or $C_{5-10}$heterocyclic, and is independently unsubstituted or substituted.

In one embodiment, A is independently monocyclic or bicyclic $C_{3-12}$carbocyclic (e.g., saturated $C_{3-12}$cycloalkyl, $C_{3-17}$cycloalkenyl) or monocyclic or bicyclic $C_{3-12}$heterocyclic, and is independently unsubstituted or substituted.

In one embodiment, A is independently $C_{5-8}$carbocyclic (e.g., saturated $C_{5-8}$cycloalkyl, $C_{5-8}$cycloalkenyl) or $C_{5-8}$heterocyclic, and is independently unsubstituted or substituted.

In one embodiment, A is independently monocyclic $C_{5-8}$carbocyclic (e.g., saturated $C_{5-8}$cycloalkyl, $C_{5-8}$cycloalkenyl) or monocyclic $C_{5-8}$heterocyclic (e.g., having 1, 2, or 3 ring heteroatoms, e.g., selected from nitrogen and oxygen), and is independently unsubstituted or substituted.

In one embodiment, A is independently derived from: cyclopentane (i.e., cyclopentyl), cyclohexane (i.e., cyclohexyl), tetrahydrofuran, tetrahydropyran, dioxane, pyrrolidine, piperidine, piperzine; and is independently unsubstituted or substituted (including, e.g., piperidinone, dimethyltetrahydropyran, etc.).

In one embodiment, A is independently selected from those (core groups) exemplified under the heading "Some Preferred Embodiments" and is independently unsubstituted or substituted, for example, with one or more substituents independently selected from those substituents exemplified under the heading "Some Preferred Embodiments."

Substituents on the Group A

The group A is independently unsubstituted or substituted.
In one embodiment, A is independently unsubstituted.
In one embodiment, A is independently substituted.
In one embodiment, A is independently unsubstituted or substituted with one or more (e.g., 1 to 5; 1 to 4; 1 to 3; 1 or 2; 2 to 5; 2 to 4; 2 or 3; 1; 2; 3; 4; 5) substituents.

In one embodiment, the substituents are independently selected from the following:

(1) carboxylic acid; (2) ester; (3) amido or thioamido; (4) acyl; (5) halo; (6) cyano; (7) nitro; (8) hydroxy; (9) ether; (10) thiol; (11) thioether; (12) acyloxy; (13) carbamate; (14) amino; (15) acylamino or thioacylamino; (16) aminoacylamino or aminothioacylamino; (17) sulfonamino; (18) sulfonyl; (19) sulfonate; (20) sulfonamido; (21) $C_{5-20}$aryl-$C_{1-7}$alkyl; (22) $C_{5-20}$aryl; (23) $C_{3-20}$heterocyclyl; (24) $C_{1-7}$alkyl; (25) oxo; (26) imino; (27) hydroxyimino; (28) phosphate.

In one embodiment, the substituents are independently selected from the following:

(1) —C(=O)OH;
(2) —C(=O)OR$^1$, wherein R$^1$ is independently as defined in (21), (22), (23) or (24);
(3) —C(=O)NR$^2$R$^3$ or —C(=S)NR$^2$R$^3$, wherein each of R$^2$ and R$^3$ is independently —H; or as defined in (21), (22), (23) or (24); or R$^2$ and R$^3$ taken together with the nitrogen atom to which they are attached form a ring having from 3 to 7 ring atoms;
(4) —C(=O)R$^4$, wherein R$^4$ is independently —H, or as defined in (21), (22), (23) or (24);
(5) —F, —Cl, —Br, —I;
(6) —CN;
(7) —NO$_2$;
(8) —OH;
(9) —OR$^5$, wherein R$^5$ is independently as defined in (21), (22), (23) or (24);
(10) —SH;
(11) —SR$^6$, wherein R$^6$ is independently as defined in (21), (22), (23) or (24);
(12) —OC(=O)R$^7$, wherein R$^7$ is independently as defined in (21), (22), (23) or (24);
(13) —OC(=O)NR$^8$R$^9$, wherein each of R$^8$ and R$^9$ is independently —H; or as defined in (21), (22), (23) or (24); or R$^8$ and R$^9$ taken together with the nitrogen atom to which they are attached form a ring having from 3 to 7 ring atoms;
(14) —NR$^{10}$R$^{11}$, wherein each of R$^{10}$ and R$^{11}$ is independently —H; or as defined in (21), (22), (23) or (24); or R$^{10}$ and R$^{11}$ taken together with the nitrogen atom to which they are attached form a ring having from 3 to 7 ring atoms;
(15) —NR$^{12}$C(=O)R$^{13}$ or —NR$^{12}$C(=S)R$^{13}$, wherein R$^{12}$ is independently —H; or as defined in (21), (22), (23) or (24); and R$^{13}$ is independently —H, or as defined in (21), (22), (23) or (24);
(16) —NR$^{14}$C(=O)NR$^{15}$R$^{16}$ or —NR$^{14}$C(=S)NR$^{15}$R$^{16}$, wherein R$^{14}$ is independently —H; or as defined in (21), (22), (23) or (24); and each of R$^{15}$ and R$^{16}$ is independently —H; or as defined in (21), (22), (23) or (24); or R$^{15}$ and R$^{16}$ taken together with the nitrogen atom to which they are attached form a ring having from 3 to 7 ring atoms;
(17) —NR$^{17}$SO$_2$R$^{18}$, wherein R$^{17}$ is independently —H; or as defined in (21), (22), (23) or (24); and R$^{18}$ is independently —H, or as defined in (21), (22), (23) or (24);
(18) —SO$_2$R$^{19}$, wherein R$^{19}$ is independently as defined in (21), (22), (23) or (24);
(19) —OSO$_2$R$^{20}$ and wherein R$^{20}$ is independently as defined in (21), (22), (23) or (24);
(20) —SO$_2$NR$^{21}$R$^{22}$, wherein each of R$^{21}$ and R$^{22}$ is independently —H; or as defined in (21), (22), (23) or (24); or R$^{21}$ and R$^{22}$ taken together with the nitrogen atom to which they are attached form a ring having from 3 to 7 ring atoms;
(21) $C_{5-20}$aryl-$C_{1-7}$alkyl, for example, wherein $C_{5-20}$aryl is as defined in (22); unsubstituted or substituted, e.g., with one or more groups as defined in (1) to (28);
(22) $C_{5-20}$aryl, including $C_{6-20}$carboaryl and $C_{5-20}$heteroaryl; unsubstituted or substituted, e.g., with one or more groups as defined in (1) to (28);
(23) $C_{3-20}$heterocyclyl; unsubstituted or substituted, e.g., with one or more groups as defined in (1) to (28);
(24) $C_{1-7}$alkyl, including:
   saturated $C_{1-7}$alkyl;
   unsaturated $C_{1-7}$alkyl, e.g., $C_{2-7}$alkenyl and $C_{2-7}$alkynyl;
   cyclic $C_{1-7}$alkyl, e.g., $C_{3-7}$cycloalkyl $C_{3-7}$cycloalkenyl, $C_{3-7}$cycloalkynyl;
   aliphatic (linear or branched) $C_{1-7}$alkyl;
   unsubstituted $C_{1-7}$alkyl;
   substituted $C_{1-7}$alkyl, e.g., substituted with one or more groups as defined in (1) to (23) and (25) to (28),
   e.g., halo-$C_{1-7}$alkyl;
   e.g., amino-$C_{1-7}$alkyl (e.g., —(CH$_2$)$_w$-amino, w is 1, 2, 3, or 4);
   e.g., carboxy-$C_{1-7}$alkyl (e.g., —(CH$_2$)$_w$—COOH, w is 1, 2, 3, or 4);
   e.g., acyl-$C_{1-7}$alkyl (e.g., —(CH$_2$)$_w$—C(=O)R$^4$, w is 1, 2, 3, or 4);
   e.g., hydroxy-$C_{1-7}$alkyl (e.g., —(CH$_2$)$_w$—OH, w is 1, 2, 3, or 4);
   e.g., $C_{1-7}$alkoxy-$C_{1-7}$alkyl (e.g., —(CH$_2$)$_w$—O—$C_{1-7}$alkyl, w is 1, 2, 3, or 4);
(25) =O;
(26) =NR$^{23}$, wherein R$^{23}$ is independently —H; or as defined in (21), (22), (23) or (24);
(27) =NOH;
(28) —P(=O)(OR$^{24}$)$_2$ and —OP(=O)(OR$^{24}$)$_2$ wherein each R$^{24}$ is independently —H; or as defined in (21), (22), (23) or (24).

In one embodiment, the substituents are independently selected from the following:
(1) —C(=O)OH;
(2) —C(=O)OMe, —C(=O)OEt, —C(=O)O(iPr), —C(=O)O(tBu); —C(=O)O(cPr);

—C(=O)OCH$_2$CH$_2$OH, —C(=O)OCH$_2$CH$_2$OMe, —C(=O)OCH$_2$CH$_2$OEt;
—C(=O)OPh, —C(=O)OCH$_2$Ph;

(3) —(C=O)NH$_2$, —(C=O)NMe$_2$, —(C=O)NEt$_2$, —(C=O)N(iPr)$_2$, —(C=O)N(CH$_2$CH$_2$OH)$_2$;
—(C=O)-morpholino, —(C=O)NHPh, —(C=O)NHCH$_2$Ph;

(4) —C(=O)H, —(C=O)Me, —(C=O)Et, —(C=O)(tBu), —(C=O)-cHex, —(C=O)Ph; —(C=O)CH$_2$Ph;

(5) —F, —Cl, —Br, —I;

(6) —CN;

(7) —NO$_2$;

(8) —OH;

(9) —OMe, —OEt, —O(iPr), —O(tBu), —OPh, —OCH$_2$Ph; —OCF$_3$, —OCH$_2$CF$_3$;
—OCH$_2$CH$_2$OH, —OCH$_2$CH$_2$OMe, —OCH$_2$CH$_2$OEt;
—OCH$_2$CH$_2$NH$_2$, —OCH$_2$CH$_2$NMe$_2$, —OCH$_2$CH$_2$N(iPr)$_2$;
—OPh—Me, —OPh-OH, —OPh-OMe, —OPh-F, —OPh-Cl, —OPh—Br, —OPh-I;

(10) —SH;

(11) —SMe, —SEt, —SPh, —SCH$_2$Ph;

(12) —OC(=O)Me, —OC(=O)Et, —OC(=O)(iPr), —OC(=O)(tBu); —OC(=O)(cPr);
—OC(=O)CH$_2$CH$_2$OH, —OC(=O)CH$_2$CH$_2$OMe, —OC(=O)CH$_2$CH$_2$OEt;
—OC(=O)Ph, —OC(=O)CH$_2$Ph;

(13) —OC(=O)NH$_2$, —OC(=O)NHMe, —OC(=O)NMe$_2$, —OC(=O)NHEt, —OC(=O)NEt$_2$, —OC(=O)NHPh, —OC(=O)NCH$_2$Ph;

(14) —NH$_2$, —NHMe, —NHEt, —NH(iPr), —NMe$_2$, —NEt$_2$, —N(iPr)$_2$, —N(CH$_2$CH$_2$OH)$_2$;
—NHPh, —NHCH$_2$Ph; piperidino, piperazino, morpholino;

(15) —NH(C=O)Me, —NH(C=O)Et, —NH(C=O)$_n$Pr, —NH(C=O)Ph, —NHC(=O)CH$_2$Ph;
—NMe(C=O)Me, —NMe(C=O)Et, —NMe(C=O)Ph, —NMeC(=O)CH$_2$Ph;

(16) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;

(17) —NHSO$_2$Me, —NHSO$_2$Et, —NHSO$_2$Ph, —NHSO$_2$PhMe, —NHSO$_2$CH$_2$Ph;
—NMeSO$_2$Me, —NMeSO$_2$Et, —NMeSO$_2$Ph, —NMeSO$_2$PhMe, —NMeSO$_2$CH$_2$Ph;

(18) —SO$_2$Me, —SO$_2$CF$_3$, —SO$_2$Et, —SO$_2$Ph, —SO$_2$PhMe, —SO$_2$CH$_2$Ph;

(19) —OSO$_2$Me, —OSO$_2$CF$_3$, —OSO$_2$Et, —OSO$_2$Ph, —OSO$_2$PhMe, —OSO$_2$CH$_2$Ph;

(20) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;

(21) —CH$_2$Ph, —CH$_2$Ph—Me, —CH$_2$Ph-OH, —CH$_2$Ph-F, —CH$_2$Ph-Cl;

(22) -Ph, —Ph—Me, —Ph—OH, —Ph—OMe, —Ph—NH$_2$, —Ph—F, —Ph—Cl, —Ph—Br, —Ph—I;
pyridyl, pyrazinyl, pyrimidinyl, pyridazinyl; furanyl, thiophenyl, pyrrolyl, imidazolyl, pyrazolyl, oxazolyl, thiazolyl, thiadiazolyl;

(23) pyrrolidinyl, imidazolidinyl, pyrazolidinyl, piperidinyl, piperazinyl, azepinyl, tetrahydrofuranyl, tetrahydropyranyl, morpholinyl, azetidinyl;

(24) —Me, —Et, —nPr, —iPr, —nBu, —iBu, —sBu, —tBu, —nPe;
—cPr, —cHex; —CH=CH$_2$, —CH$_2$—CH=CH$_2$;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$;

(25) =O;

(26) =NH, =NMe; =NEt;

(27) =NOH;

(28) —OP(=O)(OH)$_2$, —P(=O)(OH)$_2$, —OP(=O)(OMe)$_2$, —P(=O)(OMe)$_2$.

In one embodiment, the substituents are independently selected from those defined above in groups (3), (5), (6), (9), (14), (15), (18), (20), (21), (22), (23), (24), and (25).

In one embodiment, the substituents are independently selected from those defined under the heading "Substituents on the Group R$^{N1}$", above.

In one embodiment, the substituents are independently selected from those substituents exemplified under the heading "Some Preferred Embodiments."

In one embodiment, A is optionally substituted phenyl, and the substituents on the phenyl group are independently selected from:

(2) —C(=O)OMe, —C(=O)OEt, —C(=O)O(iPr), —C(=O)O(tBu); —C(=O)O(cPr);
—C(=O)OCH$_2$CH$_2$OH, —C(=O)OCH$_2$CH$_2$OMe, —C(=O)OCH$_2$CH$_2$OEt;
—C(=O)OCH$_2$Ph;

(3) —(C=O)NH$_2$, —(C=O)NMe$_2$, —(C=O)NEt$_2$, —(C=O)N(iPr)$_2$, —(C=O)N(CH$_2$CH$_2$OH)$_2$;
—(C=O)-morpholino, —(C=O)NHPh, —(C=O)NHCH$_2$Ph;

(5) —F, —Cl, —Br, —I;

(6) —CN;

(9) —OMe, —OEt, —O(iPr), —O(tBu), —OPh, —OCH$_2$Ph; —OCF$_3$, —OCH$_2$CF$_3$;
—OCH$_2$CH$_2$OH, —OCH$_2$CH$_2$OMe, —OCH$_2$CH$_2$OEt;
—OCH$_2$CH$_2$NH$_2$, —OCH$_2$CH$_2$NMe$_2$, —OCH$_2$CH$_2$N(iPr)$_2$;
—OPh—Me, —OPh-OMe, —OPh-F, —OPh-Cl, —OPh—Br, —OPh-I;

(11) —SMe, —SEt, —SPh, —SCH$_2$Ph;

(13) —OC(=O)NH$_2$, —OC(=O)NHMe, —OC(=O)NMe$_2$, —OC(=O)NHEt, —OC(=O)NEt$_2$, —OC(=O)NHPh, —OC(=O)NCH$_2$Ph;

(14) —NH$_2$, —NHMe, —NHEt, —NH(iPr), —NMe$_2$, —NEt$_2$, —N(iPr)$_2$, —N(CH$_2$CH$_2$OH)$_2$;
—NHPh, —NHCH$_2$Ph; piperidino, piperazino, morpholino;

(15) —NH(C=O)Me, —NH(C=O)Et, —NH(C=O)nPr, —NH(C=O)Ph, —NHC(=O)CH$_2$Ph;
—NMe(C=O)Me, —NMe(C=O)Et, —NMe(C=O)Ph, —NMeC(=O)CH$_2$Ph;

(17) —NHSO$_2$Me, —NHSO$_2$Et, —NHSO$_2$Ph, —NHSO$_2$PhMe, —NHSO$_2$CH$_2$Ph;

(18) —SO$_2$Me, —SO$_2$CF$_3$, —SO$_2$Et, —SO$_2$Ph, —SO$_2$PhMe, —SO$_2$CH$_2$Ph;

(20) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;

(21) —CH$_2$Ph, —CH$_2$Ph—Me, —CH$_2$Ph-OH, —CH$_2$Ph-F, —CH$_2$Ph—Cl;

(22) —Ph, —Ph—Me, —Ph—OH, —Ph—OMe, —Ph—NH$_2$, —Ph—F, —Ph—Cl, —Ph—Br, —Ph—I;

pyridyl, pyrazinyl, pyrimidinyl, pyridazinyl; furanyl, thiophenyl, pyrrolyl, imidazolyl, pyrazolyl, oxazolyl, thiazolyl, thiadiazolyl;

(23) pyrrolidinyl, imidazolidinyl, pyrazolidinyl, piperidinyl, piperazinyl, azepinyl, tetrahydrofuranyl, tetrahydropyranyl, morpholinyl, azetidinyl;

(24) —Me, —Et, —nPr, —iPr, —nBu, —iBu, —sBu, —tBu, —nPe;
—cPr, —cHex; —CH=CH$_2$, —CH$_2$—CH=CH$_2$;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$.

In one embodiment, A is optionally substituted phenyl, and the substituents on the phenyl group are independently selected from:

(5) —F, —Cl, —Br, —I;
(9) —OMe, —OEt, —O(iPr), —O(tBu), —OPh, —OCH$_2$Ph; —OCF$_3$, —OCH$_2$CF$_3$;
—OCH$_2$CH$_2$OH, —OCH$_2$CH$_2$OMe, —OCH$_2$CH$_2$OEt; —OCH$_2$CH$_2$NH$_2$, —OCH$_2$CH$_2$NMe$_2$,
(14) —NH$_2$, —NHMe, —NHEt, —NH(iPr), —NMe$_2$, —NEt$_2$, —N(iPr)$_2$, —N(CH$_2$CH$_2$OH)$_2$;
—NHPh, —NHCH$_2$Ph; piperidino, piperazino, morpholino;
(22) —Ph, —Ph—Me, —Ph—OMe, —Ph—F, —Ph—Cl;
pyridyl, pyrazinyl, pyrimidinyl, pyridazinyl; furanyl, thiophenyl, pyrrolyl, imidazolyl, pyrazolyl, oxazolyl, thiazolyl, thiadiazolyl;
(23) pyrrolidinyl, piperazinyl, azepinyl, tetrahydrofuranyl, tetrahydropyranyl, morpholinyl, azetidinyl;
(24) —Me, —Et, —nPr, —iPr, —nBu, —iBu, —sBu, —tBu, —nPe;
—cPr, —cHex; —CH=CH$_2$, —CH$_2$—CH=CH$_2$;
—CF$_3$, —CHF$_2$, —CH$_2$F, —CH$_2$CH$_2$F, —CH$_2$CHF$_2$, and —CH$_2$CF$_3$;
—CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$.

In one embodiment, A is optionally substituted pyrazolyl, and has the following formula:

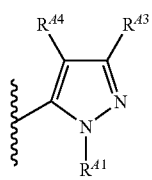

wherein:

R$^{A4}$ is H;

R$^{A3}$ is independently selected from:
(5) —F, —Cl, —Br, —I;
(22) —Ph;
(24) —Me, —Et, —nPr, —iPr, —nBu, —iBu, —sBu, —tBu, —nPe;
—cPr, —cHex;
—CF$_3$, —CHF$_2$, —CH$_2$F, —CH$_2$CH$_2$F, —CH$_2$CHF$_2$, and —CH$_2$CF$_3$;

R$^{A1}$ is independently selected from:
(22) —Ph, —Ph—Me, —Ph—OH, —Ph—OMe, —Ph—NH$_2$, —Ph—F, —Ph—Cl, —Ph—Br, —Ph—I;
pyridyl, pyrazinyl, pyrimidinyl, pyridazinyl; furanyl, thiophenyl, pyrrolyl, imidazolyl, pyrazolyl, oxazolyl, thiazolyl, thiadiazolyl;
(23) pyrrolidinyl, piperidinyl, piperazinyl, azepinyl, tetrahydrofuranyl, tetrahydropyranyl, morpholinyl, azetidinyl;
(24) —Me, —Et, —nPr, —iPr, —nBu, —iBu, —sBu, —tBu, —nPe;
—cPr, —cHex; —CH=CH$_2$, —CH$_2$—CH=CH$_2$;
—CF$_3$, —CHF$_2$, —CH$_2$F, —CH$_2$CH$_2$F, —CH$_2$CHF$_2$, and —CH$_2$CF$_3$;
—CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$.

Some Preferred Classes of Compounds

One particularly preferred class of compounds are compounds of the following formula:

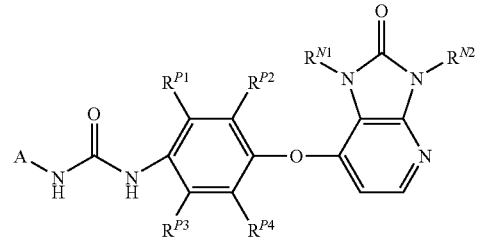

wherein:

R$^{N1}$ is independently as defined herein;

R$^{N2}$ is independently as defined herein;

each of R$^{P1}$, R$^{P2}$, R$^{P3}$, and R$^{P4}$ is independently as defined herein;

A is independently as defined herein;

and pharmaceutically acceptable salts, solvates, amides, esters, ethers, N-oxides, chemically protected forms, and prodrugs thereof.

In one embodiment, each of R$^{P1}$, R$^{P2}$, R$^{P3}$, and R$^{P4}$ is independently —H, —Me, —F, —Cl, or —SMe.

In one embodiment, R$^{P1}$ and R$^{P2}$ taken together are —CH=CH—CH=CH—; and each of R$^{P3}$ and R$^{P4}$ is independently —H.

In one embodiment, A is independently derived from: benzene, pyridine, thiadiazole, thiazole, pyrazole; and is independently unsubstituted or substituted.

In one embodiment, A is independently phenyl, and is independently unsubstituted or substituted.

In one embodiment, A is independently pyrazolyl, and is independently unsubstituted or substituted.

In one embodiment, R$^{N1}$ is independently —H or —Me.

In one embodiment, R$^{N1}$ is independently —H.

In one embodiment, R$^{N2}$ is independently —H or —Me.

In one embodiment, R$^{N2}$ is independently —H.

In one embodiment, A is a pyrazolyl group of the following formula:

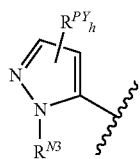

wherein:
  h is independently 0, 1 or 2;
  each $R^{PY}$ is independently a substituent as defined under the heading "Substituents on the Group A"; and
  $R^{N3}$ is independently as defined for $R^{N1}$ or $R^{A1}$.

One particularly preferred class of compounds are compounds of the following formula:

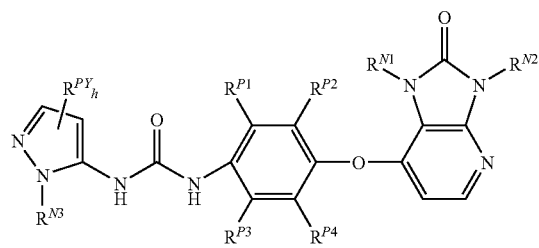

wherein:
  $R^{N1}$ is independently as defined herein;
  $R^{N2}$ is independently as defined herein;
  each of $R^{P1}$, $R^{P2}$, $R^{P3}$, and $R^{P4}$ is independently as defined herein;
  h is independently 0, 1 or 2;
  each $R^{PY}$ is independently a substituent as defined under the heading "Substituents on the Group A";
  $R^{N3}$ is independently as defined for $R^{N1}$ or $R^{A1}$;
  and pharmaceutically acceptable salts, solvates, amides, esters, ethers, N-oxides, chemically protected forms, and prodrugs thereof.

In one embodiment, A is a pyrazolyl group of selected from groups of the following formulae:

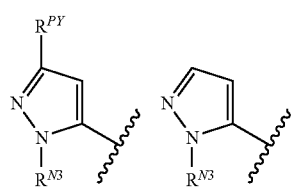

In one embodiment, $R^{N1}$ is independently —H or —Me.
In one embodiment, $R^{N1}$ is independently —H.
In one embodiment, $R^{N2}$ is independently —H or —Me.
In one embodiment, $R^{N2}$ is independently —H.
In one embodiment, each of $R^{P1}$, $R^{P2}$, $R^{P3}$, and $R^{P4}$ is independently —H, —Me, —F, —Cl, or —SMe.
In one embodiment, each of $R^{P1}$, $R^{P2}$, $R^{P3}$, and $R^{P4}$ is independently —H, —Me, —F, or —Cl.
In one embodiment, h is independently 0 or 1.
In one embodiment, h is independently 0.
In one embodiment, h is independently 1.

In one embodiment, h is independently 1 and $R^{PY}$ is independently (24) $C_{1-7}$alkyl.
In one embodiment, h is independently 1 and $R^{PY}$ is independently saturated $C_{1-7}$alkyl.
In one embodiment, $R^{N3}$ is independently as defined for $R^{N1}$.
In one embodiment, $R^{N3}$ is independently as defined for $R^{A1}$.
In one embodiment, $R^{N3}$ is independently (21) $C_{5-20}$aryl-$C_{1-7}$alkyl or (22) $C_{5-20}$aryl, and is independently unsubstituted or substituted, for example, with one or more (e.g., 1, 2, 3, 4, etc.) substituents, e.g., selected from substituents as defined under the heading "Substituents on the Group A", e.g., (5) halo, (24) $C_{1-7}$alkyl, etc.
In one embodiment, $R^{N3}$ is independently phenyl, and is independently unsubstituted or substituted, for example, with one or more (e.g., 1, 2, 3, 4, etc.) substituents, e.g., selected from substituents as defined under the heading "Substituents on the Group A", e.g., (5) halo, (24) $C_{1-7}$alkyl, including, e.g., halo-$C_{1-7}$alkyl, etc., e.g., —F, —Cl, —Br, —I, —Me, —CF$_3$.

One particularly preferred class of compounds are compounds of the following formula:

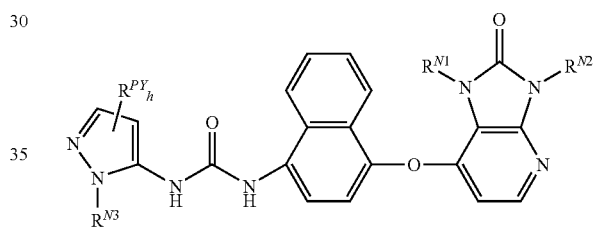

wherein:
  $R^{N1}$ is independently as defined herein;
  $R^{N2}$ is independently as defined herein;
  h is independently 0, 1 or 2;
  each $R^{PY}$ is independently a substituent as defined under the heading "Substituents on the Group A";
  $R^{N3}$ is independently as defined for $R^{N1}$;
  and pharmaceutically acceptable salts, solvates, amides, esters, ethers, N-oxides, chemically protected forms, and prodrugs thereof.

In one embodiment, A is a pyrazolyl group of selected from groups of the following formulae:

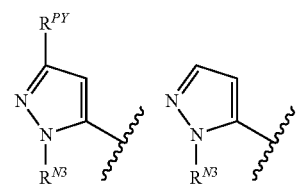

In one embodiment, $R^{N1}$ is independently —H or —Me.
In one embodiment, $R^{N1}$ is independently —H.

In one embodiment, $R^{N2}$ is independently —H or —Me.
In one embodiment, $R^{N2}$ is independently —H.
In one embodiment, h is independently 0 or 1.
In one embodiment, h is independently 0.
In one embodiment, h is independently 1.
In one embodiment, h is independently 1 and $R^{PY}$ is independently (24) $C_{1-7}$alkyl.
In one embodiment, h is independently 1 and $R^{PY}$ is independently saturated $C_{1-7}$alkyl.
In one embodiment, $R^{N3}$ is independently (21) $C_{5-20}$aryl-$C_{1-7}$alkyl or (22) $C_{5-20}$aryl, and is independently unsubstituted or substituted, for example, with one or more (e.g., 1, 2, 3, 4, etc.) substituents, e.g., selected from substituents as defined under the heading "Substituents on the Group A", e.g., (5) halo, (24) $C_{1-7}$alkyl, etc.
In one embodiment, $R^{N3}$ is independently phenyl, and is independently unsubstituted or substituted, for example, with one or more (e.g., 1, 2, 3, 4, etc.) substituents, e.g., selected from substituents as defined under the heading "Substituents on the Group A", e.g., (5) halo, (24) $C_{1-7}$alkyl, including, e.g., halo-$C_{1-7}$alkyl, etc., e.g., —F, —Cl, —Br, —I, —Me, —$CF_3$.

One particularly preferred class of compounds are compounds of the following formula:

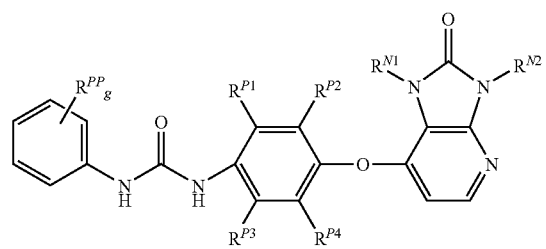

wherein:
$R^{N1}$ is independently as defined herein;
$R^{N2}$ is independently as defined herein;
each of $R^{P1}$, $R^{P2}$, $R^{P3}$, and $R^{P4}$ is independently as defined herein;
g is independently 0, 1, 2, 3, 4, or 5;
each $R^{PP}$ is independently a substituent as defined under the heading "Substituents on the Group A";
and pharmaceutically acceptable salts, solvates, amides, esters, ethers, N-oxides, chemically protected forms, and prodrugs thereof.

In one embodiment, $R^{N1}$ is independently —H or —Me.
In one embodiment, $R^{N1}$ is independently —H.
In one embodiment, $R^{N2}$ is independently —H or —Me.
In one embodiment, $R^{N2}$ is independently —H.
In one embodiment, each of $R^{P1}$, $R^{P2}$, $R^{P3}$, and $R^{P4}$ is independently —H, —Me, —F, —Cl, or —SMe.
In one embodiment, each of $R^{P1}$, $R^{P2}$, $R^{P3}$, and $R^{P4}$ is independently —H, —Me, —F, or —Cl.
In one embodiment, g is independently 0, 1, or 2.
In one embodiment, g is independently 0.
In one embodiment, g is independently 1.
In one embodiment, g is independently 2.
In one embodiment, each $R^{PP}$ is independently (5) halo or (24) $C_{1-7}$alkyl, including, e.g., halo-$C_{1-7}$alkyl, etc., e.g., —F, —Cl, —Br, —I, —Me, —$CF_3$.

One particularly preferred class of compounds are compounds of the following formula:

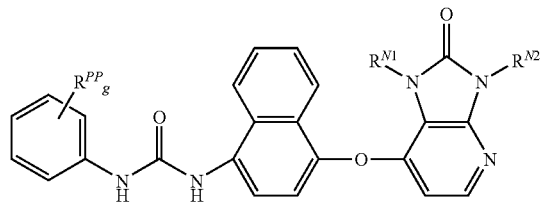

wherein:
$R^{N1}$ is independently as defined herein;
$R^{N2}$ is independently as defined herein;
g is independently 0, 1, 2, 3, 4, or 5;
each $R^{PP}$ is independently a substituent as defined under the heading "Substituents on the Group A";
and pharmaceutically acceptable salts, solvates, amides, esters, ethers, N-oxides, chemically protected forms, and prodrugs thereof.

In one embodiment, $R^{N1}$ is independently —H or —Me.
In one embodiment, $R^{N1}$ is independently —H.
In one embodiment, $R^{N2}$ is independently —H or —Me.
In one embodiment, $R^{N2}$ is independently —H.
In one embodiment, g is independently 0, 1, or 2.
In one embodiment, g is independently 0.
In one embodiment, g is independently 1.
In one embodiment, g is independently 2.
In one embodiment, each $R^{PP}$ is independently (5) halo or (24) $C_{1-7}$alkyl, including, e.g., halo-$C_{1-7}$alkyl, etc., e.g., —F, —Cl, —Br, —I, —Me, —$CF_3$.

Molecular Weight

In one embodiment, the compound has a molecular weight of 300 to 1000.
In one embodiment, the bottom of range is 325; 350; 375; 400; 425; 450.
In one embodiment, the top of range is 900; 800; 700; 600; 500.
In one embodiment, the range is 300 to 900.
In one embodiment, the range is 300 to 800.
In one embodiment, the range is 300 to 700.
In one embodiment, the range is 300 to 600.
In one embodiment, the range is 300 to 500.

Some Preferred Embodiments

All plausible combinations of the embodiments described above are explicitly disclosed herein.
Examples of some preferred compounds (where A-L is A—NH—C(=O)—NH—, Q is —O—, and Y is —CH=) (here each R is independently —H or —Me) are shown below.

1.
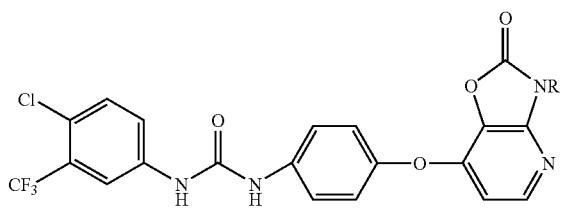
2.
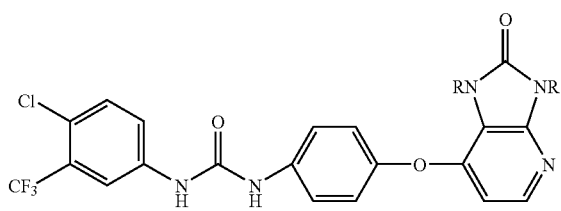
3.
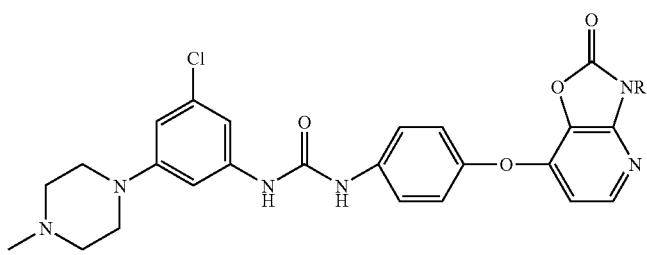
4.
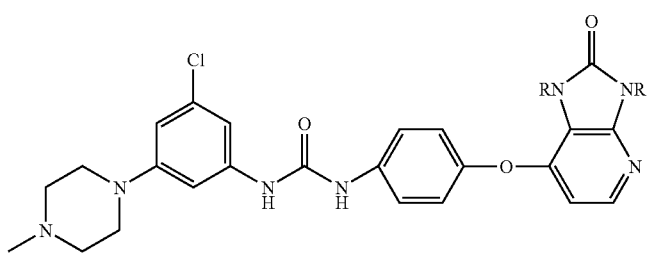
5.
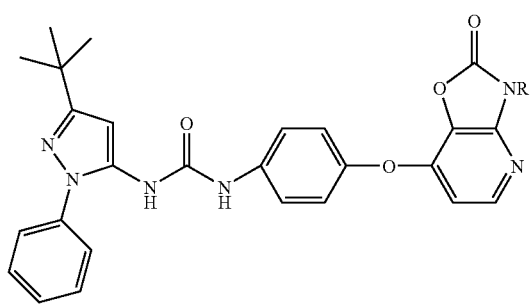
6.
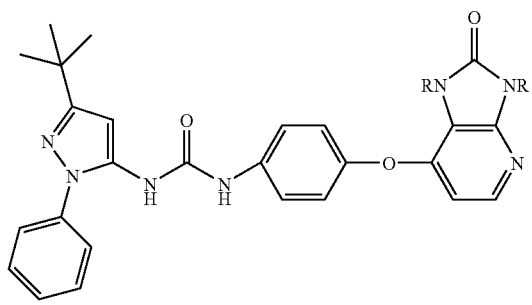

-continued
7.
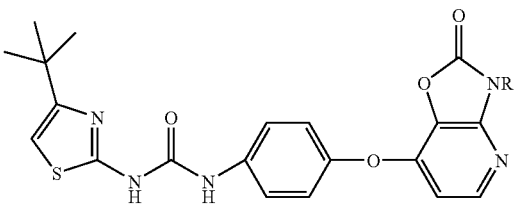
8.
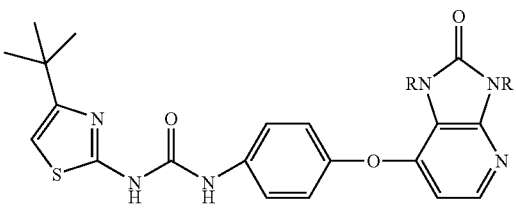
9.
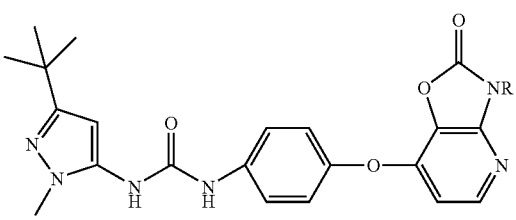
10.
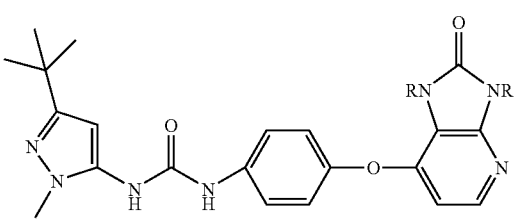
11.
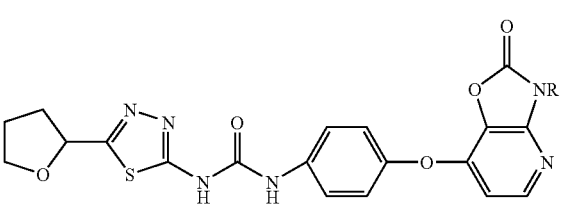
12.
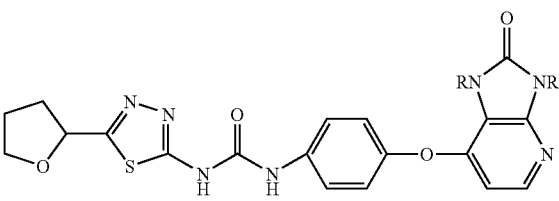
13.
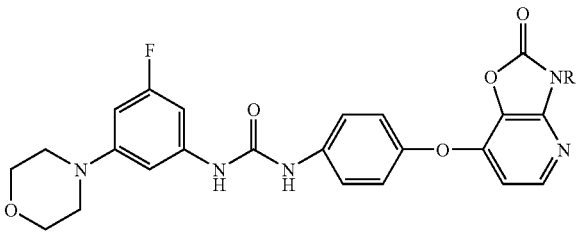

-continued
14. 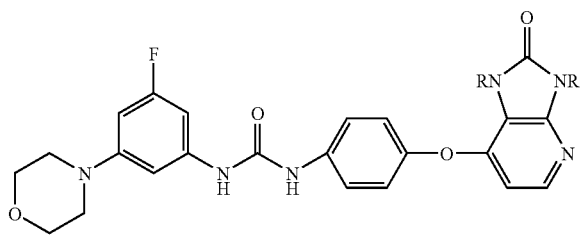
15. 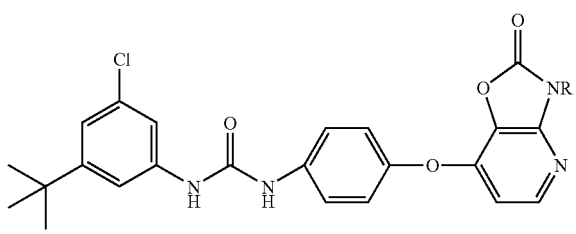
16. 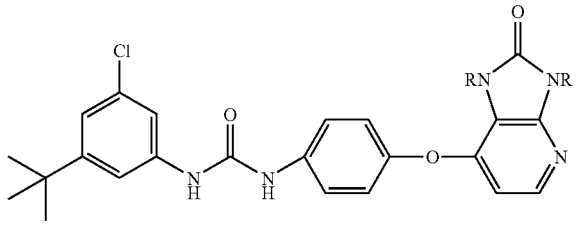
17. 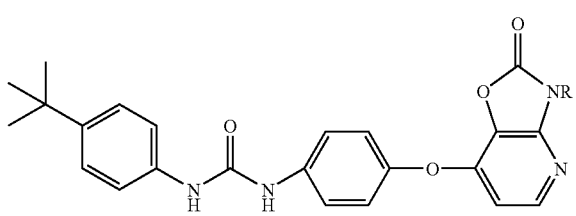
18. 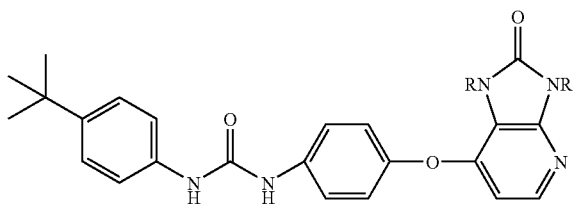
19. 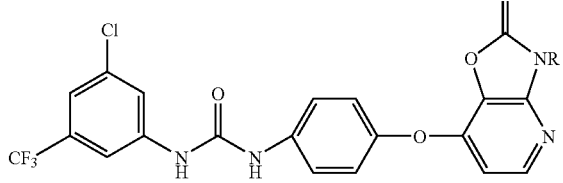
20. 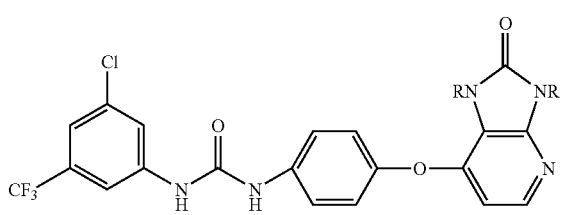

-continued
21. 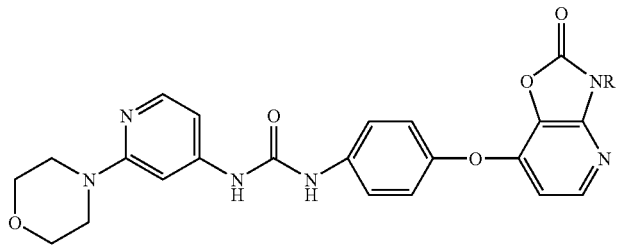
22. 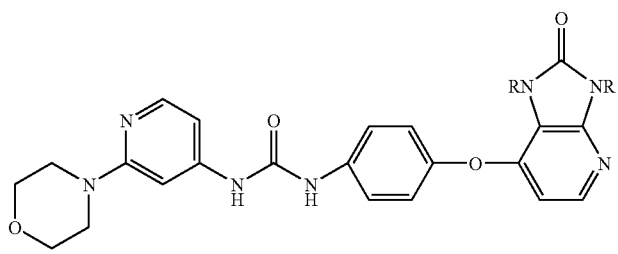
23. 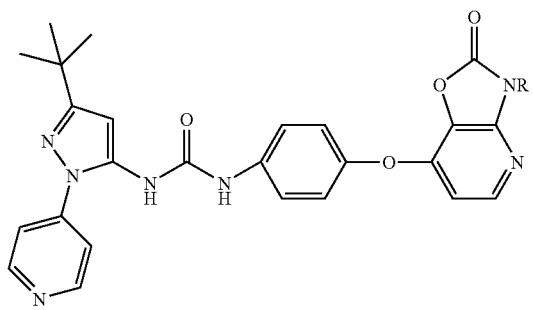
24. 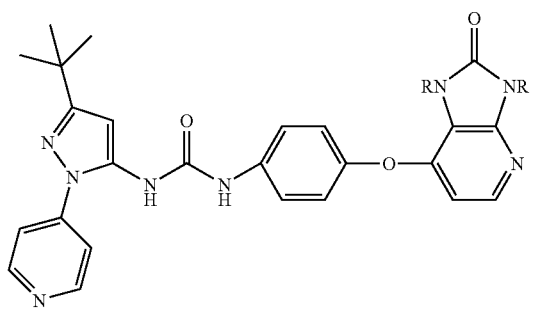
25. 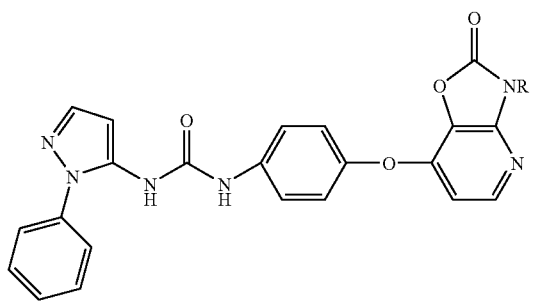

-continued
26.
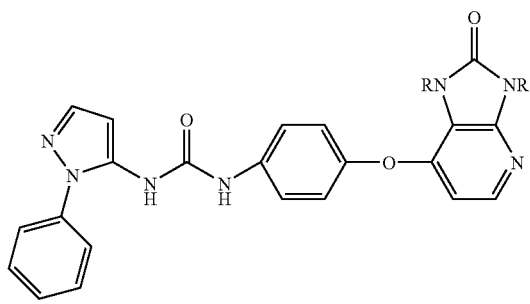
27.
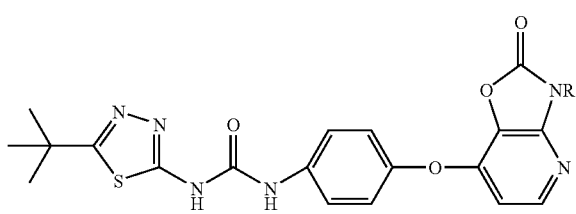
28.
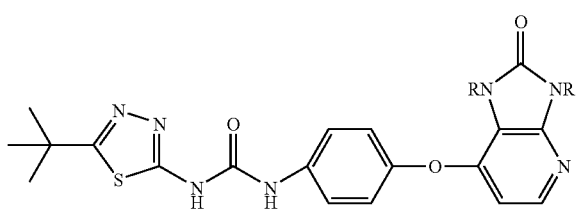
Examples of some preferred compounds (where A-L is A—NH—C(=O)—NH—, Q is —O—, and Y is —N=) (here each R is independently —H or —Me) are shown below.
Examples of some preferred compounds (where A-L is A—C(=O)—NH—, Q is —O—, and Y is —CH=) (here each R is independently —H or —Me) are shown below.
29.
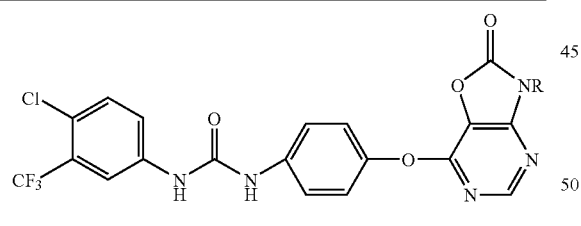
31.
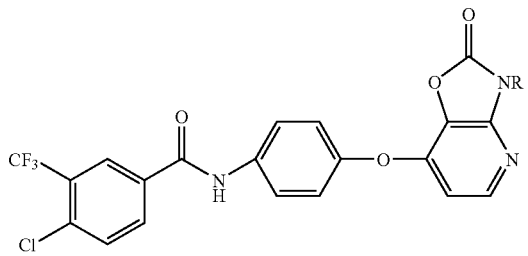
30.
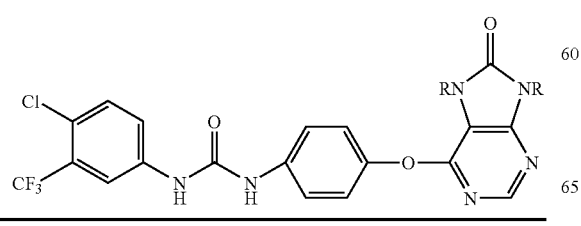
32.
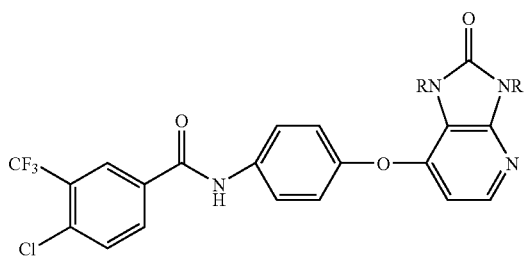

-continued
33. 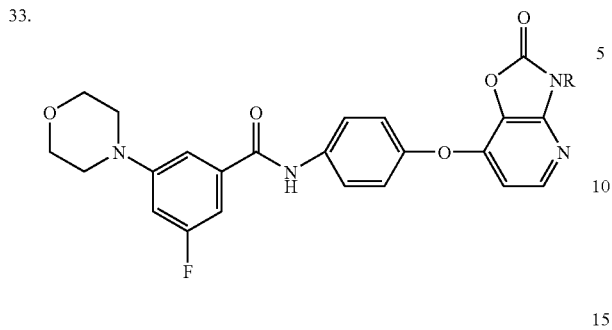
34. 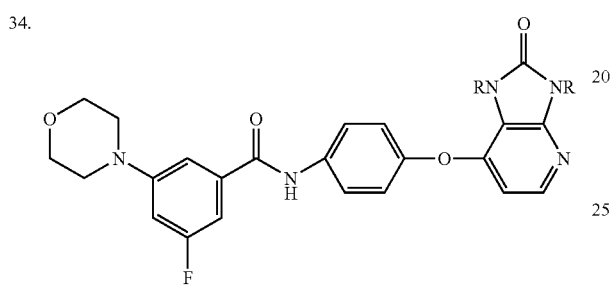
35. 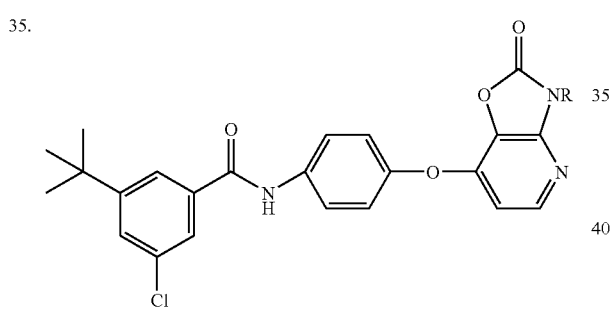
36. 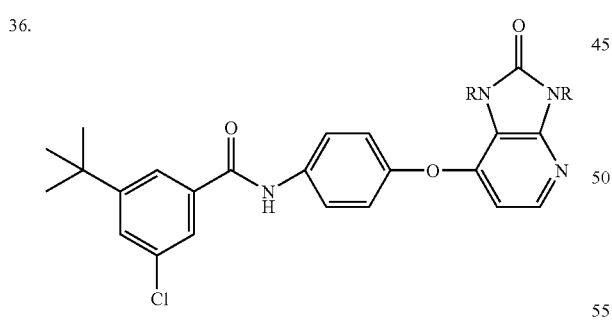
37. 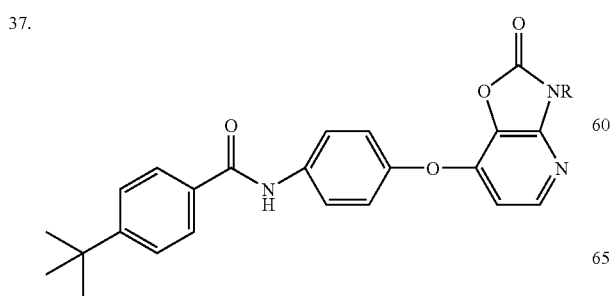
-continued
38. 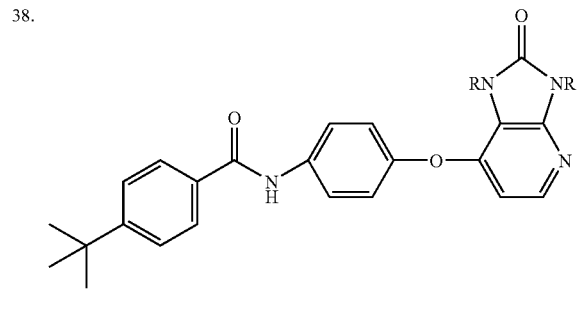
39. 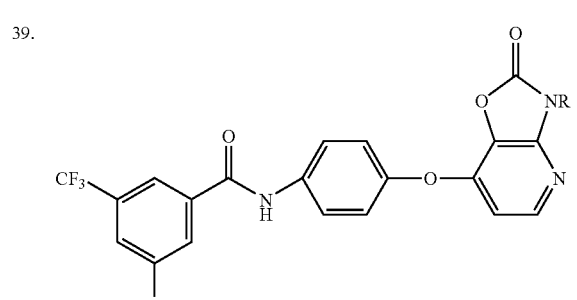
40. 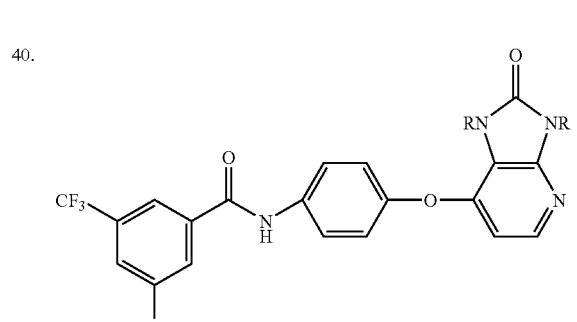
41. 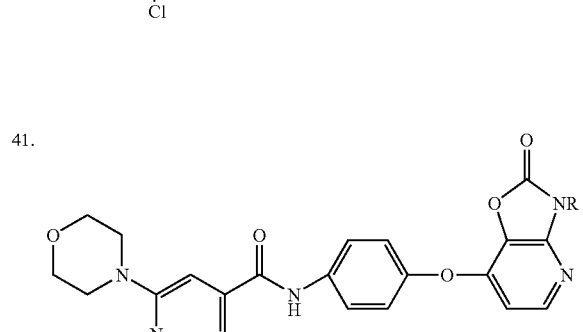
42. 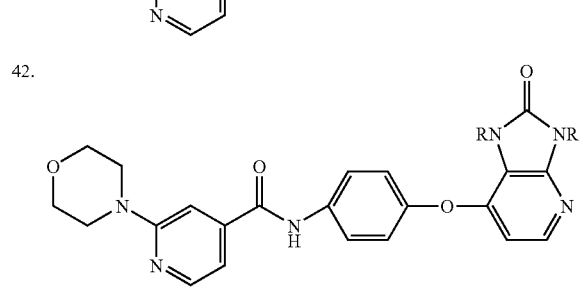

-continued
43.
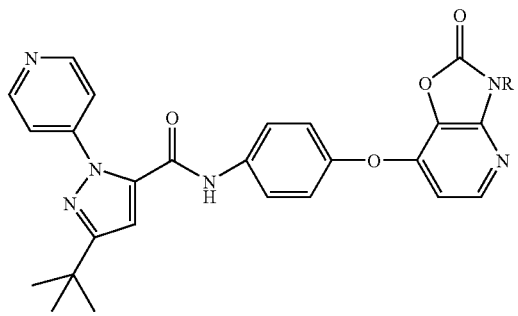
44.
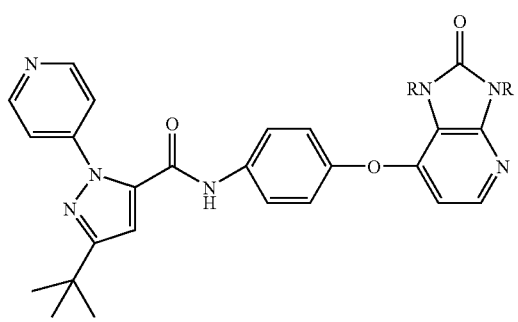
45.
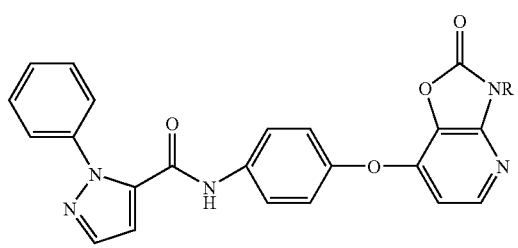
46.
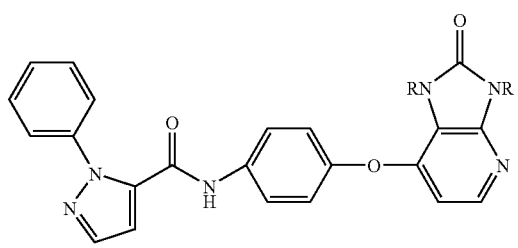
47.
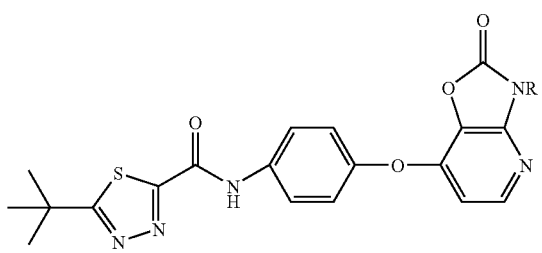
-continued
48.
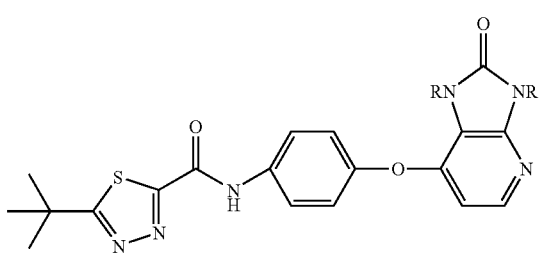
Examples of some preferred compounds (where A-L is A-S(=O)$_2$NH—, Q is —O—, and Y is —CH=) (here each R is independently —H or —Me) are shown below.
49.
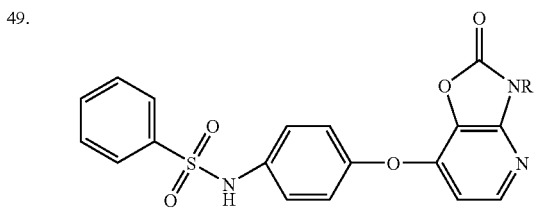
50.
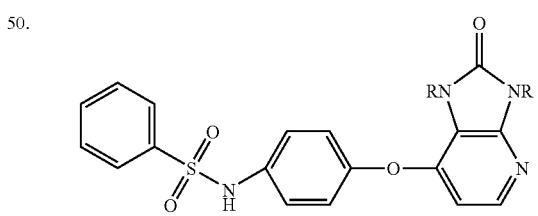
51.
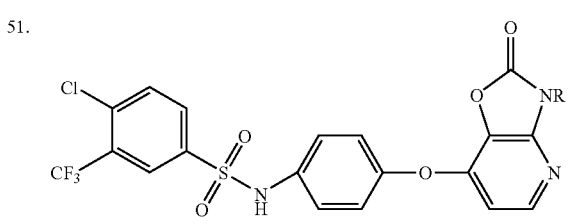
52.
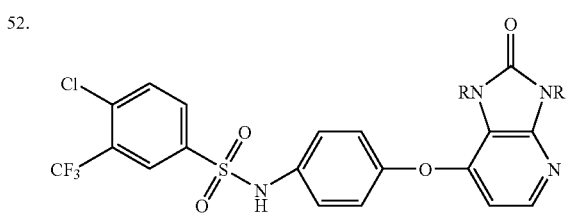

Examples of some preferred compounds (where A-L is A—NH—S(=O)₂—NH—, Q is —O—, and Y is —CH=) (here each R is independently —H or —Me) are shown below.
53.
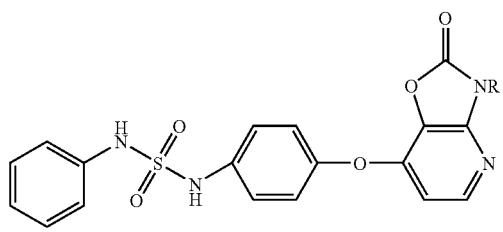
54.
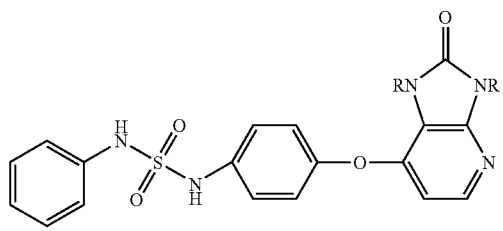
55.
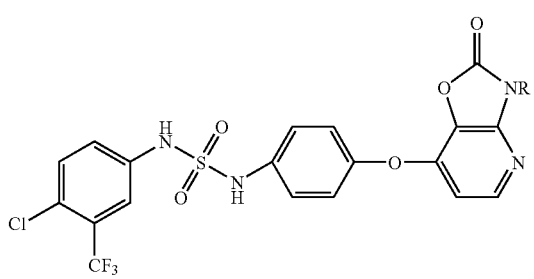
56.
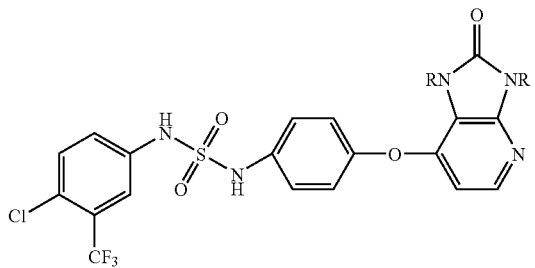
Examples of some preferred compounds (where A-L is A—NH—C(=O)—CH₂—NH—, Q is —O—, and Y is —CH=) (here each R is independently —H or —Me) are shown below.
57.
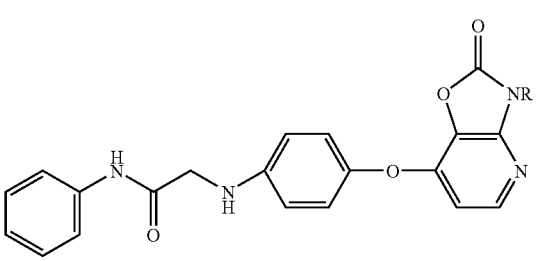
58.
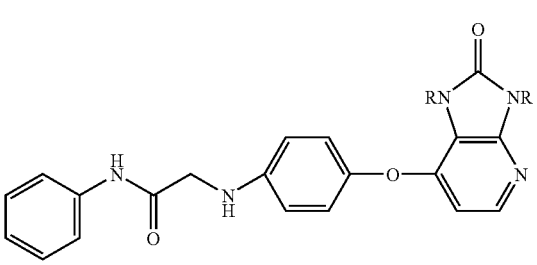
59.
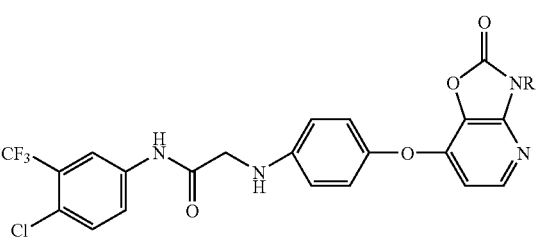
60.
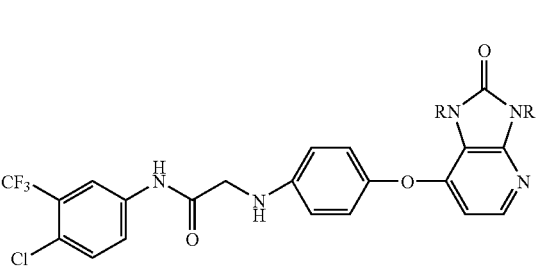

Additional examples of compounds include the following:
| | | |
|---|---|---|
| 1 | 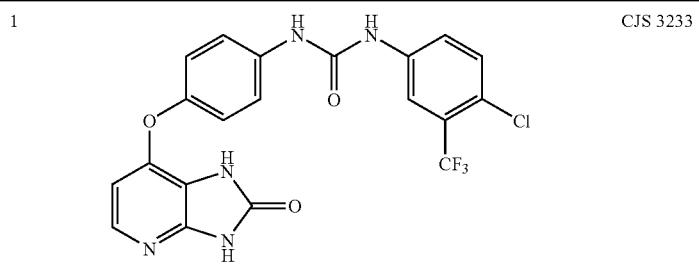 | CJS 3233 |
| 2 | 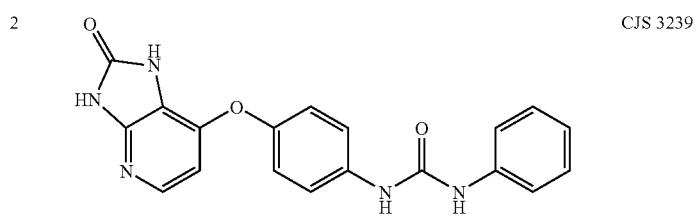 | CJS 3239 |
| 3 | 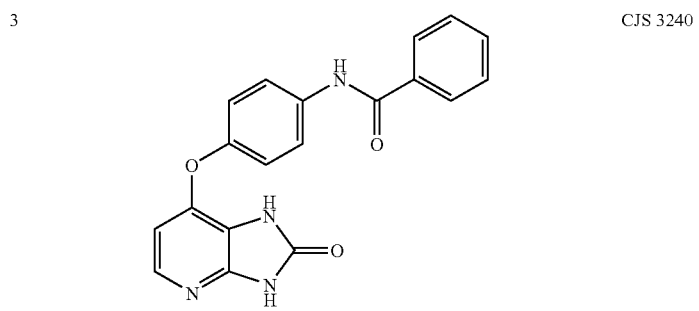 | CJS 3240 |
| 4 | 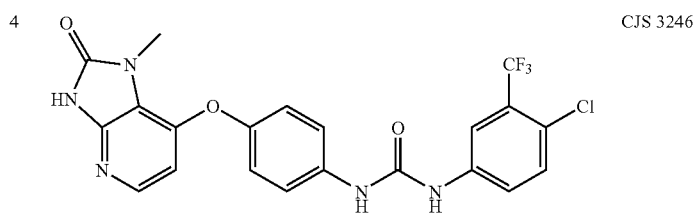 | CJS 3246 |
| 5 | 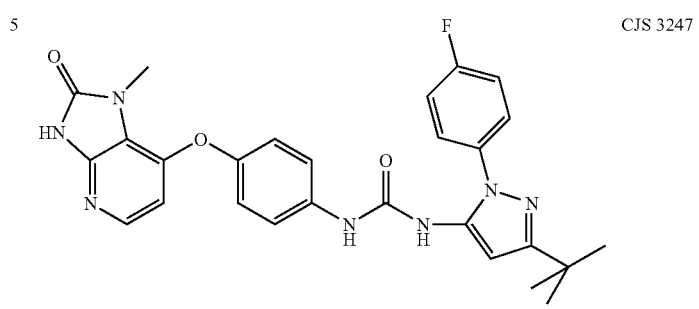 | CJS 3247 |
| 6 | 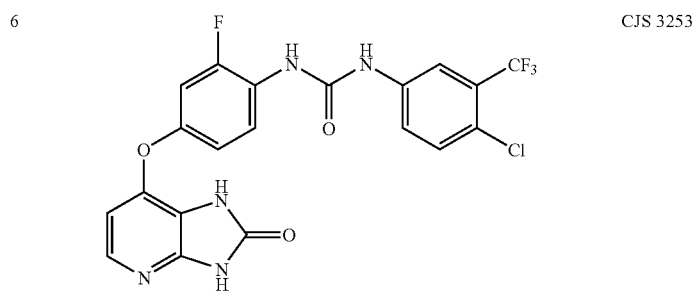 | CJS 3253 |

| | | |
|---|---|---|
| 7 | 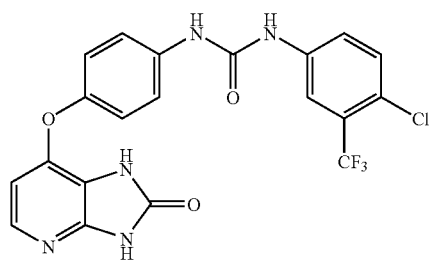 | CJS 3254 |
| 8 | 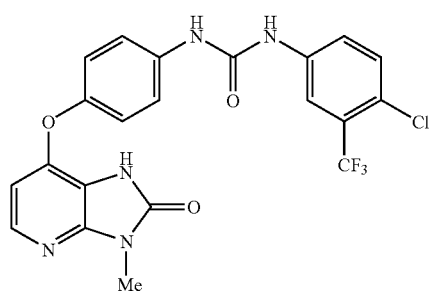 | CJS 3255 |
| 9 | 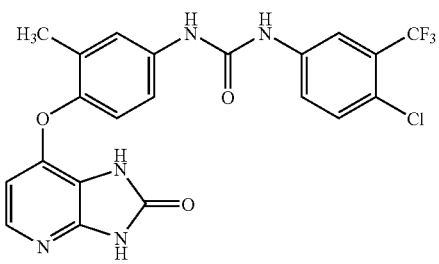 | CJS 3410 |
| 10 | 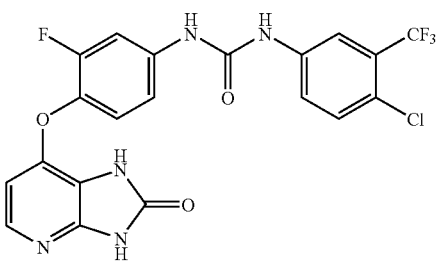 | CJS 3418 |
| 11 | 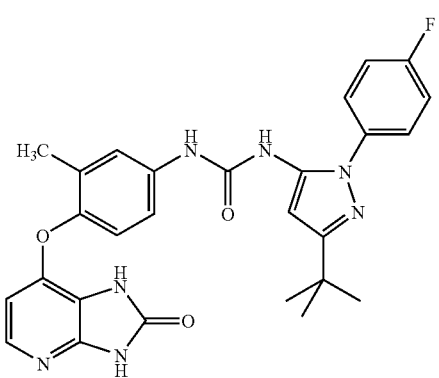 | CJS 3419 |

-continued
| | | |
|---|---|---|
| 12 | 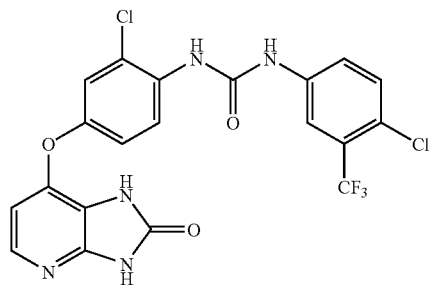 | CJS 3502 |
| 13 | 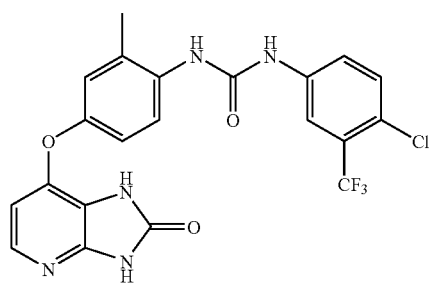 | CJS 3505 |
| 14 | 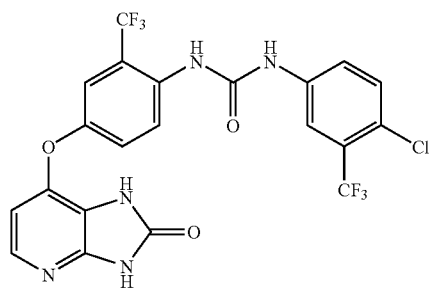 | CJS 3506 |
| 15 | 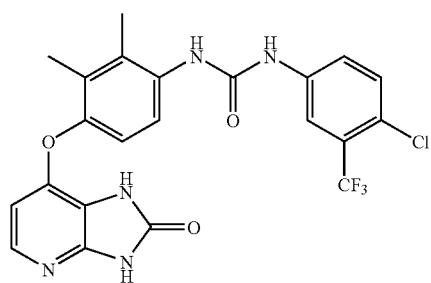 | CJS 3510 |
| 16 | 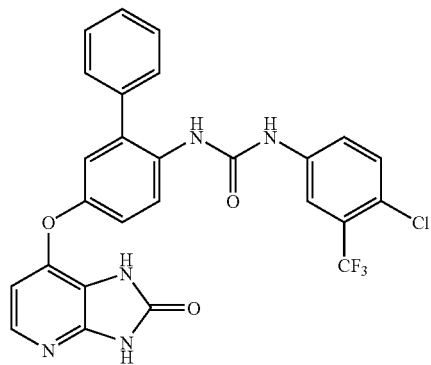 | CJS 3511 |

-continued
| | | |
|---|---|---|
| 17 | 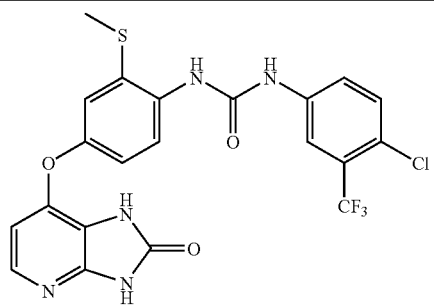 | CJS 3512 |
| 18 | 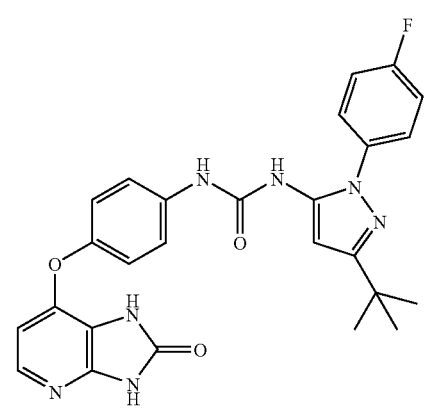 | CJS 3600 |
| 19 | 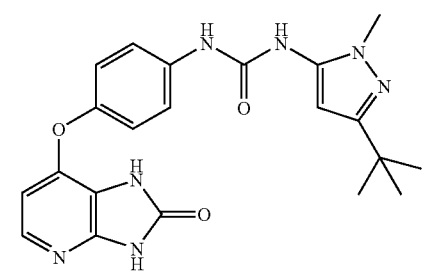 | CJS 3601 |
| 20 | 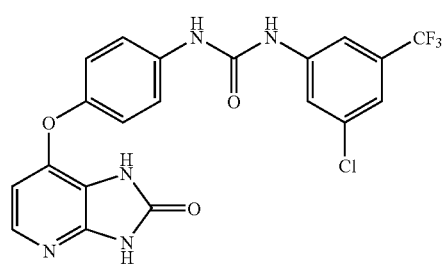 | CJS 3602 |
| 21 | 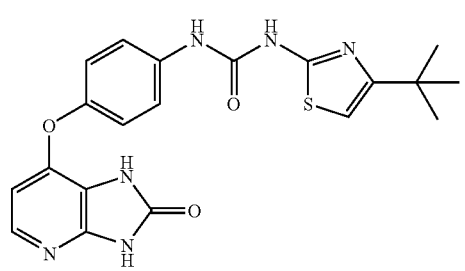 | CJS 3603 |

-continued
| | | |
|---|---|---|
| 22 | 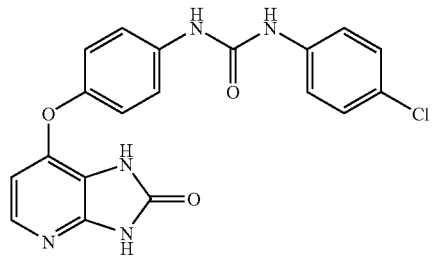 | CJS 3604 |
| 23 | 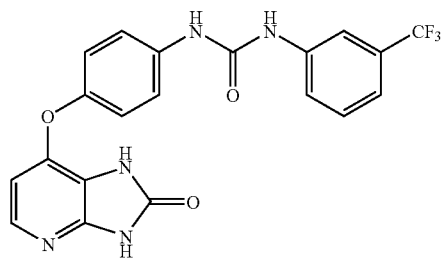 | CJS 3605 |
| 24 | 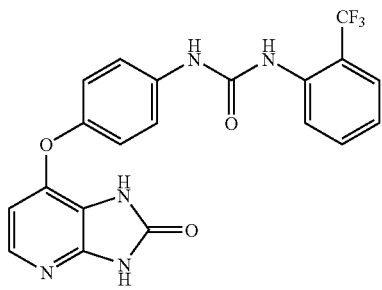 | CJS 3606 |
| 25 | 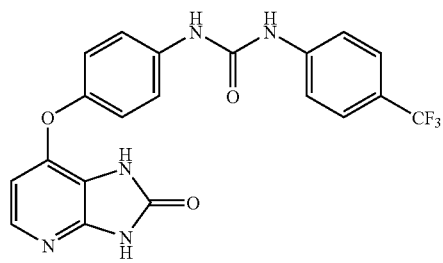 | CJS 3607 |
| 26 | 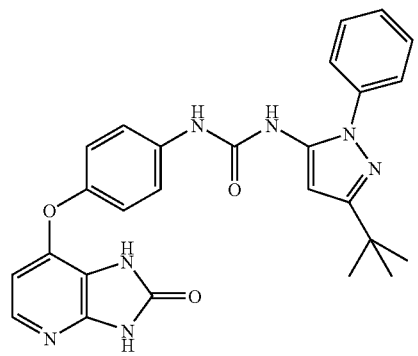 | CJS 3608 |

-continued
| | | |
|---|---|---|
| 27 | 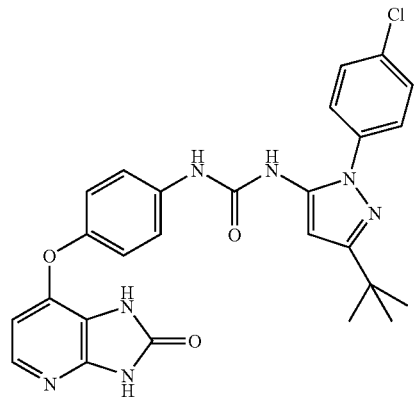 | CJS 3609 |
| 28 | 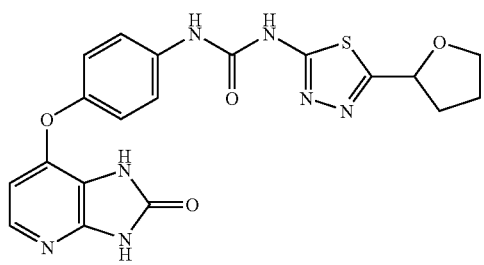 | CJS 3610 |
| 29 | 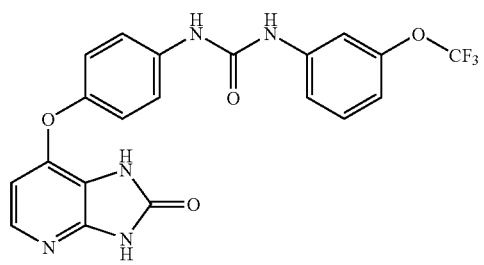 | CJS 3611 |
| 30 | 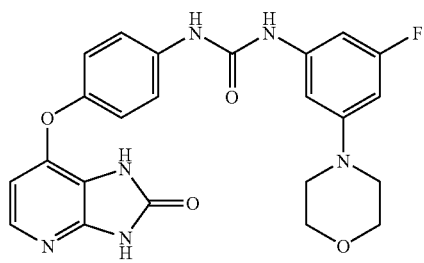 | CJS 3612 |
| 31 | 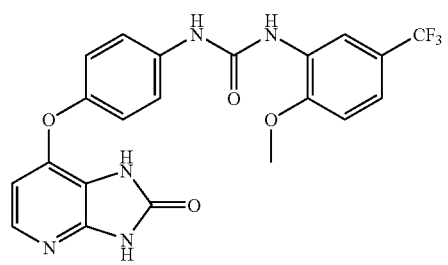 | CJS 3613 |

-continued
32 CJS 3614
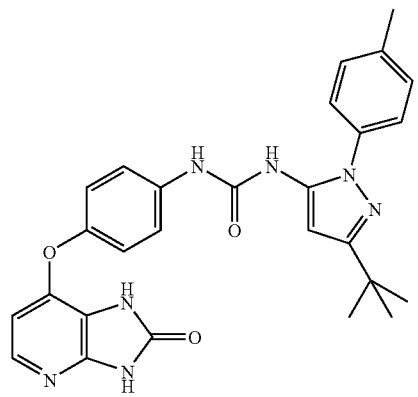
33 CJS 3615
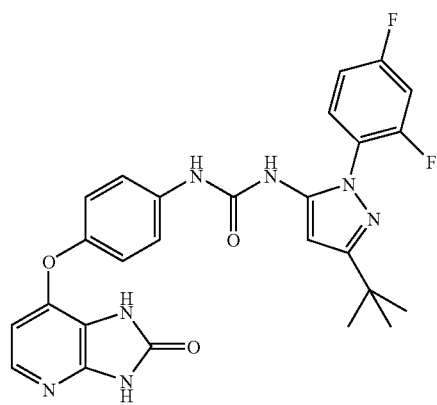
34 CJS 3616
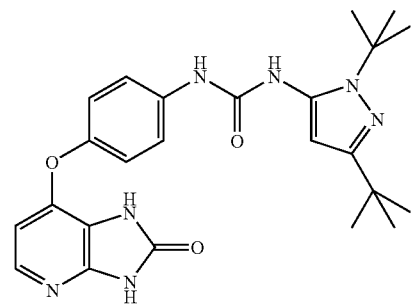
35 CJS 3617
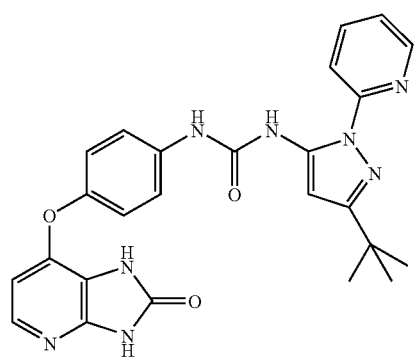

-continued
| 36 | 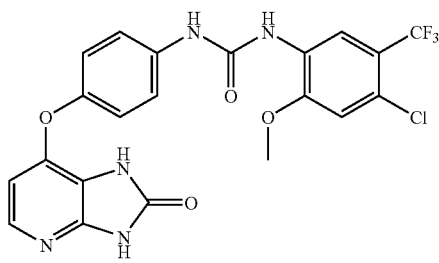 | CJS 3618 |
| 37 | 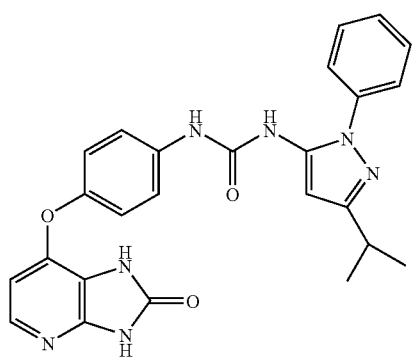 | CJS 3619 |
| 38 | 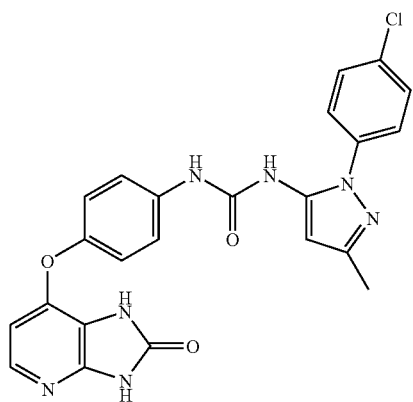 | CJS 3620 |
| 39 | 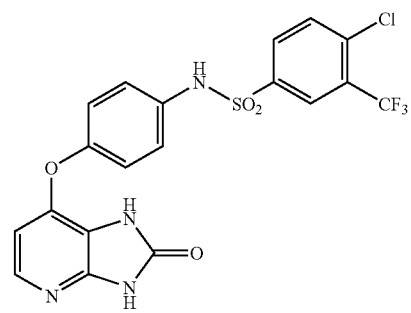 | CJS 3650 |
| 40 | 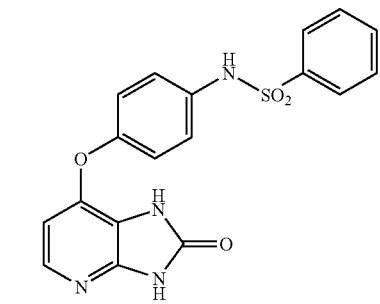 | CJS 3651 |

-continued
| 41 | 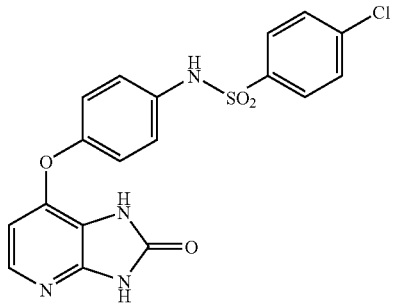 | CJS 3652 |
| 42 | 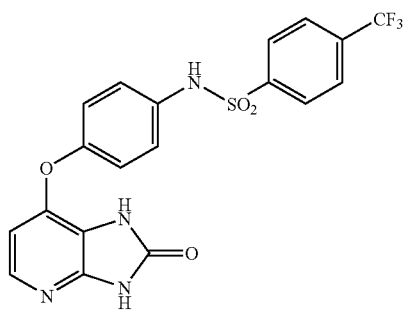 | CJS 3653 |
| 43 | 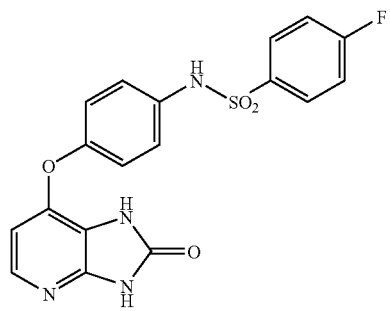 | CJS 3654 |
| 44 | 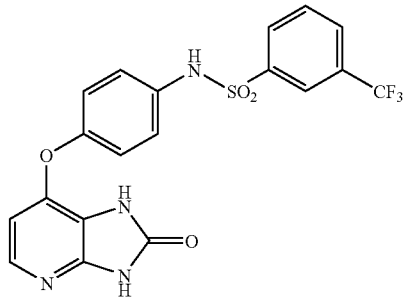 | CJS 3655 |
| 45 | 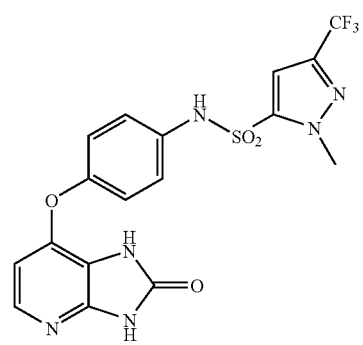 | CJS 3656 |

-continued
| | | |
|---|---|---|
| 46 | 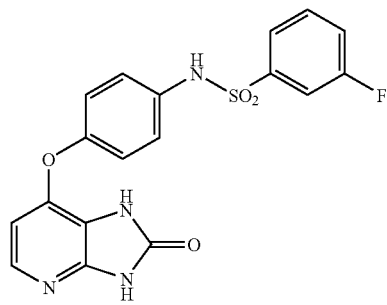 | CJS 3657 |
| 47 | 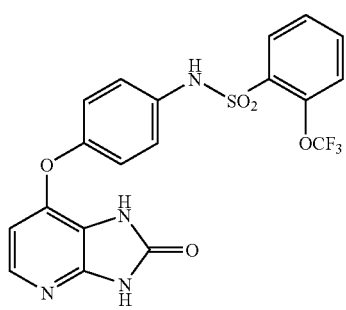 | CJS 3659 |
| 48 | 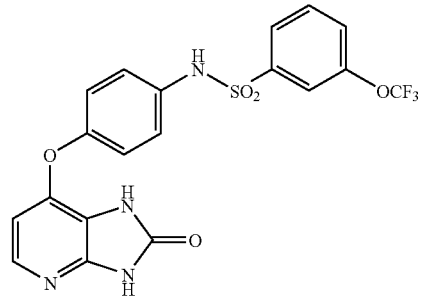 | CJS 3660 |
| 49 | 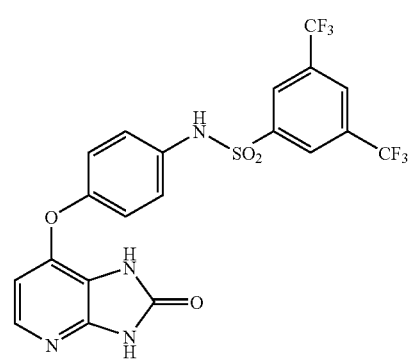 | CJS 3661 |
| 50 | 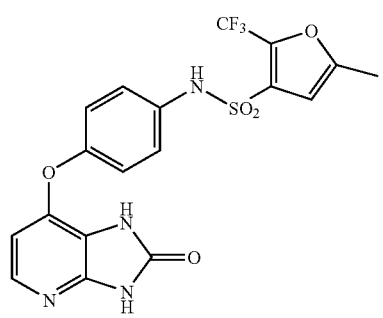 | CJS 3662 |

-continued
| | | |
|---|---|---|
| 51 | 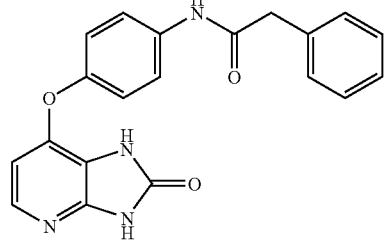 | CJS 3665 |
| 52 | 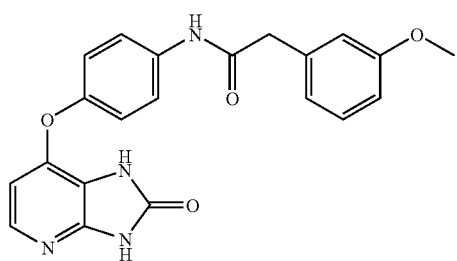 | CJS 3666 |
| 53 | 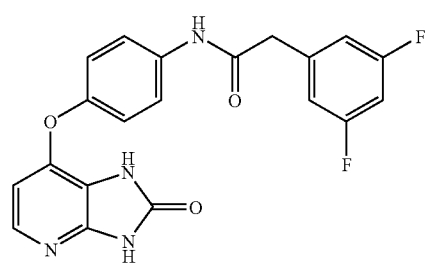 | CJS 3668 |
| 54 | 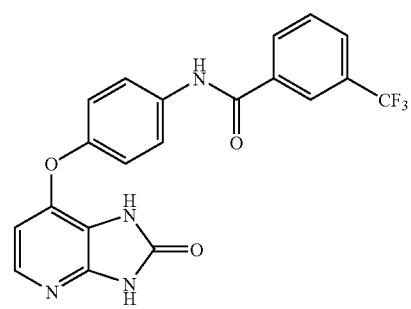 | CJS 3669 |
| 55 | 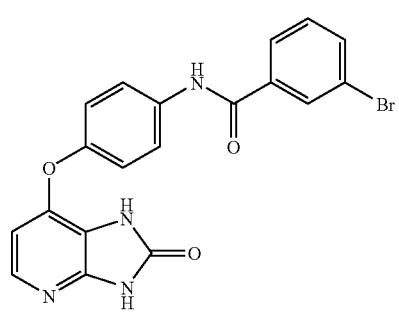 | CJS 3670 |

| | | |
|---|---|---|
| 56 | 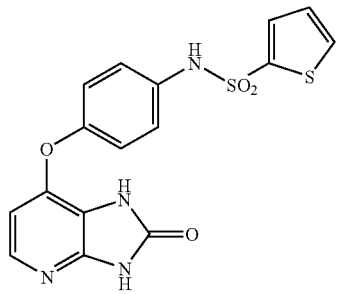 | CJS 3671 |
| 57 | 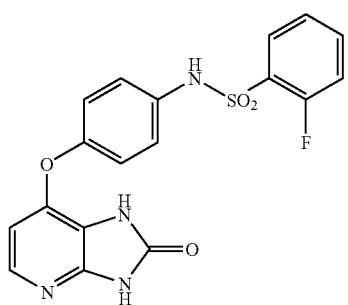 | CJS 3672 |
| 58 | 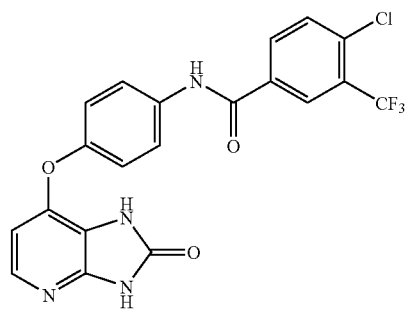 | CJS 3673 |
| 59 | 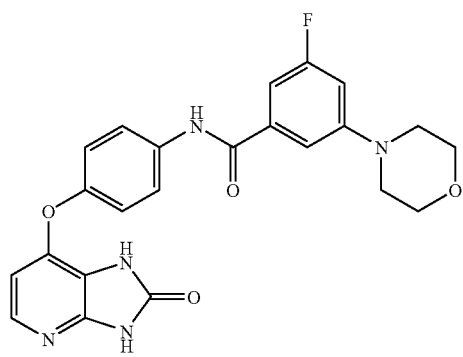 | CJS 3674 |
| 60 | 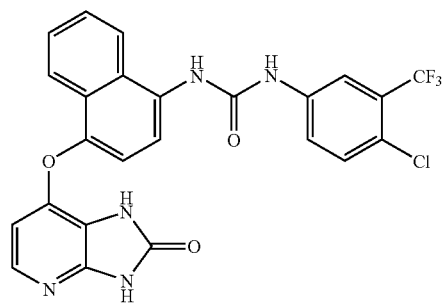 | CJS 3675 |

-continued
| 61 | 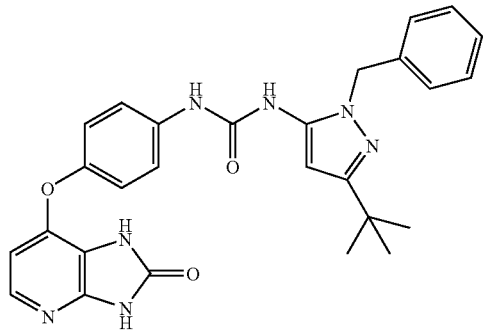 | CJS 3676 |
| 62 | 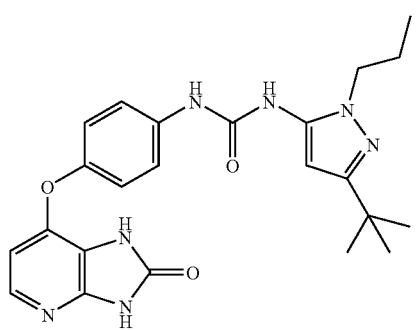 | CJS 3677 |
| 63 | 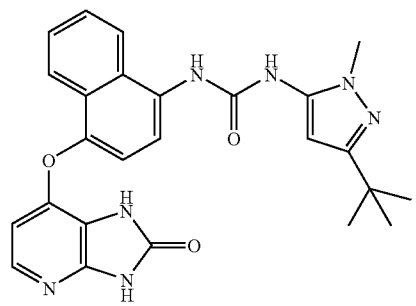 | CJS 3679 |
| 64 | 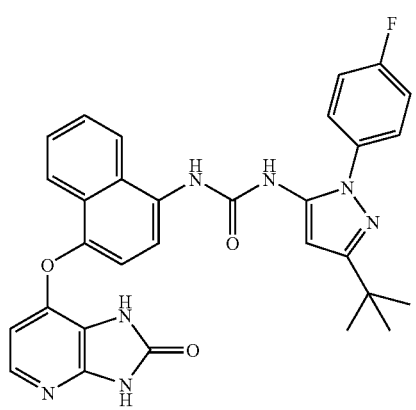 | CJS 3680 |

-continued

65                                                                          CJS 3681

[Chemical structure]

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond. Compounds and/or groups may be partially unsaturated or fully unsaturated.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked ring atoms, more preferably 3 to 8 covalently linked ring atoms, yet more preferably 5 to 6 covalently linked ring atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 ring heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene, decalin, etc.), bridged (e.g., as in norbornane, adamantane, etc.), Spiro (e.g., as in spiro [3,3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms.

Examples of groups of alkyl groups include $C_{1-4}$alkyl ("lower alkyl"), $C_{1-7}$alkyl, and $C_{1-20}$alkyl. Note that the first prefix may vary according to other limitations; for example, for unsaturated alkyl groups, the first prefix must be at least 2; for cyclic and branched alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-2}$alkenyl.

Examples of (unsubstituted) unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —$CH_2$—C≡CH).

Cycloalkyl: The term "cycloalkyl," as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of cycloalkyl groups include $C_{3-20}$cycloalkyl, $C_{3-15}$cycloalkyl, $C_{3-10}$cycloalkyl, $C_{3-7}$cycloalkyl.

Examples of cycloalkyl groups Include, but are not limited to, those derived from:

saturated monocyclic hydrocarbon compounds:

cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds:

cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:

thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds:

camphene ($C_{10}$), limonene ($C_{10}$), pinene ($C_{10}$);

polycyclic hydrocarbon compounds having an aromatic ring:

indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Carbocyclyl: The term "carbocyclyl," as used herein, pertains to a monovalent moiety obtained by removing a hydrogen atom from a non-aromatic ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{5-20}$heterocyclyl, $C_{3-15}$heterocyclyl, $C_{5-15}$heterocyclyl, $C_{3-12}$heterocyclyl, $C_{5-12}$heterocyclyl, $C_{3-10}$heterocyclyl, $C_{5-10}$heterocyclyl, $C_{3-7}$heterocyclyl, $C_{5-7}$heterocyclyl, and $C_{5-6}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{6-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{5-20}$aryl, $C_{5-15}$aryl, $C_{5-12}$aryl, $C_{5-10}$aryl, $C_{5-7}$aryl, $C_{5-6}$aryl, $C_5$aryl, and $C_6$aryl.

The ring atoms may be all carbon atoms, as in "carboaryl groups." Examples of carboaryl groups include $C_{3-20}$carboaryl, $C_{5-20}$carboaryl, $C_{5-15}$carboaryl, $C_{5-12}$carboaryl, $C_{5-10}$carboaryl, $C_{5-7}$carboaryl, $C_{5-6}$carboaryl, $C_5$carboaryl, and $C_6$carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups." Examples of heteroaryl groups include $C_{3-20}$heteroaryl, $C_{5-20}$heteroaryl, $C_{5-15}$heteroaryl, $C_{5-12}$heteroaryl, $C_{5-10}$heteroaryl, $C_{5-7}$heteroaryl, $C_{5-6}$heteroaryl, $C_5$heteroaryl, and $C_6$heteroaryl.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$); $C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$); $C_{13}$heterocyclic groups (with 2 fused rings) derived from benzodiazepine ($N_2$); $C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline (N2), phenazine ($N_2$).

Heterocyclic groups (including heteroaryl groups) that have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N═ group may be substituted in the form of an N-oxide, that is, as —N(→O)═ (also denoted —N⁺(→O⁻)═). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (═O) groups on ring carbon atoms.

Monocyclic examples of such groups include, but are not limited to, those derived from:

$C_5$: cyclopentanone, cyclopentenone, cyclopentadienone;

$C_6$: cyclohexanone, cyclohexenone, cyclohexadienone;

$O_1$: furanone ($C_5$), pyrone ($C_6$);

$N_1$: pyrrolidone (pyrrolidinone) ($C_5$), piperidinone (piperidone) ($C_6$), piperidinedione ($C_6$);

$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);

$N_1S_1$: thiazolone ($C_5$), isothiazolone ($C_5$);

$N_1O_1$: oxazolinone ($C_5$).

Polycyclic examples of such groups include, but are not limited to, those derived from:

$C_9$: indenedione;

$C_{10}$: tetralone, decalone;

$C_{14}$: anthrone, phenanthrone;

$N_1$: oxindole ($C_9$);

$O_1$: benzopyrone (e.g., coumarin, isocoumarin, chromone) ($C_{10}$);

$N_1O_1$: benzoxazolinone ($C_{10}$), benzoxazolinone ($C_{10}$);

$N_2$: quinazolinedione ($C_{10}$); benzodiazepinone ($C_{11}$); benzodiazepinedione ($C_{11}$);

N4: purinone (C9) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride (C5), succinic anhydride (C5), and glutaric anhydride (C6);

cyclic carbonates (—O—C(=O)—O— in a ring), such as ethylene carbonate (C5) and 1,2-propylene carbonate (C5);

imides (—C(=O)—NR—C(=O)— in a ring), including but not limited to, succinimide (C5), maleimide (C5), phthalimide, and glutarimide (C6);

lactones (cyclic esters, —O—C(=O)— in a ring), including, but not limited to, β-propiolactone, γ-butyrolactone, δ-valerolactone (2-piperidone), and ε-caprolactone; lactams (cyclic amides, —NR—C(=O)— in a ring), including, but not limited to, β-propiolactam (C4), γ-butyrolactam (2-pyrrolidone) (C5), δ-valerolactam (C6), and ε-caprolactam (C7);

cyclic carbamates (—O—C(=O)—NR— in a ring), such as 2-oxazolidone (C5); cyclic ureas (—NR—C(=O)—NR— in a ring), such as 2-imidazolidone (C5) and pyrimidine-2,4-dione (e.g., thymine, uracil) (C6).

Includes Other Forms

Unless otherwise specified, a reference to a particular group also includes the well known ionic, salt, solvate, and protected forms thereof. For example, a reference to carboxylic acid (—COOH) also includes the anionic (carboxylate) form (—COO−), a salt or solvate thereof, as well as conventional protected forms. Similarly, a reference to an amino group includes the protonated form (—N+HR1R2), a salt or solvate of the amino group, for example, a hydrochloride salt, as well as conventional protected forms of an amino group. Similarly, a reference to a hydroxyl group also includes the anionic form (—O−), a salt or solvate thereof, as well as conventional protected forms.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH3, is not to be construed as a reference to its structural isomer, a hydroxymethyl group, —CH2OH. Similarly, a reference to ortho-chlorophenyl is not to be construed as a reference to its structural isomer, meta-chlorophenyl. However, a reference to a class of structures may well include structurally isomeric forms falling within that class (e.g., C1-7alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

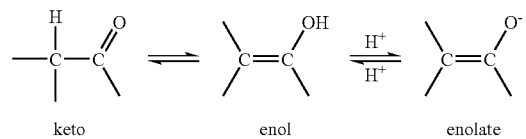

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO−), then a salt may be formed with a suitable cation. Examples of suitable inorganic cations include, but are not limited to, alkali metal ions such as Na+ and K+, alkaline earth cations such as Ca$^{2+}$ and Mg$^{2+}$, and other cations such as Al$^{+3}$. Examples of suitable organic cations include, but are not limited to, ammonium ion (i.e., NH4+) and substituted ammonium ions (e.g., NH3R+, NH2R2+, NHR3+, NR4+). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH3)4+.

If the compound is cationic, or has a functional group which may be cationic (e.g., —NH2 may be —NH3+), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate forms thereof.

Chemically Protected Forms

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$-trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

Unless otherwise specified, a reference to a particular compound also includes prodrugs thereof.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of compounds of the present invention are described herein. These and/or other well known methods may be modified and/or adapted in known ways in order to facilitate the synthesis of additional compounds within the scope of the present invention.

Descriptions of general laboratory methods and procedures, useful for the preparation of the compounds described herein, are provided in *Vogel's Textbook of Practical Organic Chemistry*, 5th Edition, 1989, (Editors: Furniss, B. S., Hannaford, A. J., Smith, P. W. G., Tatchell, A. R.) (published by Longmann, UK).

Methods for the synthesis of pyridine compounds in particular are described in *Heterocyclic Chemistry*, 3rd Edition, 1998, Joule, J. A, Mills, R. and Smith, G. F. (published by Chapman & Hall, UK).

Many of the compounds described herein can be prepared via a key intermediate: 4-(4-amino-phenoxy)-3-nitro-pyridin-2-ylamine (2), which may be conveniently substituted on the phenyl ring. This intermediate can be prepared from commercially available starting material, 4-chloro-3-nitro-pyridin-2-yl-amine (1) and substituted 4-amino-phenols. An example of such a method is illustrated in the following scheme.

Scheme 1

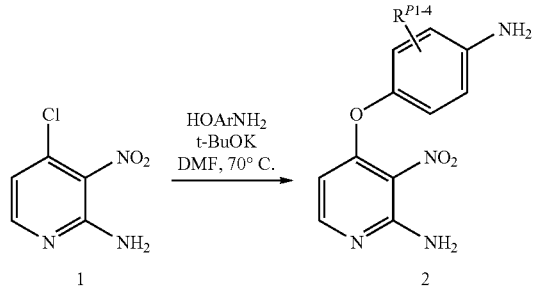

Note that compounds with substituted or unsubstituted phenyl groups have been synthesised and are described herein. The following Schemes are illustrated using unsubstituted phenyl, but it should be understood that these methods are also suitable for the preparation of compounds with substituted phenyl rings.

In one approach, the key intermediate 2 is protected, converted to an imidazo[4,5-b]pyridine-2-one, and then deprotected, to give another key intermediate: 7-(4-amino-phenoxy)-1,3-dihydro-imidazo[4,5-b]pyridin-2-one, 6.

For example, the 4-aminophenyl group of the intermediate 2 is protected selectively with Boc or trifluoroacetyl, the nitro group reduced to amino with Pd/C and ammonium formate or hydrogen, then the imidazolone 5 formed. Deprotection of the Boc group with TFA or trifluoroacetamide with ammonia affords the common intermediate 6. An example of such a method is illustrated in the following scheme.

Scheme 2

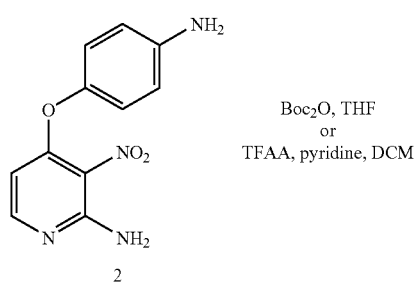

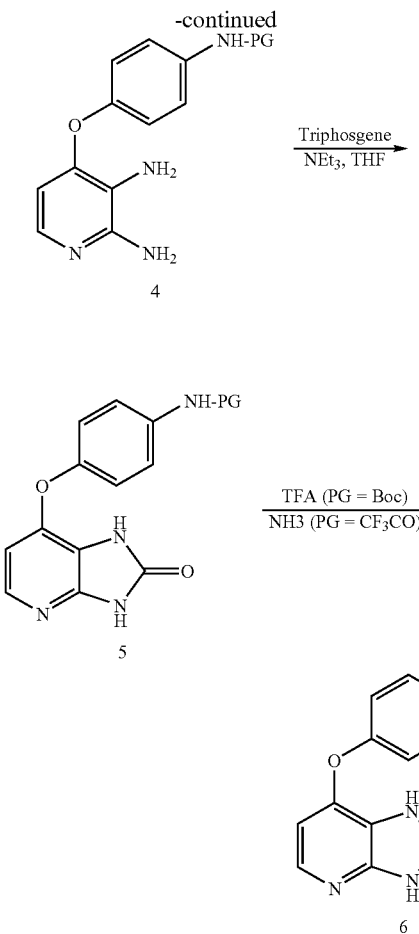

This key intermediate 6 may then be used to prepare a range of compounds with different linker groups, L, and different terminal groups, A.

For example, the intermediate can be reacted with activated carboxylic acids or acid chloride to afford amides (NHCO); with activated thioacetic acids to afford thioamide (NHCS); with isocyanates to afford ureas (NHCONH); with activated carbamates to afford ureas (NHCONH); with isothiocyanates to afford thioureas (NHCSNH); with sulfonyl chlorides to afford sulfonamides ($SO_2NH$); with activated sulfamoyl derivatives to afford sulfamides ($NHSO_2NH$); with haloacetic amide to afford glycinamides ($NHCH_2CONH$). Examples of such methods are illustrated in the following scheme.

Scheme 3

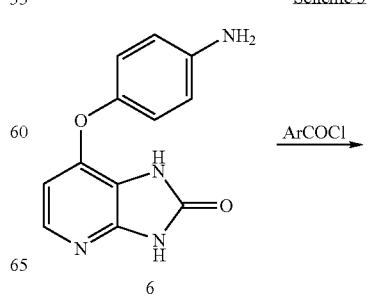

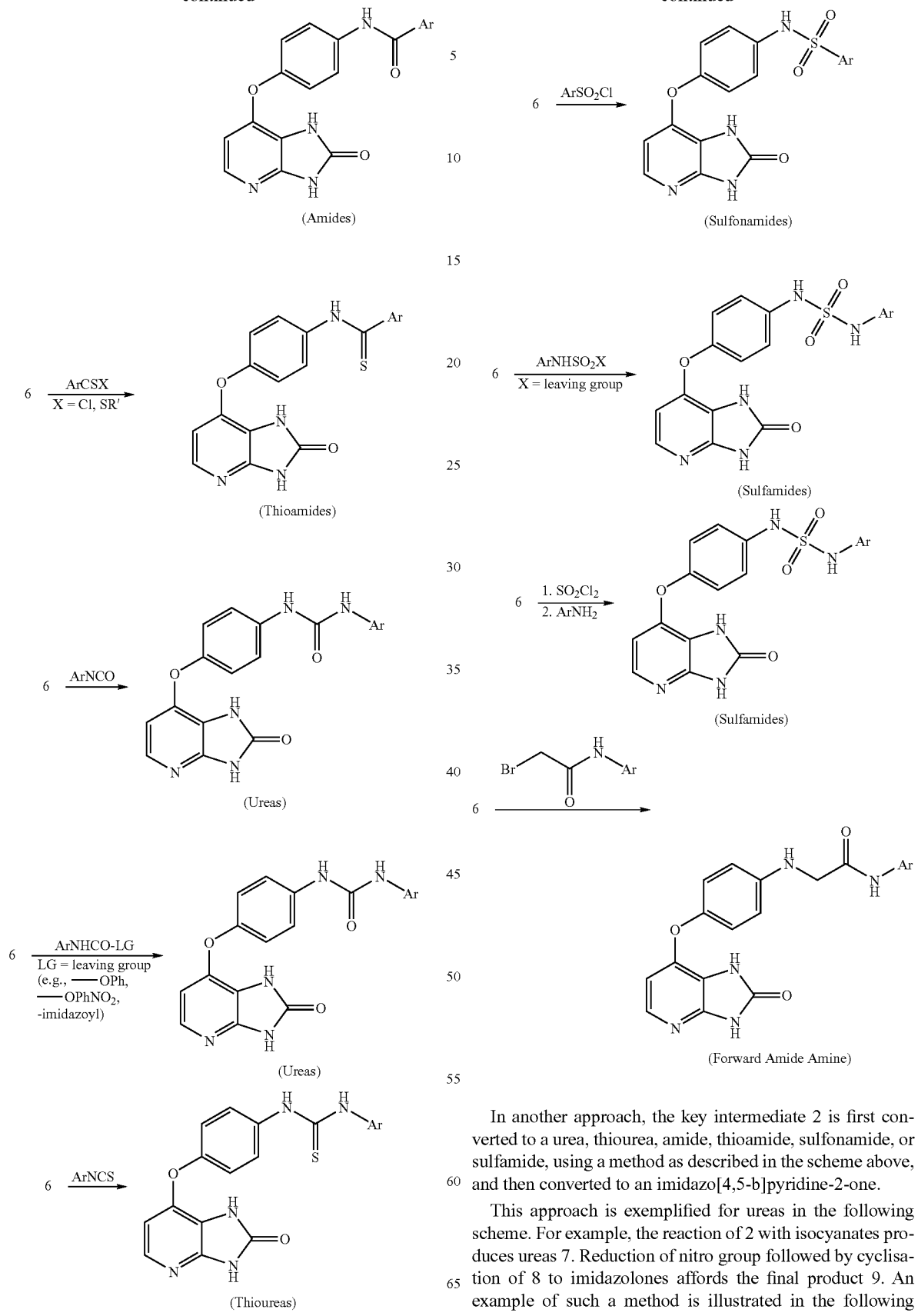

In another approach, the key intermediate 2 is first converted to a urea, thiourea, amide, thioamide, sulfonamide, or sulfamide, using a method as described in the scheme above, and then converted to an imidazo[4,5-b]pyridine-2-one.

This approach is exemplified for ureas in the following scheme. For example, the reaction of 2 with isocyanates produces ureas 7. Reduction of nitro group followed by cyclisation of 8 to imidazolones affords the final product 9. An example of such a method is illustrated in the following scheme.

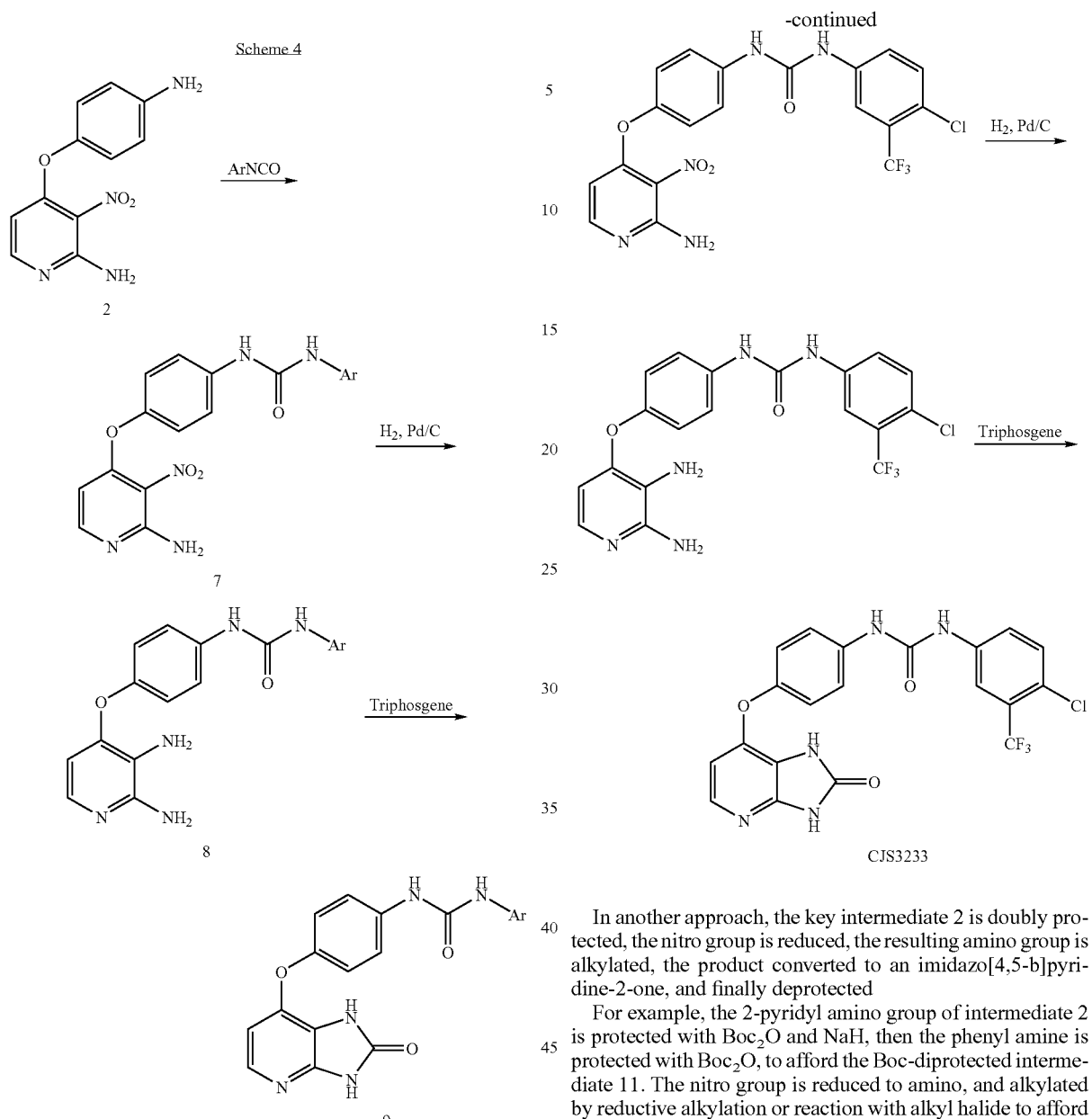

In another approach, the key intermediate 2 is doubly protected, the nitro group is reduced, the resulting amino group is alkylated, the product converted to an imidazo[4,5-b]pyridine-2-one, and finally deprotected For example, the 2-pyridyl amino group of intermediate 2 is protected with Boc$_2$O and NaH, then the phenyl amine is protected with Boc$_2$O, to afford the Boc-diprotected intermediate 11. The nitro group is reduced to amino, and alkylated by reductive alkylation or reaction with alkyl halide to afford 13. The 2-pyridyl Boc-carbamate is then cyclised to imidazolone in the presence of base to produce 14. Cleavage of the remaining Boc protection affords the common intermediate 15. An example of such a method is illustrated in the following scheme.

For example, in one approach, a method as illustrated in the following scheme is used.

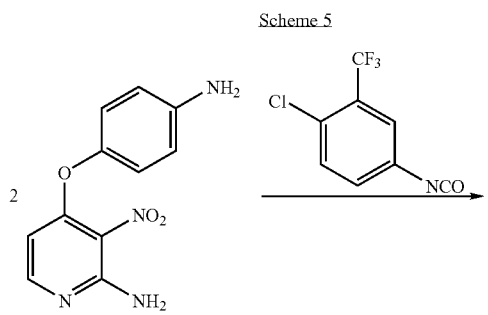

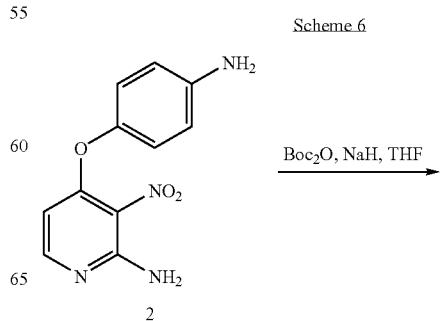

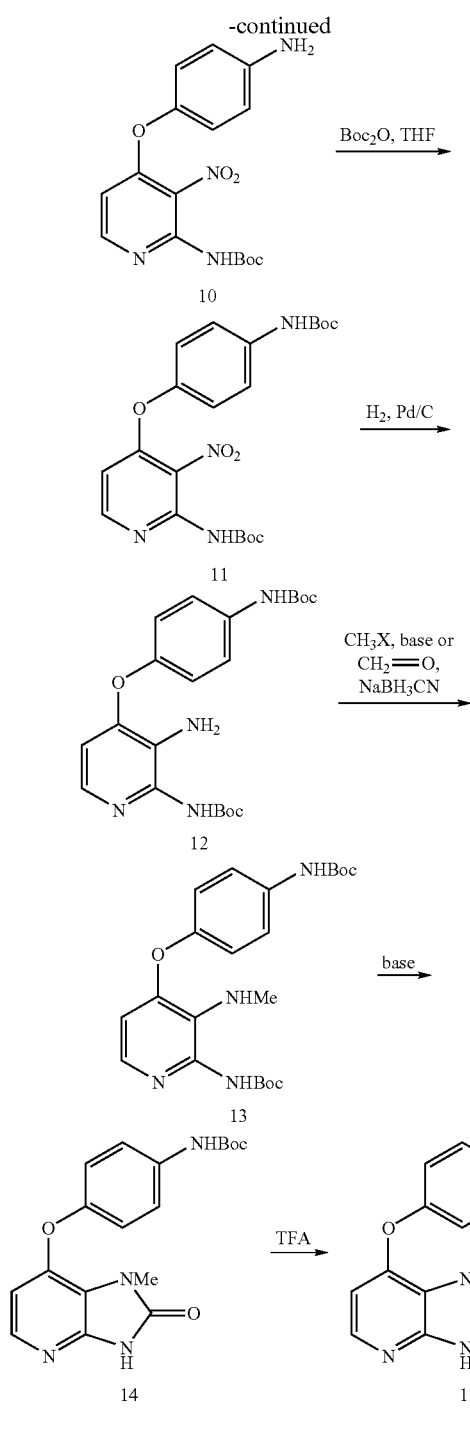

Again, this intermediate 15 may then be used to prepare a range of compounds with different linker groups, L, and different terminal groups, A.

In another approach, the key intermediate 15 is prepared starting from the commercially available reagent 4-chloro-pyridin-3-yl-amine. The amino group is converted to a carbamate, the pyridine ring is nitrated, the carbamate is alkylated, the chloro group is replaced with a para-aminophenoxy group, the nitro group is reduced to form an amino group, and the ring is closed to form an imidazo[4,5-b]pyridine-2-one.

For example, 3-Amino-4-chloropyridine 16 is converted to ethyl carbamate 17, nitrated selectively in 2-position to afford 18, then alkylated to afford the key intermediate 19. Displacement of 4-chloro with 4-aminophenolate affords 20. The nitro group is reduced, and the diamine 21 is cyclised to the common intermediate 15 in the presence of base. An example of such a method is illustrated in the following scheme.

Scheme 7

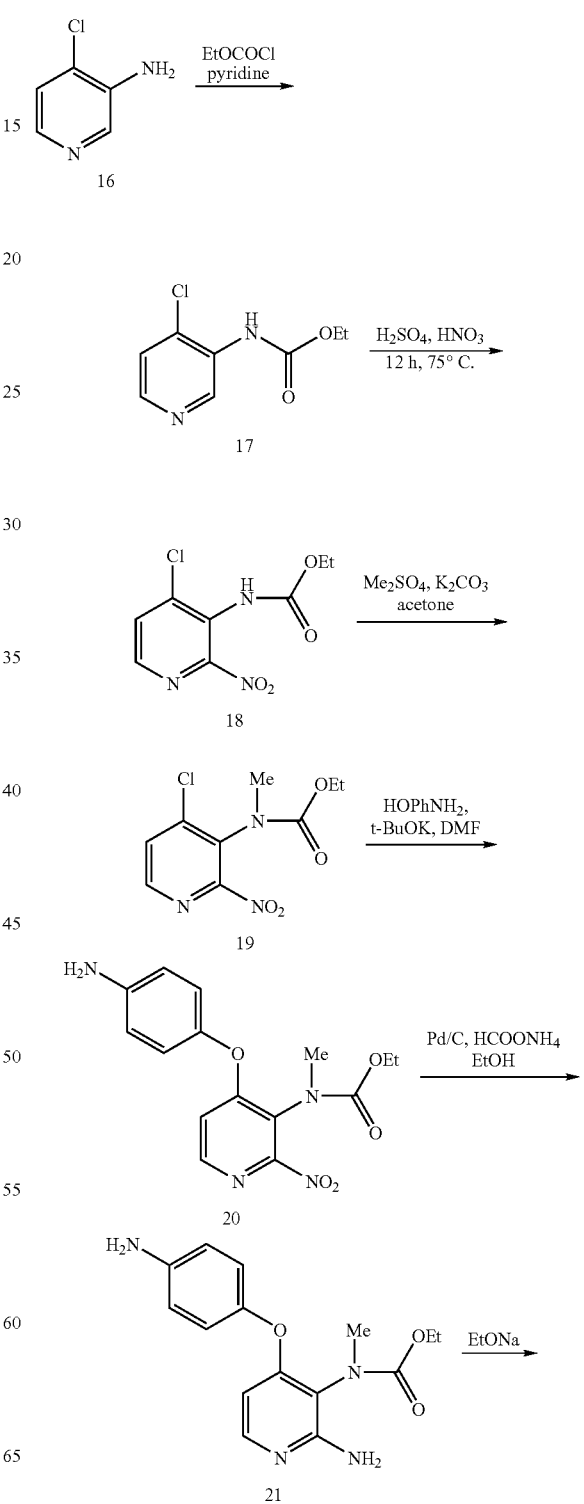

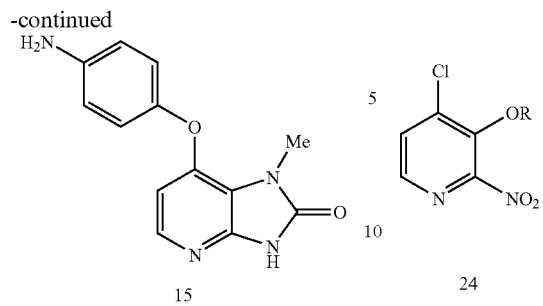

15

Again, this intermediate 15 may then be used to prepare a range of compounds with different linker groups, L, and different terminal groups, A.

In another approach, another key intermediate is prepared from the commercially available reagent 4-chloro-pyridin-3-ol. The reagent is nitrated, the hydroxyl group is protected, and the chloro group is replaced with a para-amino-phenoxy group. Then, either the hydroxyl group is deprotected (when it was protected as MOM or methyl ether), the amino group is protected as Boc carbamate and the nitro group reduced to yield an amino group, or the amino group is protected as Boc carbamate (when the hydroxyl is protected as benzyl ether) and the benzyl group is removed concomitant with the reduction of the nitro. Then, the ring is closed using triphosgene, phosgene or carbonyldiimidazole, and the initial amino group is deprotected to give the desired intermediate: 7-(4-Aminophenoxy)-3H-oxazolo[4,5-b]pyridin-2-one.

For example, 4-chloro-3-hydroxypyridine 22 is nitrated selectively in the 2-position, then the phenol protected as MOM, Me or Bn ether to afford 24. Displacement of the 4-chloro with 4-aminophenolate yields 25. Removal of the phenol protection, followed by protection of amine with Boc affords 27. Reduction of nitro group, followed by cyclisation of the resulting 2-amino-3-hydroxy motif with triphosgene to produce 30. Removal of the Boc group generates the desired intermediate 31. Alternatively, when R is benzyl (Bn), the intermediate 25 is protected first with Boc to afford 29, which is then reduced to convert the nitro group to amino simultaneously with the removal of benzyl protection to generate 28. Examples of such methods are illustrated in the following schemes.

Scheme 8

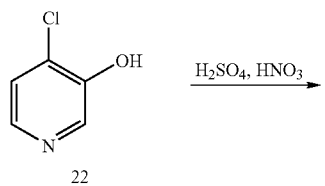

22

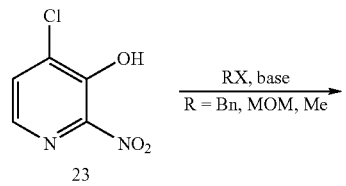

23

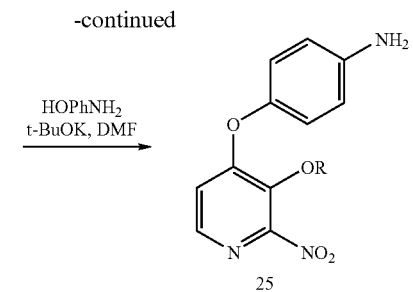

24

25

Scheme 9

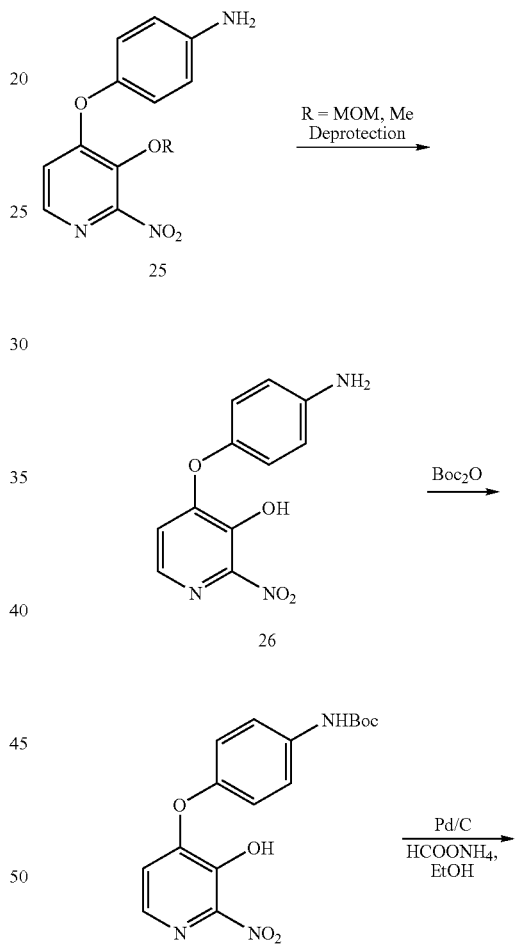

Scheme 10

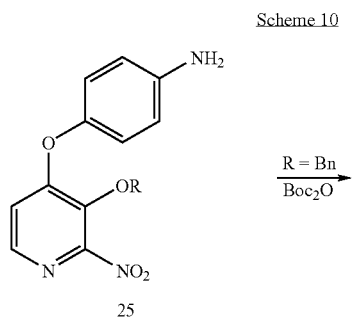

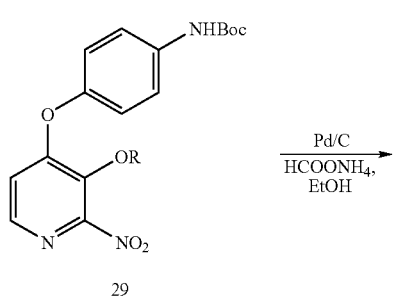

Again, this key intermediate 31 may then be used to prepare a range of compounds with different linker groups, L, and different terminal groups, A.

In another approach, another key intermediate is prepared from the commercially available reagent pyridine-2-carboxylic acid (2-picolinic acid). The ring is chlorinated and the acid group is converted to an acid chloride. The acid chloride is then converted to a secondary amide using a primary amine linked to a tertiary carbon (e.g., aniline, cumylamine, t-butyl amine). The pyridine ring is iodinated, and the amide converted back to a carboxylic acid, and then to a carboxamide, the chloro group is replaced with a para-amino-phenoxy group, and the associated amino group is then protected, to give the desired intermediate.

For example, 2-picolinic acid 32 is converted to 4-chloro-2-picolinyl chloride 33, which when treated with amine generate the amide 34. When the amine is aniline, 34a is produced, and with cumyl amine, 34b is formed. Either of these amides is lithiated selectively in position 3, and quenched with iodine. The amide 35a is then cleaved to give the carboxylic acid 36, and converted to the key intermediate carboxamide 37. The amide 35b can be converted directly to 37 using acidic conditions. The 4-chloro group in 37 is displaced with 4-aminophenolate, and the amine protected with Boc to afford 39. An example of such a method is illustrated in the following scheme.

Scheme 12

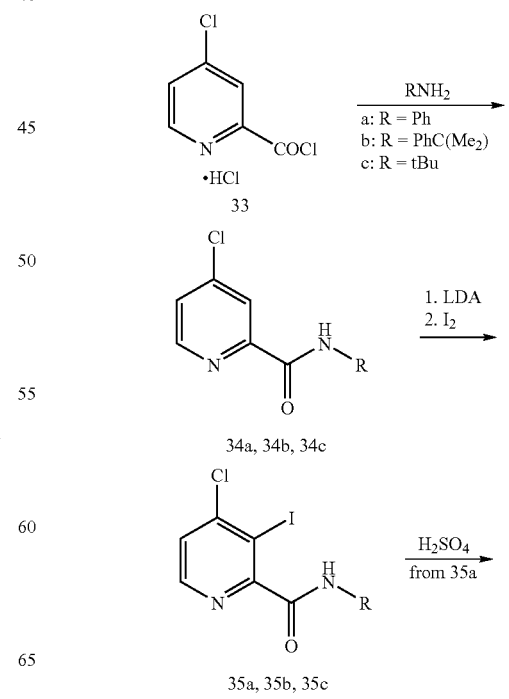

Scheme 11

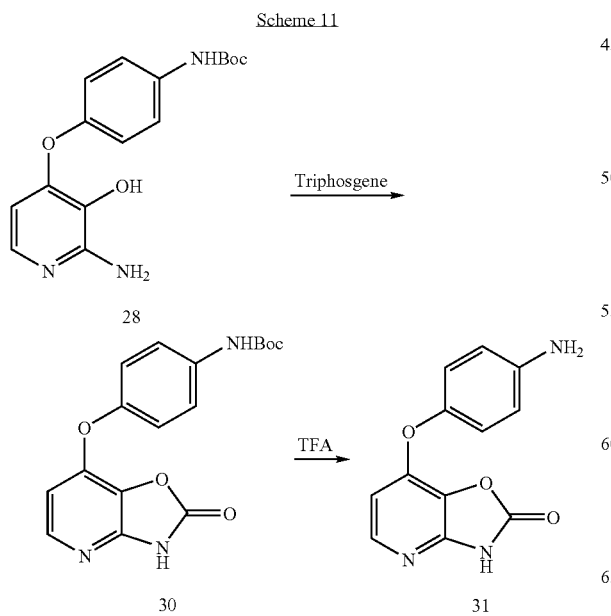

-continued

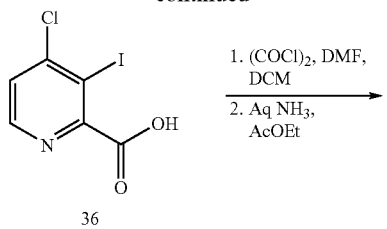

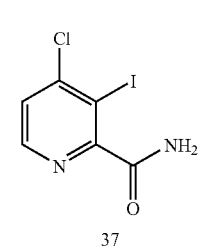

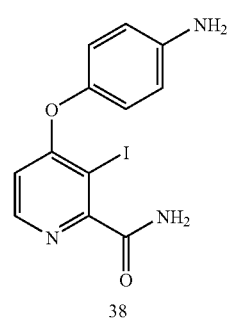

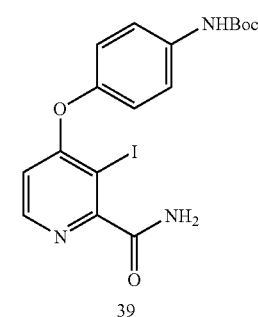

The resulting key intermediate may then be used to prepare oxazolo[4,5-b]pyridinone intermediates, by reaction with hydroxide followed by Hoffman rearrangement. For example, the iodo substituent is replaced with hydroxy to generate the phenol 40. The phenol 40 is cyclised to form 41 via a Hoffman rearrangement, by intramolecular quenching of the formed isocyanate, and deprotected to form 31. An example of such a method is illustrated in the following scheme.

Scheme 13

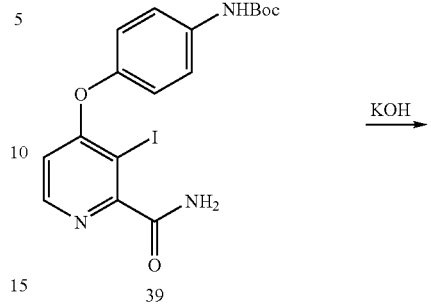

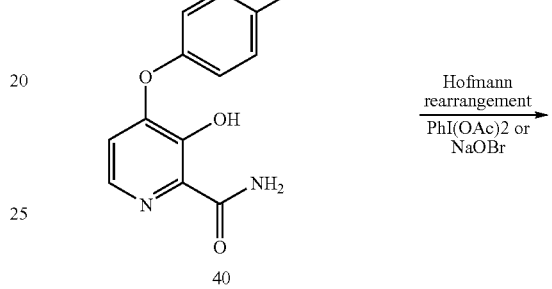

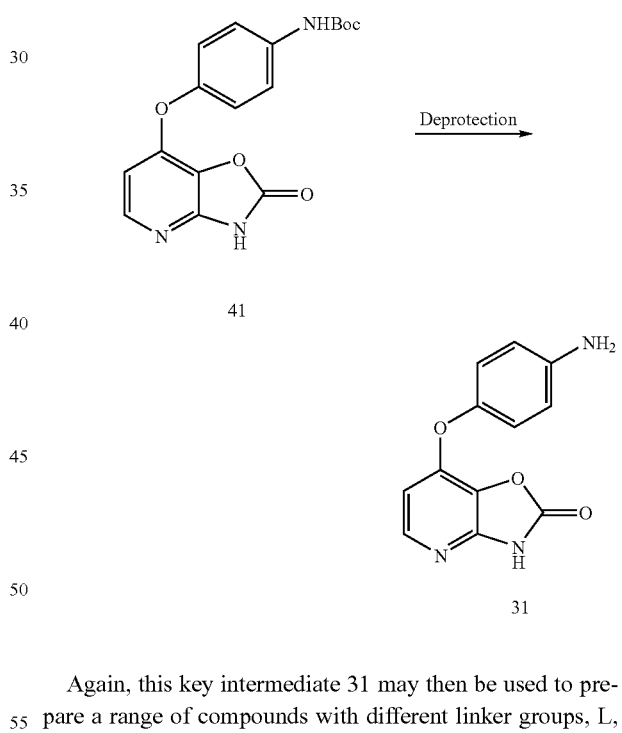

Again, this key intermediate 31 may then be used to prepare a range of compounds with different linker groups, L, and different terminal groups, A.

The resulting key intermediate may then be used to prepare imidazo[4,5-b]pyridine-2-one intermediates, by reaction with an amine followed by Hoffman rearrangement. For example, the iodo substituent is replaced with amine to generate the 3-pyridinylamine 42. The amine 42 is cyclised to form 43 via a Hoffman rearrangement, by intramolecular quenching of the formed isocyanate, and deprotected to form 44. An example of such a method is illustrated in the following scheme.

Scheme 14

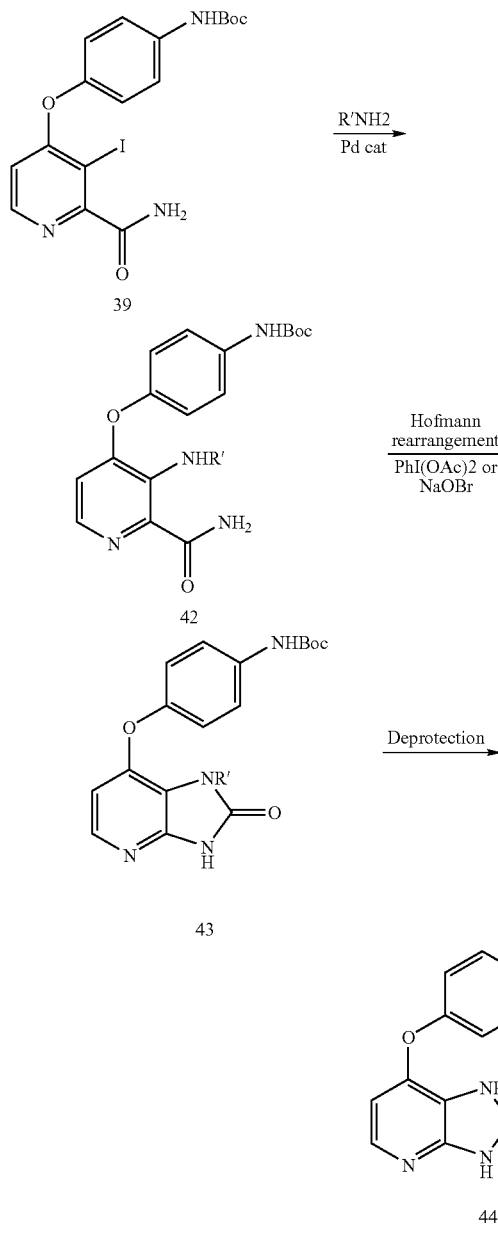

Again, this key intermediate 44 may then be used to prepare a range of compounds with different linker groups, L, and different terminal groups, A.

In another approach, yet another key intermediate is prepared using 4-hydroxybenzyl amine instead of 4-aminophenol. An example of such a method is illustrated in the following scheme.

In another approach, yet another key intermediate is prepared using 4-hydroxybenzyl amine instead of 4-aminophenol. In the starting material, the amino group may be free or protected, for example, as Boc, trityl or phthalimide. Deprotection can be achieved in the subsequent step using known methods. An example of such a method is illustrated in the following scheme.

Scheme 15

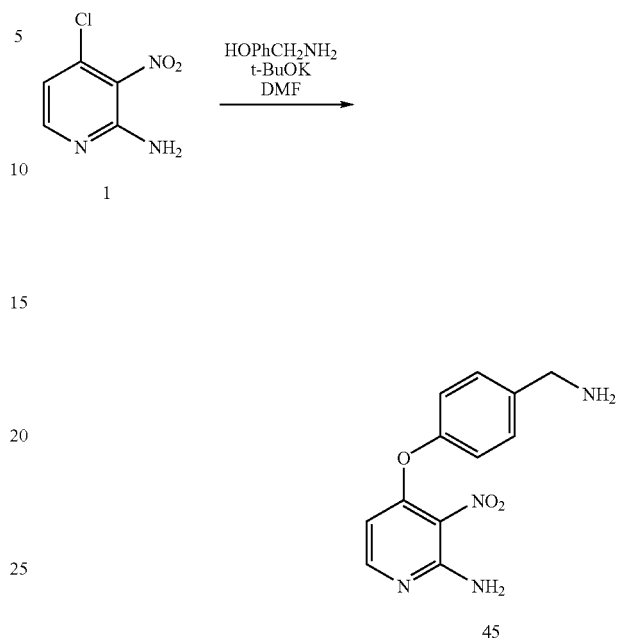

Once again, this key intermediate 45 may then be used to prepare a range of compounds with different linker groups, L, and different terminal groups, A.

For, example, benzylic amides (CH$_2$NHCO) and benzylic ureas (CH$_2$NHCONH) can be obtained as described above. Examples of such methods are illustrated in the following scheme.

Scheme 16

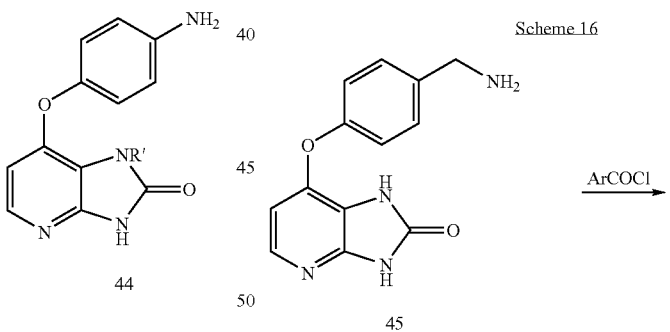

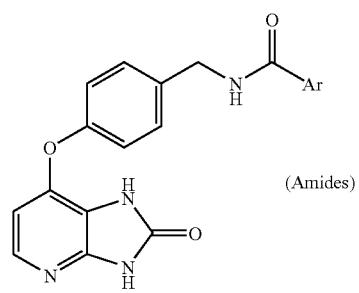

(Amides)

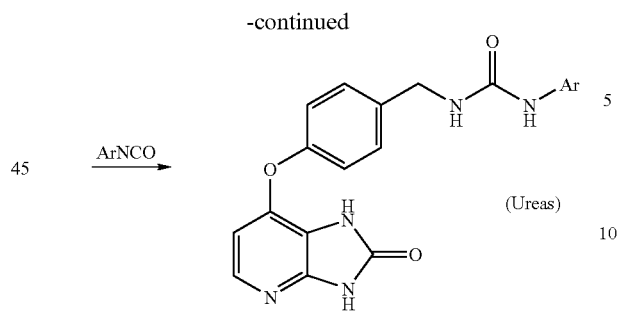

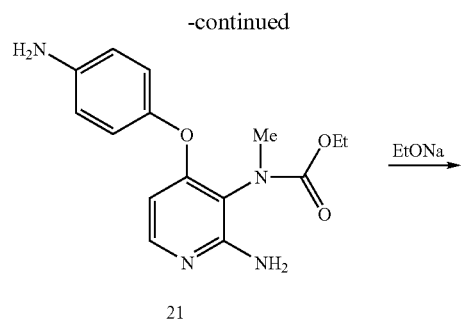

In another approach, the key intermediate 15 is prepared starting from intermediate 4. The more nucleophilic 3-amino group on the pyridine is selectively converted to a carbamate, the Boc group is deprotected, and the carbamate is alkylated. The ring closure under basic conditions affords imidazo[4,5-b]pyridine-2-one.

For example, intermediate 4 is converted to ethyl carbamate 46 and the Boc group is removed with TFA to afford 47. Deprotonation of the acidic carbamate proton with NaH creates an anion on N-3 that is alkylated to afford the intermediate 21. Intermediate 21 is cyclised to the common intermediate 15 in the presence of base. An example of such a method is illustrated in the following scheme.

Scheme 17

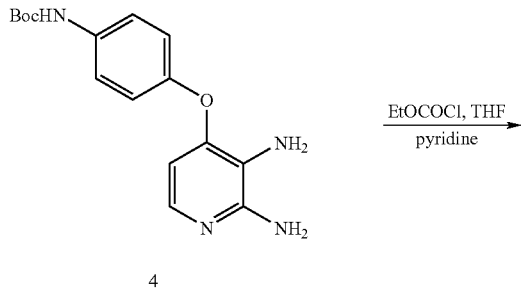

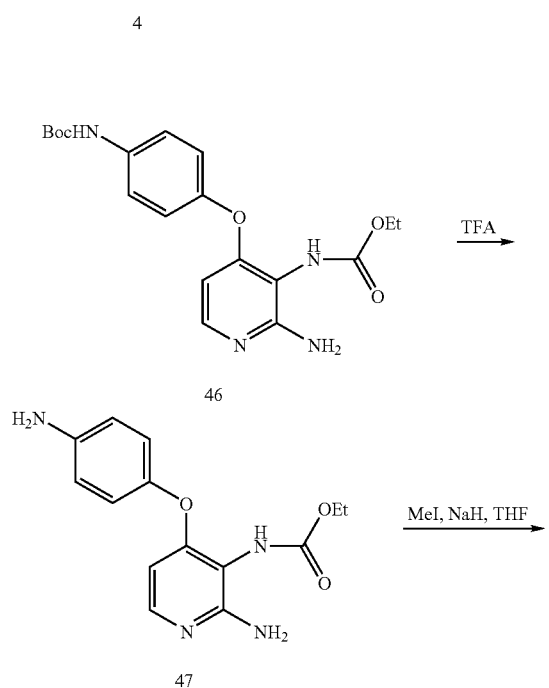

Compounds containing one of the preferred groups A, pyrazole-5-yl, can be obtained using the activated carbamates as exemplified by compound 51.

For example, 5-Aminopyrazoles 50 can be obtained from 2-keto-nitriles 48 and hydrazines 49. Reaction with phenyl chloroformate affords the activated phenylcarbamates 51. An example of such a method is illustrated in the following scheme.

Scheme 18

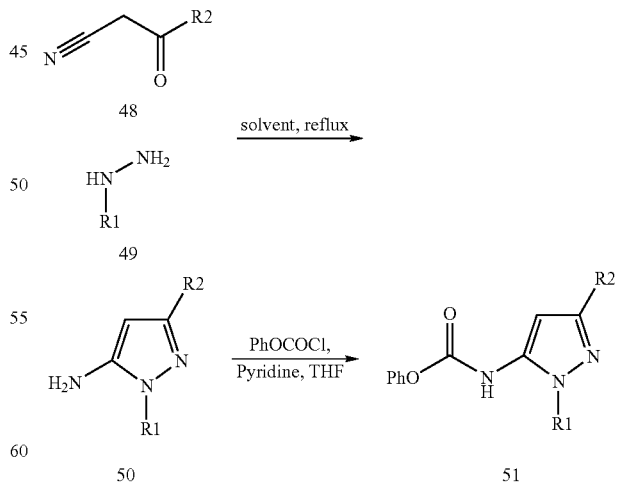

In another approach, activated carbamates, such as 51, can be reacted with key intermediates, such as 6 or 15, to afford ureas, such as CJS 3247. An example of such a method is illustrated in the following scheme.

Scheme 19

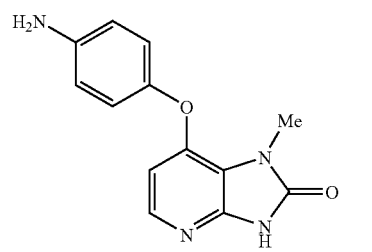

15

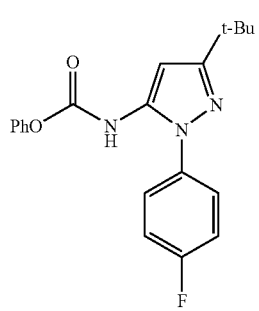

51

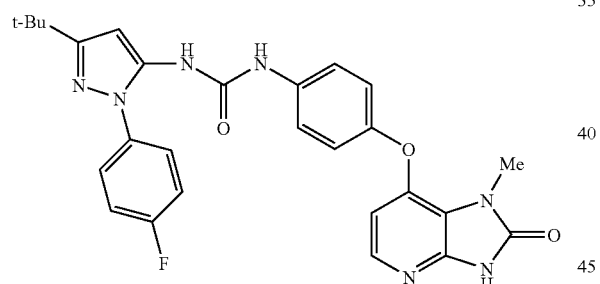

CJS3247

In another approach, compounds substituted at the N2 position (with respect to the pyridine ring) can be obtained by alkylation of the amino group of the starting material-one.

For example, 2-amino-3-nitro-4-chloropyridine, 1, is methylated with MeI and NaH to afford 52. Replacement of chloro with N-Boc protected aminophenolate produces 53 directly. (Note that N-Boc protected aminophenolate can be used in all the Schemes above instead of aminophenolate.) Reduction of the nitro group, formation of cyclic imidazolone, and removal of Boc group affords the intermediate 56. This key intermediate may be used to prepare a range of compounds with different linker groups, L, and different terminal groups, A. For example, reaction with 4-chloro-3-(trifluoromethyl)phenyl isocyanate affords compound CJS 3255. An example of such a method is illustrated in the following scheme.

Scheme 20

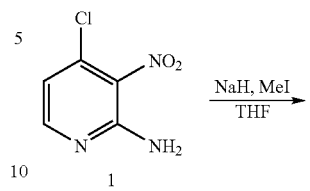
1

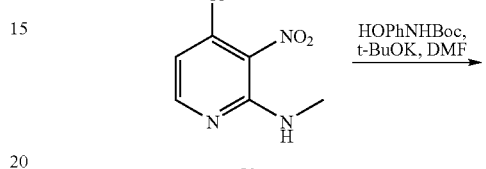
52

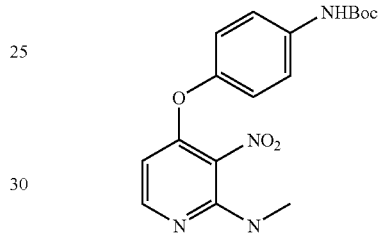
53

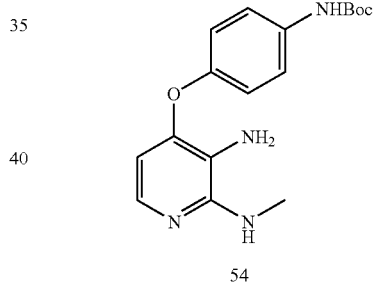
54

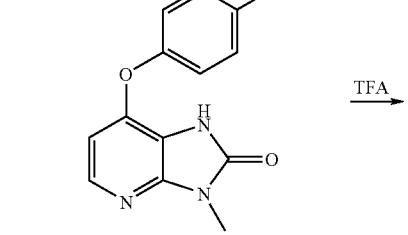
55

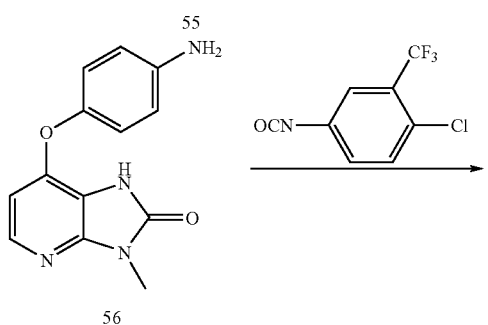
56

-continued

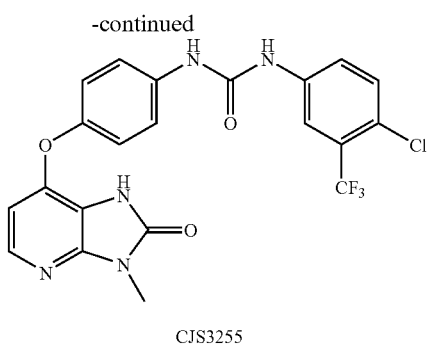

CJS3255

N2,N3-Disubstituted imidazolone compounds can be obtained from intermediate 55 by alkylation in the presence of NaH. An example of such a method is illustrated in the following scheme.

Scheme 21

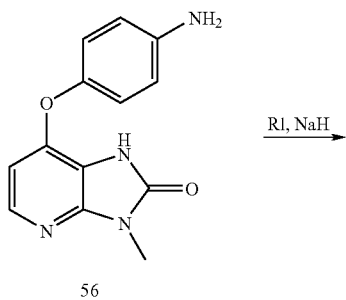

In each of the above synthetic routes, the phenylene ring of the reagents/intermediates which becomes the "central" phenylene ring of the imidazo[4,5-b]pyridin-2-one and oxazolo[4,5-b]pyridin-2-one compounds and analogs (shown below) may be suitably substituted (e.g., with $R^{P1}$, $R^{P2}$, $R^{P3}$, $R^4$, as described herein).

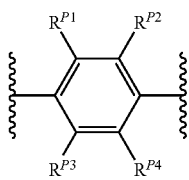

Additional synthetic routes (to vary the group Q) are described in, or may readily be derived from the synthetic routes described in, the following documents:

| -Q- | Literature Reference(s) |
|---|---|
| —(CH$_2$)$_0$—X—(CH$_2$)$_1$— | Tetrahedron, 1987, 43(11), 2557-2564. |
| —(CH$_2$)$_0$—X—(CH$_2$)$_2$— | Tetrahedron Letters, 1994, 35(40), 7343-7346. |
| —(CH$_2$)$_1$—X—(CH$_2$)$_0$— | U.S. Pat. No. 6,492,529, 10 Dec. 2002 |
| —(CH$_2$)$_2$—X—(CH$_2$)$_0$— | Tetrahedron, 1988, 44(21), 6677-6680. |
| —(CH$_2$)$_1$—X—(CH$_2$)$_1$— | U.S. Pat. No. 6,492,529, 10 Dec. 2002 |

Additional synthetic routes (to vary the group L) are described in, or may readily be derived from the synthetic routes described in, the following documents:

| A-L- | Literature Reference(s) |
|---|---|
| A-NHC(=X)— | Tetrahedron Letters, 1995, 36(37), 6745-6756. |
| A-C(=X)NH— | Tetrahedron Letters, 1995, 36(37), 6745-6746. |
| A-NHC(=X)NH— | Eur. J. of Medicinal Chemistry, 1981, 16 (4), 321-326; Tetrahedron, 2000, 56(4), 629-637; Synthetic Communications, 1997, 27(13), 2255-2260. |
| A-NHSO$_2$— | J. Med. Chem., 1991, 34(4), 1356-1362; Japanese Patent No 57-038777; J. Het. Chem., 1980, 17(1), 11-16. |
| A-NHSO$_2$NH— | Polish Journal of Chemistry, 1991, 65(11), 2053-2055; International (PCT) Patent Publication No WO 2001/036383. |
| A-CH$_2$NHC(=X)— | Tetrahedron Letters, 1995, 36(37), 6745-6746. |
| A-CH$_2$NHC(=X)NH— | Eur. J. of Medicinal Chemistry, 1981, 16 (4), 321-326; Tetrahedron, 2000, 56(4), 629-637; Synthetic Communications, 1997, 27(13), 2255-2260. |
| A-NHCH$_2$C(=X)NH— | J. Organic Chemistry, 1978, 43(17), 3394-3396; Journal of the Chemical Society, Perkin Transactions 1: Organic and Bio-Organic Chemistry, 1987, (8), 1841-1843; |

-continued

| A-L- | Literature Reference(s) |
| --- | --- |
|  | Indian Journal of Chemistry, Section B: Organic Chemistry Including Medicinal Chemistry, 1992, 31B(6), 349-350; Tetrahedron Letters, 1995, 36(37), 6745-6746. |
| A-NHCH$_2$C(=X)— | Journal of the Chemical Society, Perkin Transactions 1: Organic and Bio-Organic Chemistry (8), 1987, 1841-1843; Journal of Organic Chemistry, 1978, 43(17), 3394-3396; Bulletin of the Chem. Soc. of Japan, 1997, 70(3), 509-523. |

Additional synthetic routes (to vary the group L) are described in, or may readily be derived from the synthetic routes described in, the following documents:

| A-L- | Literature Reference(s) |
| --- | --- |
| A-NR$^N$—CO—CH$_2$— | Biorganic & Medicinal Chem Lett., 2003, 13(12), 1989-1992. |
| A-CH$_2$—CO—NR$^N$— | Biorganic & Medicinal Chemistry, 2001, 9(8), 2061-71. |
| A-CH$_2$—NR$^N$—CO— | Il Farmaco, 1999, 54(6), 364-374. |
| A-NR$^N$—CH$_2$—CO— | Journal of Organic Chemistry, 1978, 43(17), 3394-3396. |
| A-CO—CH$_2$—NR$^N$— | Journal of Medicinal Chemistry, 1989, 32(10), 2363-2367. |
| A-CH$_2$—CO—NR$^N$—CH$_2$— | Journal of Medicinal Chemistry, 2003, 46(20), 4297-4312. |
| A-CH$_2$—NR$^N$—CO—CH$_2$— | Journal of Organic Chemistry, 2003, 68(3), 1165-1167. |
| A-CH$_2$—CH$_2$—CO—NR$^N$— | Polish J. of Pharmacology & Pharmacy, 1990, 42(1), 69-77. |
| A-CH$_2$—CH$_2$—NR$^N$—CO— | J. American Chemical Society, 2002, 124(11), 2560-2567. |
| A-CH$_2$—CO—CH$_2$—NR$^N$— | Journal of Heterocyclic Chemistry, 1981, 18(3), 561-563. |
| A-CH$_2$—NR$^N$—CH$_2$—CO— | Tetrahedron, 2002, 58(49), 9865-9870. |
| A-NR$^N$—CO—CH$_2$—CH$_2$— | Tetrahedron Letters, 2003, 44(9), 1951-1955. |
| A-CO—CH$_2$—CH$_2$—NR$^N$— | Chemical & Pharmaceutical Bulletin, 1985, 3(9), 3775-3786. |
| A-CO—CH$_2$—CH$_2$—NR$^N$— | Indian Journal of Chemistry, Section B: 1988, 27B(2), 156-157. |
| A-NR$^N$—CH$_2$—CH$_2$—CO— | Indian Journal of Chemistry, Section B: 1988, 27B(2), 156-157. |
| A-NR$^N$—CH$_2$—CO—CH$_2$— | Tetrahedron Letters, 1981, 22(20), 2799-2802. |
| A-CO—CH$_2$—NR$^N$—CH$_2$— | Tetrahedron, 2002, 58(49), 9865-9870. |
| A-NR$^N$—CH$_2$—CO—NR$^N$— | Indian Journal of Chemistry, Section B: 1988, 27B(2), 156-157. |
| A-NR$^N$—CH$_2$—NR$^N$—CO— | J. of the Institute of Chemists (India), 1980. 52(3), 113-114. |
| A-CO—NR$^N$—CH$_2$—NR$^N$— | Journal of heterocyclic Chemistry, 1985, 22(1), 137-140. |
| A-NR$^N$—SO$_2$—CH$_2$— | Journal of Organic Chemistry, 1979, 44(13), 2055-2061. |
| A-CH$_2$—SO$_2$—NR$^N$— | International (PCT) Patent Publication No WO 2004/014300. |
| A-CH$_2$—NR$^N$—SO$_2$— | Organic Letters, 2003, 5(2), 105-107. |
| A-NR$^N$—CH$_2$—SO$_2$— | Archive Der Pharmazie, 1974, 307(8), 653-655. |
| A-SO$_2$—CH$_2$—NR$^N$— | Archive Der Pharmazie, 1974, 307(8), 653-655. |
| A-CH$_2$—SO$_2$—NR$^N$—CH$_2$— | Journal of medicinal Chemistry, 2003, 46(20), 4297-4312. |
| A-CH$_2$—NR$^N$—SO$_2$—CH$_2$— | Journal of medicinal Chemistry, 2001, 44(13), 2253-2258. |
| A-CH$_2$—CH$_2$—SO$_2$—NR$^N$— | Bioorganic & Medicinal Chemistry, 2002, 10(8), 2597-2610. |
| A-CH$_2$—CH$_2$—NR$^N$—SO$_2$— | Organic Letters, 2003, 5(2), 105-107. |
| A-CH$_2$—SO$_2$—CH$_2$—NR$^N$— | Chemistry of heterocyclic Compounds, 2002, 38(9), 1077-1088. |
| A-NR$^N$—CH$_2$—SO$_2$—CH$_2$— | Chemistry of heterocyclic Compounds, 2002, 38(9), 1077-1088. |
| A-SO$_2$—CH$_2$—NR$^N$—CH$_2$— | Chemical & Pharmaceutical Bulletin, 1977, 25(11), 2964-2968. |
| A-CH$_2$—NR$^N$—CH$_2$—SO$_2$— | Synlett, 2003, 8, 1129-1132. |
| A-NR$^N$—SO$_2$—CH$_2$—CH$_2$— | Bioorganic & Medicinal Chemistry, 2002, 10(8), 2597-2610. |
| A-SO$_2$—NR$^N$—CH$_2$—CH$_2$— | Chemical & Pharmaceutical Bulletin, 1985, 33(9), 3775-3786. |
| A-SO$_2$—CH$_2$—CH$_2$—NR$^N$— | Tetrahedron, 1988, 44(19), 6095-6106. |
| A-NR$^N$—CH$_2$—CH$_2$—SO$_2$— | Tetrahedron, 1988, 44(19), 6095-6106. |
| A-CH$_2$—NR$^N$—SO$_2$—NR$^N$— | Journal of Organic Chemistry, 1980, 45(26), 5373, 5375. |
| A-NR$^N$—CH$_2$—SO$_2$—NR$^N$— | Japanese Patent No 56-65863, 3 Jun. 1981. |
| A-NR$^N$—CH$_2$—NR$^N$—SO$_2$— | Current science, 1981, 50(7), 305-307. |
| A-NR$^N$—SO$_2$—CH$_2$—NR$^N$— | Japanese Patent No 56-65863, 3 Jun. 1981. |
| A-SO$_2$—NR$^N$—CH$_2$—NR$^N$— | Journal of Heterocyclic Chemistry, 2003, 40(4), 569-573. |

Uses

The imidazo[4,5-b]pyridin-2-one and oxazolo[4,5-b]pyridin-2-one compounds and analogs thereof, described herein, are useful, for example, in the treatment of diseases and conditions that are ameliorated by the inhibition of RAF (e.g., B-RAF), such as, for example, proliferative conditions, cancer, etc.

Use in Methods of Inhibiting RAF (e.g., B-RAF)

One aspect of the present invention pertains to a method of inhibiting RAF (e.g., B-RAF) activity in a cell, in vitro or in vivo, comprising contacting the cell with an effective amount of a compound, as described herein.

Suitable assays for determining RAF (e.g., B-RAF) inhibition are described below, as well as in the Examples below.

B-RAF Assays:

B-raf kinase activity is measured using a 4-tiered cascade enzyme assay similar to that described by Marais R., et al., 1997, *J. Biol. Chem.*, Vol. 272, pp. 4378-4383. B-Raf containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:100 into an assay mixture containing GST-MEK-H6 (6.5 µg/ml) and GST-ERK-H6 (100 µg/ml) in a buffer containing 800 µM ATP and appropriate concentrations of inhibitor or diluent as control. The mixture is incubated for up to 10 minutes at 30° C. to activate the ERK in a B-Raf dependent manner within the cascade. The reaction is then stopped by addition of 20 mM EDTA. The extent of activation of the GST-ERK is then determined by adding a portion of this quenched reaction mixture to a further reaction mixture containing MBP and 100 µM ATP/gamma [$^{32}$P]ATP. After 12 minutes' incubation at 30° C., the incorporation of [$^{32}$P] into the MBP substrate, as a measure of B-raf activity, is determined by precipitation with phosphoric acid and isolation by filtration on p81 phosphocellulose paper. The % inhibition of the B-raf kinase activity is calculated and plotted in order to determine the concentration of test compound required to inhibit 50% of the B-raf kinase activity ($IC_{50}$).

Alternatively, B-raf kinase activity is measured using a different 4-tiered cascade enzyme assay. B-Raf containing the V600E mutation (Davies, H., et al., 2002, *Nature*, Vol. 417, pp. 949-954) and an N-terminal MDRGSH6 tag is expressed in SF9 insect cells. Detergent soluble extracts from these cells are diluted 1:250 into an assay mixture containing GST-MEK-H6 (25 µg/ml), GST-ERK-H6 (281.25 µg/ml) and MBP in a buffer containing appropriate concentrations of inhibitor or diluent as control. 0.03 µL (100 µM) ATP is added and the mixture is incubated for up to 10 minutes at 30° C. to activate the ERK in a B-Raf dependent manner within the cascade. The extent of activation of the GST-ERK is then determined by adding 0.033 µL (100 µM) HOT $^{32}$ Pα. After 10 minutes' incubation at 30° C., the reaction is stopped by isolation of a portion of the reaction mixture on p81 phosphocellulose paper and submersion of this paper in 0.4% orthophosphoric acid. Incorporation of [$^{32}$P] Into the MBP substrate, as a measure of B-raf activity, is determined using a Packard Cernekov counter. The % inhibition of the B-raf kinase activity is calculated and plotted in order to determine the concentration of test compound required to inhibit 50% of the B-raf kinase activity ($IC_{50}$).

C-RAF Assay:

C-raf (human) is diluted to a 10× working stock in 50 mM Tris pH 7.5, 0.1 mM EGTA, 0.1 mM sodium vanadate, 0.1% β-mercaptoethanol, 1 mg/ml BSA. One unit equals the incorporation of 1 nmol of phosphate per minute into myelin basic protein per minute. In a final reaction volume of 25 µl, c-raf (5-10 mU) is incubated with 25 mM Tris pH 7.5, 0.02 mM EGTA, 0.66 mg/ml myelin basic protein, 10 mM MgAcetate, [γ-$^{33}$P-ATP] (specific activity approx 500 cpm/pmol, concentration as required) and appropriate concentrations of inhibitor or diluent as control. The reaction is initiated by the addition of Mg$^{2+}$+[γ-$^{33}$P-ATP]. After incubation for 40 minutes at room temperature, the reaction is stopped by the addition of 5 µl of a 3% phosphoric acid solution. 10 µl of the reaction is spotted onto a P30 filtermat and washed 3 times for 5 minutes in 75 mM phosphoric acid and once in methanol prior to drying and counting to determine the C-raf activity. The % inhibition of the C-raf kinase activity is calculated and plotted in order to determine the concentration of test compound required to inhibit 50% of the C-raf kinase activity ($IC_{50}$).

Selectivity:

In one embodiment, the compound selectively inhibits one RAF (e.g., B-RAF), over at least one other RAF (e.g., A-RAF and/or C-RAF).

For example, in one embodiment, the ratio of the $IC_{50}$ value for B-RAF to the $IC_{50}$ value for the other RAF (e.g., A-RAF and/or C-RAF) is at least 10, more preferably at least 100, most preferably at least 1000.

Use in Methods of Inhibiting Cell Proliferation, Etc.

The compounds (i.e., imidazo[4,5-b]pyridin-2-one and oxazolo[4,5-b]pyridin-2-one compounds and analogs thereof) described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting cells (or the cell) with an effective amount of a compound, as described herein.

In one embodiment, the method is a method of regulating (e.g., inhibiting) cell proliferation (e.g., proliferation of a cell), in vitro or in vivo, comprising contacting cells (or the cell) with an effective amount of a compound, as described herein.

In one embodiment, the method is performed in vitro.

In one embodiment, the method is performed in vivo.

In one embodiment, the compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described in the examples below.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a compound as described herein for use in a method of treatment of the human or animal body by therapy.

Use in the Manufacture of Medicaments

Another aspect of the present invention pertains to use of a compound, as described herein, in the manufacture of a medicament for use in treatment.

Methods of Treatment

Another aspect of the present invention pertains to a method of treatment comprising administering to a patient in need of treatment a therapeutically effective amount of a compound as described herein, preferably in the form of a pharmaceutical composition.

Conditions Treated—Conditions Ameliorated by the Inhibition of RAF

In one embodiment (e.g., of use in methods of therapy, of use in the manufacture of medicaments, of methods of treatment), the treatment is treatment of a disease or condition that is characterised by the up-regulation and/or activation of RAF (e.g., B-RAF), and/or is ameliorated by the inhibition of RAF (e.g., B-RAF).

In one embodiment, the treatment is treatment of cancer that is characterised by the up-regulation and/or activation of RAF (e.g., B-RAF), and/or is ameliorated by the inhibition of RAF (e.g., B-RAF).

Conditions Treated—Conditions Ameliorated by the Inhibition of RTKs

In one embodiment (e.g., of use in methods of therapy, of use in the manufacture of medicaments, of methods of treatment), the treatment is treatment of a disease or condition that is characterised by the up-regulation and/or activation of a receptor tyrosine kinase (RTK), and/or is ameliorated by the inhibition of a receptor tyrosine kinase (RTK). Examples of RTKs include FGFR, Tie, VEGFR and/or Eph, for example, FGFR-1, FGFR-2, FGFR-3, Tie2, VEGFR-2 and/or EphB2.

In one embodiment, the treatment is treatment of cancer that is characterised by the up-regulation and/or activation of a receptor tyrosine kinase (RTK), and/or is ameliorated by the inhibition of a receptor tyrosine kinase (RTK).

Conditions Treated—Conditions Characterised by Angiogenesis

In one embodiment (e.g., of use in methods of therapy, of use in the manufacture of medicaments, of methods of treatment), the treatment is treatment of a disease or condition that is characterised by inappropriate, excessive, and/or undesirable angiogenesis (as "anti-angiogenesis agents"). Examples of such conditions are discussed above.

Conditions Treated—Prolifative Conditions and Cancer

The compounds of the present invention are useful in the treatment of proliferative conditions (as "anti-proliferative agents"), cancer (as "anti-cancer agents"), etc.

The term "antiproliferative agent" as used herein, pertain to a compound which treats a proliferative condition (i.e., a compound which is useful in the treatment of a proliferative condition). The terms "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth.

The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

One of ordinary skill in the art is readily able to determine whether or not a candidate compound treats a proliferative condition, or treats cancer, for any particular cell type. For example, assays which may conveniently be used to assess the activity offered by a particular compound are described in the examples below.

Note that active compounds includes both compounds with intrinsic activity (drugs) as well as prodrugs of such compounds, which prodrugs may themselves exhibit little or no intrinsic activity.

In one embodiment (e.g., of use in methods of therapy, of use in the manufacture of medicaments, of methods of treatment), the treatment is treatment of a proliferative condition.

In one embodiment, the treatment is treatment of a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, skin cancer, squamous cancer, Kaposi's sarcoma, melanoma, malignant melanoma, lymphoma, or leukemia.

In one embodiment, the treatment is treatment of:
- a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
- a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
- a hematopoietic tumor of myeloid lineage, for example acute and chronic myelogenous leukemias, myelodysplastic syndrome, or promyelocytic leukemia;
- a tumour of mesenchymal origin, for example fibrosarcoma or habdomyosarcoma;
- a tumor of the central or peripheral nervous system, for example astrocytoma, neuroblastoma, glioma or schwannoma;
- melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of melanoma or malignant melanoma.

In one embodiment, the treatment is treatment of colorectal cancer.

The compounds of the present invention may be used in the treatment of the cancers described herein, independent of the mechanisms discussed herein.

Conditions Treated—Prolifative Conditions and Cancer Associated with RAF

Cancers with, for example, activating mutations of ras, raf and EGFR or over expression of ras, raf and EGFR including any of the isoforms thereof, may be particularly sensitive to Inhibitors of RAF (e.g., B-RAF) activity. Patients with activating mutants of RAF (e.g., B-RAF) may also find treatment with inhibitors of RAF (e.g., B-RAF) activity particularly beneficial. Cancers with other abnormalities leading to an upregulated raf-MEK-ERK pathway signal may also be particularly sensitive to treatment with inhibitors of RAF (e.g., B-RAF) activity. Examples of such abnormalities include consitutive activation of a growth factor receptor; overexpression of one or more growth factor receptors; and overexpression of one or more growth factors.

In one embodiment (e.g., of use in methods of therapy, of use in the manufacture of medicaments, of methods of treatment), the treatment is treatment of a proliferative condition as described above, for example, cancer, that is characterised by:

(a) activating mutants of ras or raf;

(b) upregulation of ras or raf;

(c) upregulated raf-MEK-ERK pathway signals;

(d) upregulation of growth factor receptors, such as ERBB2 and EGFR.

In one embodiment, the proliferative condition is characterised by cells which overexpress RAF (e.g., B-RAF) or express or overexpress mutant raf (e.g., B-RAF). In one embodiment, the proliferative condition is characterised by cells which overexpress raf (e.g., B-RAF). In one embodiment, the proliferative condition is characterised by cells which express or overexpress mutant RAF (e.g., B-RAF). In one embodiment, the proliferative condition is characterised by cells which overexpress RAF (e.g., B-RAF), or overexpress mutant RAF (e.g., B-RAF), as compared to corresponding normal cells. In one embodiment, the overexpression is by a factor of 1.5, 2, 3, 5, 10, or 20.

In one embodiment (e.g., of use in methods of therapy, of use in the manufacture of medicaments, of methods of treatment), the treatment is treatment of a condition associated with a mutated form of RAF (e.g., B-RAF), such as, for example, the mutations described in Wan, P., et al., 2004, *Cell*, Vol. 116, pp. 855-867 and Stratton et al., 2003, published international patent application publication number WO 03/056036.

Conditions Treated—Inflammation Etc.

The compounds of the present invention are useful in the treatment of conditions associated with inflammation (as "anti-inflammation agents"), etc.

The function of inflammatory cells is controlled by many factors the effects of which are mediated by different signal transduction pathways. Although some key pro-inflammatory functions are mediated by p38 Map kinase (e.g., TNF release), others are mediated by other pathways. The raf-MEK-ERK pathway, in particular, is an important activating and proliferative signal in many inflammatory cells. B and T lymphocytes, in particular, require activation of the raf-MEK-ERK pathway for clonal expansion and generation of effector populations (see, e.g., Cantrell, D. A., 2003, *Immunol Rev.*, Vol. 192, pp. 122-130; Genot, E. and Cantrell, D. A., 2000, *Curr. Opin. Immunol.*, Vol. 12(3), pp. 289-294).

In one embodiment, the treatment is treatment of: inflammatory diseases, such as rheumatoid arthritis, osteoarthritis, rheumatoid spondylitis, gouty arthritis, traumatic arthritis, rubella arthritis, psoriatic arthritis, and other arthritic conditions; Alzheimer's disease; toxic shock syndrome, the inflammatory reaction induced by endotoxin or inflammatory bowel disease; tuberculosis; atherosclerosis; muscle degeneration; Reiter's syndrome; gout; acute synovitis; sepsis; septic shock; endotoxic shock; gram negative sepsis; adult respiratory distress syndrome; cerebral malaria; chronic pulmonary inflammatory disease; silicosis; pulmonary sarcoisosis; bone resorption diseases; reperfusion injury; graft versus host reaction; allograft rejections; fever and myalgias due to infection, such as influenza, cachexia, in particular cachexia secondary to infection or malignancy, cachexia secondary to acquired immune deficiency syndrome (AIDS); AIDS; ARC (AIDS related complex); keloid formation; scar tissue formation; Crohn's disease; ulcerative colitis; pyresis; chronic obstructive pulmonary disease (COPD); acute respiratory distress syndrome (ARDS); asthma; pulmonary fibrosis; bacterial pneumonia.

In one preferred embodiment, the treatment is treatment of: arthritic conditions, including rheumatoid arthritis and rheumatoid spondylitis; inflammatory bowel disease, including Crohn's disease and ulcerative colitis; and chronic obstructive pulmonary disease (COPD).

In one preferred embodiment, the treatment is treatment of: an inflammatory disorder characterized by T-cell proliferation (T-cell activation and growth), for example, tissue graft rejection, endotoxin shock, and glomerular nephritis.

Screening

Prior to treatment, a patient may be screened to determine whether a disease or condition from which the patient is or may be suffering is one which would be susceptible to treatment with a compound that inhibits RAF (e.g., B-RAF) activity or has activity against an RTK (e.g., FGFR-1, FGFR-2, FGFR-3, VEGFR-2, Tie2, EphB2).

For example, a biological sample taken from a patient may be analysed to determine whether a condition or disease, such as cancer, that the patient is or may be suffering from is one which is characterised by elevated expression or activation of RAF (e.g., B-RAF), or an RTK (e.g., FGFR-1, FGFR-2, FGFR-3, VEGFR-2, Tie2, EphB2), or is the result of an activating mutation. Thus, the patient may be subjected to a diagnostic test to detect a marker characteristic of over-expression or activation of RAF (e.g., B-RAF) or an RTK (e.g., FGFR-1, FGFR-2, FGFR-3, VEGFR-2, Tie2, EphB2), or a mutation thereof.

As used herein, the term "marker" includes genetic markers (including, e.g., the measurement of DNA composition to identify mutations of raf, ras, MEK, ERK or a growth factor such as ERBB2 or EGFR) and markers which are characteristic of upregulation of raf, ras, MEK, ERK, growth factors receptors such as ERBB2 or EGFR including enzyme activity, enzyme levels, enzyme state (e.g. phosphorylated or not) and mRNA levels of the aforementioned proteins. Methods for identification and analysis of mutations are well known. See, for example, *Anticancer Research*, 1999, Vol. 19(4A), pp. 2481-2483; *Clin. Chem.*, 2002, Vol. 48, p. 428; *Cancer Research*, 2003, Vol. 63(14), pp. 3955-3957.

The term "marker" further includes genetic markers including, for example, the measurement of DNA composition to identify mutations of RTKs, e.g., FGFR-1, FGFR-2, FGFR-3, VEGFR-2, Tie2, and EphB2. The term "marker" also includes markers that are characteristic of up-regulation of RTKs, including enzyme activity, enzyme levels, enzyme state (e.g., phosphorylated or not) and mRNA levels of the aforementioned proteins.

Upregulation includes elevated expression or over expression, including gene amplification (i.e., multiple gene copies), increased expression by a transcriptional effect, hyperactivity, and activation, including activation by mutations.

Other tumours that have an upregulated raf-MEK-ERK pathway signal may also be particularly sensitive to inhibitors of RAF (e.g., B-RAF) activity. A number of assays exist which can identify tumours that exhibit upregulation in the raf-MEK-ERK pathway, including the commercially available MEK1/2 (MAPK Kinase) assay from Chemicon International. Upregulation can result from over expression or activation of growth factor receptors such as ERBB2 and EGFR, or mutant ras or raf proteins.

Typical methods for screening for over expression, upregulation or mutants include, but are not limited to, standard methods such as reverse-transcriptase polymerase chain reaction (RT-PCR) or in-situ hybridisation.

In screening by RT-PCR, the level of mRNA for the aforementioned proteins in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described, for example, in Ausubel, F. M. et al., eds., *Current Protocols in Molecular Biology*, 2004 (John Wiley & Sons Inc.); Innis, M. A. et-al., eds., *PCR Protocols: A Guide to Methods and Applications*, 1990 (Academic Press). Reactions and manipulations involving nucleic acid techniques are also described in Sambrook et al., *Molecular Cloning: A Laboratory Manual*, 3rd edition, 2001 (Cold Spring Harbor Laboratory Press). Alternatively, a commercially available kit for RT-PCR (e.g., Roche Molecular Biochemicals) may be used, or methodology as set forth in U.S. Pat. Nos. 4,666,828; 4,683,202; 4,801, 531; 5,192,659, 5,272,057, 5,882,864, and 6,218,529.

An example of an in-situ hybridisation technique would be fluorescence in situ hybridisation (FISH) (see, e.g., Angerer, 1987, *Meth. Enzymol.*, Vol. 152, p. 649). Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, in order to enable specific hybridization with the target nucleic acid(s) under stringent conditions. Standard methods for carrying out FISH are described, for example, in Ausubel, F. M. et al., eds., *Current Protocols in Molecular Biology*, 2004 (John Wiley & Sons Inc.); Bartlett, John M. S., "Fluorescence In Situ Hybridization: Technical Overview," in: *Molecular Diagnosis of Cancer, Methods and Protocols, 2nd ed.* (*Series: Methods in Molecular Medicine*), March 2004, pp. 77-88 (ISBN: 1-59259-760-2).

Alternatively, the protein products expressed from the mRNAs may be assayed by immunohistochemistry of tumour sections, solid phase immunoassay with microtiter plates, Western blotting, 2-dimensional SDS-polyacrylamide gel electrophoresis, ELISA, and other methods known in the art for detection of specific proteins. Detection methods would include the use of site specific antibodies, such as, phospho raf, phospho ERK, phospho MEK, or phosphotyrosine. In addition to tumour biopsies, other samples which could be utilised include pleural fluid, peritoneal fluid, urine, stool biopsies, sputum, blood (isolation and enrichment of shed tumour cells).

In addition, mutant forms of raf, EGFR or ras can be identified by direct sequencing of, for example, tumour biopsies using PCR and methods to sequence PCR products directly, for example, using methods as described herein. These and other well-known techniques for detection of the over expression, activation, or mutations may be used.

Also, abnormal levels of proteins such as raf, ras and EGFR can be measured using standard enzyme assays, for example for raf those assays described herein.

Alternative methods for the measurement of the over expression or activation of FGFR, Tie, VEGFR or Eph kinases, in particular VEGFR including the isoforms thereof, include the measurement of microvessel density. This can be measured, for example, using methods described by Orre and Rogers, 1999, *Int. J. Cancer*, Vol. 84(2), pp. 101-108. Assay methods also include the use of markers; for example, in the case of VEGFR, markers include CD31, CD34 and CD105 (Mineo et al., 2004, *J. Clin. Pathol.*, Vol. 57(6), pp. 591-597).

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio, when administered In accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development. Examples of such combinations are set out below.

In one embodiment, the compounds (i.e., imidazo[4,5-b]pyridin-2-one and oxazolo[4,5-b]pyridin-2-one compounds and analogs thereof described herein are combined with one or more (e.g., 1, 2, 3, 4) additional therapeutic agents, as described below.

One aspect of the present invention pertains to a compound as described herein, in combination with one or more additional therapeutic agents, as described below.

Examples of additional therapeutic agents that may be administered together (whether concurrently or at different time intervals) with the compounds described herein include:

(a) topoisomerase I inhibitors;
(b) antimetabolites;
(c) tubulin targeting agents;
(d) DNA binder and topoisomerase II inhibitors;
(e) alkylating agents;
(f) monoclonal antibodies;
(g) anti-hormones;
(h) signal transduction inhibitors;
(i) proteasome inhibitors;
(j) DNA methyl transferases;
(k) cytokines and retinoids.

The particular combination would be at the discretion of the physician who would select dosages using his common general knowledge and dosing regimens known to a skilled practitioner.

The agents (i.e., the compound described here, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use, as described below.

Other Uses

The compounds described herein may also be used as cell culture additives to inhibit cell proliferation, etc.

The compounds described herein may also be used as part of an in vitro assay, for example, in order to determine whether a candidate host is likely to benefit from treatment with the compound in question.

The compounds described herein may also be used as a standard, for example, in an assay, in order to identify other active compounds, other anti-proliferative agents, other anticancer agents, etc.

Kits

One aspect of the invention pertains to a kit comprising (a) an active compound as described herein, or a composition comprising an active compound as described herein, e.g., preferably provided in a suitable container and/or with suitable packaging; and (b) instructions for use, e.g., written instructions on how to administer the active compound or composition.

The written instructions may also include a list of indications for which the active ingredient is a suitable treatment.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus.

In one preferred embodiment, the subject/patient is a human.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 µg to about 250 mg (more typically about 100 µg to about 25 mg) per kilogram body weight of the subject per day. Where the active compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

All starting materials, reagents and solvents for reactions were reagent grade and used as purchased. Chromatography solvents were HPLC grade and were used without further purification. Reactions were monitored by thin layer chromatography (TLC) analysis using Merck silica gel 60 F-254 thin layer plates. Flash column chromatography was carried out on Merck silica gel 60 (0.015-0.040 mm) or in disposable Isolute Flash Si and Si II silica gel columns. Preparative TLC was performed on either Macherey-Nagel [809 023] pre-coated TLC plates SIL G-25 $UV_{264}$ or Analtech [2015] pre-coated preparative TLC plates, 2000 µm with $UV_{254}$. LCMS analyses were performed on a Micromass LCT/Water's Alliance 2795 HPLC system with a Discovery 5 µm, C18, 50 mm×4.6 mm i.d. column from Supelco at a temperature of 22° C. using the following solvent systems: Solvent A: Methanol; Solvent B: 0.1% formic acid in water at a flow rate of 1 mL/min. Gradient starting with 10% A/90% B from 0-0.5 minutes then 10% A/90% B to 90% A/10% B from 0.5 minutes to 6.5 minutes and continuing at 90% A/10% B up to 10 minutes. From 10-10.5 minutes the gradient reverted back to 10% A/90% where the concentrations remained until 12 minutes. UV detection was at 254 nm and ionisation was positive or negative ion electrospray. Molecular weight scan range is 50-1000. Samples were supplied as 1 mg/mL in DMSO or methanol with 3 µL injected on a partial loop fill. NMR spectra were recorded in DMSO-d$_6$ on a Bruker DPX 250 MHz or a Bruker Advance 500 MHz spectrometer.

(I) Coupling of 2-amino-3-nitro-4-chloropyridine with phenolates

Synthesis 1

4-(4-Aminophenoxy)-3-nitropyridin-2-amine (2)

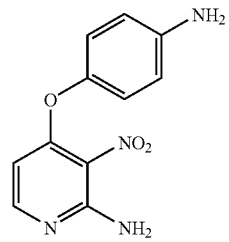

Method A. 4-Hydroxyaniline (0.7 g, 6.5 mmol) was dissolved in dry DMF (10 mL) and the solution was degassed with bubbling argon for 10 minutes. Potassium tert-butoxide (0.73 g, 6.5 mmol) was added, and the stirring and argon bubbling continued for 1 hour. 4 Chloro-3-nitropyridin-2-amine (1.0 g, 5.8 mmol) was dissolved in 5 mL dry DMF and added to the reaction mixture. The reaction mixture was heated and stirred at 70° C. for 20 hours, under argon. The solvent was evaporated and the residue was extracted between DCM and aqueous Na$_2$CO$_3$ containing 5% KOH. The extraction was repeated twice, the organic layer was dried over MgSO$_4$, and evaporated to afford the title compound (1.4 g, 98%). $^1$H-NMR (δ, ppm, DMSO-d$_6$): 5.18 (s, 2H, NH$_{2,Ph}$), 5.90 (d, 1H, H$_{Py,5}$, J=5.0 Hz), 6.65 (d, 2H, H$_{arom,Ph,3+5}$, J=10.0 Hz), 6.85 (d, 2H, H$_{arom,Ph,2+6}$), 7.07 (s, 2H, NH$_{2,Py}$), 7.95 (d, 1H, H$_{Py,6}$); LC-MS (m/z): 247 (M+H, 100).

Synthesis 2

4-(4-Aminonaphthalen-1-yl-oxy)-3-nitropyridin-2-amine

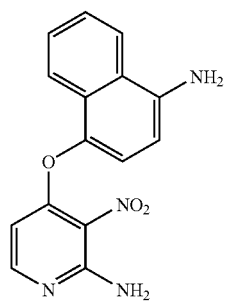

Method A was used with 4-aminonaphthalen-1-ol to afford the title compound as a brown solid (1.10 g, 64%). $^1$H-NMR (δ, ppm, DMSO-d$_6$): 5.75 (d, 1H, H$_{Py,5}$, J=5.4 Hz), 5.90 (s, 2H, NH$_2$), 6.69 (d, 1H, H$_{arom,naph}$, J=7.98 Hz), 7.13 (m, 3H, NH$_2$+H$_{arom,naph}$), 7.48 (m, 2H, H$_{arom,naph}$), 7.67 (m, 1H, H$_{arom,naph}$), 7.86 (d, 1H, H$_{Py,5}$), 8.16 (m, 1H, H$_{arom,naph}$); LC-MS (m/z): 297 (M+H, 100).

Synthesis 3

4-(4-Amino-3-fluorophenoxy)-3-nitropyridin-2-amine

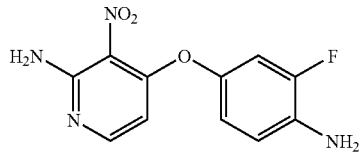

Method A was used with 2-fluoro-4-hydroxyaniline to afford the title compound (0.8 g, 59%). $^1$H-NMR (δ, ppm, DMSO-d$_6$): 5.22 (s, 2H, NH$_{2,Ph}$), 5.95 (d, 1H, H$_{Py,5}$, J=5.71 Hz), 6.75-6.83 (m, 2H, H$_{arom,Ph}$), 7.01 (dd, 1H, H$_{arom,Ph}$, J=11.80 Hz), 7.11 (s, 2H, NH$_{2,Py}$), 8.10 (d, 1H, H$_{Py,6}$, J=5.72 Hz).

Synthesis 4

4-(4-Amino-3-chlorophenoxy)-3-nitropyridin-2-amine

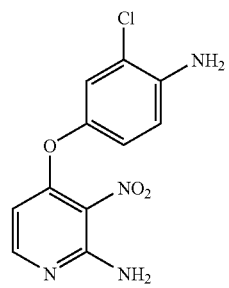

Method A was used with 4-amino-3-chlorophenol (1.027 g, 5.7 mmol) to obtain the title compound (665 mg, 46%). $^1$H-NMR (δ, ppm, DMSO-d$_6$): 4.57 (s, 2H, NH$_{2,Ph}$), 5.09 (d, 1H, H$_{Py,5}$, J=5.7 Hz), 6.03 (s, 1H, H$_{Ph,8}$), 6.05 (d, 1H, H$_{Ph,11}$, J=2.5 Hz), 6.25 (s, 2H, NH$_{2,Py}$), 6.29 (d, 1H, H$_{Ph,12}$, J=2.5 Hz), 7.13 (d, 1H, H$_{Py,6}$, J=5.7 Hz). LC-MS (m/z): 281 (M+H, 100).

Synthesis 5

4-(4-Amino-3-methylphenoxy)-3-nitropyridin-2-amine

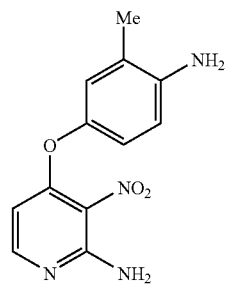

Method A was used with 4-amino-m-cresol to afford the title compound (1.083 mg, 80%). ¹H-NMR (δ, ppm, DMSO-d₆): 1.23 (s, 3H, CH₃), 4.08 (s, 2H, NH$_{2,Ph}$), 5.05 (d, 1H, H$_{Py,5}$, J=5.7 Hz), 5.83 (s, 1H, H$_{Ph,8}$), 5.87 (d, 1H, H$_{Ph,11\ or\ 12}$, J=2.7 Hz), 5.94 (d, 1H, H$_{Ph,11\ or\ 12}$, J=2.7 Hz), 6.19 (s, 2H, NH$_{2,Py}$), 7.10 (d, 1H, H$_{Py,6}$, J=5.7 Hz). LC-MS (m/z): 261 (M+H, 100).

Synthesis 6

4-(4-Amino-3-(trifluoromethyl)phenoxy)-3-nitropyridin-2-amine

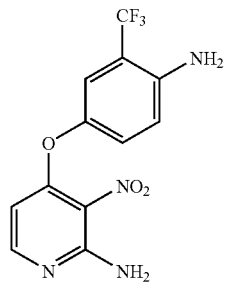

Method A was used with 4-amino-3-(trifluoromethyl)phenol to afford the title compound (946 mg, 72%). ¹H-NMR (δ, ppm, DMSO-d₆): 5.68 (s, 2H, NH$_{2,Ph}$), 5.88 (d, 1H, H$_{Py,5}$, J=5.7 Hz), 7.12 (m, 5H, H$_{Ph,8,11\ and\ 12}$+NH$_{2,Py}$), 7.95 (d, 1H, H$_{Py,6}$, J=5.7 Hz). LC-MS (m/z): 315 (M+H, 100).

Synthesis 7

4-(4-Amino-2-chlorophenoxy)-3-nitropyridin-2-amine

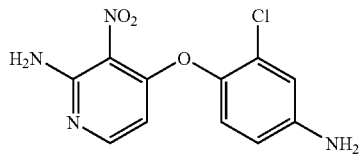

Method A was used with 4-amino-2-chlorophenol to afford the title compound (1.02 g, 57%). ¹H NMR (250 MHz, δ, ppm, DMSO-d₆): 5.50 (s, 2H), 5.81 (d, 1H, J=5.7 Hz), 6.57 (dd, 1H, Ja=8.7 Hz, Jb=2.6 Hz), 6.73 (d, 1H, J=2.6 Hz), 7.02 (d, 1H, J=8.8 Hz), 7.12 (s, 2H), 7.95 (d, 1H, J=5.7 Hz). ¹³C NMR (62.9 MHz, δ, ppm, DMSO-d₆): 99.03, 113.55, 114.13, 121.00, 123.70, 125.49, 137.44, 148.44, 152.97, 153.70, 159.22. m/z 281.1 [(M+H)⁺ calcd. for C₁₁H₉ClN₄O₃ 280.0].

Synthesis 8

4-(4-Amino-2-fluorophenoxy)-3-nitropyridin-2-amine

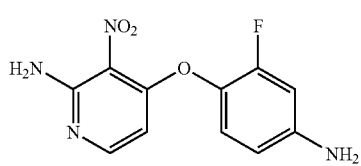

Method A was used with 4-amino-2-fluorophenol to afford the title compound (0.35 g, 29%). ¹H NMR (250 MHz, δ, ppm, DMSO-d₆): 5.53 (s, 2H), 5.92 (d, 1H, J=5.7 Hz), 6.41 (dd, 1H, Ja=8.7 Hz, Jb=2.5 Hz), 6.50 (dd, 1H, Ja=13.1 Hz, Jb=2.5 Hz), 7.00 (t, 1H, J=9.0 Hz), 7.15 (s, 2H), 7.97 (d, 1H, J=5.8 Hz). m/z 265.1 [(M+H)⁺ calcd. for C₁₁H₉FN₄O₃ 264.1].

Synthesis 9

4-(4-Amino-2-methylphenoxy)-3-nitropyridin-2-amine

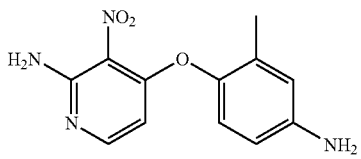

Method A was used with 4-amino-o-cresol to afford the title compound (0.57 g, 42%). ¹H NMR (250 MHz, δ, ppm, DMSO-d₆): 1.95 (s, 3H), 5.08 (s, 2H), 5.79 (d, 1H, J=5.7 Hz), 6.44 (dd, 1H, Ja=8.5 Hz, Jb=2.8 Hz), 6.49 (d, 1H, J=2.7 Hz), 6.77 (d, 1H, J=8.4 Hz), 7.04 (s, 2H), 7.92 (d, 1H, J=5.7 Hz). ¹³C NMR (62.9 MHz, δ, ppm, DMSO-d₆): 15.39, 99.04, 112.50, 116.01, 121.17, 121.67, 129.72, 140.89, 147.02, 152.84, 153.61, 159.71. m/z 261.1 [(M+H)⁺ calcd. for C₁₂H₁₂N₄O₃ 260.1].

Synthesis 10

4-(4-Amino-2,3-dimethylphenoxy)-3-nitropyridin-2-amine

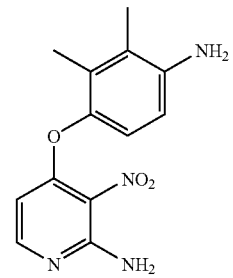

Method A was used with 4-amino-2,3-dimethylphenol to afford the title compound (1.083 mg, 80%). ¹H-NMR (δ, ppm, DMSO-d₆): 1.12 (s, 3H, CH₃), 1.17 (s, 3H, CH₃), 4.05 (s, 2H, NH$_{2,Ph}$), 4.91 (d, 1H, H$_{Py,5}$, J=5.7 Hz), 5.73 (d, 1H, H$_{Ph}$, J=8.6 Hz), 5.85 (d, 1H, H$_{Ph}$, J=8.6 Hz), 6.22 (s, 2H, NH$_{2,Py}$), 7.06 (d, 1H, H$_{Py,6}$, J=5.7 Hz). LC-MS (m/z): 275 (M+H, 100).

Synthesis 11

4-(4-Amino-2,6-difluorophenoxy)-3-nitropyridin-2-amine

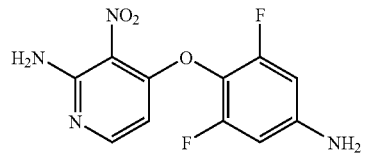

Method A was used with 4-amino-2,6-difluorophenol to afford the title compound (0.29 g, 33%). $^1$H NMR (250 MHz, δ, ppm, DMSO-$d_6$): 5.85 (s, 2H), 6.04 (d, 1H, J=5.7 Hz), 6.36 (d, 2H, J=10.7 Hz), 7.19 (s, 2H), 8.00 (d, 1H, J=5.8 Hz). m/z 283.1 [(M+H)$^+$ calcd. for $C_{11}H_8F_2N_4O_3$ 282.1].

(II) Boc Protection of Amine

Synthesis 12

4-(4-N-(tert-Butoxycarbonyl)-aminophenoxy)-3-nitropyridin-2-amine

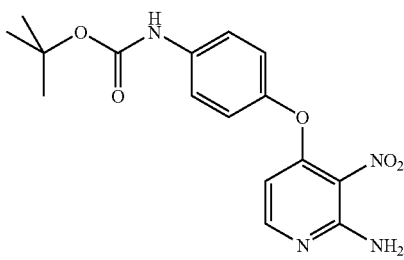

Method B. 4-(4-Aminophenoxy)-3-nitropyridin-2-amine (2.49 g, 10.1 mmol) was dissolved in THF (50 mL). Di-tert-butyl dicarbonate (4.86 g, 22.3 mmol) was added and the solution stirred for 16 hours at room temperature. The solvent was evaporated and the residue purified by column chromatography (eluent gradient DCM to DCM:AcOEt 1:1), to afford the title compound (2.92 g, 83%). $^1$H-NMR (δ, ppm, DMSO-$d_6$): 1.49 (s, 9H, t-Bu), 5.92 (d, 1H, $H_{Py,5}$, J=5.0 Hz), 7.11 (d, 2H, $H_{arom,Ph,3+5}$, J=7.50 Hz), 7.14 (s, 2H, $NH_{2,Py}$), 7.55 (d, 2H, $H_{arom,Ph,2+6}$), 7.98 (d, 1H, $H_{Py,6}$), 9.50 (s, 1H, NH); LC-MS (m/z): 247 (M+H, 100).

Synthesis 13 tert-Butyl 4-(2-amino-3-nitropyridin-4-yl-oxy)naphthalen-1-yl-carbamate

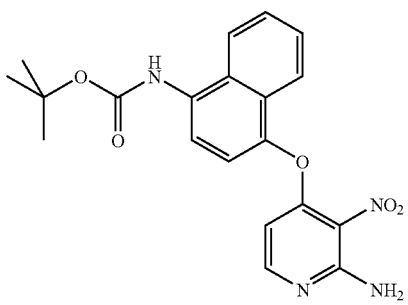

Method B was used with 4-(4-aminonaphthalen-1-yl-oxy)-3-nitropyridin-2-amine to afford the title compound (0.50 g, 34%). $^1$H-NMR (δ, ppm, DMSO-$d_6$): 1.52 (s, 9H, tBu), 5.80 (d, 1H, $H_{Py,5}$, J=5.7 Hz), 7.26 (s, 2H, $NH_2$), 7.38 (d, 1H, $H_{arom,naph}$, J=8.3 Hz), 7.58-7.69 (m, 3H, $H_{arom,naph}$), 7.86-7.89 (m, 1H, $H_{arom,naph}$), 7.93 (d, 1H, $H_{Py,5}$), 8.14-8.17 (m, 1H, $H_{arom,naph}$), 9.36 (s, 1H, NHBoc).

Synthesis 14 tert-Butyl 4-(2-amino-3-nitropyridin-4-yl-oxy)-3-methylphenyl-carbamate

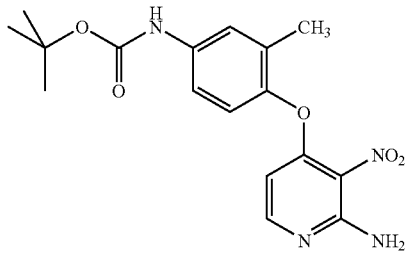

Method B was used with 4-(4-amino-2-methylphenoxy)-3-nitropyridin-2-amine (0.160 g, 0.615 mmol) to afford the title compound (0.143 g, 65%). $^1$H-NMR (500 MHz, DMSO-$d_6$) δ: 1.48 (s, 9H), 2.05 (s, 3H), 5.76 (d, 1H, J=5.4 Hz), 7.03 (d, 1H, J=8.5 Hz), 7.15 (s, 2H), 7.33 (d, 1H, J=8.9 Hz), 7.48 (s, 1H), 7.94 (d, 1H, J=5.7 Hz), 9.46 (bs, 1H). $^{13}$C NMR (125.8 MHz, DMSO-$d_6$) δ 15.50, 28.09, 79.15, 99.17, 117.30, 120.78, 121.20, 121.44, 129.85, 137.62, 145.40, 152.76, 153.04, 153.72, 158.94. m/z 383.0 [(M+Na)$^+$ calcd. for $C_{17}H_{20}N_4O_6$ 360.1].

(III) Trifluoroacetamide Protection

Synthesis 15

N-(4-(2-Amino-3-nitropyridin-4-yl-oxy)-2-fluorophenyl)-2,2,2-trifluoro-acetamide

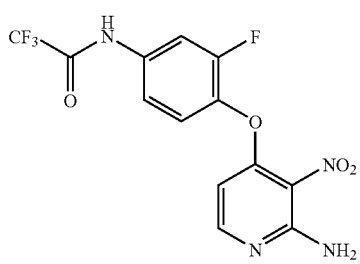

Method C. 4-(4-Amino-3-fluorophenoxy)-3-nitropyridin-2-amine (472 mg, 1.8 mmol) was suspended in dry DCM (10 mL). Pyridine (0.5 mL) and trifluoroacetic anhydride (278 μL, 2 mmol) were added, and the reaction mixture was stirred at room temperature for 2 hours. More trifluoroacetic anhydride (200 μL) was added and the stirring continued for 1 hour. The solvent was evaporated and the residue was taken up in water. The insoluble residue was recovered by filtration, dissolved in acetone, pre-adsorbed on silica and purified by column chromatography (eluent gradient DCM to DCM:MeOH 99:1), to afford the title compound (574 mg, 89%). $^1$H-NMR (δ, ppm, DMSO-$d_6$): 6.16 (d, 1H, $H_{Py,5}$, J=5.61 Hz), 7.13 (d, 1H, $H_{arom,Ph}$, J=8.75 Hz), 7.26 (s, 2H, $NH_{2,Py}$), 7.38 (d, 1H, $H_{arom,Ph}$, J=11.0 Hz), 7.59 (d, 1H, $H_{arom,Ph}$, J=8.70 Hz), 8.10 (d, 1H, $H_{Py,6}$), 11.29 (s, 1H, $NHCOCF_3$); LC-MS (m/z): 361 (M+H, 100).

(IV) Reduction of Nitro Group

1. Reduction En-Route to Common Intermediates (According to Scheme 2)

Synthesis 16

4-(4-N-(tert-Butoxycarbonyl)-aminophenoxy)-2,3-diaminopyridine

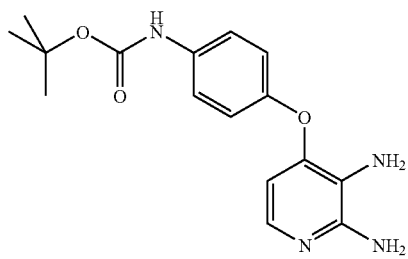

Method D1 (using ammonium formate). 4-(4-N-(tert-Butoxycarbonyl)-aminophenoxy)-3-nitropyridin-2-amine (470 mg, 1.36 mmol) was dissolved in ethanol (20 mL). Palladium 10% on activated carbon (150 mg) was added, followed by ammonium formate finely ground (1 g, 16 mmol). The reaction mixture was stirred for 1.5 hours, then filtered over Celite and concentrated. The brown solid was dissolved in an EtOAc:Water mixture (10:10 mL) and the layers were separated. The organic layers was washed with saturated $NaHCO_3$ (aq) (10 mL), dried ($MgSO_4$) and concentrated to afford the title compound (370 mg, 86%) as a brown solid. $^1$H-NMR (δ, ppm, DMSO-$d_6$): 1.49 (s, 9H, t-Bu), 4.40 (s, 2H, $NH_{2,Py3}$), 5.52 (s, 2H, $NH_{2,Py2}$), 5.93 (d, 1H, $H_{Py,5}$), 6.93 (d, 2H, $H_{arom,Ph,3+5}$, J=7.5 Hz), 7.22 (d, 1H, $H_{Py,6}$), 7.44 (d, 2H, $H_{arom,Ph,2+6}$), 9.32 (s, 1H, NH).

Synthesis 17 tert-Butyl 4-(2,3-diaminopyridin-4-yl-oxy)naphthalen-1-yl-carbamate

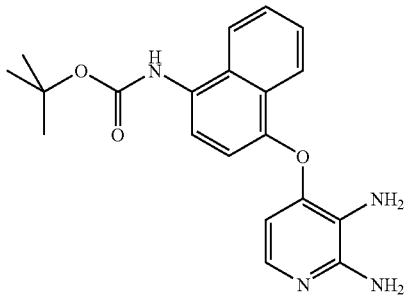

Method D1 was used with tert-butyl 4-(2-amino-3-nitropyridin-4-yl-oxy)naphthalen-1-yl-carbamate (0.50 g, 1.26 mmol), affording the title compound as a brown solid (0.38 g, 82%). $^1$H-NMR (δ, ppm, DMSO-$d_6$): 1.55 (s, 9H, tBu), 4.63 (s, 2H, $NH_2$), 5.66 (s, 2H, $NH_2$), 5.92 (d, 1H, $H_{Py,5}$, J=5.6 Hz), 7.05 (d, 1H, $H_{arom,naph}$, J=8.3 Hz), 7.24 (d, 1H, $H_{Py,5}$), 7.54 (d, 1H, $H_{arom,naph}$, J=8.3 Hz), 7.60-7.65 (m, 2H, $H_{arom,naph}$), 8.07-8.12 (m, 2H, $H_{arom,naph}$), 9.22 (s, 1H, NHBoc).

Synthesis 18

N-(4-(2,3-Diaminopyridin-4-yl-oxy)-2-fluorophenyl)-2,2,2-trifluoroacetamide

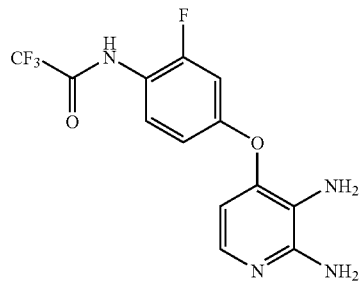

Method D2 (using hydrogen). N-(4-(2-amino-3-nitropyridin-4-yl-oxy)-2-fluorophenyl)-2,2,2-trifluoroacetamide (540 mg, 1.5 mmol) was dissolved in ethanol (15 mL) and AcOEt (5 mL). Palladium 10% on activated carbon (150 mg) was added and the reaction mixture was stirred for 2 hours under hydrogen atmosphere. The catalyst was filtered off and the filtrate evaporated to afford the title compound (490 mg, 100%). $^1$H-NMR (δ, ppm, DMSO-$d_6$): 4.65 (s, 2H, $NH_{2,Py3}$), 5.86 (s, 2H, $NH_{2,Py2}$), 6.23 (d, 1H, $H_{Py,6}$, J=5.71 Hz), 6.85 (d, 1H, $H_{arom,Ph}$, J=8.80 Hz), 7.01 (d, 1H, $H_{arom,Ph}$, J=11.51 Hz), 7.32 (d, 1H, $H_{Py,5}$, J=5.71 Hz), 7.45 (t, 1H, $H_{arom,Ph}$, J=8.76 hz), 11.37 (s, 1H, $NHCOCF_3$).

Synthesis 19 tert-Butyl 4-(2,3-diaminopyridin-4-yl-oxy)-3-methylphenyl-carbamate

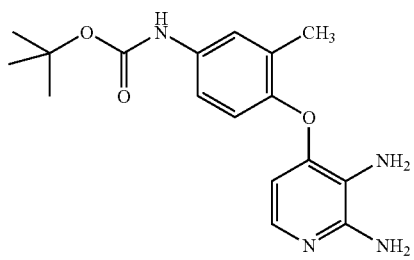

Method D2 was used with tert-butyl 4-(2-amino-3-nitropyridin-4-yl-oxy)-3-methylphenyl-carbamate (133 mg, 0.37 mmol) to afford the title compound (115 mg, 94%). $^1$H-NMR (500 MHz, DMSO-d$_6$) δ 1.47 (s, 9H), 2.08 (s, 3H), 4.38 (s, 2H), 5.45 (s, 2H), 5.73 (d, 1H, J=5.5 Hz), 6.83 (d, 1H, J=8.7 Hz), 7.18 (d, 1H, J=5.5 Hz), 7.25 (d, 1H, J=8.6 Hz), 7.41 (s, 1H), 9.26 (s, 1H). $^{13}$C NMR (125.8 MHz, DMSO-d$_6$) δ 15.82, 28.12, 78.91, 101.47, 117.11, 118.08, 120.29, 120.85, 129.48, 135.81, 135.91, 147.74, 148.63, 149.83, 152.83. m/z 331.1 [(M+H)$^+$ calcd. for C$_{17}$H$_{22}$N$_4$O$_3$ 330.2].

(V) Reduction of Nitro Group

2. Reduction of Coupled Intermediates (According to Scheme 4 and Scheme 5)

Synthesis 20

1-(4-(2,3-Diaminopyridin-4-yl-oxy)phenyl)-3-(4-chloro-3-(trifluoromethyl)phenyl)urea

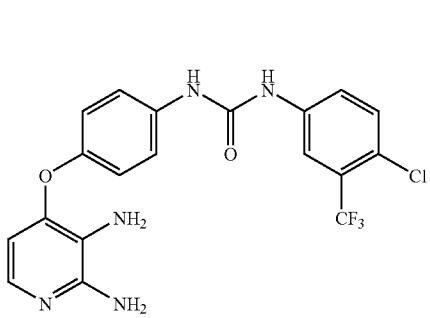

Method D2 was used with 1-(4-(2-amino-3-nitropyridin-4-yl-oxy)phenyl)-3-(4-chloro-3-(trifluoromethyl)phenyl)urea to afford the title compound (69 mg, 92%). $^1$H-NMR (δ, ppm, DMSO-d$_6$): 4.43 (s, 2H, NH$_{2,Py3}$), 5.55 (s, 2H, NH$_{2,Py2}$), 6.00 (d, 1H, H$_{Py,5}$), 6.97 (d, 2H, H$_{arom,Ph,3+5}$, J=7.5 Hz), 7.24 (d, 1H, H$_{Py,6}$), 7.46 (d, 2H, H$_{arom,Ph,2+6}$), 7.63 (broad s, 2H, H$_{arom'}$), 8.12 (s, 1H, H$_{arom'}$), 8.82 (s, 1H, NH$_{urea,1}$), 9.14 (s, 1H, NH$_{urea,3}$).

Synthesis 21

1-(4-(2,3-Diaminopyridin-4-yl-oxy)-2-chlorophenyl)-3-(4-chloro-3-(trifluoromethyl)phenyl)urea

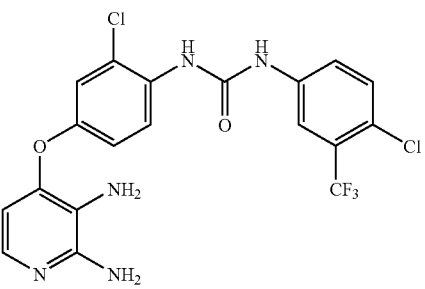

Method D2 was used with 1-(4-(2-amino-3-nitropyridin-4-yl-oxy)-2-chlorophenyl)-3-(4-chloro-3-(trifluoromethyl)phenyl)urea to afford the title compound (199 mg, 60%). $^1$H-NMR (δ, ppm, DMSO-d$_6$): 4.51 (s, 2H, NH$_{2,Py2}$), 5.65 (s, 2H, NH$_{2,Py3}$), 6.10 (d, 1H, H$_{Py,5}$, J=5.6 Hz), 6.97 (dd, 1H, H$_{arom}$, J=8.9 Hz, J=2.7 Hz), 7.11 (d, 1H, H$_{arom}$), J=2.7 Hz), 7.26 (d, 1H, H$_{Py,6}$, J=5.6 Hz), 7.62 (broad s, 2H, H$_{arom}$), 7.99 (d, 1H, H$_{arom}$, J=9.0 Hz), 8.10 (s, 1H, H$_{arom}$), 8.35 (s, 1H, NH$_{urea1}$), 9.71 (s, 1H, NH$_{urea3}$). LC-MS (m/z): 472 (M+H, 100).

Synthesis 22

1-(4-(2,3-Diaminopyridin-4-yl-oxy)-2-methylphenyl)-3-(4-chloro-3-(trifluoromethyl)phenyl)urea

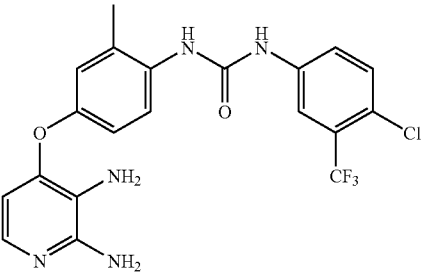

Method D2 was used with 1-(4-(2-amino-3-nitropyridin-4-yl-oxy)-2-methylphenyl)-3-(4-chloro-3-(trifluoromethyl)phenyl)urea to afford the title compound (247 mg, 75%). $^1$H-NMR (δ, ppm, DMSO-d$_6$): 1.05 (s, 3H, CH$_3$), 4.34 (broad s, 2H, NH$_{2,Py2}$), 5.62 (broad s, 2H, NH$_{2,Py3}$), 6.02 (d, 1H, H$_{Py,5}$, J=5.7 Hz), 6.85 (m, 3H, H$_{arom}$), 7.26 (d, 1H, NH$_{Py,6}$), 7.61-7.66 (m, 2H, H$_{arom}$), 8.12 (s, 1H, NH$_{urea1}$), 9.51 (s, 1H, NH$_{urea3}$). LC-MS (m/z): 452 (M+H, 100).

Synthesis 23

1-(4-Chloro-3-(trifluoromethyl)phenyl)-3-(4-(2,3-diaminopyridin-4-yl-oxy)-3-methylphenyl)urea

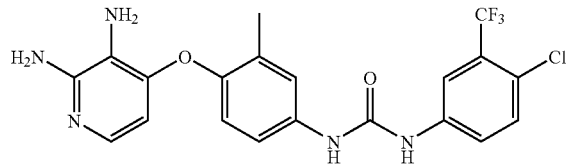

Method D2 was used with 1-(4-(2-amino-3-nitropyridin-4-yl-oxy)-3-methylphenyl)-3-(4-chloro-3-(trifluoromethyl)phenyl)urea to afford the title compound (0.25 g, 90%). $^1$H NMR (250 MHz, δ, ppm, DMSO-d$_6$): 2.13 (s, 3H), 4.43 (s, 2H), 5.50 (s, 2H), 5.77 (d, 1H, J=5.7 Hz), 6.87 (d, 1H, J=8.7 Hz), 7.19 (d, 1H, J=5.7 Hz), 7.25 (dd, 1H, Ja=8.6 Hz, Jb=2.6 Hz), 7.42 (d, 1H, J=2.4 Hz), 7.57-7.66 (m, 2H), 8.12 (d, 1H, J=1.9 Hz), 8.78 (s, 1H), 9.14 (s, 1H). m/z 452.0 [(M+H)$^+$ calcd. for C$_{20}$H$_{17}$ClF$_3$N$_5$O$_2$ 451.1].

Synthesis 24

1-(4-(2,3-diaminopyridin-4-yl-oxy)-2-(trifluoromethyl)phenyl)-3-(4-chloro-3-(trifluoromethyl)phenyl)urea

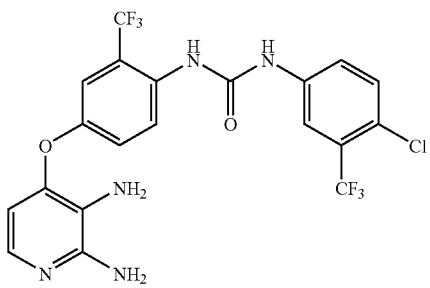

Method D2 was used with 1-(4-(2-amino-3-nitropyridin-4-yl-oxy)-2-(trifluoromethyl)phenyl)-3-(4-chloro-3-(trifluoromethyl)phenyl)urea to afford the title compound (47 mg, 60%). $^1$H-NMR (δ, ppm, DMSO-d$_6$): 4.58 (s, 2H, NH$_{2,Py2}$), 5.68 (s, 2H, NH$_{2,Py3}$), 6.14 (d, 1H, H$_{Py,5}$, J=5.5 Hz), 7.24 (s, 2H, H$_{arom}$), 7.29 (d, 1H, H$_{Py,6}$, J=5.6 Hz), 7.62 (s, 2H, H$_{arom}$), 7.75 (d, 1H, H$_{arom}$, J=8.5 Hz), 8.10 (s, 1H, H$_{arom}$), 8.17 (s, 1H, NH$_{urea1}$), 9.63 (s, 1H, NH$_{urea3}$). LC-MS (m/z): 506 (M+H, 100).

Synthesis 25

1-(4-chloro-3-(trifluoromethyl)phenyl)-3-(4-(2,3-diaminopyridin-4-yl-oxy)-3-fluorophenyl)urea

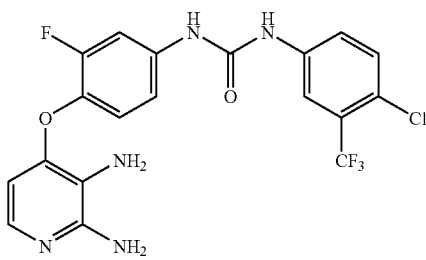

Method D2 was used with 1-(4-(2-amino-3-nitropyridin-4-yl-oxy)-3-fluorophenyl)-3-(4-chloro-3-(trifluoromethyl)phenyl)urea (181 mg, 0.373 mmol) to afford the title compound (163 mg, 96%). $^1$H-NMR (500 MHz, DMSO-d$_6$) δ: 4.48 (s, 2H), 5.56 (s, 2H), 5.89 (t, 1H, J=4.8 Hz), 7.10 (dt, 1H, J$_t$=8.8 Hz, J$_d$=4.1 Hz), 7.16-7.18 (m, 1H), 7.21 (t, 1H, J=5.0 Hz), 7.60-7.66 (m, 3H), 8.09 (s, 1H), 9.06 (s, 1H), 9.22 (s, 1H).

(VI) Formation of pyridoimidazolones from 2,3-diaminopyridyl intermediates

1. Cyclisation En-Route to Common Intermediates (According to Scheme 2)

Synthesis 26 tert-Butyl 4-(2-oxo-2,3-dihydro-1H-imidazo[4,5-b]pyridin-7-yl-oxy)phenyl-carbamate

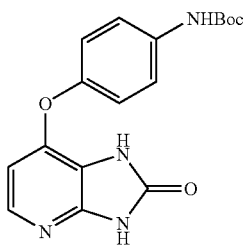

Method E1 (with triphosgene and triethylamine). 4-(4-N-(tert-Butoxycarbonyl)-aminophenoxy)-2,3-diaminopyridine (370 mg, 1.2 mmol) was dissolved in dry THF (10 mL), triethylamine (336 μL, 2.4 mmol) was added and the solution was cooled at 0° C. Triphosgene (118 mg, 0.4 mmol) was added, and the reaction mixture was stirred at 0° C. for 15 minutes and at room temperature for 16 hours. The precipitated triethylamine hydrochloride was filtered off and the solvent evaporated. The residue was pre-absorbed on silica by dissolving it in THF, adding silica and evaporating all volatiles. It was purified by column chromatography, eluting with gradient DCM to AcOEt. The fractions containing the product were evaporated, and the residue was triturated with water. The solid was recovered by filtration to afford the title compound (190 mg, 46%).

Method E2 (with phosgene and pyridine). tert-Butyl 4-(2,3-diaminopyridin-4-yl-oxy)phenyl-carbamate (1 g, 3.16 mmol) was dissolved in dry THF (32 mL, 10 mL/mmol). The solution was cooled in an ice bath under nitrogen. Pyridine (0.59 mL, 7.27 mmol) was added and followed by dropwise addition a phosgene solution 1.93 M in toluene (2 mL, 3.79 mmol) under vigourous stirring. The ice bath was removed and the mixture was stirred at room temperature overnight, then at 60° C. during 2 hours. The solvent was evaporated under reduced pressure and the solid residue was washed with water and dried to afford the title compound (952 mg, 88%) as a brown solid. $^1$H-NMR (δ, ppm, DMSO-d$_6$): 1.48 (9H, s, t-Bu), 6.29 (d, 1H, H$_{Py,5}$, J=6.0 Hz), 7.09 (d, 2H, H$_{arom,Ph,3+5}$, J=9.0 Hz), 7.51 (d, 2H, H$_{arom,Ph,2+6}$, J=9.0 Hz), 7.73 (d, 1H, $H_{Py,6}$, J=6.0 Hz), 9.43 (bs, 1H, NHBoc), 11.16 (bs, 1H, $NH_{Py3}$) 11.34 (bs, 1H, $NH_{Py2}$).; LC-MS (m/z): 343 (M+H, 100).

Synthesis 27

N-(4-(2,3-Dihydro-2-oxo-1H-imidazo[4,5-b]pyridin-7-yl-oxy)-2-fluorophenyl)-2,2,2-trifluoroacetamide (CJS 3251)

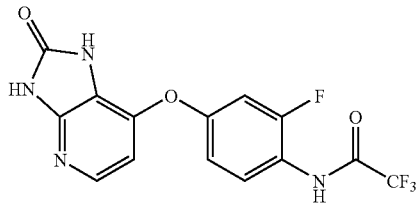

Method E3 (with triphosgene and Pyridine). N-(4-(2,3-Diaminopyridin-4-yl-oxy)-2-fluorophenyl)-2,2,2-trifluoro-acetamide (500 mg, 1.5 mmol) was dissolved in dry THF (20 mL), pyridine (1 mL) was added and the solution was cooled at 0° C. Triphosgene (445 mg, 1.5 mmol) in dry THF (10 mL) was added dropwise. The reaction mixture was stirred at room temperature for 48 hours. The solvent was evaporated and the residue washed with water. The precipitate was recovered by filtration to afford the title compound (260 mg, 49%). $^1$H-NMR (δ, ppm, DMSO-$d_6$): 6.57 (d, 1H, $H_{Py,5}$), 6.98 (d, 1H, $H_{arom,Ph}$), 7.36 (d, 1H, $H_{arom,Ph}$), 7.50 (d, 1H, $H_{arom,Ph}$), 7.75 (d, 1H, $H_{Py,6}$), 11.26 (s, 1H, $NH_{Py3}$), 11.30 (s, 1H, $NHCOCF_3$), 11.48 (s, 1H, $NH_{Py2}$). LC-MS (m/z): 356 (M, 100).

Synthesis 28 tert-Butyl 4-(2-Oxo-2,3-dihydro-1H-imidazo[4,5-b]pyridin-7-yl-oxy)naphthalen-1-yl-carbamate

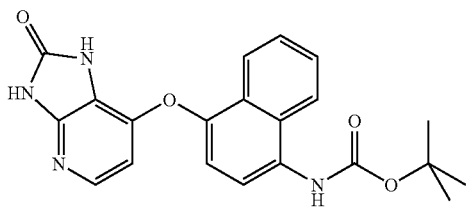

Method E2 was used with tert-butyl 4-(2,3-diaminopyridin-4-yl-oxy)naphthalen-1-yl-carbamate to afford the title compound as a solid (0.17 g, 83%). $^1$H-NMR (δ, ppm, DMSO-$d_6$): 1.51 (s, 9H, tBu), 6.26 (d, 1H, $H_{Py,5}$, J=6.1 Hz), 7.29 (d, 1H, $H_{arom,naph}$, J=8.2 Hz), 7.55-7.66 (m, 3H, $H_{arom,naph}$), 7.73 (d, 1H, $H_{Py,5}$), 7.92-7.97 (m, 1H, $H_{arom,naph}$), 8.06-8.15 (m, 1H, $H_{arom,naph}$), 9.28 (s, 1H, NHBoc), 11.48 (s, NH, $NH_{Py}$). LC-MS (m/z): 392 (M, 100).

Synthesis 29 tert-Butyl 3-methyl-4-(2-oxo-2,3-dihydro-1H-imidazo[4,5-b]pyridin-7-yl-oxy)phenyl-carbamate

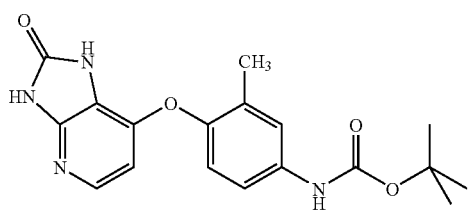

Method E3 was used with tert-butyl 4-(2,3-diaminopyridin-4-yl-oxy)-3-methylphenyl-carbamate (396 mg, 1.20 mmol) to produce the title compound (153 mg, 36%). $^1$H-NMR (500 MHz, DMSO-$d_6$) δ: 1.48 (s, 9H), 2.08 (s, 3H), 6.13 (d, 1H, J=6.0 Hz), 7.01 (d, 1H, J=8.8 Hz), 7.31 (d, 1H, J=8.8 Hz), 7.47 (s, 1H), 7.70 (d, 1H, J=6.0 Hz), 9.35 (s, 1H), 11.15 (s, 1H), 11.30 (s, 1H). $^{13}$C NMR (125.8 MHz, DMSO-$d_6$) δ 15.77, 28.11, 79.07, 104.01, 112.13, 117.33, 120.90, 121.14, 129.89, 136.97, 141.37, 146.14, 146.27, 146.71, 152.81, 154.18. m/z 357.0 [(M+H)$^+$ calcd. for $C_{18}H_{20}N_4O_4$ 356.1].

(VII) Formation of pyridoimidazolones from 2,3-diaminopyridyl intermediates

2. Cyclisation of Coupled Intermediates (According to Scheme 4 and Scheme 5)

Synthesis 30

1-(4-(2,3-Dihydro-2-oxo-1H-imidazo[4,5-b]pyridin-7-yl-oxy)phenyl)-3-(4-chloro-3-(trifluoromethyl)phenyl)urea (CJS 3233)

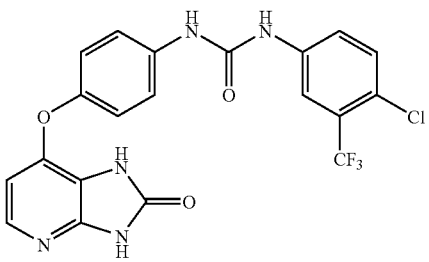

Method E1 was used with 1-(4-(2,3-diaminopyridin-4-yl-oxy)phenyl)-3-(4-chloro-3-(trifluoromethyl)phenyl)urea to afford the title compound (11 mg, 24%). $^1$H-NMR (δ, ppm, DMSO-$d_6$): 6.35 (d, 1H, $H_{Py,5}$, J=6.7 Hz), 7.14 (d, 2H, $H_{arom,Ph,3+5}$, J=10.0 Hz), 7.54 (d, 2H, $H_{arom,Ph,2+6}$), 7.64 (broad s, 2H, $H_{arom'}$), 7.77 (d, 1H, $H_{Py,6}$), 8.12 (s, 1H, $H_{arom'}$), 8.94 (s, 1H, $NH_{urea,1}$), 9.18 (s, 1H, $NH_{urea,3}$), 11.19 (s, 1H, $NH_{Py3}$), 11.36 (s, 1H, $NH_{Py2}$). LC-MS (m/z): 463 (M, 100).

Synthesis 31

1-(4-(2,3-Dihydro-2-oxo-1H-imidazo[4,5-b]pyridin-7-yl-oxy)-2-chlorophenyl)-3-(4-chloro-3-(trifluoromethyl)phenyl)urea hydrochloride (CJS 3502)

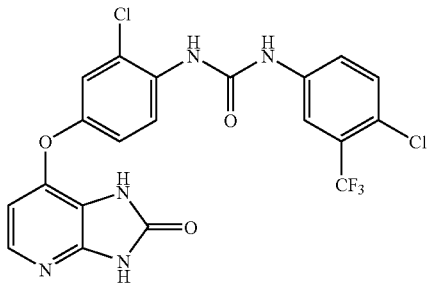

Method E3 was used with 1-(4-(2,3-diaminopyridin-4-yl-oxy)-2-chlorophenyl)-3-(4-chloro-3-(trifluoromethyl)phenyl)-urea to afford the title compound (72 mg, 96%) as a brown powder. $^1$H-NMR ($\delta$, ppm, DMSO-$d_6$): 4.16 (broad signal, HCl), 6.49 (d, 1H, $H_{Py,5}$, J=5.8 Hz), 7.16 (dd, 1H, $H_{arom}$, J=9.0 Hz, J=2.6 Hz), 7.38 (m, 1H, $H_{arom}$), 7.64 (m, 2H, $H_{arom}$), 7.79 (d, 1H, $H_{Py,6}$, J=5.8 Hz), 8.01-8.12 (m, 2H, $H_{arom}$), 8.58 (broad s, 1H, $NH_{urea1}$), 8.91 (m, 1H, $NH_{Py}$), 10.16 (s, 1H, $NH_{urea3}$), 11.25 (s, 1H, $NH_{Py}$). LC-MS (m/z): 498 (M+H, 100).

Synthesis 32

1-(4-(2,3-Dihydro-2-oxo-1H-imidazo[4,5-b]pyridin-7-yl-oxy)-2-methylphenyl)-3-(4-chloro-3-(trifluoromethyl)phenyl)urea (CJS 3505)

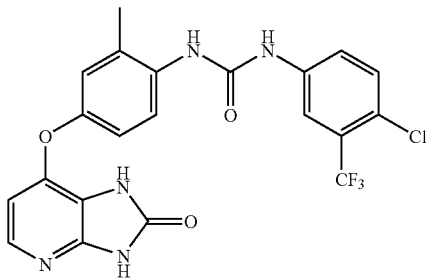

Method E3 was used with 1-(4-(2,3-diaminopyridin-4-yl-oxy)-2-methylphenyl)-3-(4-chloro-3-(trifluoromethyl)phenyl)-urea to afford the title compound (79 mg, 79%) as a brown powder. $^1$H-NMR ($\delta$, ppm, DMSO-$d_6$): 1.35 (s, 3H, $CH_3$), 6.35 (d, 1H, $H_{Py,5}$, J=6.1 Hz), 6.95-7.13 (m, 2H, $H_{arom}$), 7.62 (broad s, 2H, $H_{arom}$), 7.75-7.79 (m, 2H, $H_{arom+Py,6}$, $J_{Py,6}$=6.0 Hz), 8.12 (m, 2H, $H_{arom}$+$NH_{urea1}$), 9.48 (s, 1H, $NH_{urea3}$), 11.18 (s, 1H, $NH_{Py}$), 11.35 (s, 1H, $NH_{Py}$). LC-MS (m/z): 478 (M+H, 100).

Synthesis 33

1-(4-(2,3-Dihydro-2-oxo-1H-imidazo[4,5-b]pyridin-7-yl-oxy)-2-(trifluoromethyl)phenyl)-3-(4-chloro-3-(trifluoromethyl)phenyl)urea (CJS 3506)

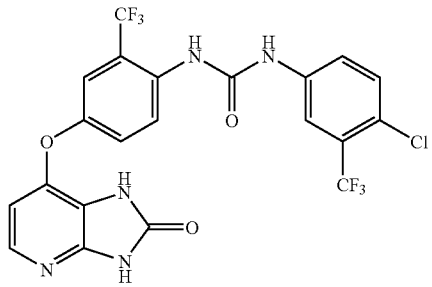

Method E3 was used with 1-(4-(2,3-diaminopyridin-4-yl-oxy)-2-(trifluoromethyl)phenyl)-3-(4-chloro-3-(trifluoromethyl)phenyl)urea to afford the title compound (76 mg, 63%) as a brown powder. $^1$H-NMR ($\delta$, ppm, DMSO-$d_6$): 6.53 (d, 1H, $H_{Py,5}$, J=5.9 Hz), 7.44 (m, 1H, $H_{arom}$, J=8.9 Hz), 7.49 (s, 1H, $H_{arom}$), 7.63 (broad s, 2H, $H_{arom}$), 7.83 (d, 1H, $H_{Py,6}$, J=5.8 Hz), 7.88 (d, 1H, $H_{arom}$, J=8.9 Hz), 8.11 (s, 1H, $NH_{urea1}$), 8.29 (s, 1H, $H_{arom}$), 9.81 (s, 1H, $NH_{urea3}$), 11.26 (s, 1H, $NH_{Py}$), 11.48 (s, 1H, $NH_{Py}$). LC-MS (m/z): 532 (M+H, 100).

(VIII) Deprotection of Boc Carbamate

Synthesis 34

7-(4-Aminophenoxy)-1H-imidazo[4,5-b]pyridin-2(3H)-one

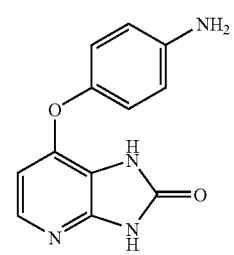

Method F. tert-Butyl 4-(2-oxo-2,3-dihydro-1H-imidazo[4,5-b]pyridin-7-yl-oxy)phenyl-carbamate (950 mg, 2.77 mmol) was dissolved in trifluoroacetic acid (TFA) (13 mL) and the solution was stirred at room temperature for 1.5 hours. TFA was evaporated in vacuo and the resulting viscous oil was taken up in water (3 mL). A saturated aqueous solution of $Na_2CO_3$ was added until pH 7. The resulting precipitate was recovered by filtration, washed with water and dried to afford the title compound (524 mg, 83%) as a brown solid. $^1$H-NMR ($\delta$, ppm, DMSO-$d_6$): 5.09 (bs, 2H, $NH_2$), 6.22 (d, 1H, $H_{Py,5}$, J=6.0 Hz), 6.61 (d, 2H, $H_{arom,Ph,3+5}$, J=8.8 Hz), 6.86 (d, 2H, H$_{arom,Ph,2+6}$, J=8.8 Hz), 7.70 (d, 1H, H$_{Py,6}$, J=6.0 Hz), 11.09 (bs, 1H, NH$_{Py,3}$), 11.26 (bs, 1H, NH$_{Py,2}$).; LC-MS (m/z): 243 (M+H, 100).

Synthesis 35

7-(4-Aminonaphthalen-1-yl-oxy)-1H-imidazo[4,5-b]pyridin-2(3H)-one

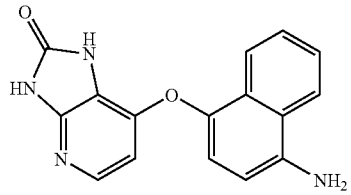

Method F was used with tert-butyl 4-(2-oxo-2,3-dihydro-1H-imidazo[4,5-b]pyridin-7-yl-oxy)naphthalen-1-yl-carbamate to afford the title compound as an off-white solid (94 mg, 74%). $^1$H-NMR (δ, ppm, DMSO-d$_6$): 5.96 (d, 1H, H$_{Py,5}$, J=5.95 Hz), 6.61 (d, 1H, H$_{arom,naph}$, J=8.15 Hz), 7.03 (d, 3H, H$_{arom,naph}$, J=8.15 Hz), 7.33-7.37 (m, 2H, H$_{arom,naph}$), 7.52 (d, 1H, H$_{Py,5}$), 7.58-7.62 (m, 1H, H$_{arom,naph}$), 8.05-8.11 (m, 1H, H$_{arom,naph}$), 11.21 (s, NH, NH$_{Py}$). LC-MS (m/z): 293 (M+H, 100).

Synthesis 36

7-(4-Amino-2-methylphenoxy)-1H-imidazo[4,5-b]pyridin-2(3H)-one

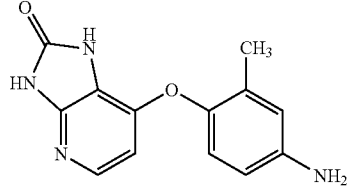

Method F was used with tert-butyl 3-methyl-4-(2-oxo-2,3-dihydro-1H-imidazo[4,5-b]pyridin-7-yl-oxy)phenyl-carbamate (135 mg, 0.379 mmol) to produce the title compound (61 mg, 63%). $^1$H-NMR (500 MHz, DMSO-d$_6$) δ: 1.95 (s, 3H), 5.05 (s, 2H), 6.08 (d, 1H, J=6.0 Hz), 6.45 (d, 1H, J=8.2 Hz), 6.50 (s, 1H), 6.79 (d, 1H, J=8.4 Hz), 7.68 (d, 1H, J=6.0 Hz), 11.15 (s, 1H), 11.29 (s, 1H). m/z 257.1 [(M+H)$^+$ calcd. for C$_{13}$H$_{12}$N$_4$O$_2$ 256.1].

(IX) Deprotection of Trifluoroacetamide

Synthesis 37

7-(4-Amino-3-fluorophenoxy)-1H-imidazo[4,5-b]pyridin-2(3H)-one

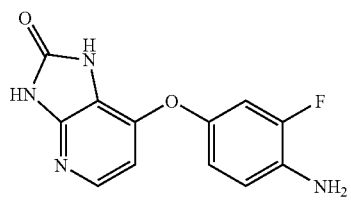

Method G. N-(4-(2,3-Dihydro-2-oxo-1H-imidazo[4,5-b]pyridin-7-yl-oxy)-2-fluorophenyl)-2,2,2-trifluoroacetamide (250 mg, 0.77 mmol) was dissolved in EtOH (7 mL) and aqueous concentrated NH$_3$ (5 mL) was added. The reaction mixture was refluxed for 16 hours. The solvent was evaporated, and the residue washed with DCM. The precipitate was recovered by filtration, washed with water and dried to afford the title compound (105 mg, 52%). $^1$H-NMR (δ, ppm, DMSO-d$_6$): 5.16 (s, 2H, NH$_2$), 6.28 (d, 1H, H$_{Py,5}$, J=5.88 Hz), 6.72-6.81 (m, 2H, H$_{arom,Ph}$), 6.99 (d, 1H, H$_{arom,Ph}$), 7.72 (d, 1H, H$_{Py,6}$), 11.16 (s, 1H, NH$_{Py,3}$), 11.33 (s, 1H, NH$_{Py,2}$).

(X) Synthesis of Ureas from Isocyanates and Amines

1. Ureas from Pyridoimidazolone Intermediates (According to Scheme 3 and Scheme 20)

Synthesis 38

1-(4-(2,3-Dihydro-2-oxo-1H-imidazo[4,5-b]pyridin-7-yl-oxy)phenyl)-3-phenyl-urea (CJS 3239)

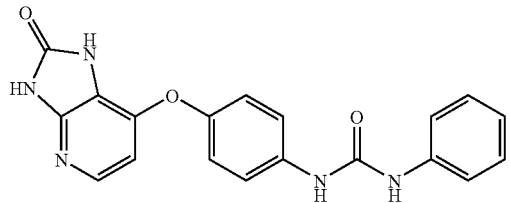

Method H1 (in Pyridine). 7-(4-Aminophenoxy)-2,3-dihydro-2-oxo-1H-imidazo[4,5-b]pyridine (65 mg, 0.27 mmol) was suspended in dry pyridine (3 mL) and heated at 50° C. Phenyl isocyanate (30 μL, 0.28 mmol) was added; the solution became clear. The reaction mixture was heated at reflux for 2 hours, then it was allowed to cool at room temperature. DCM (20 mL) was added, the precipitate formed was recovered by filtration and washed with more DCM, to afford 1-(4-(2,3-dihydro-2-oxo-1H-imidazo[4,5-b]pyridin-7-yl-oxy)phenyl)-3-phenyl-urea (67 mg, 69%). $^1$H-NMR (δ, ppm, DMSO-d$_6$): 6.34 (d, 1H, H$_{Py,5}$, J=7.5 Hz), 6.98 (t, 1H, H$_{arom,Ph',4}$, J=7.5 Hz), 7.13 (d, 2H, H$_{arom,Ph,3+5}$, J=8.75 Hz), 7.29 (t, 2H, H$_{arom,Ph',3+5}$), 7.46 (d, 2H, H$_{arom,Ph',2+6}$), 7.53 (d, 2H, H$_{arom,Ph,2+6}$), 7.76 (d, 1H, H$_{Py,6}$) 8.67 (s, 1H, NH$_{urea,1}$), 8.76 (s, 1H, NH$_{urea,3}$), 11.19 (s, 1H, NH$_{Py3}$), 11.35 (s, 1H, NH$_{Py2}$). LC-MS (m/z): 362 (M+H, 100).

Synthesis 39

1-(4-Chlorophenyl)-3-(4-(2-oxo-2,3-dihydro-1H-imidazo[4,5-b]pyridin-7-yl-oxy)phenyl)urea (CJS 3604)

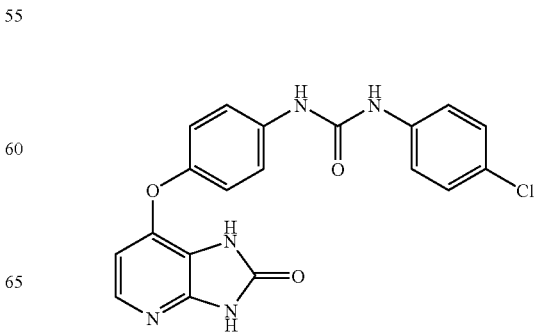

Method H2 (in THF). A mixture of p-chlorophenylisocyanate (24.5 mg, 0.16 mmol) and 7-(4-aminophenoxy)-1H-imidazo[4,5-b]pyridin-2(3H)-one (30 mg, 0.12 mmol) in anhydrous THF (1.5 mL) was stirred at room temperature for 14 hours. The solvent was evaporated and the solid residue was washed with Et$_2$O to afford the title compound (44 mg, 91%) as an off-white solid. $^1$H-NMR (δ, ppm, DMSO-d$_6$): 6.33 (d, 1H, H$_{Py,5}$, J=6.0 Hz), 7.12 (d, 2H, H$_{arom,Ph,3+5}$, J=8.9 Hz), 7.32 (d, 2H, H$_{arom,Ph,2+6}$, J=8.9 Hz), 7.50 (~t, 4H, H$_{arom'}$), 7.75 (d, 1H, H$_{Py,6}$, J=6.0 Hz), 8.82 (bs, 1H, NH$_{urea}$), 8.85 (bs, 1H, NH$_{urea}$), 11.17 (bs, 1H, NH$_{Py3}$), 11.34 (bs, 1H, NH$_{Py2}$). LC-MS (m/z): 396 (M+H, 100).

Synthesis 40

1-(4-(2-Oxo-2,3-dihydro-1H-imidazo[4,5-b]pyridin-7-yl-oxy)phenyl)-3-(3-(trifluoromethyl)phenyl)urea (CJS 3605)

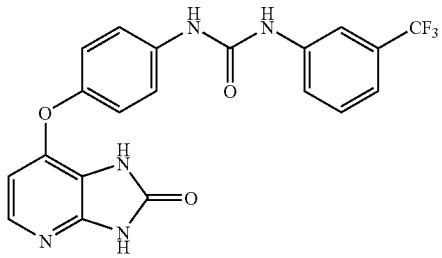

Method H2 was used with 3-(trifluoromethyl)phenyl isocyanate to afford the title compound (28 mg, 53%) as an off-white solid. $^1$H-NMR (δ, ppm, DMSO-d$_6$): 6.34 (d, 1H, H$_{Py,5}$, J=6.0 Hz), 7.12 (d, 2H, H$_{arom,Ph,3+5}$, J=8.8 Hz), 7.31 (d, 1H, H$_{arom',4}$, J=7.5 Hz), 7.48-7.61 (m, 2H, H$_{arom',5+6}$), 7.54 (d, 2H, H$_{arom,Ph,2+6}$, J=8.8 Hz), 7.76 (d, 1H, H$_{Py,6}$, J=6.0 Hz), 8.01 (bs, 1H, H$_{arom',2}$), 8.88 (bs, 1H, NH$_{urea}$), 9.05 (bs, 1H, NH$_{urea}$), 11.14 (bs, 1H, NH$_{Py3}$), 11.32 (bs, 1H, NH$_{Py2}$) LC-MS (m/z): 430 (M+H, 100).

Synthesis 41

1-(4-(2-Oxo-2,3-dihydro-1H-imidazo[4,5-b]pyridin-7-yl-oxy)phenyl)-3-(2-(trifluoromethyl)phenyl)urea (CJS 3606)

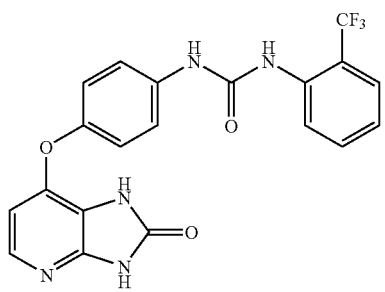

Method H2 was used with 2-(trifluoromethyl)phenyl isocyanate to afford the title compound (35 mg, 66%) as an off-white solid. $^1$H-NMR (δ, ppm, DMSO-d$_6$): 6.35 (d, 1H, H$_{Py,5}$, J=6.0 Hz), 7.12 (d, 2H, H$_{arom,Ph,3+5}$, J=8.9 Hz), 7.28 (t, 1H, H$_{arom'}$, J=7.6 Hz), 7.54 (d, 2H, H$_{arom,Ph,2+6}$, J=8.9 Hz), 7.65 (m, 2H, H$_{arom'}$), 7.76 (d, 1H, H$_{Py,6}$, J=6.0 Hz), 7.94 (d, 1H, H$_{arom'}$, J=8.2 Hz), 8.07 (bs, 1H, NH$_{urea}$), 9.44 (bs, 1H, NH$_{urea}$), 11.14 (bs, 1H, NH$_{Py3}$), 11.31 (bs, 1H, NH$_{Py2}$). LC-MS (m/z): 430 (M+H, 100).

Synthesis 42

1-(4-(2-Oxo-2,3-dihydro-1H-imidazo[4,5-b]pyridin-7-yl-oxy)phenyl)-3-(4-(trifluoromethyl)phenyl)urea (CJS 3607)

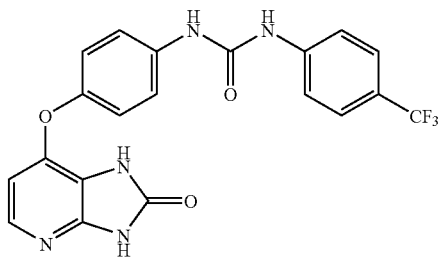

Method H2 was used with 4-(trifluoromethyl)phenyl isocyanate to afford the title compound (40 mg, 75%) as an off-white solid. $^1$H-NMR (δ, ppm, DMSO-d$_6$): 6.35 (d, 1H, H$_{Py,5}$, J=6.0 Hz), 7.13 (d, 2H, H$_{arom,Ph,3+5}$, J=8.8 Hz), 7.54 (d, 2H, H$_{arom,Ph,2+6}$, J=8.8 Hz), 7.60-7.69 (m, 4H, H$_{arom'}$), 7.76 (d, 1H, H$_{Py,6}$, J=6.0 Hz), 8.89 (bs, 1H, NH$_{urea}$), 9.10 (bs, 1H, NH$_{urea}$), 11.14 (bs, 1H, NH$_{Py3}$), 11.31 (bs, 1H, NH$_{Py2}$). LC-MS (m/z): 430 (M+H, 100).

Synthesis 43

1-(3-Fluoro-5-morpholinophenyl)-3-(4-(2-oxo-2,3-dihydro-1H-imidazo[4,5-b]pyridin-7-yl-oxy)phenyl)urea (CJS 3612)

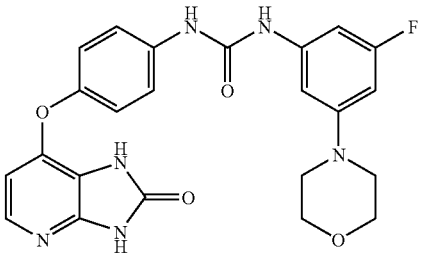

Method H2 was used with 4-(3-fluoro-5-isocyanatophenyl)morpholine. A final washing with a hot 1:1 mixture of EtOAc and THF afforded the title compound (2.1 mg, 38%) as an off-white solid. $^1$H-NMR (δ, ppm, DMSO-d$_6$): 3.10 (t, 4H, CH$_2$—N, J=4.0 Hz), 3.72 (t, 4H, CH$_2$—O, J=4.0 Hz), 6.33 (d, 1H, H$_{Py,5}$, J=5.9 Hz), 6.40 (d, 1H, H$_{arom',4}$, J=12.5 Hz), 6.80 (m, 2H, H$_{arom',2+6}$), 7.12 (d, 2H, H$_{arom,Ph,3+5}$, J=8.9 Hz), 7.52 (d, 2H, H$_{arom,Ph,2+6}$, J=8.9 Hz), 7.75 (d, 1H, H$_{Py,6}$, J=5.9 Hz), 8.82 and 8.85 (bs, 2H, NH$_{urea}$), 11.17 (bs, 1H, NH$_{Py3}$), 11.34 (bs, 1H, NH$_{Py2}$) LC-MS (m/z): 465 (M+H, 100).

Synthesis 44

1-(4-Chloro-3-(trifluoromethyl)phenyl)-3-(4-(2-oxo-2,3-dihydro-1H-imidazo[4,5-b]pyridin-7-yl-oxy)naphthalen-1-yl)urea (CJS 3675)

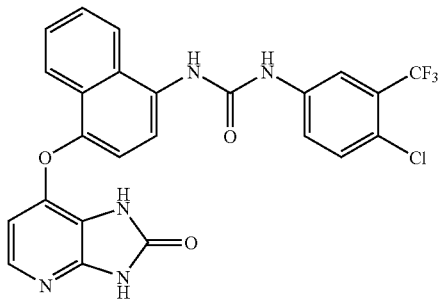

Method H2 was used with 7-(4-aminonaphthalen-1-yl-oxy)-1H-imidazo[4,5-b]pyridin-2(3H)-one (94 mg, 0.32 mmol) and 1-chloro-4-isocyanato-2-(trifluoromethyl)benzene (77 mg, 0.35 mmol) to afford the title compound as a brown solid (25 mg, 15%). $^1$H-NMR (δ, ppm, DMSO-$d_6$): 6.21 (d, 1H, $H_{Py,5}$, J=5.9 Hz), 7.20 (m, 1H, $H_{arom,Naph}$), 7.56-7.67 (m, 4H, $H_{arom,naph+Py,6}$), 7.79-7.87 (m, 2H, $H_{arom,Ph'}$), 7.94-7.97 (m, 1H, $H_{arom,naph}$), 8.23-8.31 (m, 2H, $H_{arom,naph}$), 10.52 (s, NH, $NH_{Py}$), 11.26 (s, NH, $NH_{Py'}$). LC-MS (m/z): 514 (M+H, 100).

Synthesis 45

1-(4-(2-oxo-2,3-dihydro-1H-imidazo[4,5-b]pyridin-7-yl-oxy)naphthalen-1-yl)-3-(3-(trifluoromethyl)phenyl)urea (CJS 3681)

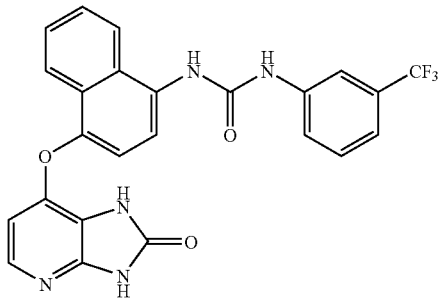

Method H2 was used with 7-(4-aminonaphthalen-1-yl-oxy)-1H-imidazo[4,5-b]pyridin-2(3H)-one (30 mg, 0.10 mmol) and 1-isocyanato-3-(trifluoromethyl)benzene (21 mg, 0.11 mmol) to afford the title compound as a brown solid (31 mg, 65%). $^1$H-NMR (δ, ppm, DMSO-$d_6$): 6.21 (d, 1H, $H_{Py,5}$, J=5.5 Hz), 7.32 (m, 2H, $H_{arom,Naph}$), 7.53-7.71 (m, 5H, $H_{arom,naph+Ph'}$), 7.96 (t, 2H, $H_{arom,naph}$), 8.09 (s, 1H, $H_{arom,Ph}$), 8.19 (d, 1H, $H_{Py,6}$, J=5.5 Hz), 8.96 and 9.46 (bs, 2H, $NH_{urea}$) 11.39 (s, NH, $NH_{Py}$), 11.44 (s, NH, $NH_{Py'}$). LC-MS (m/z): 480 (M+H, 100).

Synthesis 46

1-(4-(2,3-Dihydro-2-oxo-1H-imidazo[4,5-b]pyridin-7-yl-oxy)-2-fluorophenyl)-3-(4-chloro-3-(trifluoromethyl)phenyl)urea (CJS 3253)

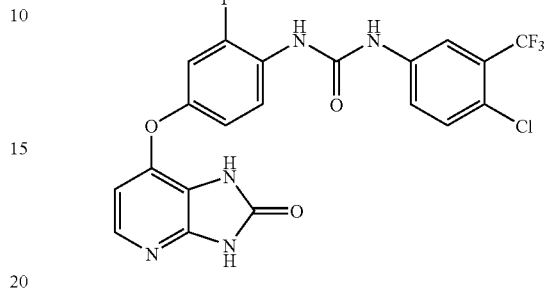

Method H2 was used with 7-(4-amino-3-fluorophenoxy)-1H-imidazo[4,5-b]pyridin-2(3H)-one (26 mg, 0.1 mmol) and 1-chloro-4-isocyanato-2-(trifluoromethyl)benzene (23 mg, 0.1 mmol) to afford the title compound (40 mg, 83%). $^1$H-NMR (δ, ppm, DMSO-$d_6$): 6.45 (d, 1H, $H_{Py,5}$, J=5.91 Hz), 6.98 (d, 1H, $H_{arom,Ph}$), 7.23 (d, 1H, $H_{arom,Ph}$), 7.63 (broad s, 2H, $H_{arom}$), 7.79 (d, 1H, $H_{Py,6}$), 8.05 (s, 1H, $H_{arom,Ph}$), 8.12 (s, 1H, $H_{arom'}$), 8.69 (s, 1H, $NH_{urea,1}$), 9.49 (s, 1H, $NH_{urea,3}$), 11.22 (s, 1H, $NH_{Py3}$), 11.42 (s, 1H, $NH_{Py2}$). LC-MS (m/z): 481 (M+H, 100).

Synthesis 47

1-(4-(2,3-Dihydro-1-methyl-2-oxo-1H-imidazo[4,5-b]pyridin-7-yl-oxy)phenyl)-3-(4-chloro-3-(trifluoromethyl)phenyl)urea (CJS 3246)

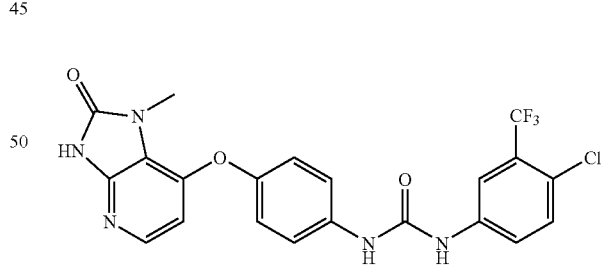

Method H2 was used with 7-(4-amino-3-fluorophenoxy)-1H-imidazo[4,5-b]pyridin-2(3H)-one (25 mg, 0.1 mmol) and 1-chloro-4-isocyanato-2-(trifluoromethyl)benzene (23 mg, 0.1 mmol) to afford the title compound (32 mg, 69%). $^1$H-NMR (δ, ppm, DMSO-$d_6$): 3.47 (s, 3H, $CH_3N$), 6.42 (d, 1H, $H_{Py,5}$, J=5.94 Hz), 7.16 (d, 2H, $H_{arom,Ph,3+5}$, J=8.94 Hz), 7.55 (d, 2H, $H_{arom,Ph,2+6}$), 7.64 (broad s, 2H, $H_{arom'}$), 7.80 (d, 1H, $H_{Py,6}$), 8.13 (s, 1H, $H_{arom'}$), 8.99 (s, 1H, $NH_{urea1}$), 9.23 (s, 1H, $NH_{urea,3}$), 11.63 (s, 1H, $NH_{Py3}$). LC-MS (m/z): 478 (M, 100).

Synthesis 48

1-(4-Chloro-3-(trifluoromethyl)phenyl)-3-(3-methyl-4-(2-oxo-2,3-dihydro-1H-imidazo[4,5-b]pyridin-7-yl-oxy)phenyl)urea (CJS 3410)

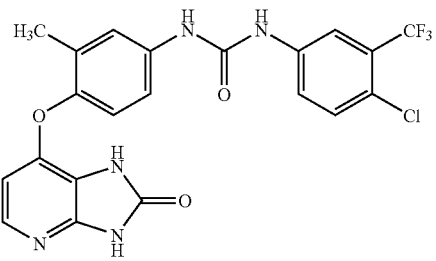

Method H2 was used with 7-(4-amino-2-methylphenoxy)-1H-imidazo[4,5-b]pyridin-2(3H)-one (20 mg, 0.078 mmol) to furnish the title compound (27 mg, 72%). $^1$H-NMR (500 MHz, DMSO-$d_6$) δ: 2.13 (s, 3H), 6.17 (d, 1H, J=5.7 Hz), 7.05 (d, 1H, J=8.6 Hz), 7.35 (d, 1H, J=8.8 Hz), 7.48 (s, 1H), 7.60-7.65 (m, 2H), 7.72 (d, 1H, J=5.7 Hz), 8.12 (s, 1H), 8.86 (s, 1H), 9.17 (s, 1H), 11.17 (s, 1H), 11.31 (s, 1H). m/z 478.1 [(M+H)$^+$ calcd. for $C_{21}H_{15}ClF_3N_5O_3$ 477.1].

(XI) Synthesis of Ureas from Isocyanates and Amines

2. Ureas from 2-amino-3-nitropyridine intermediates (according to Scheme 4 and Scheme 5)

Synthesis 49

1-(4-(2-Amino-3-nitropyridin-4-yl-oxy)phenyl)-3-(4-chloro-3-(trifluoromethyl)phenyl)urea (CJS 3231)

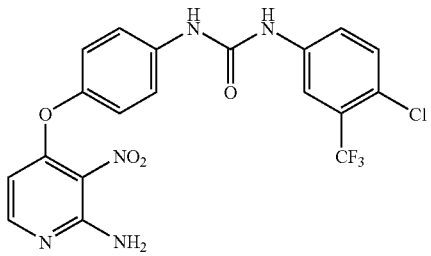

Method H3 (in DCM). 4-(4-Aminophenoxy)-3-nitropyridin-2-amine (170 mg, 0.69 mmol) was dissolved in dry DCM (5 mL) and cooled to 0° C. 4-Chloro-3-trifluoromethyl-phenyl isocyanate (153 mg, 0.69 mg) was dissolved in dry DCM (3 mL) and was added dropwise to the cooled solution. The reaction mixture was allowed to warm at room temperature and was stirred for 20 hours under argon. The resulting precipitate was recovered by filtration, washed with more DCM and dried, to afford the title compound (240 mg, 74%). $^1$H-NMR (δ, ppm, DMSO-$d_6$): 5.98 (d, 1H, $H_{Py,5}$, J=5.0 Hz), 7.14-7.18 (m, 4H, $NH_{2,Py}+H_{arom,Ph,3+5}$), 7.57 (d, 2H, $H_{arom,Ph,2+6}$), 7.64 (broad s, 2H, $H_{arom'}$), 8.00 (d, 1H, $H_{Py,6}$), 8.13 (s, 1H, $H_{arom'}$), 9.00 (s, 1H, $NH_{urea,1}$), 9.21 (s, 1H, $NH_{urea,3}$); LC-MS (m/z): 468 (M+H, 100).

Synthesis 50

1-(4-(2-Amino-3-nitropyridin-4-yl-oxy)phenyl)-3-phenylurea (CJS 3241)

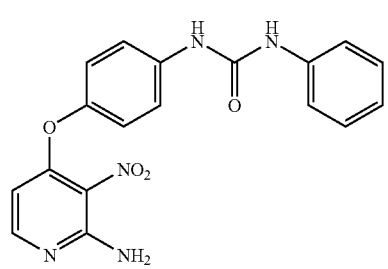

Method H3 was used with 4-(4-aminophenoxy)-3-nitropyridin-2-amine (50 mg, 0.2 mol) and phenyl isocyanate (22 μL, 0.2 mmol) to afford the title compound (54 mg, 74%). $^1$H-NMR (δ, ppm, DMSO-$d_6$): 5.96 (d, 1H, $H_{Py,5}$, J=5.72 Hz), 6.99 (t, 1H, $H_{arom,Ph',4}$), 7.13-7.16 (m, 4H, $NH_{2,Py}+H_{arom,Ph,3+5}$), 7.30 (t, 2H, $H_{arom,Ph',3+5}$, J=7.90 Hz), 7.48 (d, 2H, $H_{arom,Ph',2+6}$'J=7.69 Hz), 7.55 (d, 2H, $H_{arom,Ph,2+6}$, J=8.93 Hz), 8.00 (d, 1H, $H_{Py,6}$, J=5.78 Hz), 8.69 (s, 1H, $NH_{urea,1}$), 8.81 (s, 1H, $NH_{urea,3}$); LC-MS (m/z): 366 (M+H, 100).

Synthesis 51

1-(4-(2-amino-3-nitropyridin-4-yl-oxy)-2-chlorophenyl)-3-(4-chloro-3-(trifluoromethyl)phenyl)urea (CJS 3500)

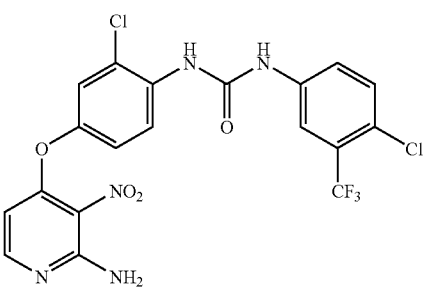

Method H3 was used with 4-(4-amino-3-chlorophenoxy)-3-nitropyridin-2-amine and 4-chloro-3-trifluoromethyl-phenyl isocyanate to afford the title compound (530 mg, 74%). $^1$H-NMR (δ, ppm, DMSO-$d_6$): 6.05 (d, 1H, $H_{Py,5}$, J=5.7 Hz), 7.19 (m, 3H, $H_{arom}$), 7.43 (d, 1H, $H_{Ph,11or12}$, J=2.7 Hz), 7.61 (s, 2H, $NH_{2,Py}$), 8.01 (d, 1H, $H_{Py,6}$, J=5.7 Hz), 8.09 (s, 1H, $H_{arom}$), 8.17 (d, 1H, $H_{arom}$, J=9.1 Hz), 8.49 (s, 1H, $NH_{urea1}$), 9.85 (s, 1H, $NH_{urea3}$). LC-MS (m/z): 502 (M+H, 100).

Synthesis 52

1-(4-(2-amino-3-nitropyridin-4-yl-oxy)-2-methylphenyl)-3-(4-chloro-3-(trifluoromethyl)phenyl) urea (CJS 3501)

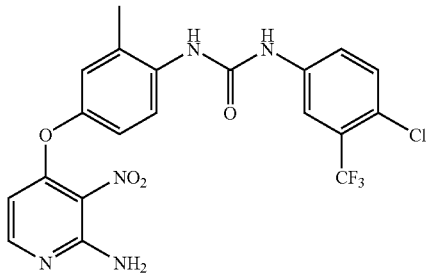

Method H3 was used with 4-(4-amino-3-methylphenoxy)-3-nitropyridin-2-amine and 4-chloro-3-trifluoromethyl-phenyl isocyanate to afford the title compound (582 mg, 78%. $^1$H-NMR (δ, ppm, DMSO-d$_6$): 2.25 (s, 3H, CH$_3$), 5.95 (d, 1H, H$_{Py,5}$, J=5.7 Hz), 6.96 (m, 2H, H$_{arom}$), 7.02 (m, 1H, H$_{arom}$), 7.12 (s, 2H, NH$_{2,Py}$), 7.48-7.68 (m, 2H, H$_{arom}$), 7.73 (d, 1H, H$_{arom}$), 7.95 (d, 1H, H$_{Py,6}$, J=5.7 Hz), 8.13 (m, 1H, H$_{arom}$), 8.65 (s, 1H, NH$_{urea1}$), 9.99 (s, 1H, NH$_{urea3}$). LC-MS (m/z): 482 (M+H, 100).

Synthesis 53

1-(4-(2-Amino-3-nitropyridin-4-yl-oxy)-2-(trifluoromethyl)phenyl)-3-(4-chloro-3-(trifluoromethyl)phenyl)urea (CJS 3503)

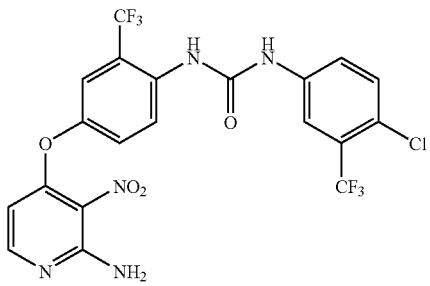

Method H3 was used with 4-(4-amino-3-(trifluoromethyl)phenoxy)-3-nitropyridin-2-amine and 4-chloro-3-trifluoromethyl-phenyl isocyanate to afford the title compound (416 mg, 99%). $^1$H-NMR (δ, ppm, DMSO-d$_6$): 6.06 (d, 1H, H$_{Py,5}$, J=5.7 Hz), 7.26 (m, 2H, H$_{arom}$), 7.54 (m, 2H, H$_{arom}$), 7.64 (s, 2H, NH$_{2,Py}$), 7.96 (m, 1H, H$_{arom}$), 8.05 (d, 1H, H$_{Py,6}$, J=5.7 Hz), 8.11 (m, 1H, H$_{arom}$), 8.28 (s, 1H, NH$_{urea1}$), 9.76 (s, 1H, NH$_{urea3}$). LC-MS (m/z): 536 (M+H, 100).

Synthesis 54

1-(4-(2-Amino-3-nitropyridin-4-yl-oxy)-2,3-dimethylphenyl)-3-(4-chloro-3-(trifluoromethyl)phenyl) urea (CJS 3504)

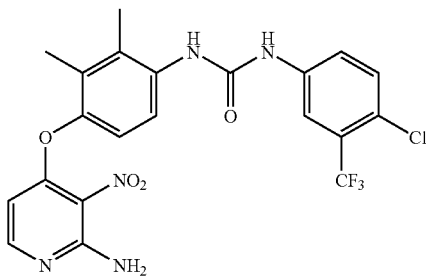

Method H3 was used with 4-(4-amino-2,3-dimethylphenoxy)-3-nitropyridin-2-amine and 4-chloro-3-trifluoromethyl-phenyl isocyanate to afford the title compound (625 mg, 86%) as a yellow powder. $^1$H-NMR (δ, ppm, DMSO-d$_6$): 2.07 (s, 3H, CH$_3$), 2.19 (s, 3H, CH$_3$), 5.77 (d, 1H, H$_{Py,5}$, J=5.7 Hz), 6.98 (d, 1H, H$_{arom}$, J=8.7 Hz), 7.14 (s, 2H, NH$_{2,Py}$), 7.57 (d, 1H, H$_{arom}$, J=8.7 Hz), 7.62 (m, 1H, H$_{arom}$), 7.96 (d, 1H, H$_{Py,6}$, J=5.7 Hz), 8.12 (m, 1H, H$_{arom}$), 8.21 (s, 1H, NH$_{urea1}$), 9.38 (s, 1H, NH$_{urea3}$). LC-MS (m/z): 496 (M+H, 100).

Synthesis 55

1-(4-(2-Amino-3-nitropyridin-4-yl-oxy)-3-chlorophenyl)-3-(4-chloro-3-(trifluoromethyl)phenyl) urea (CJS 3401)

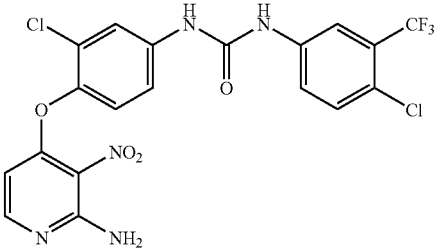

Method H3 was used with 4-(4-amino-2-chlorophenoxy)-3-nitropyridin-2-amine (0.40 g, 1.42 mmol) and 4-chloro-3-(trifluoromethyl)phenyl isocyanate (0.32 g, 1.42 mmol) to afford the title compound (0.71 g, 100%). $^1$H NMR (250 MHz, DMSO-d$_6$) δ 5.86 (d, 1H, J=5.6 Hz), 7.22 (s, 2H), 7.35 (d, 1H, J=8.8 Hz), 7.44 (dd, 1H, Ja=8.8 Hz, Jb=2.4 Hz), 7.60-7.69 (m, 2H), 7.87 (d, 1H, J=2.4 Hz), 7.99 (d, 1H, J=5.7 Hz), 8.10 (d, 1H, J=2.1 Hz), 9.17 (s, 1H), 9.29 (s, 1H). m/z 502.2 [(M+H)$^+$ calcd. for C$_{19}$H$_{12}$Cl$_2$F$_3$N$_5$O$_4$ 501.0].

Synthesis 56

1-(4-(2-Amino-3-nitropyridin-4-yl-oxy)-3-fluorophenyl)-3-(4-chloro-3-(trifluoromethyl)phenyl) urea (CJS 3404)

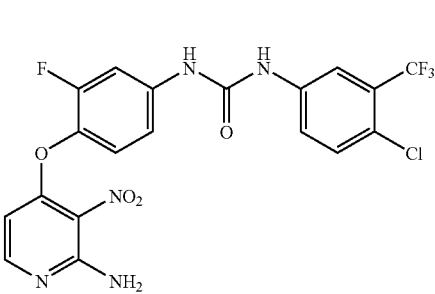

Method H3 was used with 4-(4-amino-2-fluorophenoxy)-3-nitropyridin-2-amine (0.25 g, 0.946 mmol) and 4-chloro-3-(trifluoromethyl)phenyl isocyanate (0.21 g, 0.946 mmol) to afford the title compound (0.19 g, 42%). $^1$H NMR (250 MHz, 6, ppm, DMSO-$d_6$): 5.98 (dd, 1H, Ja=5.7 Hz, Jb=1.0 Hz), 7.21 (s, 2H), 7.26 (dd, 1H, Ja=9.1 Hz, Jb=2.3 Hz), 7.34 (t, 1H, J=8.8 Hz), 7.60-7.73 (m, 3H), 8.01 (d, 1H, J=5.7 Hz), 8.10 (d, 1H, J=2.1 Hz), 9.19 (s, 1H), 9.27 (s, 1H). m/z 486.1 [(M+H)$^+$ calcd. for $C_{19}H_{12}ClF_4N_5O_4$ 485.1].

Synthesis 57

1-(4-(2-Amino-3-nitropyridin-4-yl-oxy)-3,5-difluorophenyl)-3-(4-chloro-3-(trifluoromethyl)phenyl)urea (CJS 3406)

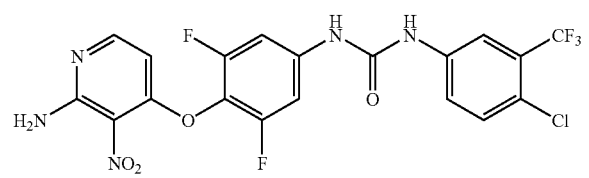

Method H3 was used with 4-(4-amino-2,6-difluorophenoxy)-3-nitropyridin-2-amine (0.20 g, 0.709 mmol) and 4-chloro-3-(trifluoromethyl)phenyl isocyanate (0.16 g, 0.709 mmol) to afford the title compound (0.085 g, 24%). $^1$H NMR (250 MHz, 6, ppm, DMSO-$d_6$): 6.11 (d, 1H, J=5.7 Hz), 7.28 (s, 2H), 7.46 (d, 2H, J=10.3 Hz), 7.61-7.71 (m, 2H), 8.04 (d, 1H, J=5.7 Hz), 8.09 (d, 1H, J=2.1 Hz), 9.36 (s, 1H), 9.40 (s, 1H). m/z 504.0 [(M+H)$^+$ calcd. for $C_{19}H_{11}ClF_5N_5O_4$ 503.0].

Synthesis 58

1-(4-(2-Amino-3-nitropyridin-4-yl-oxy)-3-methylphenyl)-3-(4-chloro-3-(trifluoromethyl)phenyl)urea (CJS 3408)

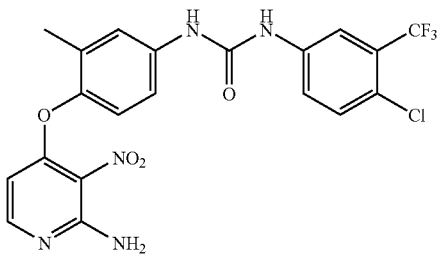

Method H3 was used with 4-(4-amino-2-methylphenoxy)-3-nitropyridin-2-amine (0.22 g, 0.991 mmol) and 4-chloro-3-(trifluoromethyl)phenyl isocyanate (0.16 g, 0.709 mmol) to afford the title compound (0.49 g, 100%). $^1$H NMR (250 MHz, 6, ppm, DMSO-$d_6$): 2.10 (s, 3H), 5.81 (d, 1H, J=5.7 Hz), 7.08 (d, 1H, J=8.7 Hz), 7.14 (s, 2H), 7.37 (dd, 1H, Ja=8.8 Hz, Jb=2.6 Hz), 7.49 (d, 1H, J=2.4 Hz), 7.58-7.66 (m, 2H), 7.96 (d, 1H, J=5.7 Hz), 8.12 (d, 1H, J=2.1 Hz), 8.89 (s, 1H), 9.16 (s, 1H). m/z 482.1 [(M+H)$^+$ calcd. for $C_{20}H_{15}ClF_3N_5O_4$ 481.1].

(XII) Synthesis of Ureas from Activated Carbamates and Amines (According to Scheme 3 and Scheme 19)

Synthesis 59

1-(3-tert-Butyl-1-(4-fluorophenyl)-1H-pyrazol-5-yl)-3-(4-(2-oxo-2,3-dihydro-1H-imidazo[4,5-b]pyridin-7-yl-oxy)phenyl)urea (CJS 3600)

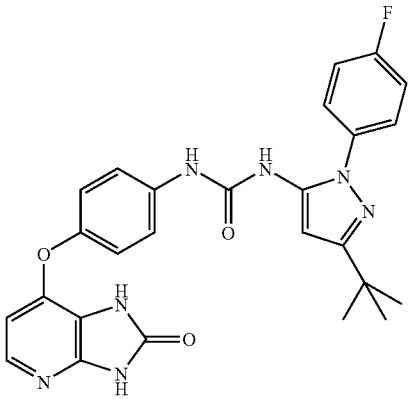

Method I1. A mixture of phenyl 3-tert-butyl-1-(4-fluorophenyl)-1H-pyrazol-5-yl-carbamate (66 mg, 0.18 mmol) and 7-(4-aminophenoxy)-1H-imidazo[4,5-b]pyridin-2(3H)-one (30 mg, 0.12 mmol) in anhydrous THF (1.5 mL) containing 4 Angstrom molecular sieves was heated at 50° C. for 14 hours. After dilution with EtOAc (10 mL) and filtration to remove the molecular sieves, the solution was washed with 0.5 M citric acid (aqueous), saturated NaHCO$_3$ (aqueous) and brine. The organic layer was dried over MgSO$_4$ and the solvent was evaporated under reduced pressure. The orange solid residue was washed with Et$_2$O to afford the title compound (52 mg, 85%) as a slightly orange solid. $^1$H-NMR (6, ppm, DMSO-$d_6$): 1.28 (s, 9H, t-Bu), 6.31 (d, 1H, H$_{Py,5}$, J=6.0 Hz), 6.35 (s, 1H, H$_{Pyz,4}$), 7.09 (d, 2H, H$_{arom,Ph,3+5}$, J=8.9 Hz), 7.37 (t, 2H, H$_{arom,4-F-Ph,3+5}$ J=8.8 Hz), 7.47 (d, 2H, H$_{arom,Ph,2+6}$, J=8.9 Hz), 7.57 (dd, 2H, H$_{arom,4-F-Ph,2+6}$ J=8.8 Hz and J=5.0 Hz), 7.74 (d, 1H, H$_{Py,6}$, J=6.0 Hz), 8.37 (bs, 1H, NH$_{urea}$), 9.06 (bs, 1H, NH$_{urea}$), 11.16 (bs, 1H, NH$_{Py3}$) 11.34 (bs, 1H, NH$_{Py2}$). LC-MS (m/z): 502 (M+H, 100).

Synthesis 60

1-(3-tert-Butyl-1-methyl-1H-pyrazol-5-yl)-3-(4-(2-oxo-2,3-dihydro-1H-imidazo[4,5-b]pyridin-7-yl-oxy)phenyl)urea (CJS 3601)

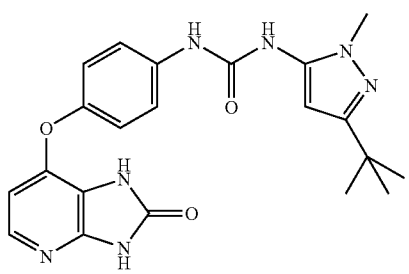

Method I2. A solution of phenyl 3-tert-butyl-1-methyl-1H-pyrazol-5-yl-carbamate (37 mg, 0.13 mmol) and 7-(4-aminophenoxy)-1H-imidazo[4,5-b]pyridin-2(3H)-one (30 mg, 0.12 mmol) in anhydrous DMSO (1 mL) was heated at 85° C. for 2 hours. After cooling to room temperature, the solution was diluted in EtOAc (10 mL), washed twice with H$_2$O and once with brine. The organic layer was dried over MgSO$_4$ and the solvent was evaporated under reduced pressure. The solid residue was washed with Et$_2$O to afford the title compound (25 mg, 49%) as an off-white solid. $^1$H-NMR (δ, ppm, DMSO-d$_6$): 1.32 (s, 9H, t-Bu), 3.60 (s, 3H, CH$_3$N), 6.04 (s, 1H, H$_{Pyz,4}$), 6.33 (d, 1H, H$_{Py,5}$, J=6.0 Hz), 7.11 (d, 2H, H$_{arom,Ph,3+5}$, J=8.8 Hz), 7.53 (d, 2H, H$_{arom,Ph,2+6}$, J=8.8 Hz), 7.75 (d, 1H, H$_{Py,6}$, J=6.0 Hz), 8.54 (bs, 1H, NH$_{urea}$), 9.02 (bs, 1H, NH$_{urea}$), 11.18 (bs, 1H, NH$_{Py3}$), 11.35 (bs, 1H, NH$_{Py2}$). LC-MS (m/z): 422 (M+H, 100).

Synthesis 61

1-(3-tert-Butyl-1-phenyl-1H-pyrazol-5-yl)-3-(4-(2-oxo-2,3-dihydro-1H-imidazo[4,5-b]pyridin-7-yl-oxy)phenyl)urea (CJS 3608)

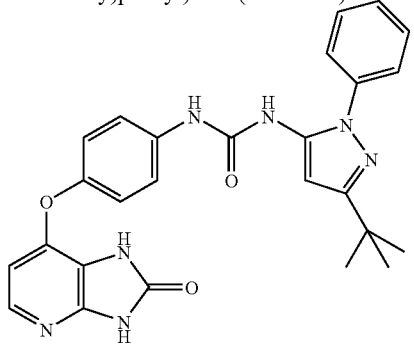

Method I2 was used with phenyl 3-tert-butyl-1-phenyl-1H-pyrazol-5-yl-carbamate to afford the title compound (43 mg, 45%) as an orange solid. $^1$H-NMR (δ, ppm, DMSO-d$_6$): 1.28 (s, 9H, t-Bu), 6.32 (d, 1H, H$_{Py,5}$, J=6.0 Hz), 6.37 (s, 1H, H$_{Pyz,4}$), 7.10 (d, 2H, H$_{arom,Ph,3+5}$, J=9.0 Hz), 7.37-7.54 (m, 5H, H$_{arom,Ph-Pyz}$), 7.47 (d, 2H, H$_{arom,Ph,2+6}$, J=9.0 Hz), 7.75 (d, 1H, H$_{Py,6}$, J=6.0 Hz), 8.40 (bs, 1H, NH$_{urea}$), 9.11 (bs, 1H, NH$_{urea}$), 11.16 (bs, 1H, NH$_{Py3}$), 11.34 (bs, 1H, NH$_{Py2}$). LC-MS (m/z): 484 (M+H, 100).

Synthesis 62

1-(3-tert-Butyl-1-(4-chlorophenyl)-1H-pyrazol-5-yl)-3-(4-(2-oxo-2,3-dihydro-1H-imidazo[4,5-b]pyridin-7-yl-oxy)phenyl)urea (CJS 3609)

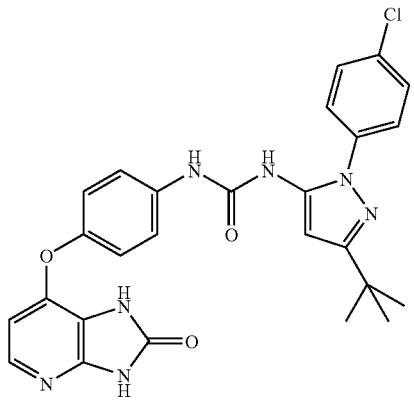

Method I2 was used with phenyl 3-tert-butyl-1-(4-chlorophenyl)-1H-pyrazol-5-yl-carbamate to afford the title compound (30 mg, 57%) as a slightly pink solid. $^1$H-NMR (δ, ppm, DMSO-d$_6$): 1.27 (s, 9H, t-Bu), 6.31 (d, 1H, H$_{Py,5}$, J=6.0 Hz), 6.37 (s, 1H, H$_{Pyz,4}$), 7.10 (d, 2H, H$_{arom,Ph,3+5}$, J=9.0 Hz), 7.48 (d, 2H, H$_{arom,Ph,2+6}$, J=9.0 Hz), 7.58 (bs, 4H, H$_{arom,4-Cl-Ph}$), 7.74 (d, 1H, H$_{Py,6}$, J=6.0 Hz), 8.52 (bs, 1H, NH$_{urea}$), 9.16 (bs, 1H, NH$_{urea}$), 11.20 (bs, 1H, NH$_{Py3}$), 11.38 (bs, 1H, NH$_{Py2}$). LC-MS (m/z): 518 (M+H, 100).

Synthesis 63

1-(3-tert-Butyl-1-p-tolyl-1H-pyrazol-5-yl)-3-(4-(2-oxo-2,3-dihydro-1H-imidazo[4,5-b]pyridin-7-yl-oxy)phenyl)urea (CJS 3614)

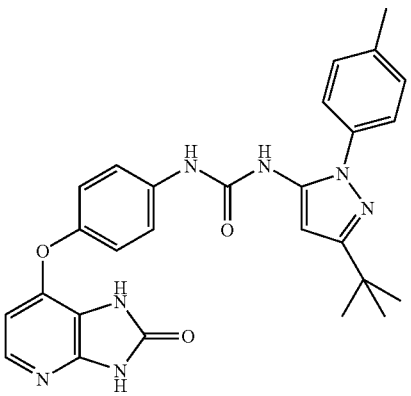

Method I2 was used with phenyl 3-tert-butyl-1-p-tolyl-1H-pyrazol-5-yl-carbamate to afford the title compound (40 mg, 67%) as an off-white solid. $^1$H-NMR (δ, ppm, DMSO-d$_6$): 1.27 (s, 9H, t-Bu), 2.37 (s, 3H, CH$_3$Ph), 6.31 (d, 1H, H$_{Py,5}$, J=6.0 Hz), 6.34 (s, 1H, H$_{Pyz,4}$), 7.09 (d, 2H, H$_{arom,Ph,3+5}$, J=8.9 Hz), 7.33 (d, 2H, H$_{arom,p-Tol-Ph}$, J=8.4 Hz), 7.40 (d, 2H, H$_{arom,p-Tol-Ph}$, J=8.4 Hz), 7.47 (d, 2H, H$_{arom,Ph,2+6}$, J=8.9 Hz), 7.74 (d, 1H, H$_{Py,6}$, J=6.0 Hz), 8.38 (bs, 1H, NH$_{urea}$), 9.14 (bs, 1H, NH$_{urea}$), 11.16 (bs, 1H, NH$_{Py3}$), 11.34 (bs, 1H, NH$_{Py2}$). LC-MS (m/z): 498 (M+H, 100).

Synthesis 64

1-(3-tert-Butyl-1-(2,4-difluorophenyl)-1H-pyrazol-5-yl)-3-(4-(2-oxo-2,3-dihydro-1H-imidazo[4,5-b]pyridin-7-yl-oxy)phenyl)urea (CJS 3615)

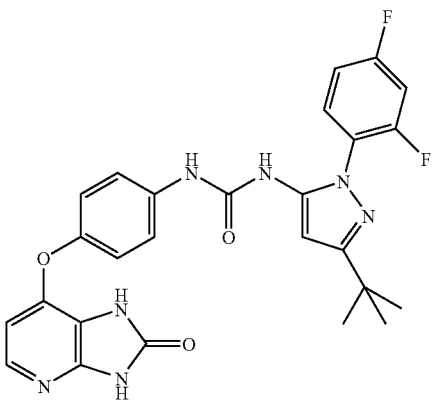

Method I2 was used with phenyl 3-tert-butyl-1-(2,4-difluorophenyl)-1H-pyrazol-5-yl-carbamate to afford the title compound (33 mg, 80%) as an off-white solid. $^1$H-NMR (δ, ppm, DMSO-d$_6$): 1.26 (s, 9H, t-Bu), 6.32 (d, 1H, H$_{Py,5}$, J=6.0 Hz), 6.36 (s, 1H, H$_{Pzy,4}$), 7.09 (d, 2H, H$_{arom,Ph,3+5}$, J=8.9 Hz), 7.29 (m, 1H, H$_{arom,2,4\text{-}diF\text{-}Ph}$), 7.46 (d, 2H, H$_{arom,Ph,2+6}$, J=8.9 Hz), 7.54-7.68 (m, 2H, H$_{arom,2,4\text{-}diF\text{-}ph}$), 7.74 (d, 1H, H$_{Py,6}$, J=6.0 Hz), 8.42 (bs, 1H, NH$_{urea}$), 8.94 (bs, 1H, NH$_{urea}$), 11.17 (bs, 1H, NH$_{Py3}$), 11.34 (bs, 1H, NH$_{Py2}$). LC-MS (m/z): 520 (M+H, 100).

Synthesis 65

1-(1,3-di-tert-Butyl-1H-pyrazol-5-yl)-3-(4-(2-oxo-2,3-dihydro-1H-imidazo[4,5-b]pyridin-7-yl-oxy)phenyl)urea (CJS 3616)

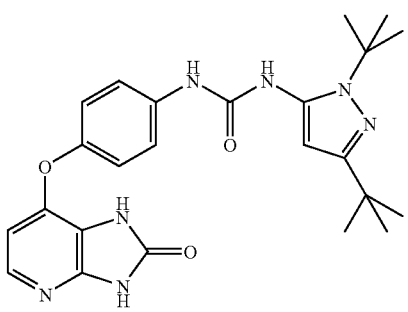

Method I1 was used with phenyl 1,3-di-tert-butyl-1H-pyrazol-5-yl-carbamate to afford the title compound (15 mg, 40%) as an off-white solid. $^1$H-NMR (δ, ppm, DMSO-d$_6$): 1.21 (s, 9H, t-Bu), 1.55 (s, 9H, t-Bu-N), 6.02 (s, 1H, H$_{Pyz,4}$), 6.32 (d, 1H, H$_{Py,5}$, J=6.0 Hz), 7.10 (d, 2H, H$_{arom,Ph,3+5}$, J=9.0 Hz), 7.52 (d, 2H, H$_{arom,Ph,2+6}$, J=9.0 Hz), 7.74 (d, 1H, H$_{Py,6}$, J=6.0 Hz), 7.84 (bs, 1H, NH$_{urea}$), 9.00 (bs, 1H, NH$_{urea}$), 11.17 (bs, 1H, NH$_{Py3}$), 11.34 (bs, 1H, NH$_{Py2}$). LC-MS (m/z): 408 (M-C$_4$H$_7$, 100).

Synthesis 66

1-(3-tert-Butyl-1-(pyridin-2-yl)-1H-pyrazol-5-yl)-3-(4-(2-oxo-2,3-dihydro-1H-imidazo[4,5-b]pyridin-7-yl-oxy)phenyl)urea (CJS 3617)

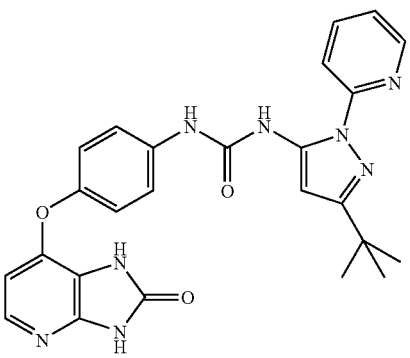

Method I2 was used with phenyl 3-tert-butyl-1-(pyridin-2-yl)-1H-pyrazol-5-yl-carbamate to afford the title compound (37 mg, 74%) as a slightly pink powder. $^1$H-NMR (δ, ppm, DMSO-d$_6$): 1.30 (s, 9H, t-Bu), 6.36 (d, 1H, H$_{Py,5}$, J=6.0 Hz), 6.61 (s, 1H, H$_{Pyz,4}$), 7.15 (d, 2H, H$_{arom,Ph,3+5}$, J=9.0 Hz), 7.34 (m, 1H, H$_{arom,Py\text{-}Pyz}$), 7.59 (d, 2H, H$_{arom,Ph,2+6}$, J=9.0 Hz), 7.77 (d, 1H, H$_{Py,6}$, J=6.0 Hz), 7.89-8.05 (m, 2H, H$_{arom,Py\text{-}Pyz}$), 8.47 (m, 2H, H$_{arom,Py\text{-}Pyz}$ and NH$_{urea}$) 9.99 (bs, 1H, NH$_{urea}$), 11.23 (bs, 1H, NH$_{Py3}$), 11.39 (bs, 1H, NH$_{Py2}$). LC-MS (m/z): 485 (M+H, 100).

Synthesis 67

1-(3-Chloro-5-(trifluoromethyl)phenyl)-3-(4-(2-oxo-2,3-dihydro-1H-imidazo[4,5-b]pyridin-7-yl-oxy)phenyl)urea (CJS 3602)

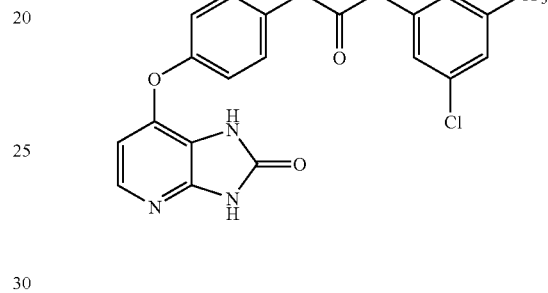

Method I2 was used with phenyl 3-chloro-5-(trifluoromethyl)phenyl-carbamate to afford the title compound (48 mg, 85%) was obtained as a white solid. $^1$H-NMR (δ, ppm, DMSO-d$_6$): 6.32 (d, 1H, H$_{Py,5}$, J=6.0 Hz), 7.12 (d, 2H, H$_{arom,Ph,3+5}$, J=9.0 Hz), 7.39 (bs, 1H, H$_{arom',4}$), 7.55 (d, 2H, H$_{arom,Ph,2+6}$, J=9.0 Hz), 7.75 (d, 1H, H$_{Py,6}$, J=6.0 Hz), 7.84 (m, 2H, H$_{arom',2+6}$), 9.27 (bs, 1H, NH$_{urea}$), 9.51 (bs, 1H, NH$_{urea}$), 11.21 (bs, 1H, NH$_{Py3}$), 11.38 (bs, 1H, NH$_{Py2}$). LC-MS (m/z): 463 (M, 100).

Synthesis 68

1-(4-(2-Oxo-2,3-dihydro-1H-imidazo[4,5-b]pyridin-7-yl-oxy)phenyl)-3-(3-(trifluoromethoxy)phenyl)urea (CJS 3611)

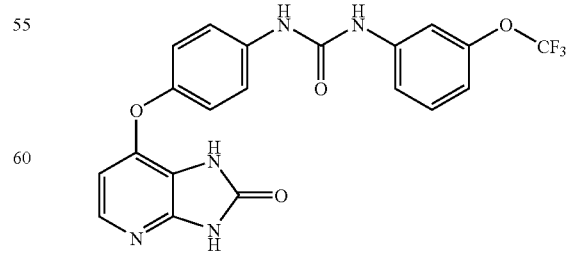

Method I2 was used with phenyl 3-(trifluoromethoxy)phenyl-carbamate to afford the title compound (22 mg, 40%) as brown solid. ¹H-NMR (δ, ppm, DMSO-d₆): 6.33 (d, 1H, H$_{Py,5}$, J=6.0 Hz), 6.94 (~d, 1H, H$_{arom'}$, J=8.0 Hz), 7.12 (d, 2H, H$_{arom,Ph,3+5}$, J=8.9 Hz), 7.30 (~d, 1H, H$_{arom'}$, J=8.4 Hz), 7.40 (t, 1H, H$_{arom'}$, J=8.1 Hz), 7.54 (d, 2H, H$_{arom,Ph,2+6}$, J=8.9 Hz), 7.70 (bs, 1H, H$_{arom',2}$), 7.75 (d, 1H, H$_{Py,6}$, J=6.0 Hz), 8.97 (bs, 1H, NH$_{urea}$), 9.13 (bs, 1H, NH$_{urea}$), 11.17 (bs, 1H, NH$_{Py3}$), 11.34 (bs, 1H, NH$_{Py2}$). LC-MS (m/z): 446 (M+H, 100).

Synthesis 69

1-(2-Methoxy-5-(trifluoromethyl)phenyl)-3-(4-(2-oxo-2,3-dihydro-1H-imidazo[4,5-b]pyridin-7-yl-oxy)phenyl)urea (CJS 3613)

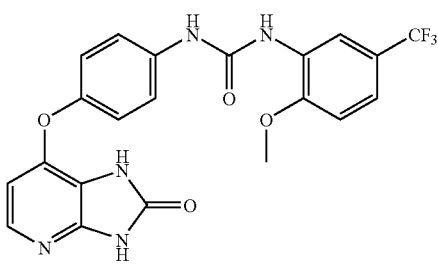

Method I2 was used with phenyl 2-methoxy-5-(trifluoromethyl)phenyl-carbamate to afford the title compound (7 mg, 13%) as an orange powder. ¹H-NMR (δ, ppm, DMSO-d₆): 3.98 (s, 3H, OCH₃), 6.34 (d, 1H, H$_{Py,5}$, J=6.0 Hz), 7.13 (d, 2H, H$_{arom,Ph,3+5}$, J=8.9 Hz), 7.20 (d, 1H, H$_{arom',3}$, J=8.5 Hz), 7.32 (dd, 1H, H$_{arom',4}$, J=8.5 Hz and J=1.6 Hz), 7.54 (d, 2H, H$_{arom,Ph,2+6}$, J=8.9 Hz), 7.75 (d, 1H, H$_{Py,6}$, J=6.0 Hz), 8.51 (bs, 1H, NH$_{urea}$), 8.55 (~d, 1H, H$_{arom',6}$, J=2.0 Hz), 9.52 (bs, 1H, NH$_{urea}$), 11.17 (bs, 1H, NH$_{Py3}$) 11.34 (bs, 1H, NH$_{Py2}$) LC-MS (m/z): 460 (M+H, 100).

Synthesis 70

1-(4-tert-Butylthiazol-2-yl)-3-(4-(2-oxo-2,3-dihydro-1H-imidazo[4,5-b]pyridin-7-yl-oxy)phenyl)urea (CJS 3603)

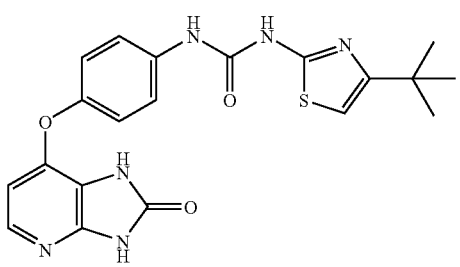

Method I2 was used with phenyl 4-tert-butylthiazol-2-yl-carbamate to afford the title compound (17 mg, 33%) as an off-white solid. ¹H-NMR (δ, ppm, DMSO-d₆): 1.25 (s, 9H, t-Bu), 6.34 (d, 1H, H$_{Py,5}$, J=6.0 Hz), 6.63 (s, 1H, H$_{Thz,5}$), 7.14 (d, 2H, H$_{arom,Ph,3+5}$, J=8.9 Hz), 7.54 (d, 2H, H$_{arom,Ph,2+6}$, J=8.9 Hz), 7.75 (d, 1H, H$_{Py,6}$, J=6.0 Hz), 9.25 (bs, 1H, NH$_{urea}$), 10.68 (bs, 1H, NH$_{urea}$), 11.17 (bs, 1H, NH$_{Py3}$), 11.34 (bs, 1H, NH$_{Py2}$). LC-MS (m/z): 425 (M+H, 100).

Synthesis 71

1-(4-(2-Oxo-2,3-dihydro-1H-imidazo[4,5-b]pyridin-7-yl-oxy)phenyl)-3-(5-(tetrahydrofuran-2-yl)-1,3,4-thiadiazol-2-yl)urea (CJS 3610)

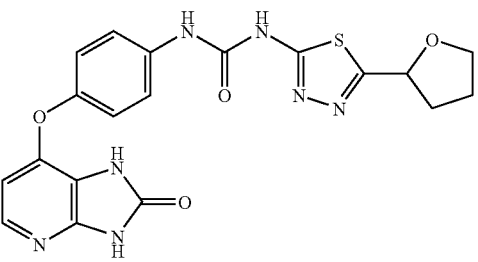

Method I2 was used with phenyl 5-(tetrahydrofuran-2-yl)-1,3,4-thiadiazol-2-yl-carbamate to afford the title compound (61 mg, 81%) as an off-white solid. ¹H-NMR (δ, ppm, DMSO-d₆): 2.00 and 2.35 (m, 4H, CHCH₂CH₂), 3.88 (m, 2H, CH₂O), 5.16 (dd, 1H, CH—O, J=7.3 Hz and J=5.5 Hz), 6.35 (d, 1H, H$_{Py,5}$, J=5.9 Hz), 7.14 (d, 2H, H$_{arom,Ph,3+5}$, J=8.9 Hz), 7.58 (d, 2H, H$_{arom,Ph,2+6}$, J=8.9 Hz), 7.76 (d, 1H, H$_{Py,6}$, J=5.9 Hz), 9.27 (bs, 1H, NH$_{urea}$), 11.18 (bs, 2H, NH$_{urea}$ and NH$_{Py3}$), 11.35 (bs, 1H, NH$_{Py2}$). LC-MS (m/z): 440 (M+H, 100).

Synthesis 72

1-(4-Chloro-2-methoxy-5-(trifluoromethyl)phenyl)-3-(4-(2-oxo-2,3-dihydro-1H-imidazo[4,5-b]pyridin-7-yl-oxy)phenyl)urea (CJS 3618)

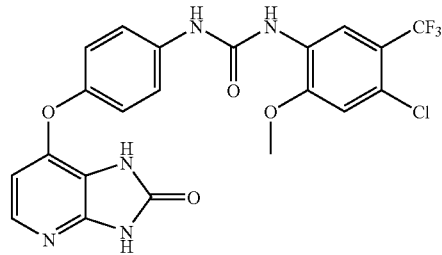

Method I2 was used with phenyl 4-chloro-2-methoxy-5-(trifluoromethyl)phenyl-carbamate to afford the title compound (47 mg, 92%) as a slightly pink powder. ¹H-NMR (δ, ppm, DMSO-d₆): 4.00 (s, 3H, CH₃—O), 6.34 (d, 1H, H$_{Py,5}$, J=5.9 Hz), 7.13 (d, 2H, H$_{arom,Ph,3+5}$, J=8.9 Hz), 7.35 (s, 1H, H$_{arom',3}$), 7.53 (d, 2H, H$_{arom,Ph,2+6}$, J=8.9 Hz), 7.76 (d, 1H, H$_{Py,6}$, J=5.9 Hz), 8.59 (bs, 1H, NH$_{urea}$), 8.68 (s, 1H, H$_{arom',6}$), 9.64 (bs, 1H, NH$_{urea}$), 11.17 (bs, 1H, NH$_{Py3}$), 11.34 (bs, 1H, NH$_{Py2}$).

Synthesis 73

1-(3-isopropyl-1-phenyl-1H-pyrazol-5-yl)-3-(4-(2-oxo-2,3-dihydro-1H-imidazo[4,5-b]pyridin-7-yl-oxy)phenyl)urea (CJS 3619)

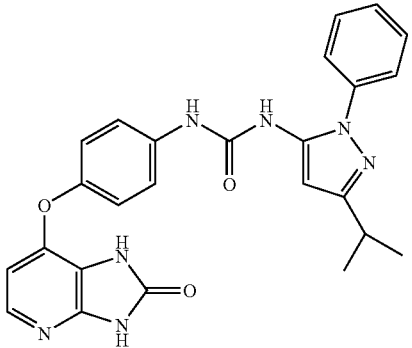

Method F was used with phenyl 3-isopropyl-1-phenyl-1H-pyrazol-5-yl-carbamate (50 mg, 0.15 mmol) to afford the title compound (23 mg, 48%) as a slightly pink solid. $^1$H-NMR (δ, ppm, DMSO-d$_6$): 1.23 (d, 6H, (CH$_3$)$_2$CH, J=6.9 Hz), 2.89 (m, 1H, CH(CH$_3$)$_2$, J=6.9 Hz), 6.31 (d, 1H, H$_{Py,5}$, J=5.9 Hz), 6.33 (s, 1H, H$_{Pyz,4}$), 7.10 (d, 2H, H$_{arom,Ph,3+5}$, J=8.9 Hz), 7.40-7.54 (m, 5H, H$_{arom,Ph-Pyz}$), 7.47 (d, 2H, H$_{arom,Ph,2+6}$, J=8.9 Hz), 7.74 (d, 1H, H$_{Py,6}$, J=5.9 Hz), 8.44 (bs, 1H, NH$_{urea}$), 9.13 (bs, 1H, NH$_{urea}$), 11.20 (bs, 1H, NH$_{Py3}$), 11.37 (bs, 1H, NH$_{Py2}$).

Synthesis 74

1-(1-(benzyl)-3-tert-butyl-1H-pyrazol-5-yl)-3-(4-(2-oxo-2,3-dihydro-1H-imidazo[4,5-b]pyridin-7-yl-oxy)phenyl)urea (CJS 3676)

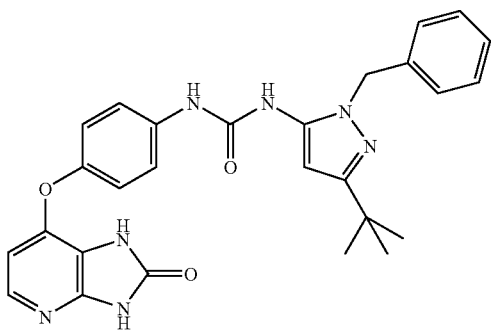

Method I2 was used with phenyl 1-(benzyl)-3-tert-butyl-1H-pyrazol-5-yl-carbamate to afford the title compound (35 mg, 46%) as an off-white solid. $^1$H-NMR (δ, ppm, DMSO-d$_6$): 1.22 (s, 9H, t-Bu), 5.20 (s, 2H, CH$_2$), 6.16 (s, 1H, H$_{Pyz,4}$), 6.32 (d, 1H, H$_{Py,5}$, J=5.5 Hz), 7.08 (d, 2H, H$_{arom,Ph'}$, J=7.5 Hz), 7.11 (d, 2H, H$_{arom,Ph,3+5}$, J=8.5 Hz), 7.24-7.35 (m, 3H, H$_{arom,Ph'}$), 7.50 (d, 2H, H$_{arom,Ph,2+6}$, J=8.5 Hz), 7.74 (d, 1H, H$_{Py,6}$, J=5.5 Hz), 8.55 (bs, 1H, NH$_{urea}$), 8.90 (bs, 1H, NH$_{urea}$), 11.20 (bs, 1H, NH$_{Py3}$), 11.37 (bs, 1H, NH$_{Py2}$).

Synthesis 75

1-(3-tert-butyl-1-(propyl)-1H-pyrazol-5-yl)-3-(4-(2-oxo-2,3-dihydro-1H-imidazo[4,5-b]pyridin-7-yl-oxy)phenyl)urea (CJS 3677)

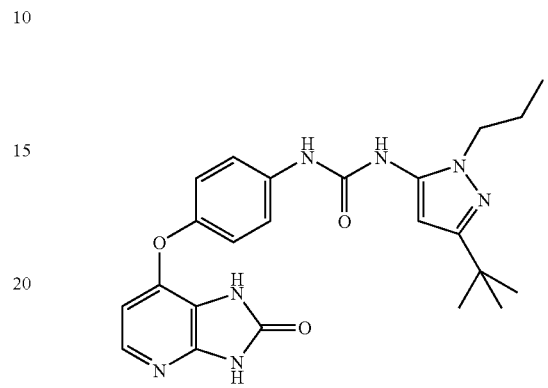

Method I2 was used with phenyl 3-tert-butyl-1-(propyl)-1H-pyrazol-5-yl-carbamate to afford the title compound (29 mg, 50%) as an off-white solid. $^1$H-NMR (δ, ppm, DMSO-d$_6$): 0.85 (t, 3H, CH$_3$, J=7.5 Hz), 1.21 (s, 9H, t-Bu), 1.66-1.74 (m, 2H, CH$_2$), 3.85 (t, 2H, CH$_2$, J=7.0 Hz), 6.06 (s, 1H, H$_{Pyz,4}$), 6.32 (d, 1H, H$_{Py,5}$, J=6.0 Hz), 7.12 (d, 2H, H$_{arom,Ph,3+5}$, J=8.5 Hz), 7.53 (d, 2H, H$_{arom,Ph,2+6}$, J=8.5 Hz), 7.75 (d, 1H, H$_{Py,6}$, J=6.0 Hz), 8.42 (bs, 1H, NH$_{urea}$), 8.95 (bs, 1H, NH$_{urea}$), 11.21 (bs, 1H, NH$_{Py3}$), 11.37 (bs, 1H, NH$_{Py2}$).

Synthesis 76

1-(4-(2,3-Dihydro-1-methyl-2-oxo-1H-imidazo[4,5-b]pyridin-7-yl-oxy)phenyl)-3-(3-tert-butyl-1-(4-fluorophenyl)-1H-pyrazol-5-yl)urea (CJS 3247)

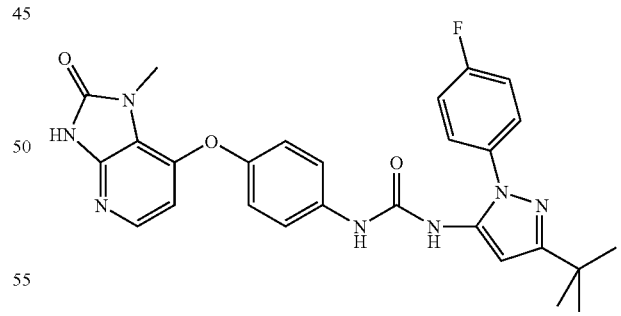

Method I2 was used with 7-(4-aminophenoxy)-1-methyl-1H-imidazo[4,5-b]pyridin-2(3H)-one (25 mg, 0.1 mmol) and phenyl 3-tert-butyl-1-(4-fluorophenyl)-1H-pyrazol-5-yl-carbamate (42 mg, 0.12 mmol) to afford the title compound (18 mg, 35%). $^1$H-NMR (δ, ppm, DMSO-d$_6$): 1.29 (s, 9H, t-Bu), 3.46 (s, 3H, CH$_3$N), 6.37 (s, 1H, H$_{Pyz,4}$), 6.41 (d, 1H, H$_{Py,6}$), 7.13 (d, 2H, H$_{arom,Ph,3+5}$), 7.38 (t, 2H, H$_{arom,4-F-Ph,3+5}$), 7.48 (d, 2H, H$_{arom,Ph,2+6}$), 7.57 (dd, 2H, H$_{arom,4-F-Ph,2+6}$), 7.80 (d, 1H, H$_{Py,6}$), 8.38 (s, 1H, NH$_{urea}$), 9.08 (s, 1H, NH$_{urea}$), 11.61

(bs, 1H, NH$_{Py3}$). LC-MS (m/z): 516 (M+H, 100). Acc. mass (C$_{27}$H$_{26}$N$_7$O$_3$F): calculated 516.2159, found 516.2086.

Synthesis 77

1-(1-(4-chlorophenyl)-3-methyl-1H-pyrazol-5-yl)-3-(4-(2-oxo-2,3-dihydro-1H-imidazo[4,5-b]pyridin-7-yl-oxy)phenyl)urea (CJS 3620)

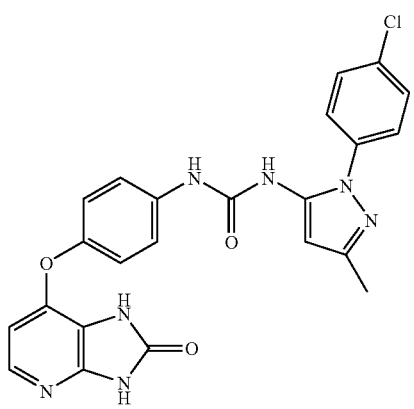

Method F was used with phenyl 1-(4-chlorophenyl)-3-methyl-1H-pyrazol-5-yl-carbamate (41 mg, 0.12 mmol) and 7-(4-aminophenoxy)-1H-imidazo[4,5-b]pyridin-2(3H)-one (20 mg, 0.08 mmol). The solid residue obtained after evaporation of the solvents was washed only with Et$_2$O to afford the title compound (31 mg, 79%) as a pale pink solid. $^1$H-NMR (δ, ppm, DMSO-d$_6$): 2.19 (s, 3H, CH$_3$), 6.28 (s, 1H, H$_{Pyz,4}$), 6.31 (d, 1H, H$_{Py,5}$, J=5.8 Hz), 7.10 (d, 2H, H$_{arom,Ph,3+5}$, J=8.9 Hz), 7.47 (d, 2H, H$_{arom,Ph,2+6}$, J=8.9 Hz), 7.57 (m, 4H, H$_{arom,4-Cl-Ph}$), 7.74 (d, 1H, H$_{Py,6}$, J=5.8 Hz), 8.47 (bs, 1H, NH$_{urea}$), 9.05 (bs, 1H, NH$_{urea}$), 11.19 (bs, 1H, NH$_{Py3}$), 11.37 (bs, 1H, NH$_{Py2}$). $^{13}$C-NMR (δ, ppm, DMSO-d$_6$): 13.7, 99.3, 105.1, 112.8, 119.8, 120.5, 125.7, 129.2, 131.5, 136.3, 137.2, 137.5, 141.2, 145.8, 146.8, 148.2, 148.5, 151.6, 154.1. LC-MS (m/z): 476 (M+H, 100). HRMS (EI): m/z [M+H]$^+$ calcd. for C$_{23}$H$_{19}$N$_7$O$_3$Cl: 476.1238; found: 476.1213.

Synthesis 78

1-(3-tert-butyl-1-methyl-1H-pyrazol-5-yl)-3-(4-(2-oxo-2,3-dihydro-1H-imidazo[4,5-b]pyridin-7-yl-oxy)naphthalen-1-yl)urea (CJS 3679)

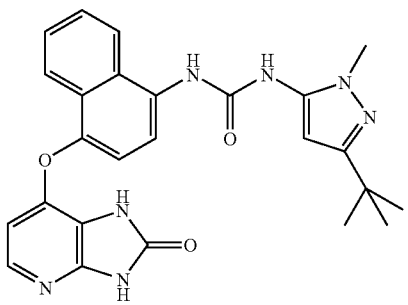

Method I1 was used with phenyl 3-tert-butyl-1-methyl-1H-pyrazol-5-yl-carbamate to afford the title compound (35 mg, 74%) as an off-white solid. $^1$H-NMR (δ, ppm, DMSO-d$_6$): 1.22 (s, 9H, t-Bu), 3.67 (s, 3H, Me), 6.10 (s, 1H, H$_{Pyz,4}$), 6.21 (d, 1H, H$_{Py,5}$, J=5.5 Hz), 7.31 (d, 2H, H$_{arom,Naph}$, J=8.5 Hz), 7.60-7.72 (m, 3H, H$_{arom,Naph}$), 7.94-7.97 (m, 2H, H$_{arom,Naph}$), 8.18 (d, 1H, H$_{Py,6}$, J=5.5 Hz), 8.85 (s, 1H, NH$_{urea}$), 9.01 (s, 1H, NH$_{urea}$), 11.38 (bs, 1H, NH$_{Py3}$), 11.43 (bs, 1H, NH$_{Py2}$). LC-MS (m/z): 471 (M, 100).

Synthesis 79

1-(3-tert-butyl-1-(4-fluorophenyl)-1H-pyrazol-5-yl)-3-(4-(2-oxo-2,3-dihydro-1H-imidazo[4,5-b]pyridin-7-yl-oxy)naphthalen-1-yl)urea (CJS 3680)

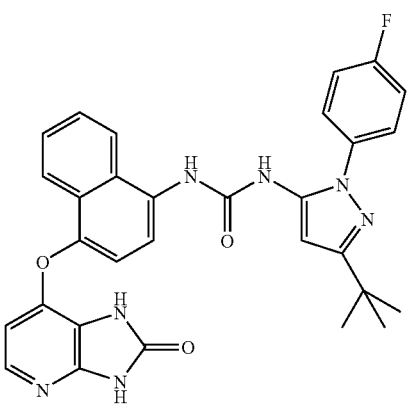

Method I1 was used with phenyl 3-tert-butyl-1-(4-fluorophenyl)-1H-pyrazol-5-yl-carbamate to afford the title compound (12 mg, 22%) as a brown solid. $^1$H-NMR (δ, ppm, DMSO-d$_6$): 1.35 (s, 9H, t-Bu), 6.20 (d, 1H, H$_{Py,5}$, J=6.0 Hz), 6.40 (s, 1H, H$_{Pyz,4}$), 7.29 (d, 2H, H$_{arom,Naph}$, J=8.5 Hz), 7.41 (t, 2H, H$_{arom,4-F-Ph,3+5}$), 7.58-7.70 (m, 5H, H$_{arom,Naph+4-F-Ph}$), 7.87 (d, 1H, H$_{arom,naph}$, J=8.5 Hz), 7.94 (d, 1H, H$_{arom,naph}$, J=8.5 Hz), 8.05 (d, 1H, H$_{Py,6}$, J=6.0 Hz), 8.76 (s, 1H, NH$_{urea}$), 9.06 (s, 1H, NH$_{urea}$), 11.37 (bs, 1H, NH$_{Py3}$), 11.43 (bs, 1H, NH$_{Py2}$). LC-MS (m/z): 552 (M+H, 100).

(XIII) Isocyanate Synthesis Via Curtius Rearrangement

Synthesis 80

4-(3-fluoro-5-isocyanatophenyl)morpholine

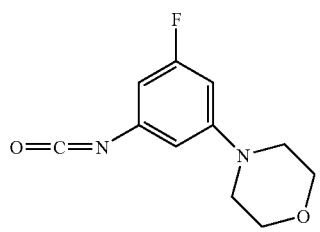

Method J. To a solution of 3-fluoro-5-morpholinobenzoic acid (200 mg, 0.89 mmol) in dry CH$_2$Cl$_2$ (1.1 mL) was added oxalylchloride 2M in CH$_2$Cl$_2$ (0.45 mL, 0.98 mmol). The mixture was stirred at room temperature during 3 hours and the solvent was evaporated under reduced pressure. The residue was diluted with THF (2 mL) and injected while stirring vigorously into an ice-cooled solution of NaN$_3$ (232 mg, 3.56 mmol) in a mixture of H$_2$O (2 mL) and acetone (5 mL). After 15 minutes at 0° C. and 1 minutes at room temperature, the solution was extracted with Et$_2$O (3×10 mL) and dried over MgSO$_4$. The solvents were evaporated under reduced pressure and the residue was refluxed in toluene for 1.5 hours. Removal of the solvent in vacuo afforded a yellow solid (150 mg) containing the expected isocyanate along with the starting 3-fluoro-5-morpholinobenzoic acid (62:38 molar ratio according to $^1$H-NMR). This mixture was used without any further purification. $^1$H-NMR (δ, ppm, CDCl$_3$): 3.14 (t, 4H, CH$_2$—N, J=4.8 Hz), 3.84 (t, 4H, CH$_2$—O, J=4.8 Hz), 6.31 (dt, 1H, H$_{arom,4}$, J=8.7 Hz and J=2.1 Hz), 6.35 (t, 1H, H$_{arom,6}$, J=2.1 Hz), 6.41 (dt, 1H, H$_{arom,2}$, J=11.8 Hz and J=2.1 Hz). IR (v, cm$^{-1}$): 2260 (N=C=O).

(XIV) Pyrazole Synthesis

Synthesis 81

3-tert-Butyl-1-(2,4-difluorophenyl)-1H-pyrazol-5-amine

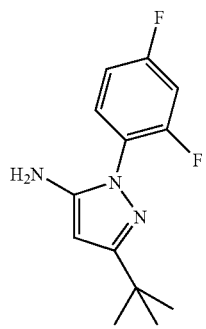

Method K. 2,4-difluorophenylhydrazine hydrochloride (500 mg, 2.8 mmol) and 4,4-dimethyl-3-oxopentanenitrile (386 mg, 3.08 mmol) were dissolved in a 0.2 M ethanolic solution of HCl (15 mL). The solution was heated under reflux for 12 hours. After cooling to room temperature, the mixture was basified with 1 M NaOH until pH 12. EtOAc was added (40 mL) and the aqueous layer was discarded. The solvents were evaporated under reduced pressure and the resulting yellow solid was dissolved in EtOAC (40 mL). The solution was washed with water and brine, and then dried over MgSO$_4$. Evaporation of the solvent in vacuo afforded the title compound (695 mg, quantitative yield) as a yellow solid. $^1$H-NMR (δ, ppm, DMSO-d$_6$): 1.19 (s, 9H, t-Bu), 5.08 (bs, 2H, NH$_2$), 5.30 (s, 1H, H$_{Pyz,4}$), 7.17 (m, 1H, H$_{arom}$), 7.38-7.53 (m, 2H, H$_{arom}$).

Synthesis 82

1,3-di-tert-Butyl-1H-pyrazol-5-amine

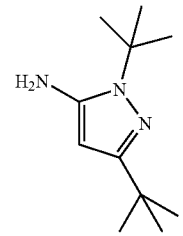

Method K was used with tert-butylhydrazine hydrochloride to afford the title compound (385 mg, 33%) as a pale orange solid. $^1$H-NMR (δ, ppm, DMSO-d$_6$): 1.14 (s, 9H, t-Bu), 1.48 (s, 9H, t-Bu-N), 4.61 (bs, 2H, NH$_2$), 5.23 (s, 1H, H$_{Pyz,4}$). LC-MS (m/z): 196 (M+H, 100).

Synthesis 83

3-tert-Butyl-1-(pyridin-2-yl)-1H-pyrazol-5-amine

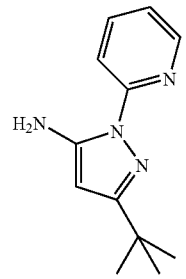

Method K was used with 2-hydrazinopyridine to afford the title compound (165 mg, 27%) as a brown oil. $^1$H-NMR (δ, ppm, DMSO-d$_6$): 1.23 (s, 9H, t-Bu), 5.31 (s, 1H, H$_{Pyz,4}$), 6.67 (bs, 2H, NH$_2$), 7.17 (m, 1H, H$_{arom,Py}$), 7.79-7.93 (m, 2H, H$_{arom,Py}$), 8.35 (m, 1H, H$_{arom,Py}$). LC-MS (m/z): 217 (M+H, 100).

Synthesis 84

1-benzyl-3-tert-butyl-1H-pyrazol-5-amine

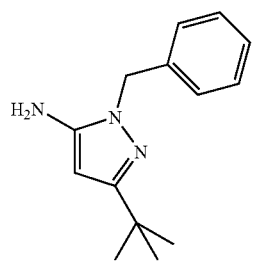

Method K was used with benzylhydrazine dihydrochloride to afford the title compound (585 mg, quantitative yield) as an off-white solid. $^1$H-NMR (δ, ppm, DMSO-d$_6$): 1.16 (s, 9H, t-Bu), 5.04 (s, 4H, NH$_2$ and CH$_2$), 5.18 (s, 1H, H$_{Pyz,4}$), 7.10 (d, 2H, H$_{arom,o}$, J=7.4 Hz), 7.21-7.33 (m, 3H, H$_{arom,p+m}$).

Synthesis 85

3-tert-butyl-1-propyl-1H-pyrazol-5-amine

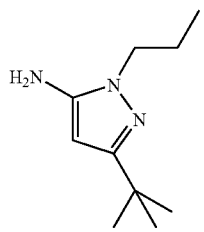

Method K was used with n-propylhydrazine oxalate to afford the title compound (330 mg, quantitative yield) as an off-white solid. ¹H-NMR (δ, ppm, DMSO-$d_6$): 0.83 (t, 3H, $CH_3$—$CH_2$, J=7.4 Hz), 1.14 (s, 9H, t-Bu), 1.63 (m, 2H, $CH_2$—$CH_3$), 3.70 (t, 2H, $CH_2$—N, J=7.4 Hz), 4.86 (bs, 2H, $NH_2$), 5.11 (s, 1H, $H_{Pyz,4}$).

Synthesis 86

3-tert-butyl-1-(pyridin-4-yl)-1H-pyrazol-5-amine

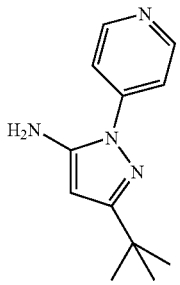

4-hydrazinopyridine hydrochloride (400 mg, 2.74 mmol) was dissolved in MeOH and passed through a column filled with the ion-exchange resin Ambersep 900-OH (Fluka). MeOH was eluted until no product remains in the column (checked by TLC). Concentration of the resulting methanolic solution afforded 4-hydrazinopyridine (285 mg, 95%) as a red oil. ¹H-NMR (δ, ppm, DMSO-$d_6$): 4.14 (s, 2H, $NH_2$), 6.62 (d, 2H, $H_{arom,Py}$, J=6.2 Hz), 7.51 (s, 1H, NH), 8.00 (d, 2H, $H_{arom,Py}$, J=6.2 Hz). A mixture of 4-hydrazinopyridine (285 mg, 2.61 mmol) and 4,4-dimethyl-3-oxopentanenitrile (327 mg, 2.61 mmol) in toluene (1 mL) was heated under reflux during 16 h. After cooling to room temperature, evaporation of the solvent in vacuo afforded a brown residue which was purified by chromatography on silica gel (cyclohexane-EtOAc, 6:4 until 3:7). The title compound (291 mg, 51%) was obtained as a pale yellow solid ($R_f$ 0.27, cyclohexane-EtOAc, 3:7). ¹H-NMR (δ, ppm, DMSO-$d_6$): 1.22 (s, 9H, t-Bu), 5.46 (s, 1H, $H_{Pyz,4}$), 5.56 (s, 2H, $NH_2$), 7.70 (s, 2H, $H_{arom,Py}$), 8.56 (s, 2H, $H_{arom,Py}$). ¹³C-NMR (δ, ppm, DMSO-$d_6$): 29.8 (($CH_3$)$_3$), 31.9 (C($CH_3$)$_3$), 88.7 ($C_{Pyz,4}$), 114.6 ($C_{Py,3+5}$), 146.0 and 148.5 ($C_{Pyz,5}$ and $C_{Pyz,3}$), 150.4 ($C_{Py,2+6}$), 162.5 ($C_{Pyz,4}$). LC-MS (m/z): 217 (M+H, 100).

(XV) Synthesis of Activated Phenyl Carbamates

Synthesis 87

Phenyl 3-tert-butyl-1-(4-fluorophenyl)-1H-pyrazol-5-yl-carbamate

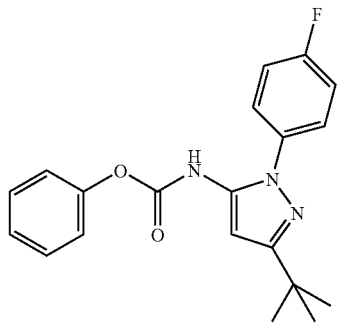

Method L. 3-tert-butyl-1-(4-fluorophenyl)-1H-pyrazol-5-amine (200 mg, 0.86 mmol) was dissolved in dry THF (9 mL). The solution was cooled with an ice bath under nitrogen. Pyridine (90 μL, 1.11 mmol) and phenyl chloroformate (129 μL, 1.03 mmol) were then successively added. The mixture was stirred at 0° C. for 5 minutes and at room temperature for 1.5 hours. The THF was evaporated under reduced pressure and the residue was dissolved in EtOAc (15 mL). The resulting suspension was washed successively with 1M HCl (aqueous), $H_2O$, saturated. $NaHCO_3$ (aqueous) and brine. The organic layer was dried over $MgSO_4$ and the solvent was evaporated under reduced pressure to afford the title compound (300 mg, quantitative yield) as a brown solid. ¹H-NMR (δ, ppm, DMSO-$d_6$): 1.28 (s, 9H, t-Bu), 6.36 (s, 1H, $H_{Pyz,4}$), 7.10-7.60 (m, 9H, $H_{arom}$), 10.03 (bs, 1H, NH).

Synthesis 88

Phenyl 3-tert-butyl-1-methyl-1H-pyrazol-5-yl-carbamate

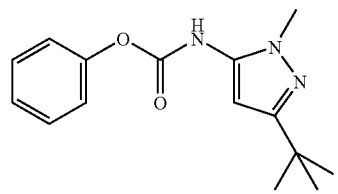

Method L was used with 5-amino-3-tert-butyl-1-methylpyrazole (200 mg, 1.30 mmol), and the title compound (355 mg, quantitative yield) was obtained as a slightly pink powder. ¹H-NMR (δ, ppm, DMSO-$d_6$): 1.20 (s, 9H, t-Bu), 3.65 (s, 3H, CH₃N), 6.04 (s, 1H, H$_{Pyz,4}$), 7.12-7.36 (m, 3H, H$_{arom,o+p}$), 7.43 (t, 2H, H$_{arom,m}$, J=7.8 Hz), 10.11 (bs, 1H, NH).

Synthesis 89

Phenyl 3-tert-butyl-1-phenyl-1H-pyrazol-5-yl-carbamate

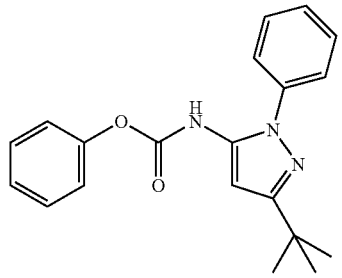

Method L was used with 5-amino-3-tert-butyl-1-phenylpyrazole (200 mg, 0.93 mmol), and the title compound (310 mg, quantitative yield) was obtained as a brown powder. ¹H-NMR (δ, ppm, DMSO-d₆): 1.30 (s, 9H, t-Bu), 6.35 (s, 1H, H$_{Pyz,4}$), 7.12-7.56 (m, 10H, H$_{arom}$), 9.94 (bs, 1H, NH).

Synthesis 90

Phenyl 3-tert-butyl-1-(4-chlorophenyl)-1H-pyrazol-5-yl-carbamate

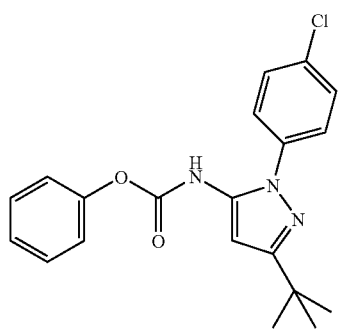

Method L was used with 3-tert-butyl-1-(4-chlorophenyl)-1H-pyrazol-5-amine (230 mg, 0.92 mmol) to afford the title compound (340 mg, quantitative yield) as a slightly yellow solid. ¹H-NMR (δ, ppm, DMSO-d₆): 1.29 (s, 9H, t-Bu), 6.37 (s, 1H, H$_{Pyz,4}$), 7.12-7.60 (m, 9H, H$_{arom}$), 10.00 (bs, 1H, NH).

Synthesis 91

Phenyl 3-tert-butyl-1-p-tolyl-1H-pyrazol-5-yl-carbamate

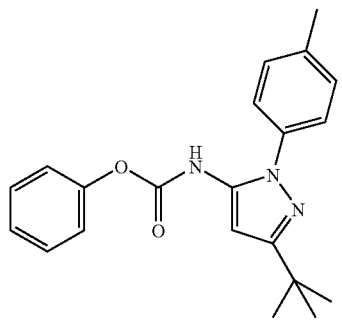

Method L was used with 3-tert-butyl-1-p-tolyl-1H-pyrazol-5-amine (200 mg, 0.87 mmol) to afford the title compound (317 mg, quantitative yield) as a slightly yellow solid. ¹H-NMR (δ, ppm, DMSO-d₆): 1.28 (s, 9H, t-Bu), 2.37 (s, 3H, CH₃Ph), 6.33 (s, 1H, H$_{Pyz,4}$), 7.12-7.44 (m, 9H, H$_{arom}$), 9.93 (bs, 1H, NH).

Synthesis 92

Phenyl 3-tert-butyl-1-(2,4-difluorophenyl)-1H-pyrazol-5-yl-carbamate

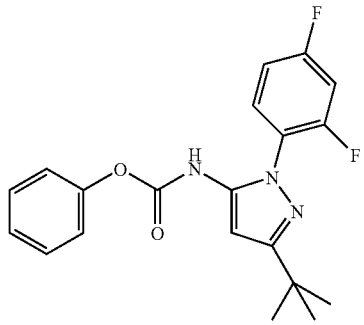

Method L was used with 3-tert-butyl-1-(2,4-difluorophenyl)-1H-pyrazol-5-amine (200 mg, 0.79 mmol), the title compound (293 mg, quantitative yield) was obtained as a yellow foam. ¹H-NMR (δ, ppm, DMSO-d₆): 1.27 (s, 9H, t-Bu), 6.33 (s, 1H, H$_{Pyz,4}$), 7.12-7.60 (m, 8H, H$_{arom}$), 10.17 (bs, 1H, NH).

Synthesis 93

Phenyl 1,3-di-tert-butyl-1H-pyrazol-5-yl-carbamate

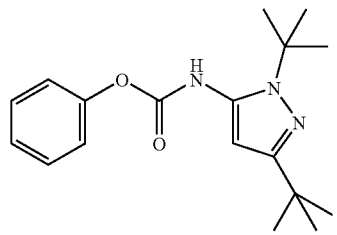

Method L was used with 1,3-di-tert-butyl-1H-pyrazol-5-amine (150 mg, 0.77 mmol) to afford the title compound (243 mg, quantitative yield) as a white powder. ¹H-NMR (δ, ppm, DMSO-d₆): 1.21 (s, 9H, t-Bu), 1.57 (s, 9H, t-Bu-N), 6.06 (s, 1H, H$_{Pyz,4}$), 7.12-7.28 (m, 3H, H$_{arom,o+p}$), 7.42 (t, 2H, H$_{arom,m}$, J=7.7 Hz), 9.55 (bs, 1H, NH).

Synthesis 94

Phenyl 3-tert-butyl-1-(pyridin-2-yl)-1H-pyrazol-5-yl-carbamate

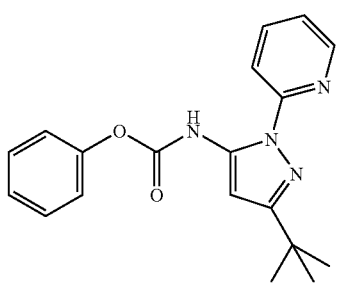

Method L was used with 3-tert-butyl-1-(pyridin-2-yl)-1H-pyrazol-5-amine (133 mg, 0.61 mmol) to afford the title compound (207 mg, quantitative yield) as a brown solid. $^1$H-NMR (δ, ppm, DMSO-d$_6$): 1.30 (s, 9H, t-Bu), 6.49 (s, 1H, H$_{Pyz,4}$), 7.12-7.37 (m, 4H, H$_{arom,o+p}$ and H$_{arom,Py}$), 7.46 (t, 2H, H$_{arom,m}$, J=7.7 Hz), 7.93-8.07 (m, 2H, H$_{arom,Py}$), 8.48 (m, 1H, H$_{arom,Py}$), 11.56 (bs, 1H, NH).

Synthesis 95

Phenyl 3-chloro-5-(trifluoromethyl)phenyl-carbamate

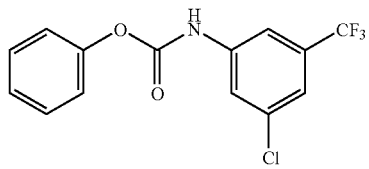

Method L was used with 3-chloro-5-(trifluoromethyl)benzenamine (200 mg, 1.02 mmol) to afford the title compound (309 mg, 96%) as a brown powder. $^1$H-NMR (δ, ppm, DMSO-d$_6$): 7.25-7.53 (m, 6H, H$_{arom}$), 7.85 (s, 2H, H$_{arom}$), 10.80 (bs, 1H, NH).

Synthesis 96

Phenyl 3-(trifluoromethoxy)phenyl-carbamate

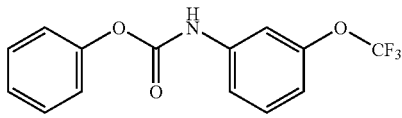

Method L was used with 3-(trifluoromethoxy)aniline (200 mg, 1.13 mmol) to afford the title compound (264 mg, 79%) as a yellow solid. $^1$H-NMR (δ, ppm, DMSO-d$_6$): 7.04 (m, 1H. H$_{arom}$), 7.23-7.51 (m, 7H, H$_{arom}$), 7.61 (s, 1H, H$_{arom}$), 10.54 (bs, 1H, NH). LC-MS (m/z): 320 (M+Na, 100).

Synthesis 97

Phenyl 2-methoxy-5-(trifluoromethyl)phenyl-carbamate

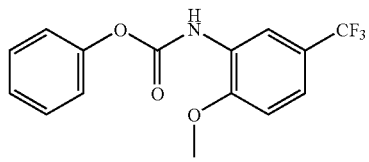

Method L was used with 2-methoxy-5-(trifluoromethyl)aniline (200 mg, 1.04 mmol) to afford the title compound (292 mg, 90%) as a yellow solid. $^1$H-NMR (δ, ppm, DMSO-d$_6$): 3.93 (s, 3H, OCH$_3$), 7.21-7.51 (m, 7H, H$_{arom}$), 8:06 (s, 1H, H$_{arom}$), 9.49 (bs, 1H, NH).

Synthesis 98

Phenyl 4-tert-butylthiazol-2-yl-carbamate

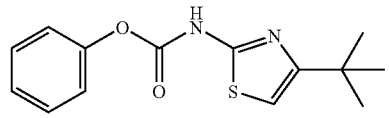

Method L was used with 4-tert-butylthiazol-2-amine (300 mg, 1.92 mmol) to afford the title compound (530 mg, quantitative yield) as a white solid. $^1$H-NMR (δ, ppm, DMSO-d$_6$): 1.26 (s, 9H, t-Bu), 6.77 (s, 1H, H$_{ThZ,5}$), 7.20-7.51 (m, 5H, H$_{arom}$), 12.23 (bs, 1H, NH).

Synthesis 99

Phenyl 5-(tetrahydrofuran-2-yl)-1,3,4-thiadiazol-2-yl-carbamate

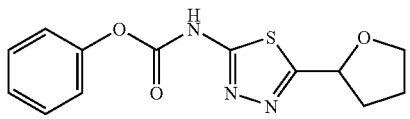

Method L was used with 5-(tetrahydrofuran-2-yl)-1,3,4-thiadiazol-2-amine (140 mg, 0.82 mmol) to afford the title compound (124 mg, 52%) as a white powder. $^1$H-NMR (δ, ppm, DMSO-d$_6$): 2.00 and 2.35 (m, 4H, CHCH$_2$CH$_2$), 3.86 (m, 2H, CH$_2$O), 5.20 (dd, 1H, CH—O, J=7.3 Hz and J=5.4 Hz), 7.28 (m, 3H, H$_{arom,o+p}$), 7.45 (t, 2H, H$_{arom,m}$, J=7.6 Hz), 12.76 (bs, 1H, NH).

Synthesis 100

Phenyl 4-chloro-2-methoxy-5-(trifluoromethyl)phenyl-carbamate

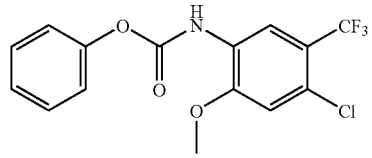

Method L was used with 4-chloro-2-methoxy-5-(trifluoromethyl)benzenamine to afford the title compound (270 mg, quantitative yield) as a yellow oil. $^1$H-NMR (δ, ppm, DMSO-d$_6$): 3.96 (s, 3H, CH$_3$—O), 7.20-7.46 (2m, 6H, H$_{arom}$), 8.17 (s, 1H, H$_{arom}$), 9.62 (bs, 1H, NH).

Synthesis 101

Phenyl 3-isopropyl-1-phenyl-1H-pyrazol-5-yl-carbamate

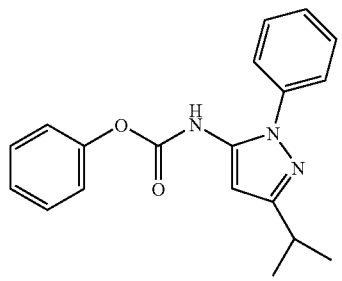

Method L was used with 3-isopropyl-1-phenyl-1H-pyrazol-5-amine to afford the title compound (319 mg, quantitative yield) as an orange oil. $^1$H-NMR (δ, ppm, DMSO-d$_6$): 1.24 (d, 6H, (CH$_3$)$_2$CH, J=6.9 Hz), 2.91 (m, 1H, CH(CH$_3$)$_2$, J=6.9 Hz), 6.32 (s, 1H, H$_{Pyz,4}$), 7.06-7.55 (m, 10H, H$_{arom}$), 10.06 (bs, 1H, NH).

Synthesis 102

Phenyl 3-tert-butyl-1-benzyl-1H-pyrazol-5-yl-carbamate

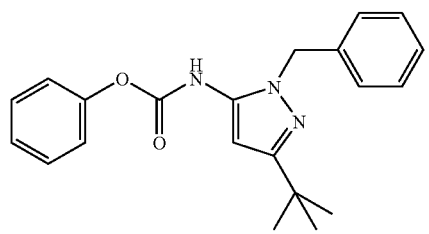

Method L was used with 5-amino-3-tert-butyl-1-benzylpyrazole to afford the title compound (128 mg, 75%) as a yellow solid. $^1$H-NMR (δ, ppm, DMSO-d$_6$): 1.22 (s, 9H, t-Bu), 5.29 (s, 2H, CH$_2$), 6.15 (s, 1H, H$_{Pyz,4}$), 7.10-7.41 (m, 10H, H$_{arom}$), 10.23 (bs, 1H, NH). LC-MS (m/z): 350 (M+H, 100).

Synthesis 103

Phenyl 3-tert-butyl-1-propyl-1H-pyrazol-5-yl-carbamate

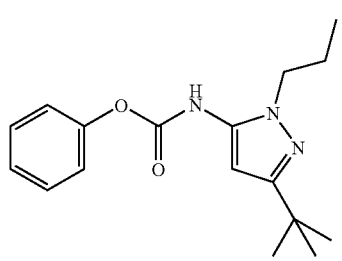

Method L was used with 5-amino-3-tert-butyl-1-propyl pyrazole to afford the title compound (98 mg, 55%) as a white solid. $^1$H-NMR (δ, ppm, DMSO-d$_6$): 0.91 (t, J=7.4 Hz, 3H, CH$_3$), 1.26 (s, 9H, t-Bu), 5.29 (s, 2H, CH$_2$), 1.73-1.80 (m, 2H, CH$_2$), 3.98 (t, J=7.0 Hz) 6.11 (s, 1H, H$_{Pyz,4}$), 7.27-7.34 (m, 3H, H$_{arom}$), 7.47-7.50 (m, 2H, H$_{arom}$), 10.16 (bs, 1H, NH). LC-MS (m/z): 302 (M+H, 100).

Synthesis 104

Phenyl 1-(4-chlorophenyl)-3-methyl-1H-pyrazol-5-yl-carbamate

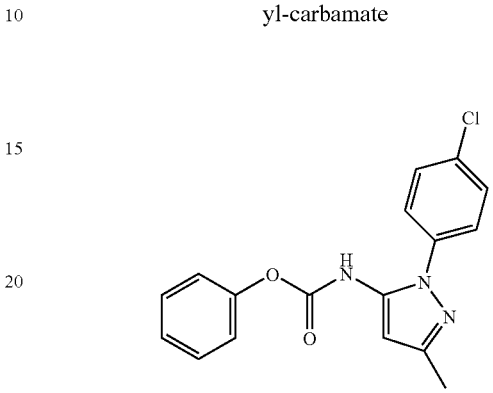

1-(4-chlorophenyl)-3-methyl-1H-pyrazol-5-amine (100 mg, 0.48 mmol) was dissolved in dry THF (6 mL). Pyridine (51 μL, 0.62 mmol) was added and the solution was cooled in an ice bath under nitrogen surpressure. Phenyl chloroformate (73 μL, 0.58 mmol) was slowly added and the mixture was stirred at 0° C. during 5 min and at room temperature during 1.5 h. The mixture was then diluted in EtOAc (10 mL) and the salts remaining were filtrated off. The filtrate was concentrated under reduced pressure. The resulting white solid was washed with a little amount of cold EtOAc and water to afford the title compound (41 mg, 26%) as a white solid. $^1$H-NMR (δ, ppm, DMSO-d$_6$): 2.22 (s, 3H, CH$_3$), 6.28 (s, 1H, H$_{Pyz,4}$), 7.11-7.60 (m, 9H, H$_{arom}$), 10.14 (bs, 1H, NH). LC-MS (m/z): 328 (M+H, 100).

(XVI) Synthesis of Amides

Synthesis 105

N-(4-(2-Oxo-2,3-dihydro-1H-imidazo[4,5-b]pyridin-7-yl-oxy)phenyl)benzamide (CJS 3240)

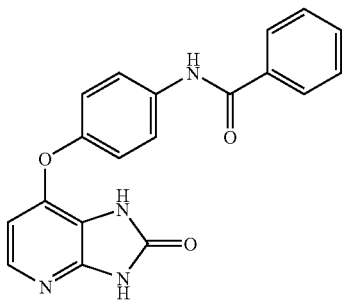

Method M. 7-(4-Aminophenoxy)-2,3-dihydro-2-oxo-1H-imidazo[4,5-b]pyridine (30 mg, 0.13 mmol) and triethylamine (22.3 μL, 0.16 mmol) were mixed in dry THF (3 mL) and benzoyl chloride (19.0 μL, 0.16 mmol) was added. This mixture was heated to reflux for 20 hours and subsequently the solvent was removed in vacuo. The obtained residue was dissolved in acetone (2 mL) and upon addition of water a solid precipitated. This solid was collected, washed with water (2×2 mL) and Et$_2$O (2×2 mL) and dried. The title compound was obtained as a light brown solid (44 mg, 80%). $^1$H-NMR (δ, ppm, DMSO-d$_6$): 6.39 (d, 1H, H$_{Py,5}$, J=5.0 Hz), 7.19 (d, 2H, H$_{arom,Ph,3+5}$, J=7.50 Hz), 7.51-7.63 (m, 3H, H$_{arom,Ph',3+4+5}$), 7.78 (d, 1H, H$_{Py,6}$) 7.86 (d, 2H, H$_{arom,Ph,2+6}$), 7.97 (d, 2H, H$_{arom,Ph',2+6}$), 10.36 (s, 1H, NH$_{amide}$). 11.22 (s, 1H, NH$_{Py3}$) 11.39 (s, 1H, NH$_{Py2}$). LC-MS (m/z): 347 (M+H, 100).

Synthesis 106

N-(4-(2-Oxo-2,3-dihydro-1H-imidazo[4,5-b]pyridin-7-yl-oxy)phenyl)-2-phenyl acetamide (CJS 3665)

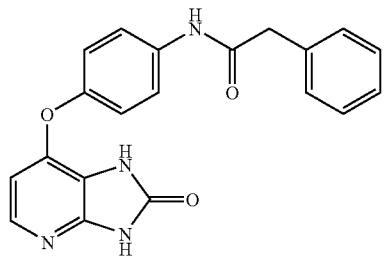

Method M was used with 2-phenylacetyl chloride to afford the title compound as an off-white solid (34 mg, 72%). $^1$H-NMR (δ, ppm, DMSO-d$_6$): 3.64 (s, 2H, CH$_2$), 6.32 (br s, 1H, H$_{Py,5}$), 7.12-7.33 (m, 6H, H$_{arom,Ph',2+3+6}$+H$_{arom,Ph,3+5}$+H$_{arom,Ph',5}$), 7.66 (s, 2H, H$_{arom,Ph,2+6}$), 7.74 (s, 1H, H$_{Py,6}$) 10.29 (s, 1H, NH$_{amide}$), 11.19 (s, 1H, NH$_{Py3}$), 11.37 (s, 1H, NH$_{Py2}$). LC-MS (m/z): 362 (M+2H, 100).

Synthesis 107

2-(3—Methoxyphenyl)-N-(4-(2-oxo-2,3-dihydro-1H-imidazo[4,5-b]pyridin-7-yl-oxy)phenyl)acetamide (CJS 3666)

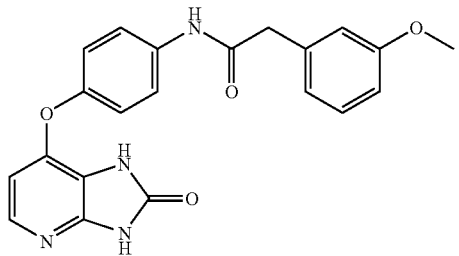

Method M was used with 2-(3-methoxyphenyl)acetyl chloride to afford the title compound as an off-white solid (41 mg, 81%). $^1$H-NMR (δ, ppm, DMSO-d$_6$): 3.61 (s, 2H, CH$_2$), 3.75 (s, 3H, CH$_3$), 6.33 (d, 1H, H$_{Py,5}$, J=6.0 Hz), 6.80-6.93 (m, 3H, H$_{arom,Ph',2+4+6}$), 7.12 (d, 2H, H$_{arom,Ph,3+5}$, J=9.0 Hz), 7.24 (t, 1H, H$_{arom,Ph',3}$, J=8.25 Hz), 7.67 (d, 2H, H$_{arom,Ph,2+6}$), 7.74 (d, 1H, H$_{Py,6}$), 10.23 (s, 1H, NH$_{amide}$), 11.16 (s, 1H, NH$_{Py3}$), 11.34 (s, 1H, NH$_{Py2}$). LC-MS (m/z): 391 (M+H, 100).

Synthesis 108

2-(3,5-Difluorophenyl)-N-(4-(2-oxo-2,3-dihydro-1H-imidazo[4,5-b]pyridin-7-yl-oxy)phenyl)acetamide (CJS 3668)

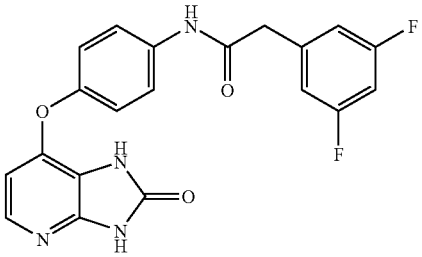

Method M was used with 2-(3,5-difluorophenyl)acetyl chloride to afford the title compound as an off-white solid (32 mg, 62%). $^1$H-NMR (δ, ppm, DMSO-d$_6$): 3.72 (s, 2H, CH$_2$), 6.34 (d, 1H, H$_{Py,5}$, J=5.95 Hz), 7.07-7.25 (m, 5H, H$_{arom,Ph',2+4+6}$+H$_{arom,Ph,3+5}$), 7.67 (d, 2H, H$_{arom,Ph,2+6}$, J=9.0 Hz), 7.76 (d, 1H, H$_{Py,6}$), 10.30 (s, 1H, NH$_{amide}$), 11.18 (s, 1H, NH$_{Py3}$), 11.36 (s, 1H, NH$_{Py2}$) LC-MS (m/z): 397 (M+H, 100).

Synthesis 109

N-(4-(2-Oxo-2,3-dihydro-1H-imidazo[4,5-b]pyridin-7-yl-oxy)phenyl)-3-(trifluoro methyl)benzamide (CJS 3669)

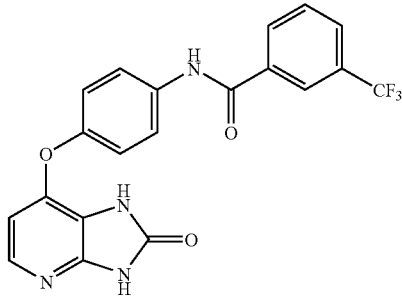

Method M was used with 3-(trifluoromethyl)benzoyl chloride to afford the title compound as an off-white solid (40 mg, 72%). $^1$H-NMR (δ, ppm, DMSO-d$_6$): 6.40 (d, 1H, H$_{Py,5}$, J=5.95 Hz), 7.21 (d, 2H, H$_{arom,Ph,3+5}$, J=8.95 Hz), 7.79 (d, 1H, H$_{Py,6}$), 7.86 (d, 2H, H$_{arom,Ph,2+6}$), 7.96-8.01 (m, 1H, H$_{arom,Ph',6}$), 8.26-8.32 (m, 3H, H$_{arom,Ph',2+4+5}$), 10.57 (s, 1H, NH$_{amide}$), 11.21 (s, 1H, NH$_{Py3}$), 11.38 (s, 1H, NH$_{Py2}$). LC-MS (m/z): 416 (M+2H, 100).

Synthesis 110

3-Bromo-N-(4-(2-oxo-2,3-dihydro-1H-imidazo[4,5-b]pyridin-7-yl-oxy)phenyl)-benzamide (CJS 3670)

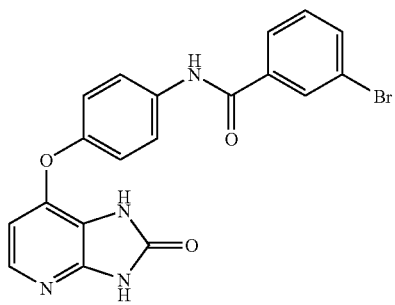

Method M was used with 3-bromobenzoyl chloride to afford the title compound as an off-white solid (41 mg, 60%). $^1$H-NMR (δ, ppm, DMSO-d$_6$): 6.40 (d, 1H, H$_{Py,5}$, J=5.95 Hz), 7.20 (d, 2H, H$_{arom,Ph,3+5}$, J=9.0 Hz), 7.52 (pseudo t, 1H, H$_{arom,Ph',5}$), 7.79 (d, 1H, H$_{Py,6}$), 7.85 (d, 2H, H$_{arom,Ph,2+6}$), 7.95-8.00 (m, 2H, H$_{arom,Ph',4+6}$), 8.15-8.17 (m, 1H, H$_{arom,Ph',2}$), 10.45 (s, 1H, NH$_{amide}$), 11.22 (s, 1H, NH$_{Py3}$), 11.41 (s, 1H, NH$_{Py2}$). LC-MS (m/z): 425 (M+H, 100).

Synthesis 111

4-Chloro-N-(4-(2-oxo-2,3-dihydro-1H-imidazo[4,5-b]pyridin-7-yl-oxy)phenyl)-3-(trifluoromethyl)benzamide (CJS 3673)

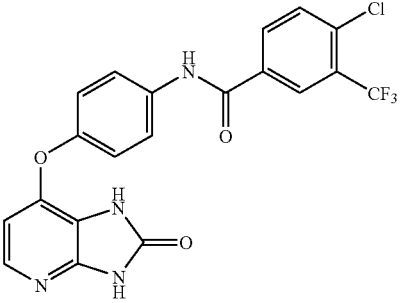

Method M was used with 4-chloro-3-(trifluoromethyl) benzoyl chloride to afford the title compound as an light brown solid (52 mg, 89%). $^1$H-NMR (δ, ppm, DMSO-d$_6$): 6.40 (d, 1H, H$_{Py,5}$, J=5.88 Hz), 7.21 (d, 2H, H$_{arom,Ph,3+5}$, J=8.73 Hz), 7.80-8.00 (m, 3H, H$_{aromPh,2+6}$+H$_{Py,6}$), 8.25-8.46 (m, 3H, H$_{arom,Ph',2+5+6}$), 10.62 (s, 1H, NH$_{amide}$), 11.18 (s, 1H, NH$_{Py3}$), 11.35 (s, 1H, NH$_{Py2}$). LC-MS (m/z): 449 (M+H, 100).

Synthesis 112

3-Fluoro-5-morpholino-N-(4-(2-oxo-2,3-dihydro-1H-imidazo[4,5-b]pyridin-7-yl-oxy)phenyl)benzamide (CJS 3674)

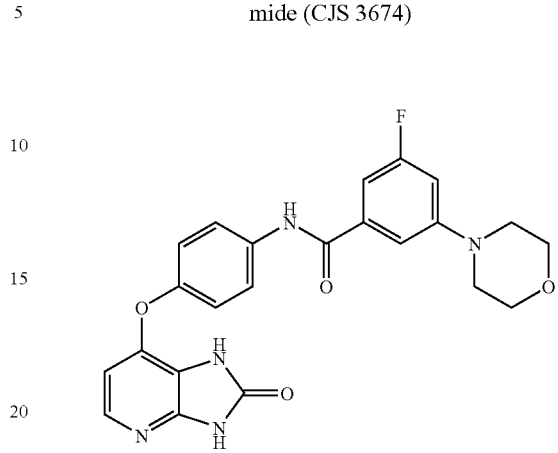

Method M was used with 3-fluoro-5-morpholinobenzoyl chloride to afford the title compound as a light brown solid (52 mg, 89%). $^1$H-NMR (δ, ppm, DMSO-d$_6$): 3.25 (m, 4H, CH$_2$N), 3.76 (m, 4H, CH$_2$O), 6.38 (d, 1H, H$_{Py,5}$, J=5.93 Hz), 6.98-7.10 (m, 2H, H$_{arom,Ph'}$), 7.20 (d, 2H, H$_{arom,Ph,3+5}$, J=8.98 Hz), 7.31 (m, 1H, H$_{arom,Ph'}$), 7.78 (d, 1H, H$_{Py,6}$), 7.83 (d, 2H, H$_{arom,Ph,2+6}$), 10.32 (s, 1H, NH$_{amide}$), 11.24 (s, 1H, NH$_{Py3}$), 11.41 (s, 1H, NH$_{Py2}$). LC-MS (m/z): 450 (M+H, 100).

(XVII) Synthesis of Sulfonamides

Synthesis 113

4-Chloro-N-(4-(2-oxo-2,3-dihydro-1H-imidazo[4,5-b]pyridin-7-yl-oxy)phenyl)-3-(trifluoromethyl)benzenesulfonamide (CJS 3650)

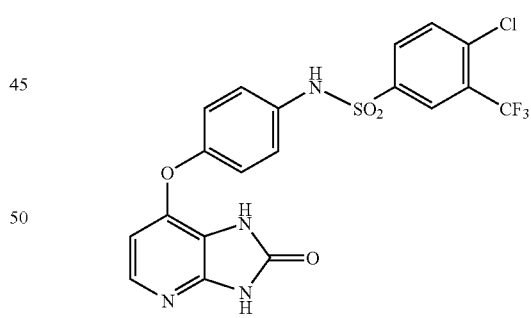

Method N. 7-(4-Aminophenoxy)-2,3-dihydro-2-oxo-1H-imidazo[4,5-b]pyridine (30 mg, 0.13 mmol) was suspended in dry pyridine (3 mL) and 4-chloro-3-(trifluoromethyl)benzene-1-sulfonyl chloride (44.4 mg, 0.16 mmol) was added. The resulting solution was stirred at room temperature for 20 hours and subsequently the solvent was removed in vacuo. The obtained residue was dissolved in acetone (4 mL) and upon addition of water a solid precipitated. This solid was collected, washed with water (2×2 mL) and Et$_2$O (2×2 mL) and dried to give the title compounds as an off-white solid (44 mg, 57%). $^1$H-NMR (δ, ppm, DMSO-d$_6$): 6.28 (d, 1H, H$_{Py,5}$, J=5.8 Hz), 7.12 (s, 4H, H$_{arom,Ph}$), 7.75 (d, 1H, H$_{Py,6}$), 7.98 (s, 2H, H$_{arom,Ph'}$), 8.05 (s, 1H, H$_{arom,Ph'}$), 10.47 (s, 1H, NHSO$_2$), 11.17 (s, 1H, NH$_{Py3}$), 11.40 (s, 1H, NH$_{Py2}$). LC-MS (m/z): 485 (M+H, 100).

Synthesis 114
N-(4-(2-Oxo-2,3-dihydro-1H-imidazo[4,5-b]pyridin-7-yl-oxy)phenyl)benzene sulphonamide (CJS 3651)

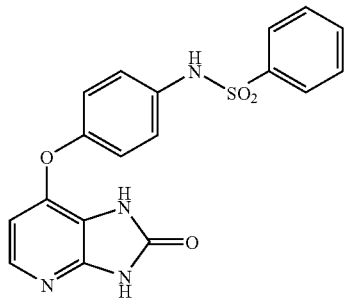

Method N was used with benzenesulfonyl chloride to afford the title compound as an off-white solid (44 mg, 89%). $^1$H-NMR (δ, ppm, DMSO-d$_6$): 6.28 (d, 1H, H$_{Py,5}$, J=5.78 Hz), 7.10 (dd$_{AB}$, 4H, H$_{arom,Ph}$, J=8.75 Hz), 7.52-7.68 (m, 3H, H$_{arom,Ph'}$), 7.73-7.83 (m, 3H, H$_{Py,6+arom,Ph'}$), 10.28 (s, 1H, NHSO$_2$), 11.15 (s, 1H, NH$_{Py3}$), 11.37 (s, 1H, NH$_{Py2}$). LC-MS (m/z): 383 (M+H, 100).

Synthesis 115
4-Chloro-N-(4-(2-oxo-2,3-dihydro-1H-imidazo[4,5-b]pyridin-7-yl-oxy)phenyl)benzene sulphonamide (CJS 3652)

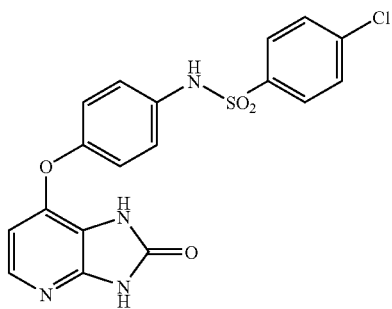

Method N was used with 4-chlorobenzenesulfonyl chloride to afford the title compound as an off-white solid (27 mg, 50%). $^1$H-NMR (δ, ppm, DMSO-d$_6$): 6.30 (d, 1H, H$_{Py,5}$, J=5.95 Hz), 7.10 (dd$_{AB}$, 4H, H$_{arom,Ph}$, J=9 Hz), 7.64-7.77 (m, 5H, H$_{Py,6+arom,Ph'}$), 10.35 (s, 1H, NHSO$_2$), 11.15 (s, 1H, NH$_{Py3}$), 11.38 (s, 1H, NH$_{Py2}$). LC-MS (m/z): 417 (M+H, 100).

Synthesis 116
4-Fluoro-N-(4-(2-oxo-2,3-dihydro-1H-imidazo[4,5-b]pyridin-7-yl-oxy)phenyl)benzene sulphonamide (CJS 3654)

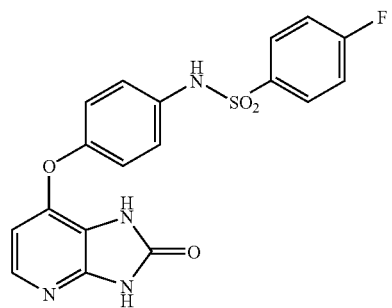

Method N was used with 4-fluorobenzenesulfonyl chloride to afford the title compound as an off-white solid (30 mg, 58%). $^1$H-NMR (δ, ppm, DMSO-d$_6$): 6.31 (d, 1H, H$_{Py,5}$, J=5.95 Hz), 7.10 (dd$_{AB}$, 4H, H$_{arom,Ph}$, J=9.0 Hz), 7.42 (pseudo t, 2H, H$_{arom,Ph'}$), 7.74-7.84 (m, 3H, H$_{Py,6+Ph'}$), 10.24 (s, 1H, NHSO$_2$), 11.09 (s, 1H, NH$_{Py3}$), 11.32 (s, 1H, NH$_{Py2}$) LC-MS (m/z): 401 (M+H, 100).

Synthesis 117
N-(4-(2-Oxo-2,3-dihydro-1H-imidazo[4,5-b]pyridin-7-yl-oxy)phenyl)-4-(trifluoro methyl)benzene-sulfonamide (CJS 3653)

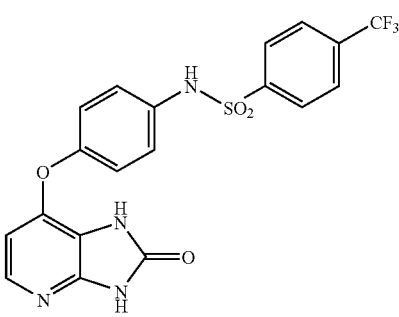

Method N was used with 4-(trifluoromethyl)benzenesulfonyl chloride to afford the title compound as an off-white solid (33 mg, 56%). $^1$H-NMR (δ, ppm, DMSO-d$_6$): 6.31 (d, 1H, H$_{Py,5}$, J=5.83 Hz), 7.11 (dd$_{AB}$, 4H, H$_{arom,Ph}$, J=8.45 Hz), 7.75 (d, 1H, H$_{Py,6}$), 7.97 (s, 4H, H$_{Ph'}$), 10.50 (s, 1H, NHSO$_2$), 11.12 (s, 1H, NH$_{Py3}$), 11.36 (s, 1H, NH$_{Py2}$). LC-MS (m/z): 451 (M+H, 100).

Synthesis 118
1—Methyl-N-(4-(2-oxo-2,3-dihydro-1H-imidazo[4,5-b]pyridin-7-yl-oxy)phenyl)-3-(trifluoromethyl)-1H-pyrazole-5-sulfonamide (CJS 3656)

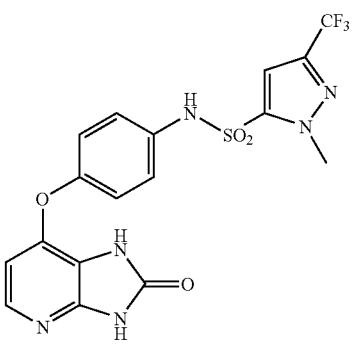

Method N was used with 1-methyl-3-(trifluoromethyl)-1H-pyrazole-5-sulfonyl chloride to afford the title compound as a brown solid (38 mg, 64%). $^1$H-NMR (δ, ppm, DMSO-d$_6$): 3.93 (s, 3H, CH$_3$), 6.31 (s, 1H, H$_{Py,5}$), 7.12 (m, 4H, H$_{arom,Ph}$), 7.76 (s, 1H, H$_{Py,6}$), 8.51 (s, 1H, H$_{Pyrazole}$), 10.42 (s, 1H, NHSO$_2$), 11.16 (s, 1H, NH$_{Py3}$), 11.38 (s, 1H, NH$_{Py2}$). LC-MS (m/z): 455 (M+H, 100).

Synthesis 119

N-(4-(2-Oxo-2,3-dihydro-1H-imidazo[4,5-b]pyridin-7-yl-oxy)phenyl)-3-(trifluoro methyl)benzene-sulfonamide (CJS 3655)

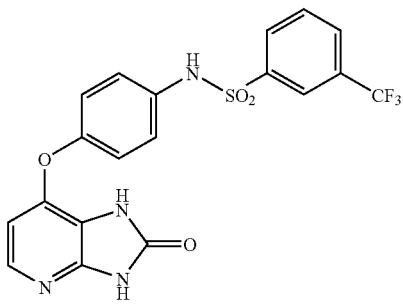

Method N was used with 3-(trifluoromethyl)benzenesulfonyl chloride to afford the title compound as an off-white solid (33 mg, 56%). $^1$H-NMR ($\delta$, ppm, DMSO-d$_6$): 6.31 (d, 1H, H$_{Py,5}$, J=5.83 Hz), 7.11 (dd$_{AB}$, 4H, H$_{arom,Ph}$, J=8.45 Hz), 7.75 (d, 1H, H$_{Py,6}$), 7.97 (s, 4H, H$_{Ph'}$), 10.50 (s, 1H, NHSO$_2$), 11.12 (s, 1H, NH$_{Py3}$), 11.36 (s, 1H, NH$_{Py2}$). LC-MS (m/z): 451 (M+H, 100).

Synthesis 120

3-Fluoro-N-(4-(2-oxo-2,3-dihydro-1H-imidazo[4,5-b]pyridin-7-yl-oxy)phenyl)benzene sulphonamide (CJS 3657)

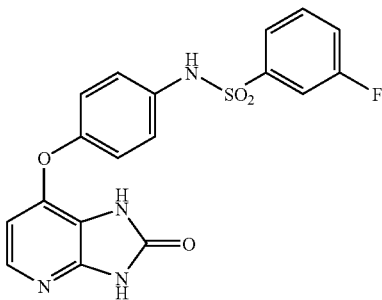

Method N was used with 3-fluorobenzenesulfonyl chloride to afford the title compound as a light brown solid (34 mg, 64%). $^1$H-NMR ($\delta$, ppm, DMSO-d$_6$): 6.29 (d, 1H, H$_{Py,5}$, J=5.93 Hz), 7.11 (dd$_{AB}$, 4H, H$_{arom,Ph}$, J=8.98 Hz), 7.51-7.66 (m, 4H, H$_{Ph'}$), 7.75 (d, 1H, H$_{Py,6}$), 10.38 (s, 1H, NHSO$_2$), 11.15 (s, 1H, NH$_{Py3}$) 11.37 (s, 1H, NH$_{Py2}$). LC-MS (m/z): 401 (M+H, 100).

Synthesis 121

N-(4-(2-Oxo-2,3-dihydro-1H-imidazo[4,5-b]pyridin-7-yl-oxy)phenyl)-2-(trifluoro methoxy)benzene-sulfonamide (CJS 3659)

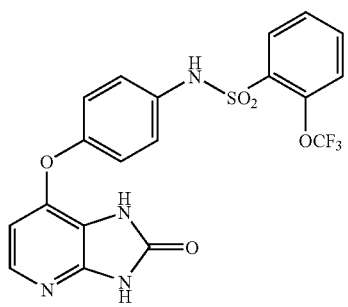

Method N was used with 2-(trifluoromethoxy)benzene-sulfonyl chloride to afford the title compound as an off-white solid (45 mg, 74%). $^1$H-NMR ($\delta$, ppm, DMSO-d$_6$): 6.25 (d, 1H, H$_{Py,5}$, J=5.95 Hz), 7.10 (dd$_{AB}$, 4H, H$_{arom,Ph}$, J=8.98 Hz), 7.58 (m, 2H, H$_{Ph'}$), 7.75 (m, 2H, H$_{Py,6+ph'}$), 7.96 (d, 1H, H$_{arom,Ph}$, J=7.5 Hz), 10.55 (s, 1H, NHSO$_2$), 11.15 (s, 1H, NH$_{Py3}$), 11.36 (s, 1H, NH$_{Py2}$). LC-MS (m/z): 467 (M+H, 100).

Synthesis 122

N-(4-(2-Oxo-2,3-dihydro-1H-imidazo[4,5-b]pyridin-7-yl-oxy)phenyl)-3-(trifluoro methoxy)benzene-sulfonamide (CJS 3660)

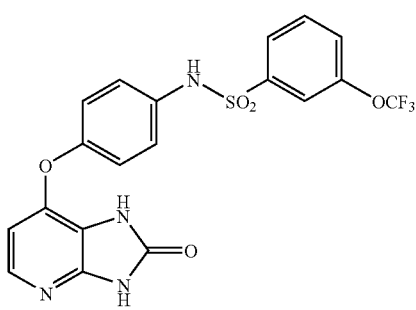

Method N was used with 3-(trifluoromethoxy)benzene-sulfonyl chloride to afford the title compound as a light brown solid (41 mg, 68%). $^1$H-NMR ($\delta$, ppm, DMSO-d$_6$): 6.26 (d, 1H, H$_{Py,5}$, J=6.03 Hz), 7.11 (dd$_{AB}$, 4H, H$_{arom,Ph}$, J=9.15 Hz), 7.63-7.76 (m, 5H, H$_{Py,6+ph'}$), 10.42 (s, 1H, NHSO$_2$), 11.16 (s, 1H, NH$_{Py3}$), 11.37 (s, 1H, NH$_{Py2}$). LC-MS (m/z): 467 (M+H, 100).

Synthesis 123

N-(4-(2-Oxo-2,3-dihydro-1H-imidazo[4,5-b]pyridin-7-yl-oxy)phenyl)-3,5-bis(trifluoro methyl)benzene-sulfonamide (CJS 3661)

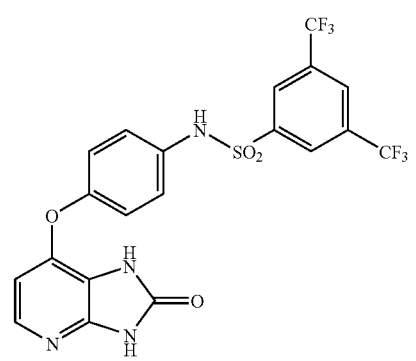

Method N was used with 3,5-bis(trifluoromethyl)benzene-1-sulfonyl chloride to afford the title compound as white solid (46 mg, 68%). $^1$H-NMR (δ, ppm, DMSO-$d_6$): 6.22 (d, 1H, $H_{Py,5}$, J=5.83 Hz), 7.11 (s, 4H, $H_{arom,Ph}$), 7.73 (m, 2H, $H_{Py,6}$), 8.22 (s, 2H, $H_{arom,Ph'}$), 8.53 (s, 1H, $H_{arom,Ph'}$), 10.52 (s, 1H, NHSO$_2$), 11.17 (s, 1H, NH$_{Py3}$), 11.38 (s, 1H, NH$_{Py2}$). LC-MS (m/z): 519 (M+H, 100).

Synthesis 124

5—Methyl-N-(4-(2-oxo-2,3-dihydro-1H-imidazo[4,5-b]pyridin-7-yl-oxy)phenyl)-2-(trifluoromethyl)furan-3-sulfonamide (CJS 3662)

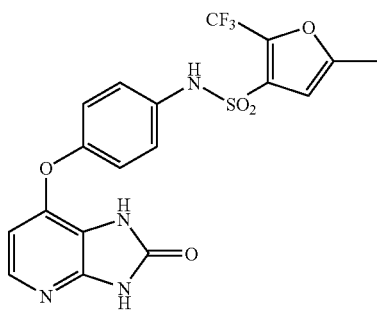

Method N was used with 5-methyl-2-(trifluoromethyl)furan-3-sulfonyl chloride to afford the title compound as a light brown solid (37 mg, 63%). $^1$H-NMR (δ, ppm, DMSO-$d_6$): 6.33 (d, 1H, $H_{Py,5}$, J=5.93 Hz), 7.16 (dd$_{AB}$, 4H, $H_{arom,Ph}$, J=9.1 Hz), 7.33 (s, 1H, $H_{furan}$), 7.76 (d, 1H, $H_{Py,6}$), 10.37 (s, 1H, NHSO$_2$), 11.17 (s, 1H, NH$_{Py3}$), 11.39 (s, 1H, NH$_{Py2}$). LC-MS (m/z): 455 (M+H, 100).

Synthesis 125

N-(4-(2-Oxo-2,3-dihydro-1H-imidazo[4,5-b]pyridin-7-yl-oxy)phenyl)thiophene-2-sulfonamide (CJS 3671)

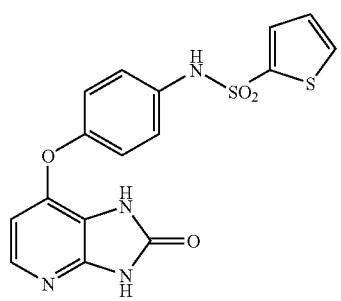

Method N was used with thiophene-2-sulfonyl chloride to afford the title compound as a light brown solid (28 mg, 55%). $^1$H-NMR (δ, ppm, DMSO-$d_6$): 6.31 (d, 1H, $H_{Py,5}$, J=5.95 Hz), 7.08-7.21 (m, 5H, $H_{arom,Ph+Thio}$), 7.52-7.56 (m, 1H, $H_{thio}$), 7.76 (d, 1H, $H_{Py,6}$) 7.91-7.94 (m, 1H, $H_{thio}$), 10.41 (s, 1H, NHSO$_2$), 11.16 (s, 1H, NH$_{Py3}$), 11.37 (s, 1H, NH$_{Py2}$). LC-MS (m/z): 389 (M+H, 100).

Synthesis 126

2-Fluoro-N-(4-(2-oxo-2,3-dihydro-1H-imidazo[4,5-b]pyridin-7-yl-oxy)phenyl)benzene sulphonamide (CJS 3672)

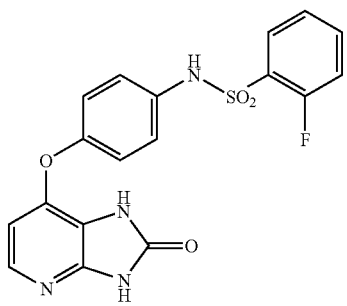

Method N was used with 2-fluorobenzenesulfonyl chloride to afford the title compound as a light brown solid (33 mg, 63%). $^1$H-NMR (δ, ppm, DMSO-$d_6$): 6.26 (d, 1H, $H_{Py,5}$, J=5.9 Hz), 7.11 (dd$_{AB}$, 4H, $H_{arom,Ph}$, J=8.8 Hz), 7.35-7.48 (m, 2H, $H_{Ph'}$), 7.73-7.85 (m, 3H, $H_{Py,6+Ph'}$), 10.62 (s, 1H, NHSO$_2$), 11.14 (s, 1H, NH$_{Py3}$), 11.36 (s, 1H, NH$_{Py2}$). LC-MS (m/z): 401 (M+H, 100).

Synthesis 127

N-(4-(2,3-Dihydro-2-oxo-1H-imidazo[4,5-b]pyridin-7-yl-oxy)phenyl)benzene sulfonamide

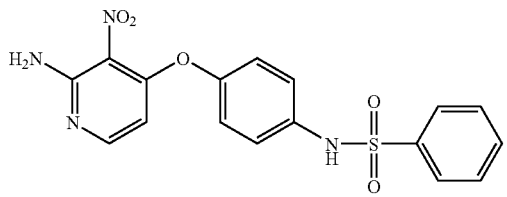

Method N was used with 4-(4-aminophenoxy)-3-nitropyridin-2-amine (300 mg, 1.2 mmol) and benzenesulfonyl chloride (153 μL, 1.2 mmol) to afford the title compound (150 mg, 32%). $^1$H-NMR (δ, ppm, DMSO-$d_6$): 5.85 (d, 1H, $H_{Py,5}$, J=5.68 Hz), 7.05-7.20 (m, 6H, NH$_{2,Py}$+$H_{arom,Ph,3+5}$+2H$_{arom,Ph'}$), 7.52-7.67 (m, 3H, $H_{arom,Ph'}$), 7.55 (d, 2H, H$_{arom,Ph,2+6}$, J=8.27 Hz), 7.98 (d, 1H, H$_{Py,6}$, J=5.70 Hz), 10.37 (s, 1H, NH$_{sulfonamide}$); LC-MS (m/z): 387 (M+H, 100).

(XVIII) Synthesis of Aromatic Amines Starting Materials

Synthesis 128

4-Chloro-2-methoxy-5-(trifluoromethyl)benzenamine

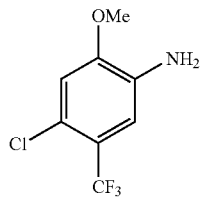

1-Chloro-5-methoxy-4-nitro-2-(trifluoromethyl)benzene (306 mg, 1.19 mmol) was dissolved in acetic acid (5 mL). Iron (436 mg, 7.78 mmol) was added and the mixture was heated under reflux for 1.5 hour. After cooling to room temperature, the mixture was filtered through celite. The filtrate was concentrated under reduced pressure and the residue was taken up in EtOAc. The solution was washed with saturated NaHCO$_3$ (aqueous) and brine, and then dried over MgSO$_4$. Evaporation of the solvent in vacuo afforded an oily residue which was purified by flash chromatography on silica gel (cyclohexane-EtOAc, 7:3) to afford the title compound (177 mg, 66%) as a yellow oil (R$_f$ 0.45, cyclohexane-EtOAc, 7:3). $^1$H-NMR (δ, ppm, DMSO-d$_6$): 3.85 (s, 3H, CH$_3$—O), 5.27 (bs, 2H, NH$_2$), 7.02 (s, 2H, H$_{arom}$). LC-MS (m/z): 226 (M+H, 100).

(XIX) Synthesis of N1-alkylated Pyridoimidazolone Common Intermediate

1. Via Acylation of Diamine (According to Scheme 17

Synthesis 129

Ethyl 4-(4-N-(tert-butoxycarbonyl)-aminophenoxy)-2-aminopyridin-3-yl-carbamate

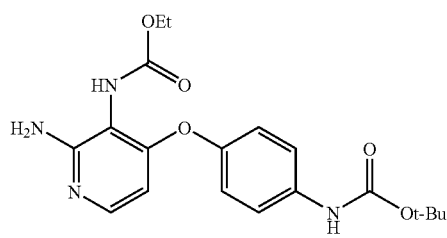

4-(4-N-(tert-Butoxycarbonyl)-aminophenoxy)-2,3-diaminopyridine (1.07 g, 3.4 mmol) was dissolved in dry THF (10 mL), pyridine (400 μL, 5 mmol) was added and the solution was cooled at 0° C. Ethyl chloroformate (335 μL, 3.5 mmol) was added, and the reaction mixture was stirred at 0° C. for 2 hours. The solvent was evaporated, the residue was taken up in DCM and was extracted with saturated aqueous Na$_2$CO$_3$. The organic layer was dried (over MgSO$_4$) and evaporated, to afford a mixture containing 50% product and 50% starting material. This mixture was dissolved in dry THF (10 mL), pyridine (400 μL, 5 mmol) was added and the solution was cooled at 0° C. Ethyl chloroformate (200 μL, 2.1 mmol) was added, and the reaction mixture was stirred at 0° C. for 2 hours. Extraction between DCM and saturated aqueous Na$_2$CO$_3$ was performed as described before. The residue from evaporation still contains 20% starting material. The reaction (THF 10 mL, pyridine 400 μL and ethyl chloroformate 100 μL) and work-up was repeated once more. The residue was purified by column chromatography (eluent AcOEt) to afford the title compound (700 mg, 53%). $^1$H-NMR (δ, ppm, DMSO-d$_6$): 1.17 (t, 3H, CH$_{3,Et}$, J=6.82 Hz), 1.49 (s, 9H, t-Bu), 4.04 (q, 2H, CH$_{2,Et}$, J=7.07 Hz), 5.78 (s, 2H, NH$_{2,Py2}$), 5.86 (d, 1H, H$_{Py,5}$, J=5.65 Hz), 6.96 (d, 2H, H$_{arom,Ph,3+5}$, J=8.85 Hz), 7.49 (d, 2H, H$_{arom,Ph,2+6}$, J=8.85 Hz), 7.69 (d, 1H, H$_{Py,6}$, J=5.70 Hz), 8.29 (s, 1H, NH$_{Py3}$), 9.39 (s, 1H, NH$_{Ph}$). $^{13}$C-NMR (δ, ppm, DMSO-d$_6$): 160.55, 158.47, 154.79, 152.81, 149.09, 146.86, 136.31, 120.59, 119.49, 106.59, 101.32, 79.03, 60.22, 54.87, 28.09, 14.49. LC-MS (m/z): 388 (M$^+$, 100).

Synthesis 130

Ethyl 4-(4-aminophenoxy)-2-aminopyridin-3-yl-carbamate

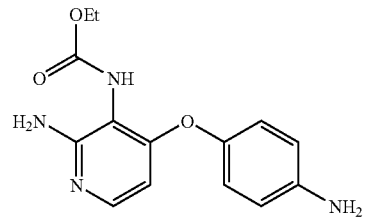

Method F was used with ethyl 4-(4-N-(tert-butoxycarbonyl)-aminophenoxy)-2-aminopyridin-3-yl-carbamate (386 mg, 1.0 mmol). The work-up was modified: the residue was extracted between saturated Na$_2$CO$_3$ and DCM. The organic layer was dried and evaporated to afford the title compound (250 mg, 87%). $^1$H-NMR (δ, ppm, DMSO-d$_6$): 1.20 (t, 3H, CH$_{3,Et}$, J=6.64 Hz), 4.05 (q, 2H, CH$_{2,Et}$, J=7.04 Hz), 5.04 (s, 2H, NH$_{2,Ph}$), 5.68 (s, 2H, NH$_{2,Py2}$), 5.81 (d, 1H, H$_{Py,5}$, J=5.70 Hz), 6.59 (d, 2H, H$_{arom,Ph,3+5}$, J=8.72 Hz), 6. (d, 2H, H$_{arom,Ph,2+6}$, J=8.70 Hz), 7.66 (d, 1H, H$_{Py,6}$, J=5.72 Hz), 8.22 (s, 1H, NH$_{Py3}$). $^{13}$C-NMR (□, ppm, DMSO-d$_6$): 161.47, 158.32, 154.85, 146.75, 146.02, 144.20, 121.33, 114.61, 105.97, 100.74, 60.17, 14.52. LC-MS (m/z): 288 (M$^+$, 100).

(XX) Synthesis of N1-Alkylated Pyridoimidazolone Common Intermediate

2. Via Nitration of Ethyl 4-chloropyridin-3-yl-carbamate (According to Scheme 7)

Synthesis 131

Ethyl 4-chloro-2-nitropyridin-3-yl-carbamate

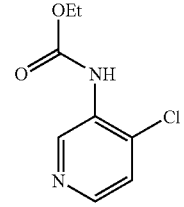

3-Amino-4-chloropyridine (6.7 g, 52 mmol) was dissolved in pyridine (90 mL) and ethyl chloroformate (9.7 mL, 101 mmol), was added dropwise. When the addition was finished, the reaction mixture was stirred for further 5 minutes, then the pyridine was evaporated. The residue was taken in water, and the precipitate recovered by filtration. The filtrate was extracted with chloroform, the organic layer was dried and evaporated. The residue was washed with water, the precipitate recovered by filtration and pooled with the solid from the first washing. After drying in dessicator over $P_2O_5$, the title product was obtained (5.15 g, 49%). $^1$H-NMR ($\delta$, ppm, DMSO-$d_6$): 1.25 (t, 3H, $CH_{3,Et}$, J=7.09 Hz), 4.15 (q, 2H, $CH_2$,Et), 7.59 (d, 1H, $H_{Py,5}$, J=5.28 Hz), 8.34 (d, 1H, $H_{Py,6}$, J=5.32 Hz), 8.69 (s, 1H, $H_{Py,2}$), 9.36 (s, 1H, $NH_{Py3}$).

Synthesis 132

Ethyl 4-chloro-2-nitropyridin-3-yl-methyl-carbamate

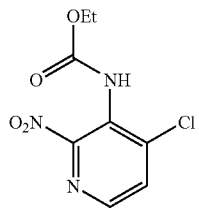

Ethyl 4-chloropyridin-3-yl-carbamate (2.15 g, 10.7 mmol) was dissolved in concentrated sulphuric acid (10 mL), cooled at 0° C. and fuming nitric acid (5 mL) was added dropwise. After addition, the reaction mixture was stirred at 0° C. for 10 minutes, then it was slowly heated at 75° C. The reaction mixture was stirred at this temperature for 18 hours and subsequently poured over ice. The obtained precipitate was collected by filtration, washed with water and dried to afford the title compound (0.35 g, 13%). $^1$H-NMR ($\delta$, ppm, DMSO-$d_6$): 1.22 (t, 3H, $CH_{3,Et}$, J=6.85 Hz), 4.12 (q, 2H, $CH_{2,Et}$), 8.11 (d, 1H, $H_{Py,5}$, J=5.13 Hz), 8.46 (d, 1H, $H_{Py,6}$, J=5.11 Hz), 10.00 (s, 1H, $NH_{Py3}$).

Synthesis 133

Ethyl 4-chloro-2-nitropyridin-3-yl-methyl-carbamate

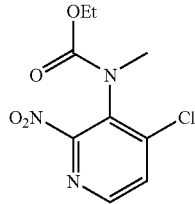

Ethyl 4-chloro-2-nitropyridin-3-yl-carbamate (350 mg, 1.4 mmol) was dissolved in acetone and potassium carbonate (280 mg, 2 mmol) was added followed by dimethyl sulfate (161 μL, 1.7 mmol). The reaction mixture was heated to reflux for 5 hours, cooled at room temperature, diluted with water and extracted with DCM. The organic layer was dried and evaporated to afford the title compound (340 mg, 93%). $^1$H-NMR ($\delta$, ppm, DMSO-$d_6$): 1.02+1.25 (t+t, rotamers, 3H, $CH_{3,Et}$), 3.14+3.19 (s+s, rotamers, 3H, $NCH_3$), 4.05+4.14 (q+q, rotamers, 2H, $CH_{2,Et}$), 8.21 (d, 1H, $H_{Py,5}$, J=5.70 Hz), 8.60 (d, 1H, $H_{Py,6}$, J=5.20 Hz). LC-MS (m/z): 259 (M+H, 100).

Synthesis 134

Ethyl 4-(4-aminophenoxy)-2-nitropyridin-3-yl-methyl-carbamate

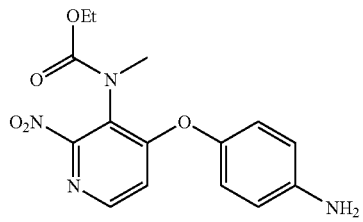

Method A was used with ethyl 4-chloro-2-nitropyridin-3-yl-methyl-carbamate (400 mg, 1.5 mmol) and 4-hydroxyaniline (196 mg, 1.8 mmol) to afford the title compound (56 mg, 12%) after purification by column chromatography, eluent gradient DCM to DCM:AcOEt 1:1. $^1$H-NMR ($\delta$, ppm, DMSO-$d_6$): 1.06+1.23 (t+t, rotamers, 3H, $CH_{3,Et}$), 3.18+3.23 (s+s, rotamers, 3H, $NCH_3$), 4.04+4.12 (q+q, rotamers, 2H, $CH_{2,Et}$), 5.44 (s, 2H, $NH_{2,Ph}$), 5.97 (s, 2H, $NH_{2,Py2}$), 6.92 (d, 2H, $H_{arom,Ph,3+5}$, J=8.79 Hz), 6.92 (d, 2H, $H_{arom,Ph,2+6}$, J=8.82 Hz), 7.04 (d, 1H, $H_{Py,5}$, J=5.60 Hz), 8.33 (d, 1H, $H_{Py,6}$, J=5.59 Hz). LC-MS (m/z): 332 ($M^+$, 100).

(XXI) Synthesis of N1-Alkylated Pyridoimidazolone Common Intermediate

3. Cyclisation (According to Scheme 7 and Scheme 17)

Synthesis 135

Ethyl 4-(4-aminophenoxy)-2-aminopyridin-3-yl-methyl-carbamate

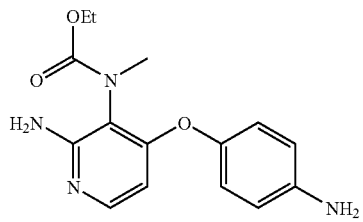

Method O1. Ethyl 4-(4-aminophenoxy)-2-aminopyridin-3-yl-carbamate (72 mg, 0.25 mmol) was dissolved in dry THF (3 mL) and cooled at 0° C. Sodium hydride (11 mg, 0.28 mmol) was added, and the reaction mixture was stirred for 25 minutes. Methyl iodide (18 μL, 0.25 mmol) was added. The mixture was stirred at 0° C. for 30 minutes and at room temperature for 1.5 hours. The solvent was evaporated and the residue extracted between DCM and saturated $Na_2CO_3$. The organic layer was dried and evaporated, and the residue purified by column chromatography (eluent AcOEt) to afford the title compound (40 mg, 53%). $^1$H-NMR ($\delta$, ppm, DMSO-$d_6$): 1.10 (t, 3H, CH$_{3,Et}$, J=7.04 Hz), 3.01 (s, 3H, CH$_3$N), 3.90-4.10 (m, 2H, CH$_{2,Et}$), 5.06 (s, 2H, NH$_{2,Ph}$), 5.78 (d, 1H, H$_{Py,5}$, J=6.68 Hz), 5.97 (s, 2H, NH$_{2,Py2}$), 6.59 (d, 2H, H$_{arom,Ph,3+5}$, J=8.76 Hz), 6.73 (d, 2H, H$_{arom,Ph,2+6}$, J=8.79 Hz), 7.67 (d, 1H, H$_{Py,6}$, J=5.73 Hz). LC-MS (m/z): 302 (M$^+$, 100). Acc. mass (C$_{15}$H$_{19}$N$_4$O$_3$): calculated 303.1457, found 303.1453.

Method O2. Ethyl 4-(4-aminophenoxy)-2-nitropyridin-3-yl-methyl-carbamate (56 mg, 0.17 mmol) was dissolved in ethanol (3 mL). Pd 10% on carbon (30 mg) was added followed by ammonium formate (150 mg). The reaction mixture was stirred for 1.5 hours, and then the catalyst was filtered off and the filtrate evaporated to afford the title compound (44 mg, 86%).

Synthesis 136

7-(4-Aminophenoxy)-1-methyl-1H-imidazo[4,5-b]pyridin-2(3H)-one

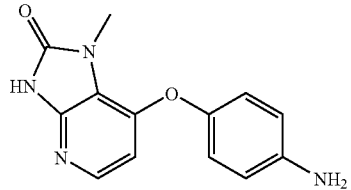

Ethyl 4-(4-aminophenoxy)-2-aminopyridin-3-yl-methyl-carbamate (180 mg, 0.6 mmol) was suspended in a solution of sodium ethoxide in ethanol, obtained from dissolving sodium (480 mg, 21 mmol) in ethanol (9 ml). The suspension was heated under microwave irradiation for 40 minutes (100° C., 150 W). The mixture was cooled at room temperature, diluted with water and evaporated. The residue was triturated with acetone, and the washings discarded. The solid was dissolved in water and the insoluble solid was filtered off. The filtrate was acidified with HCl 1 M to pH 1, then brought to pH 10 with saturated aqueous Na$_2$CO$_3$. The precipitate formed was recovered by filtration, to afford the title compound (52 mg, 34%). $^1$H-NMR ($\delta$, ppm, DMSO-$d_6$): 3.49 (s, 3H, CH$_3$N), 5.11 (s, 2H, NH$_2$), 6.29 (d, 1H, H$_{Py,6}$, J=6.0 Hz), 6.63 (d, 2H, H$_{arom,Ph,3+5}$, J=8.69 Hz), 6.90 (d, 2H, H$_{arom,Ph,2+6}$, J=8.73 Hz), 7.74 (d, 1H, H$_{Py,6}$, J=5.96 Hz), 11.53 (s, 1H, NH$_{Py2}$). LC-MS (m/z): 257 (M+H, 100).

Synthesis 137

4-Amino-2,3-dimethylphenol

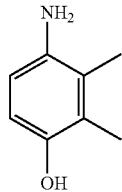

A mixture of 2,3-dimethyl-4-nitrophenol (2 g, 1.2 mmol) and Pd(C) (10%) (1.83 g) in EtOH (80 mL) was stirred at room temperature under H$_2$ atmosphere for 5 hours. The crude mixture was then filtered using celite and washed with DCM. After evaporating the solvent, the title compound (1.60 g, 97%) was obtained as a brown powder. $^1$H-NMR (6, ppm, DMSO-$d_6$): 1.94 (s, 3H, H$_{Me}$), 2.01 (s, 3H, H$_{Me}$), 4.06 (s, 2H, NH$_2$), 6.32 (d, 1H, H$_{arom\ 6}$, J$_{6-5}$=8.1 Hz), 6.40 (d, 1H, H$_{arom\ 5}$, J$_{6-5}$=8.1 Hz), 6.61 (s, 1H, H$_{arom\ 2}$), 8.10 (broad s, 1H, OH).

Synthesis 138

4-(4-Amino-2,3-dimethylphenoxy)-3-nitropyridin-2-amine

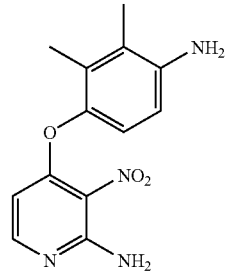

Method A was used with 4-amino-2,3-dimethylphenol (682 mg, 5 mmol) to afford the title compound (1.083 mg, 80%) after purification by chromatography on silica gel (EtOAc-DCM, 1:1) as a mustard-coloured solid (R$_f$ 0.40, EtOAc-DCM, 1:1). $^1$H-NMR ($\delta$, ppm, DMSO-$d_6$): 1.12 (s, 3H, CH$_3$), 1.17 (s, 3H, CH$_3$), 4.05 (s, 2H, NH$_{2,Ph}$), 4.91 (d, 1H, H$_{Py,5}$ J=5.7 Hz), 5.73 (d, 1H, H$_{Ph}$, J=8.6 Hz), 5.85 (d, 1H, H$_{Ph}$, J=8.6 Hz), 6.22 (s, 2H, NH$_{2,Py}$), 7.06 (d, 1H, H$_{Py,6}$, J=5.7 Hz). LC-MS (m/z): 275 (M+H, 100).

Synthesis 139

1-(4-(2-Amino-3-nitropyridin-4-yl-oxy)-2,3-dimethylphenyl)-3-(4-chloro-3-(trifluoromethyl)phenyl)urea

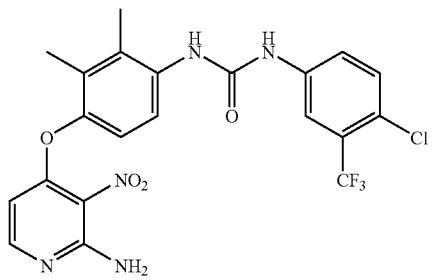

Method H3 was used with 4-(4-amino-2,3-dimethylphenoxy)-3-nitropyridin-2-amine (400 mg, 1.5 mmol) to afford the title compound (625 mg, 86%) as a yellow powder. $^1$H-NMR ($\delta$, ppm, DMSO-$d_6$): 2.07 (s, 3H, CH$_3$), 2.19 (s, 3H, CH$_3$), 5.77 (d, 1H, H$_{Py,5}$, J=5.7 Hz), 6.98 (d, 1H, H$_{arom}$, J=8.7 Hz), 7.14 (s, 2H, NH$_{2,Py}$), 7.57 (d, 1H, H$_{arom}$, J=8.7 Hz), 7.62

(m, 1H, H$_{arom}$), 7.96 (d, 1H, H$_{Py,6}$, J=5.7 Hz), 8.12 (m, 1H, H$_{arom}$), 8.21 (s, 1H, NH$_{urea1}$), 9.38 (s, 1H, NH$_{urea3}$). LC-MS (m/z): 496 (M+H, 100).

Synthesis 140

1-(4-(2,3-Diaminopyridin-4-yl-oxy)-2,3-dimethylphenyl)-3-(4-chloro-3-(trifluoromethyl)phenyl)urea

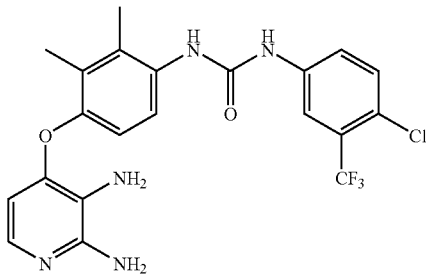

Method D2 was used with 1-(4-(2-amino-3-nitropyridin-4-yl-oxy)-2,3-dimethylphenyl)-3-(4-chloro-3-(trifluoromethyl)phenyl)urea (300 mg, 1.5 mmol) to afford the title compound (67 mg, 24%) after purification by chromatography on silica gel (EtOAc—MeOH, 95:5) as a yellow powder (R$_f$ 0.73, EtOAc—MeOH, 95:5). $^1$H-NMR (δ, ppm, DMSO-d$_6$): 2.09 (s, 3H, CH$_3$), 2.19 (s, 3H, CH$_3$), 4.59 (broad s, 2H, NH$_{2,Py2}$), 5.81 (bs, 1H, H$_{Py,5}$), 6.75-6.81 (m, 1H, H$_{arom}$), 7.39-7.44 (m, 1H, H$_{arom}$), 7.58-7.63 (m, 3H, H$_{arom}$ & NH$_{2,Py}$), 8.11 (m, 1H, H$_{arom}$), 8.17 (s, 1H, NH$_{urea}$), 9.39 (s, 1H, NH$_{urea3}$). LC-MS (m/z): 466 (M+H, 100).

Synthesis 141

1-(4-(2,3-Dihydro-2-oxo-1H-benzo[d]imidazol-4-yl-oxy)-2,3-dimethylphenyl)-3-(4-chloro-3-(trifluoromethyl)phenyl)urea (CJS 3510)

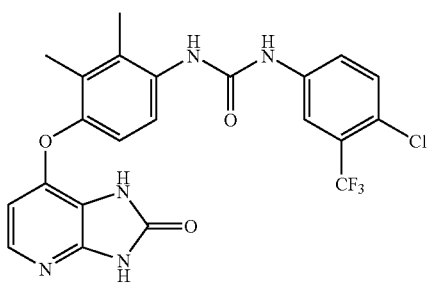

Method E3 was used with 1-(4-(2,3-diaminopyridin-4-yl-oxy)-2,3-dimethylphenyl)-3-(4-chloro-3-(trifluoromethyl)phenyl)urea to afford the title compound (20 mg, 27%) as a yellow powder. $^1$H-NMR (δ, ppm, DMSO-d$_6$): 2.09 (s, 3H, CH$_3$), 2.19 (s, 3H, CH$_3$), 6.12 (d, 1H, H$_{Py,5}$, J=5.8 Hz), 6.95 (d, 1H, H$_{arom}$, J=8.4 Hz), 7.48 (d, 1H, H$_{arom}$, J=8.6 Hz), 7.58 (d, 1H, H$_{arom}$, J=8.5 Hz), 7.65-7.72 (m, 2H, H$_{Py,6}$, H$_{arom}$), 8.14 (s, 1H, H$_{arom}$), 8.46 (s, 1H, NH$_{urea1}$), 9.64 (s, 1H, NH$_{urea3}$), 11.21 (s, 1H, NH$_{Py}$), 11.32 (s, 1H, NH$_{Py}$). LC-MS (m/z): 492 (M+H, 100).

Synthesis 142

3-(Methylthio)-4-nitrophenol

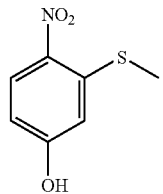

To a solution of 3-fluoro-4-nitrophenol (2 g, 12.7 mmol) in dry DMF (67 mL) was added, by aliquots, 2 equivalents of sodium thiomethoxide (1.78 g, 25.5 mmol) followed by 3 equivalents of potassium carbonate (5.27 g, 38.2 mmol). The mixture was stirred at room temperature for 23 hours and then water (100 mL) was added. The mixture was extracted with EtOAc, and the combined organic layers washed successively with water (60 mL) and brine (60 mL) and then dried over MgSO$_4$. The solvent was evaporated under vacuum to provide the title compound (2.12 g, 90%) as a yellow powder. $^1$H-NMR (δ, ppm, DMSO-d$_6$): 2.44 (s, 3H, H$_{Me}$), 6.72 (d, 1H, H$_{arom\ 6}$, J$_{6-5}$=9.0 Hz), 6.79 (s, 1H, H$_{arom\ 2}$), 8.19 (d, 1H, H$_{arom\ 5}$, J$_{5-8}$=9.1 Hz), 11.20 (broad s, 1H, OH).

Synthesis 143

4-Amino-3-(methylthio)phenol

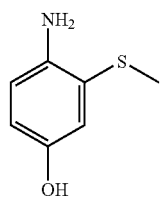

Iron powder (1.59 g, 28.5 mmol) was added slowly to a solution of 3-(methylthio)-4-nitrophenol (1.76 g, 9.5 mmol) in acetic acid (50 mL) and ethanol (5 mL). The mixture was stirred 17 hours at room temperature.v Then iron was removed with a magnet and the slurry mixture filtered. The filtrate was diluted in water (100 mL) and neutralised with a saturated solution of Na$_2$CO$_3$. The mixture was extracted with DCM, and the combined organic layer dried over Na$_2$SO$_4$. Then, the solvent was evaporated under vacuum to provide the title compound (780 mg, 53%) as a grey powder. $^1$H-NMR (δ, ppm, DMSO-d$_6$): 2.29 (s, 3H, H$_{Me}$), 4.48 (bs, 2H, NH$_2$), 6.44 (d, 1H, H$_{arom\ 5}$, J$_{6-5}$=8.5 Hz), 6.54 (d, 1H, H$_{arom\ 6}$, J$_{6-5}$=8.5 Hz), 6.61 (s, 1H, H$_{arom\ 2}$), 8.58 (broad s, 1H, OH). GC-MS (m/z): 155.09

Synthesis 144

4-(4-Amino-3-(methylthio)phenoxy)-3-nitropyridin-2-amine

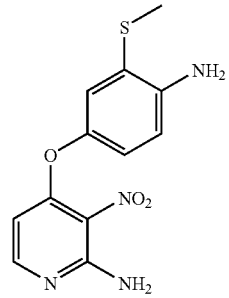

Method A was used with 4-amino-3-(methylthio)phenol (573 mg, 3.7 mmol) to afford the title compound (657 mg, 61%) after purification by chromatography on silica gel (EtOAc-DCM, 1:1) as a red brown solid ($R_f$ 0.56, EtOAc-DCM, 1:1). $^1$H-NMR ($\delta$, ppm, DMSO-$d_6$): 2.36 (s, 3H, CH$_3$); 5.18 (s, 2H, NH$_{2,ph}$), 5.92 (d, 1H, H$_{Py,6}$, J=5.8 Hz), 6.75 (dd, 1H, H$_{Ph,11or12}$, J=8.6 Hz and J=2.1 Hz), 6.81 (d, 1H, H$_{Ph,11or12}$, J=8.7 and J=2.6 Hz), 6.98 (d, 1H, H$_{Ph,8}$, J=2.6 Hz), 7.07 (bs, 2H, NH$_{2,Py}$), 7.95 (d, 1H, H$_{Py,6}$, J=5.7 Hz). LC-MS (m/z): 293 (M+H, 100).

Synthesis 145

1-(4-(2-Amino-3-nitropyridin-4-yl-oxy)-2-(methylthio)phenyl)-3-(4-chloro-3-(trifluoromethyl)phenyl)urea (CJS 3507)

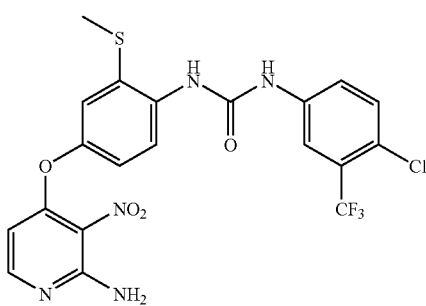

Method H3 was used with 4-(4-amino-3-(methylthio)phenoxy)-3-nitropyridin-2-amine (150 mg, 0.5 mmol) to afford the title compound (247 mg, 93%) as a orange powder. $^1$H-NMR ($\delta$, ppm, DMSO-$d_6$): 2.47 (s, 3H, CH$_3$), 6.02 (d, 1H, H$_{Py,5}$, J=5.7 Hz), 7.04 (d, 1H, H$_{arom}$, J=8.8 Hz), 7.16 (s, 2H, NH$_{2,Py}$), 7.21 (m, 1H, H$_{arom}$, J=8.8 Hz), 7.62 (m, 2H, H$_{arom}$), 7.85 (m, 1H, H$_{arom}$), 8.01 (d, 1H, H$_{arom}$, J=8.8 Hz), 8.11 (d, 1H, H$_{Py,6}$, J=5.7 Hz), 8.20 (s, 1H, NH$_{urea1}$), 9.75 (s, 1H, NH$_{urea3}$). LC-MS (m/z): 514 (M+H, 100).

Synthesis 146

1-(4-(2,3-Diaminopyridin-4-yl-oxy)-2-(methylthio)phenyl)-3-(4-chloro-3-(trifluoromethyl)phenyl)urea

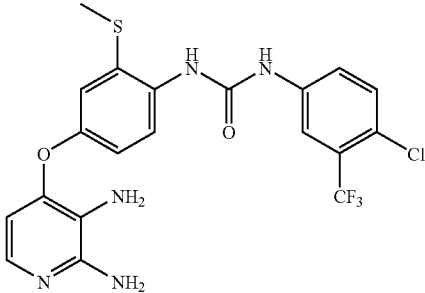

A suspension of iron powder (4 equivalents, 78 mg, 1.4 mmol) and ammonium chloride (5.8 equivalents, 109 mg, 2 mmol) in ethanol (400 μL) and water (438 μL) was heated to reflux. 1-(4-(2-amino-3-nitropyridin-4-yl-oxy)-2-(methylthio)phenyl)-3-(4-chloro-3-(trifluoromethyl)phenyl)urea (180 mg, 0.35 mmol) was added in portions and the mixture stirred at reflux for 24 hours. After cooling to room temperature, the slurry mixture was filtered and washed with ethanol. After removal of the solvent, the crude powder was dissolved into EtOAc, filtered to removed the precipitate, and evaporated to provide the title compound (100 mg, 59%) as a sticky dark oil. $^1$H-NMR ($\delta$, ppm, DMSO-$d_6$): 2.41 (s, 3H, CH$_3$), 5.61 (s, 2H, NH$_{2,Py}$), 6.06 (d, 1H, H$_{Py,5}$, J=5.6 Hz), 6.79 (d, 1H, H$_{arom}$, J=8.7 Hz), 7.01 (s, 1H, H$_{arom}$), 7.26 (d, 1H, H$_{Py,6}$, J=5.6 Hz), 7.58-7.69 (m, 4H, H$_{arom}$), 8.12 (s, 2H, NH$_{2,Py}$), 8.27 (s, 1H, NH$_{urea1}$), 10.02 (s, 1H, NH$_{urea3}$). LC-MS (m/z): 484 (M+H, 100).

Synthesis 147

1-(4-(2,3-Dihydro-2-oxo-1H-imidazo[4,5-b]pyridin-7-yl-oxy)-2-(methylthio)phenyl)-3-(4-chloro-3-(trifluoromethyl)phenyl)urea (CJS 3512)

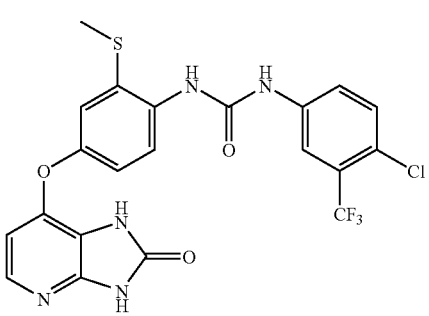

Method E3 was used with 1-(4-(2,3-diaminopyridin-4-yl-oxy)-2-(methylthio)phenyl)-3-(4-chloro-3-(trifluoromethyl)phenyl)urea to afford the title compound (56 mg, 55%) as a brown powder. $^1$H-NMR ($\delta$, ppm, DMSO-$d_6$): 2.45 (s, 3H, CH$_3$), 6.42 (d, 1H, H$_{Py,5}$, J=4.2 Hz), 6.99 (d, 1H, H$_{arom}$, J=8.4 Hz), 7.19 (s, 1H, H$_{arom}$), 7.63 (s, 2H, H$_{arom}$), 7.78 (s, 2H, H$_{arom}$), 8.12 (s, 1H, H$_{arom}$), 8.26 (s, 1H, NH$_{urea3}$), 9.91 (s, 1H, NH$_{urea3}$), 11.25 (s, 1H, NH$_{Py}$), 11.44 (bs, 1H, NH$_{Py}$). LC-MS (m/z): 510 (M+H, 100).

Synthesis 148

4-Amino-3-phenylphenol

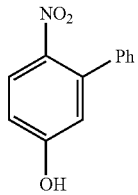

The title compound was prepared in three steps, following the method shown in synthesis on 3 steps, is based on the work of Avenova et al., 1995 (Avenoza, A., Busto, J. H., Cativiela, C., Peregrina, J. M., 1995, *Synthesis*, pp. 671-674). $^1$H-NMR (δ, ppm, CDCl$_3$): 6.60-6.73 (m, 3H, Arom.), 7.30-7.48 (m, 5H, Arom.). GC-MS (m/z): 185.08.

Synthesis 149

4-(4-Amino-3-phenylphenoxy)-3-nitropyridin-2-amine

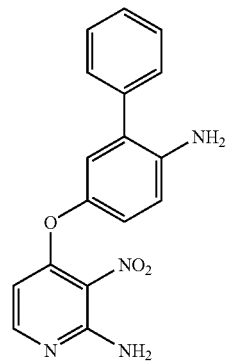

Method A was used with 4-amino-3-phenylphenol (764 mg, 0.4 mmol) to afford the title compound (1.26 g, 95%) without any purification as a red brown solid. $^1$H-NMR (δ, ppm, DMSO-d$_6$): 4.89 (bs, 2H, NH$_{2,Ph}$), 6.02 (d, 1H, H$_{Py,5}$, J=5.7 Hz), 6.83 (m, 2H, H$_{arom}$), 6.91 (m, 1H, H$_{arom}$), 7.05 (bs, 2H, NH$_{2,Py}$), 7.35 (m, 1H, H$_{arom}$), 7.44 (m, 4H, H$_{arom}$), 7.96 (d, 1H, H$_{Py,6}$, J=5.7 Hz). LC-MS (m/z): 322 (M+H, 100).

Synthesis 150

1-(4-(2-Amino-3-nitropyridin-4-yl-oxy)-2-phenylphenyl)-3-(4-chloro-3-(trifluoromethyl)phenyl)urea (CJS 3509)

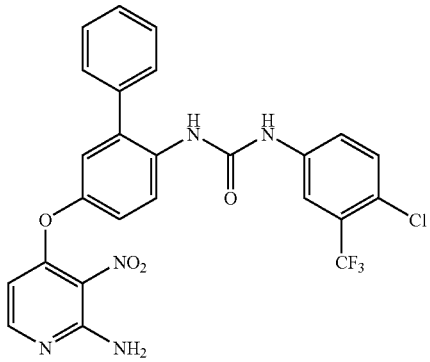

Method H3 was used with 4-(4-amino-3-phenylphenoxy)-3-nitropyridin-2-amine (583 mg, 1.8 mmol) to afford the title compound (613 mg, 62%) as a yellow powder. $^1$H-NMR (δ, ppm, DMSO-d$_6$): 6.11 (d, 1H, H$_{Py,6}$, J=5.7 Hz), 7.07 (d, 1H, H$_{arom}$, J=2.7 Hz), 7.15 (s, 1H,H$_{arom}$), 7.21 (dd, 1H, H$_{arom}$, J=8.8 Hz, J=2.7 Hz), 7.40-7.52 (m, 6H, H$_{arom}$), 7.57 (s, 2H, NH$_{2,Py}$), 7.92 (d, 1H, H$_{arom}$, J=8.8 Hz), 7.99 (s, 1H, NH$_{urea1}$), 8.03 (d, 1H, H$_{Py,6}$, J=5.7 Hz), 9.75 (s, 1H, NH$_{urea3}$). LC-MS (m/z): 544 (M+H, 100).

Synthesis 151

1-(4-(2,3-Diaminopyridin-4-yl-oxy)-2-(phenyl)phenyl)-3-(4-chloro-3-(trifluoromethyl)phenyl)urea

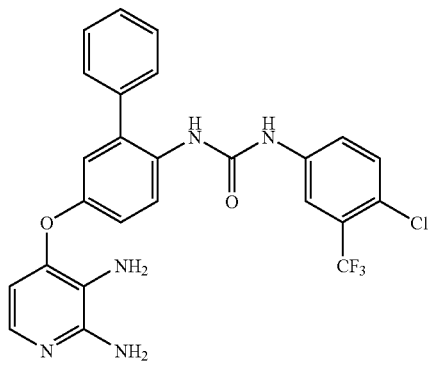

Method D2 was used with 1-(4-(2-amino-3-nitropyridin-4-yl-oxy)-2-phenylphenyl)-3-(4-chloro-3-(trifluoromethyl) phenyl)urea (400 mg, 1.5 mmol) to afford the title compound (377 mg, 99%) without any purification as a pale brown powder. $^1$H-NMR (δ, ppm, DMSO-d$_6$): 4.52 (bs, 2H, NH$_{2,Py}$), 5.57 (bs, 1H,), 6.22 (d, 1H, H$_{Py,5}$, J=5.9 Hz), 6.85 (s, 1H, H$_{arom}$), 6.99 (m, 1H, H$_{arom}$), 7.40 (m, 4H, H$_{arom}$), 7.46 (m, 3H, H$_{arom}$), 7.55 (bs, 2H, NH$_{2,Py}$), 7.72 (d, 1H, H$_{arom}$, J=8.8 Hz), 7.88 (s, 1H, H$_{arom}$), 8.02 (s, 1H, NH$_{urea1}$), 9.41 (s, 1H, NH$_{urea3}$). LC-MS (m/z): 514 (M+H, 100).

Synthesis 152

1-(4-(2,3-Dihydro-2-oxo-1H-imidazo[4,5-b]pyridin-7-yl-oxy)-2-phenylphenyl)-3-(4-chloro-3-(trifluoromethyl)phenyl)urea (CJS 3511)

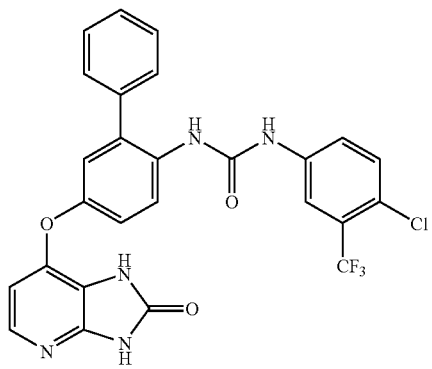

Method E3 was used with 1-(4-(2,3-diaminopyridin-4-yl-oxy)-2-(phenyl)phenyl)-3-(4-chloro-3-(trifluoromethyl)phenyl)urea to afford the title compound (24 mg, 15%) as a grey powder. $^1$H-NMR ($\delta$, ppm, DMSO-d$_6$): 6.50 (bs, 1H, H$_{Py,5}$), 7.04 (s, 1H, H$_{arom}$), 7.12 (s, 1H, H$_{arom}$, J=7.6 Hz), 7.37-7.60 (m, 5H, H$_{arom}$), 7.75-7.95 (m, 1H, H$_{arom}$), 8.03 (s, 1H, NH$_{urea1}$), 9.42 (s, 1H, NH$_{urea3}$), 11.19 (s, 1H, NH$_{Py}$), 11,35 (s, 1H, NH$_{Py}$). LC-MS (m/z): 540 (M+H, 100).

Synthesis 153

1-(4-(2,3-Dihydro-2-oxo-1H-imidazo[4,5-b]pyridin-7-yl-oxy)phenyl)-3-(4-chloro-3-(trifluoromethyl)phenyl)thiourea (CJS 3254)

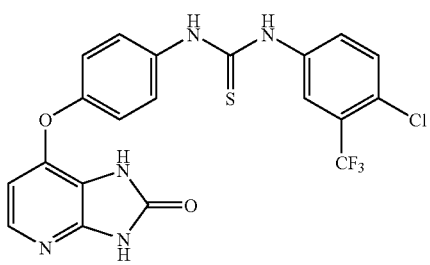

A mixture of 4-chloro-3-trifluoromethylphenyl-isothiocyanate (20 μL, 0.12 mmol) and 7-(4-aminophenoxy)-1H-imidazo[4,5-b]pyridin-2(3H)-one (29 mg, 0.12 mmol) in anhydrous THF (2 mL) was stirred at room temperature for 3 days. The solvent was evaporated and the solid residue was washed with DCM to afford the title compound (47 mg, 82%). $^1$H-NMR ($\delta$, ppm, DMSO-d$_6$): 6.40 (d, 1H, H$_{Py,6}$, J=5.8 Hz), 7.15 (d, 2H, H$_{arom,Ph,3+5}$, J=8.70 Hz), 7.54 (d, 2H, H$_{arom,Ph,2+6}$, J=8.75 Hz), 7.67 (d, 1H, H$_{Py,6}$, J=8.55 Hz), 7.80 (broad s, 2H, H$_{arom'}$), 8.08 (s, 1H, H$_{arom'}$), 10.03 (s, 1H, NH$_{thiourea,1}$), 10.10 (s, 1H, NH$_{thiourea,3}$), 11.18 (s, 1H, NH$_{Py3}$), 11.36 (s, 1H, NH$_{Py2}$).

Synthesis 154

1-(3-tert-Butyl-1-(4-fluorophenyl)-1H-pyrazol-5-yl)-3-methyl-4-(2-oxo-2,3-dihydro-1H-imidazo[4,5-b]pyridin-7-yl-oxy)phenyl)urea (CJS 3419)

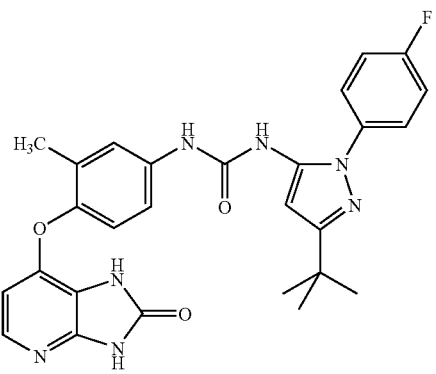

Method I2 was used with phenyl 3-tert-butyl-1-(4-fluorophenyl)-1H-pyrazol-5-yl-carbamate and 7-(4-amino-2-methylphenoxy)-1H-imidazo[4,5-b]pyridin2(3H)-one to afford the title compound (3 mg, 7%). $^1$H-NMR ($\delta$, ppm, DMSO-d$_6$): 1.28 (s, 9H), 2.10 (s, 3H), 6.15 (d, 1H, J=6.0 Hz), 6.36 (s, 1H), 7.01 (d, 1H, J=8.8 Hz), 7.27 (d, 1H, J=9.4 Hz), 7.35-7.39 (m, 2H), 7.43 (s, 1H), 7.55-7.58 (m, 2H), 7.71 (d, 1H, J=6.0 Hz), 8.36 (s, 1H), 8.99 (s, 1H), 11.16 (s, 1H), 11.31 (s, 1H). LC-MS (m/z): 516 (M+H, 100).

Synthesis 155

1-(4-Chloro-3-(trifluoromethyl)phenyl)-3-(3-fluoro-4-(2-oxo-2,3-dihydro-1H-imidazo[4,5-b]pyridin-7-yl-oxy)phenyl)urea (CJS 3418)

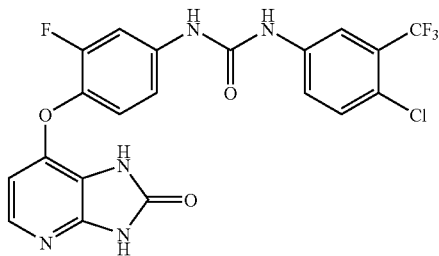

Method E3 was used with 1-(4-chloro-3-(trifluoromethyl)phenyl)-3-(4-(2,3-diaminopyridin-4-yl-oxy)-3-fluorophenyl)urea (0.14 g, 0.316 mmol) to produce the title compound (4 mg, 3%). m/z 482.0 [(M+H)$^+$ calcd for C$_{20}$H$_{12}$ClF$_4$N$_5$O$_3$ 481.1].

Synthesis 156

4-Chloro-N-methyl-3-nitropyridin-2-amine

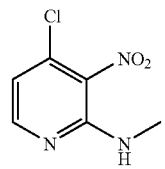

2-Amino-4-chloro-3-nitropyridine (590 mg, 4 mmol) was dissolved in dry THF (15 mL), the solution was cooled to 0° C. and NaH (240 mg, 6 mmol) was added. The reaction mixture was stirred for 2 hours, and allowed to warm at room temperature. The solvent was evaporated and the residue extracted between AcOEt and water. The organic layer was dried (MgSO$_4$) and evaporated. The crude mixture was purified by column chromatography (eluent DCM) to afford the title compound (190 mg, 25%). $^1$H-NMR ($\delta$, ppm, DMSO-d$_6$): 2.88 (d, 3H, Me, J=4.55 Hz), 6.86 (d, 1H, H$_{Py,5}$, J=5.31 Hz), 7.44 (broad s, 1H, NH), 8.21 (d, 1H, H$_{Py,5}$, J=5.30 Hz).

Synthesis 157 tert-Butyl 4-(2-(methylamino)-3-nitropyridin-4-yl-oxy)phenylcarbamate

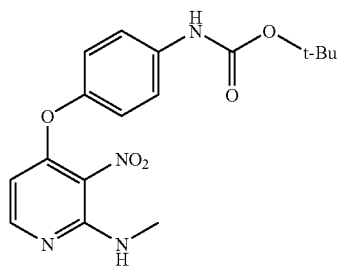

N-Boc-4-hydroxyaniline (334 mg, 1.6 mmol) was dissolved in dry DMF (5 mL) and the solution was degassed by argon bubbling for 10 minutes. Potassium tert-butoxide (179 mg, 1.6 mmol) was added, and the stirring and argon bubbling continued for 50 minutes. 4-Chloro-N-methyl-3-nitropyridin-2-amine (260 mg, 1.4 mmol) was added to the reaction mixture. The reaction mixture was heated and stirred at 80° C. for 9 hours, under argon. The solvent was evaporated and the residue was extracted between DCM and aqueous NaOH 1M. The extraction was repeated twice, the organic layer was dried over $MgSO_4$, and evaporated. The residue was purified by column chromatography (eluent gradient DCM to DCM:AcOEt 15:1) to afford the title compound (300 mg, 60%). $^1$H-NMR (δ, ppm, DMSO-$d_6$): 1.48 (s, 9H, t-Bu), 2.91 (d, 3H, Me, J=4.60 Hz), 5.94 (d, 1H, $H_{Py,5}$, J=5.70 Hz), 7.09 (d, 2H, $H_{arom,Ph,3+5}$, J=9.00 Hz), 7.45 (m, 1H, $NH_{Py}$), 7.53 (d, 2H, $H_{arom,Ph,2+6}$), 8.07 (d, 1H, $H_{Py,6}$), 9.46 (s, 1H, NH).

Synthesis 158 tert-Butyl 4-(3-amino-2-(methylamino)pyridin-4-yl-oxy)phenylcarbamate

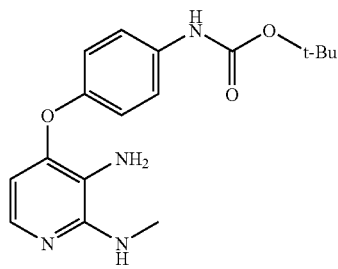

Method D1 was used with tert-butyl 4-(2-(methylamino)-3-nitropyridin-4-yl-oxy)phenylcarbamate (300 mg, 0.83 mmol) to afford the title compound as a brown solid (260 mg, 95%). $^1$H-NMR (δ, ppm, DMSO-$d_6$): 1.47 (s, 9H, t-Bu), 2.85 (s, 3H, Me), 4.34 (s, 2H, $NH_{2,Py}$) 5.75 (t, 1H, $NH_{Py}$, J=2.95 Hz), 5.95 (d, 1H, $H_{Py,5}$, J=3.50 Hz), 6.90 (d, 2H, $H_{arom,Ph,3+5}$, J=8.30 Hz), 7.33 (d, 1H, $H_{Py,6}$), 7.42 (d, 2H, $H_{arom,Ph,2+6}$), 9.27 (s, 1H, NH).

Synthesis 159 tert-Butyl 4-(2,3-dihydro-3-methyl-2-oxo-1H-imidazo[4,5-b]pyridin-7-yl-oxy)phenyl carbamate

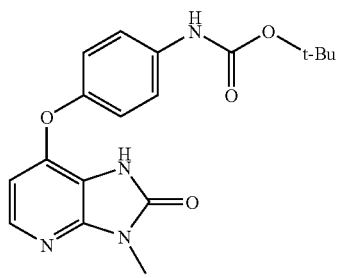

Method E3 was used with tert-butyl 4-(3-amino-2-(methylamino)pyridin-4-yl-oxy)phenylcarbamate (250 mg, 0.76 mmol) to afford the title compound as a brown solid (245 mg, 91%). $^1$H-NMR (δ, ppm, DMSO-$d_6$): 1.47 (s, 9H, t-Bu), 3.30 (s, 3H, Me), 6.35 (d, 1H, $H_{Py,5}$, J=5.95 Hz), 7.10 (d, 2H, $H_{arom,Ph,3+5}$, J=6.7 Hz), 7.52 (d, 2H, $H_{arom,Ph,2+6}$), 7.82 (d, 1H, $H_{Py,6}$), 9.46 (s, 1H, NHBoc), 11.46 (s, 1H, $NH_{Py2}$).

Synthesis 160

7-(4-Aminophenoxy)-3-methyl-1H-imidazo[4,5-b]pyridin-2(3H)-one

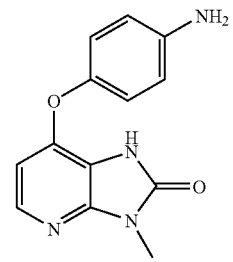

Method F was used with tert-butyl 4-(2,3-dihydro-3-methyl-2-oxo-1H-imidazo[4,5-b]pyridin-7-yl-oxy)phenyl carbamate (245 mg, 0.76 mmol) to afford the title compound as a solid (47 mg, 27%). $^1$H-NMR (δ, ppm, DMSO-$d_6$): 3.29 (s, 3H, Me), 5.13 (s, 2H, $NH_2$), 6.35 (d, 1H, $H_{Py,5}$, J=5.25 Hz), 6.61 (d, 2H, $H_{arom,Ph,3+5}$, J=8.65 Hz), 6.87 (d, 2H, $H_{arom,Ph,2+6}$), 7.79 (d, 1H, $H_{Py,6}$), 11.41 (s, 1H, $NH_{Py2}$).

Synthesis 161

1-(4-(2,3-Dihydro-3-methyl-2-oxo-1H-imidazo[4,5-b]pyridin-7-yl-oxy)phenyl)-3-(4-chloro-3-(trifluoromethyl)phenyl)urea (CJS 3255)

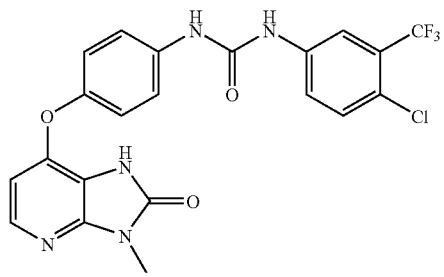

Method H2 was used with 7-(4-aminophenoxy)-3-methyl-1H-imidazo[4,5-b]pyridin-2(3H)-one (20 mg, 0.08 mmol) and 1-chloro-4-isocyanato-2-(trifluoromethyl)benzene (17 mg, 0.08 mmol) to afford the title compound as a solid (32 mg, 84%). $^1$H-NMR ($\delta$, ppm, DMSO-$d_6$): 3.30 (s, 3H, CH$_3$), 6.40 (d, 1H, H$_{Py,5}$, J=5.55 Hz), 7.13 (d, 2H, H$_{arom,Ph,3+5}$, J=8.05 Hz), 7.54 (d, 2H, H$_{arom,Ph,2+6}$), 7.61-7.65 (m, 2H, H$_{arom'}$), 7.84 (d, 1H, H$_{Py,6}$), 8.11 (s, 1H, H$_{arom'}$), 8.97 (s, 1H, NH$_{urea1}$), 9.20 (s, 1H, NH$_{urea,3}$), 11.48 (s, 1H, NH$_{Py3}$).

Biological Methods—Kinase Assay No. 1

Compounds were assessed by a kinase assay performed according to the following protocol.

1. Prepare three stock solutions: AB Solution, Start Mix, and Dilution Buffer.

| AB solution: 1 ml | |
|---|---|
| Tris pH 7.5 (1M) | 50 µL |
| β-Mercaptoethanol | 3 µL |
| EDTA pH 8 (0.5M) | 2 µL |
| Triton (10%) | 10 µL |
| NaF (5 mM) | 30 µL |
| NaVO$_4$ (20 µM) | 25 µL |
| Bovine Serum Albumin (20 mg/ml) | 50 µL |
| *Myelin Basic Protein (30 mg/mL) | 60 µL |
| *MEK (5 mg/ml) | 5 µL |

| AB solution: 1 ml (continued) | |
|---|---|
| *ERK (7.5 mg/ml) | 37.5 µL |
| H$_2$O | 727.5 µL |

*= Added just prior to use

| Start mix: 300 µL | |
|---|---|
| ATP (100 mM) | 1.8 µL |
| MgCl$_2$ (1M) | 14.4 µL |
| H$_2$O | 281.8 µL |
| HOT $^{32}$Pα | 2 µL |

| Dilution buffer: 1 ml | |
|---|---|
| Tris pH 7.5 (1M) | 50 µL |
| EDTA pH 8 (0.5M) | 0.2 µL |
| NaCl (5M) | 20 µL |
| Triton (10%) | 10 µL |
| NaF (5 mM) | 10 µL |
| NaVO$_4$ (20 µM) | 10 µL |
| β-Mercaptoethanol | 3 µL |
| Bovine Serum Albumin (20 mg/mL) | 50 µL |
| H$_2$O | 847 µL |

2. Prepare the B-RAF dilutions:
   B-RAF dilution (1)=Mix 7.5 µL $^{V600E}$B-RAF+30 µL dilution buffer.
   (This is a 1 in 5 dilution.)
   B-RAF dilution (0.1)=Mix 20 µL $^{V600E}$B-RAF dilution (1)+180 µL dilution buffer.
   (This is a further 1 in 10 dilution, so the total B-RAF dilution is 50×.)

3. Mix 700 µL AB solution+175 µL B-RAF dilution (0.1). This solution is now referred to as AB0.1.

4. Add 24.5 µL AB 0.1 solution into numbered tubes, as indicated below.
   (Note: each reaction is tested in triplicate.)

5. Add 20 µL AB solution to the blowout and empty vector control tubes.

6. Add DMSO, H$_2$O etc. to the control tubes, as below.

7. Add 0.5 µL of test compound of the desired concentration (diluted in DMSO) to the appropriate tubes, as below. (Note: stock test compound concentration is 100 mM.)

| Tube | AB0.1 | AB | Test Compound concentration | Controls | Amount of B-RAF per tube |
|---|---|---|---|---|---|
| 1 | 24.5 µL | — | 1000 µM | — | 0.1 µL |
| 2 | 24.5 µL | — | 100 µM | — | 0.1 µL |
| 3 | 24.5 µL | — | 10 µM | — | 0.1 µL |
| 4 | 24.5 µL | — | 1 µM | — | 0.1 µL |
| 5 | 24.5 µL | — | 0.1 µM | — | 0.1 µL |
| 6 | 24.5 µL | — | 0.01 µM | — | 0.1 µL |

-continued

| Tube | AB0.1 | AB | Test Compound concentration | Controls | Amount of B-RAF per tube |
|---|---|---|---|---|---|
| 7 | 24.5 µL | — | — | DMSO 0.5 µL | 0.1 µL |
| 8 | 24.5 µL | — | — | H$_2$O 0.5 µL | 0.1 µL |
| 9 (blowout) | — | 20 µL | — | B-raf dilution (1) 5 µL | 1 µL |
| 10 | — | 20 µL | — | Empty vector 5 µL | 0 µL |
| 11 (positive control) | 24.5 µL | — | — | PD (10 µM) 0.5 µL | 0.1 µL |

8. Incubate the tubes at 30° C. for 10 minutes.

9. Add 5 µL of start mix to each tube in 15-second intervals, gently spinning each tube after adding the start solution, and incubate at 30° C. for 10 minutes.

10. Stop the reaction by placing 20 µL of the reaction solution in the tube onto a small piece of P81 paper (pre-numbered), and drop this paper into 75 mM orthophosphoric acid. Repeat this every 15 seconds with each tube.

11. When all reactions have been stopped, replace the acid with fresh acid.

12. Do two more of these washes every 15 minutes.

13. Remove the paper from the acid and put into pre-numbered tubes.

14. Count the radiation levels using a Packard Cerenkov counter.

Biological Methods—Kinase Assay No. 2 (DELFIA)

Compounds were assessed by a kinase assay performed according to the following protocol.

The following reagents were prepared:

DELFIA Kinase Buffer (DKB):

| Reagent | Stock Concentration | Volume per mL (µL) | Volume per 10 mL plate (µL) |
|---|---|---|---|
| 20 mM MOPS pH 7.2 | 0.2 M | 100 | 1000 |
| 0.5 M EGTA pH 8.0 | 0.5 M | 10 | 100 |
| 10 mM MgCl$_2$ | 1 M | 10 | 100 |
| 0.1% β-mercaptoethanol | | 1 | 10 |
| 25 mM β-glycerophosphate | 0.5 M | 50 | 500 |
| Water | 100% | 829 | 8290 |

MOPS = 3-[N-Morpholino] propanesulfonic acid (Sigma M3183).
EGTA = Ethylene glycol-bis(2-aminoethylether)-N,N,N',N'-tetraacetic acid (Sigma E3889).

DKB1 (DKB with B-RAF and MEK Protein):

Combine 4950 µL of DKB and 50 µL of 2.5 mg/ml GST-MEK stock (to give 1 mg of MEK per 40 µL). Then add 22.5 µL of B-RAF to give ~0.2 µL of B-RAF per 40 µL.

DKB2 (DKB with MEK Protein):

Combine 4950 µL of DKB and 50 µL of 2.5 mg/ml GST-MEK stock (to give 1 mg of MEK per 40 µL). Use 500 µL of this for the blow out (BO) and the empty vector (EV) control.

ATP:

100 mM stock, dilute to 500 µM to give 100 µM final concentration in assay.

Inhibitors (Test Compounds):

100 mM stock, dilute to 10, 3, 1, 0.3, 0.1, 0.03, 0.01, 0.003, 0.001, 0.0003, 0.0001 mM in DMSO in drug plate, resulting in concentration of 100, 30, 10, 3, 1, 0.3, 0.1, 0.03, 0.01, 0.003, 0.001 µM in the assay.

Primary Antibody:

Phospho-MEK1/2 CST #9121S diluted 1:1000 in DELFIA assay buffer (AB). Preincubate antibody in the AB for 30 minutes at room temperature prior to use.

Secondary Antibody:

Anti-rabbit-Eur labelled secondary Perkin Elmer #AD0105 diluted 1:1000 in DELFIA assay buffer (AB). Preincubate antibody in the AB for 30 minutes at room temperature prior to use. (Primary and secondary antibodies were incubated together,)

Tween:

0.1% Tween 20 in water

Assay Buffer:

DELFIA assay buffer Perkin Elmer #4002-0010

Enhancement Solution:

DELFIA enhancement solution Perkin Elmer 94001-0010

Assay Plates:

96 well glutathione-coated black plate Perbio #15340

Procedure:

1. Preblock wells with 5% milk in TBS for 1 hour.

2. Wash wells with 3× with 200 µL TBS.

3. Plate out 40 µL of DKB1 for all inhibitors (test compounds), DMSO control, and optionally other control compounds.

4. Plate out 40 µL of DKB2 for BO and EV wells.

5. Add inhibitors (test compounds) at 0.5 µL per well according to desired plate layout.

6. Add 0.5 µL DMSO to vehicle control wells.

7. Add 2 µL of B-RAF to BO and EV wells.

8. Pre-incubate with inhibitors (test compounds) for 10 minutes at room temperature with shaking.

9. Add 10 µL of 500 µM ATP stock, in DKB, to give 100 µM assay concentration.

10. Seal plates with TopSeal and incubate at room temperature with shaking for 45 minutes.

11. Wash plates 3× with 200 µL 0.1% Tween20/Water to terminate reaction.

12. Add 50 μL per well of antibody mix and incubate for 1 hour at room temperature with shaking.

13. Wash plates 3× with 200 μL 0.1% Tween20/Water.

14. Add 100 μL DELFIA enhancement solution per well, cover in foil, and incubate at room temperature for 30 minutes with shaking.

15. Read on Victor using Europium protocol.

Biological Methods—Cell Based Assays

Compounds were assessed using cell-based assays which were performed according to the following protocol.

Day 0:

Plate out 16,000 cells/well in 99 μL medium in a 96-well plate.

Day 1:

1. Add 1 μL inhibitor to the cells (total 1 μL solution).

2. Incubate the cells with test compound for 6 hours at 37° C.

3. Aspirate off the solution from all of the wells.

4. Fixate the cells with 100 μL 4% formaldehyde/0.25% Triton X-100 PBS per well.

5. Incubate the plate for 1 hour at 4° C.

6. Aspirate off the fixing solution and add 300 μL TBS per well.

7. Leave the plate overnight at 4° C.

Day 2:

1. Wash the plate 2× with 200 μL PBS per well.

2. Block with 100 μL 5% dried milk in TBS.

3. Incubate the plate for 20 minutes at 37° C.

4. Wash the plate 2× with 0.1% tween/$H_2O$.

5. Add 50 μL of 3 μg/mL primary antibody ppERK (Sigma M8159), diluted in 5% milk powder/TBS, to each well.

6. Incubate the plate for 2 hours at 37° C.

7. Wash the plate 3× with 0.1% tween/$H_2O$.

8. Add 50 μL of 0.45 μg/mL secondary Europium-labelled anti-mouse antibody (Perkin Elmer) to each well.

9. Incubate the plate for 1 hour at 37° C.

10. Wash the plate 3× with 0.1% tween/$H_2O$.

11. Add 100 μL enhancement solution (Perkin Elmer) to each well.

12. Leave the plate for approximately 10 minutes at room temperature before gently shaking the plate.

13. Read Europium Time Resolved Fluorescence in Victor2.

14. Wash the plate 2× with 0.1% tween/$H_2O$.

15. Measure the protein concentration with BCA (Sigma) by adding 200 μL of solution per well.

16. Incubate the plate for 30 minutes at 37° C.

17. Read absorbance levels at 570 nm in a plate reader.

Note that Europium counts are normalised for protein levels by dividing counts by absorbance.

Biological Methods—Cell Proliferation Assay (SRB $IC_{50}$)

Cultures of WM266.4 melanoma cells are routinely cultured in DMEM/10% foetal bovine serum, at 37° C., in 5% $CO_2$ water saturated atmosphere. Cultures are maintained in exponential growth phase by sub-culturing before having become confluent (3-5 day intervals). Single cell suspensions are prepared by harvesting an 80 $cm^2$ tissue culture flask with 5 mL commercial trypsin EDTA. After 5 minutes, the detached cells are mixed with 5 mL fully complemented culture medium and centrifugally pelleted (1000 rpm for 7 minutes). After aspirating the supernatant, the cell pellet is re-suspended in 10 mL fresh medium and the cells fully disaggregated by drawing the whole volume up/down 5 times through a 19-gauge needle. The concentration of the cells is determined using a haemocytometer (1/10 dilution). A suitable volume to give at least a 2-fold excess for the number of tests being conducted, typically 100-200 mL, is prepared by diluting the cell suspension to 10,000/mL, and 100 μL/well dispensed into 96 well plates using a programmable 8-channel peristaltic pump, giving 1000 cells/well, leaving column 12 blank. The plates are returned to the incubator for 24 hours to allow the cells to re-attach. The compounds being tested are prepared at 20 mM in dimethylsulphoxide. Aliquots (200 μL) are diluted into 20 mL culture medium giving 200 μM, and 10 serial dilutions of 3× performed by transferring 5 mL to 10 mL. Aliquots (100 μL) of each dilution are added to the wells, using an 8-channel pipettor, thus performing a final further 2× dilution, and giving doses ranging from 100 μM to 0.005 μM. Column 11 receives plain culture medium only. Each compound is tested in quadruplicate, each replicate being the average of four wells, and two plates per compound. After a further 6 days growth, the plates are emptied, and the cells are fixed in 10% trichloroacteic acid for 10 minutes on ice. After thorough rinsing in running tap water, the plates are dried, and stained by adding 50 μL of a solution of 0.1% sulphorhodamine-B in 1% acetic acid, for 10 minutes at room temperature. The stain is poured out and the plates thoroughly rinsed under a stream of 1% acetic acid, thus removing unbound stain, and dried. The bound stain is taken into solution by addition of 150 μL Tris buffer pH 8, followed by 10 minutes on a plate-shaker (approximately 500 rpm). The absorbance at 540 nm in each well (being proportional to the number of cells present) is determined using a plate reader. After averaging the results in rows A-D and E-H, the blank value (row 12) is subtracted, and results expressed as percentage of the untreated value (row 11). The 10 values so derived (in quadruplicate) are plotted against the logarithm of the drug concentration, and analysed by non-linear regression to a four parameter logistic equation, setting constraints if suggested by inspection. The $IC_{50}$ generated by this procedure is the concentration of the drug that produces a percentage control $A_{540}$ midway between the saturation, and zero-effect plateaus.

Biological Methods—BRAF High Throughput Screen $^{V600E}$BRAF was used in a cascade assay that included MEK1, ERK2 and Elk. Phosphorylation through this cascade was measured using a specific phospho-Elk antibody and a Europium-labelled anti-mouse IgG secondary antibody in a DELFIA ELISA assay.

High-binding 384-well clear polystyrene plates (Greiner 00360148) were coated overnight (4° C.) with 25 μL Elk (2.5 μg/mL in PBS).

The plates were washed three times with PBS and the wells blocked with 5% milk (Marvel) in PBS. After 30 minutes at room temperature, the plates were again washed three times with PBS.

$^{V600E}$BRAF lysate, MEK1 and ERK2 were pre-mixed in BRAF buffer (Tris 50 mM, pH 7.5, containing 10 mM MgCl$_2$, 100 µM EGTA, 0.1% mercaptoethanol, 5 mM sodium fluoride, 200 µM sodium orthovanadate and 0.5 mg/ml BSA) so that the equivalent of 0.05 µL BRAF, 81.25 ng MEK1 and 1 µg ERK2 were added to each well in a total volume of 17 µL. Inhibitors (200 µM) or DMSO control (2%) 3 µL were added to the plates prior to enzyme mix. The enzyme reaction was started by the addition of 5 µL ATP solution (125 µM in BRAF buffer) (final concentration 25 µM) and the reaction stopped by washing the plates three times in 0.1% Tween/water. Anti-phospho Elk (Ser 383 monoclonal antibody) (Cell Signalling Technology #9186) diluted 1/4000 and Eu-labelled anti-mouse IgG (Perkin Elmer Life Sciences, AD0124) diluted to 1/50, were pre-mixed (30 minutes at room temperature) in DELFIA assay buffer (Perkin Elmer Life Sciences 4002-0010) and 25 µL added to each well. After 1.5 hours, the plates were washed again (3×) in 0.1% Tween/water.

35 µL of Enhancement solution (Perkin Elmer Life Sciences 4001-0010) was then added and after 20 minutes at room temperature, the plates were read on a Victor2 at 615 nm (excitation 340 nm in time resolved fluorescence mode). Percent inhibition was calculated in relation to DMSO only controls. Staurosporin was used as a positive control.

In a high throughput screen (HTS) context, hits were identified as compounds that inhibited the enzyme cascade by more than 3 standard deviations of the mean of the compound wells (n=320) on each plate.

Biological Data

Biological data were obtained (using one or more of: BRAF V600E Kinase Assay; Phospho-ERK Cell-based Assay; Cell proliferation (SRB) assay) for the following 65 compounds:

| No. | ID No. |
|---|---|
| 1 | CJS 3233 |
| 2 | CJS 3239 |
| 3 | CJS 3240 |
| 4 | CJS 3246 |
| 5 | CJS 3247 |
| 6 | CJS 3253 |
| 7 | CJS 3254 |
| 8 | CJS 3255 |
| 9 | CJS 3410 |
| 10 | CJS 3418 |
| 11 | CJS 3419 |
| 12 | CJS 3502 |
| 13 | CJS 3505 |
| 14 | CJS 3506 |
| 15 | CJS 3510 |
| 16 | CJS 3511 |
| 17 | CJS 3512 |
| 18 | CJS 3600 |
| 19 | CJS 3601 |
| 20 | CJS 3602 |
| 21 | CJS 3603 |
| 22 | CJS 3604 |
| 23 | CJS 3605 |
| 24 | CJS 3606 |
| 25 | CJS 3607 |
| 26 | CJS 3608 |
| 27 | CJS 3609 |
| 28 | CJS 3610 |
| 29 | CJS 3611 |
| 30 | CJS 3612 |
| 31 | CJS 3613 |
| 32 | CJS 3614 |
| 33 | CJS 3615 |
| 34 | CJS 3616 |
| 35 | CJS 3617 |
| 36 | CJS 3618 |
| 37 | CJS 3619 |
| 38 | CJS 3620 |
| 39 | CJS 3650 |
| 40 | CJS 3651 |
| 41 | CJS 3652 |
| 42 | CJS 3653 |
| 43 | CJS 3654 |
| 44 | CJS 3655 |
| 45 | CJS 3656 |
| 46 | CJS 3657 |
| 47 | CJS 3659 |
| 48 | CJS 3660 |
| 49 | CJS 3661 |
| 50 | CJS 3662 |
| 51 | CJS 3665 |
| 51 | CJS 3666 |
| 52 | CJS 3669 |
| 53 | CJS 3670 |
| 54 | CJS 3671 |
| 55 | CJS 3672 |
| 56 | CJS 3673 |
| 57 | CJS 3674 |
| 58 | CJS 3675 |
| 59 | CJS 3676 |
| 60 | CJS 3677 |
| 61 | CJS 3679 |
| 62 | CJS 3680 |
| 62 | CJS 3681 |
| 64 | CJS 3680 |
| 65 | CJS 3681 |

For the BRAF V600E Kinase Assay, the IC50 (µM) values are as follows:

at least 3 compounds tested have an IC50 of less than 0.01 µM;

at least 23 of the compounds tested have an IC50 of less than 0.1 µM;

at least 37 of the compounds tested have an IC50 of less than 1 µM.

For the Phospho-ERK Cell-based Assay, the IC50 (µM) values are as follows:

at least 11 of the compounds tested have an IC50 of less than 5 µM;

at least 14 of the compounds tested have an IC50 of less than 10 µM;

at least 19 of the compounds tested have an IC50 of less than 50 µM.

For the Cell proliferation (SRB) assay, the IC50 (µM) values are as follows:

at least 14 of the compounds tested have an IC50 of less than 1 µM;

at least 29 of the compounds tested have an IC50 of less than 10 µM;

at least 47 of the compounds tested have an IC50 of less than 50 µM.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:
1. A compound of the following formula:

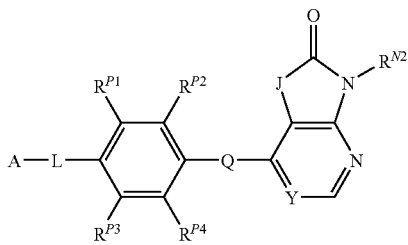

wherein:
J is independently —O— or —NR$^{N1}$—;
R$^{N1}$, if present, is independently —H or a group selected from:
aliphatic saturated C$_{1-5}$alkyl,
aliphatic C$_{2-5}$alkenyl,
aliphatic C$_{2-5}$alkynyl,
saturated C$_{3-6}$cycloalkyl,
C$_{3-6}$cycloalkenyl;
C$_6$-carboaryl;
C$_{5-6}$heteroaryl;
C$_{5-6}$heterocyclic;
and is independently unsubstituted or substituted;
R$^{N2}$ is independently —H or a group selected from:
aliphatic saturated C$_{1-5}$alkyl,
aliphatic C$_{2-5}$alkenyl,
aliphatic C$_{2-5}$alkynyl,
saturated C$_{3-6}$cycloalkyl,
C$_{3-6}$cycloalkenyl;
C$_6$-carboaryl;
C$_{5-6}$heteroaryl;
C$_{5-6}$heterocyclic;
and is independently unsubstituted or substituted;
Y is independently —CH= or —N=;
Q is independently —(CH$_2$)$_j$—M—(CH$_2$)$_k$— wherein:
j is independently 0, 1 or 2;
k is independently 0, 1, or 2;
j+k is 0, 1, or 2;
M is independently —O—, —S—, —NH—, —NMe—, or —CH$_2$—;
each of R$^{P1}$, R$^{P2}$, R$^{P3}$, and R$^{P4}$ is independently —H or a group selected from:
aliphatic saturated C$_{1-5}$alkyl;
aliphatic C$_{2-5}$alkenyl;
aliphatic C$_{2-5}$alkynyl;
saturated C$_{3-6}$cycloalkyl;
C$_{3-6}$cycloalkenyl;
aliphatic saturated C$_{1-5}$haloalkyl;
—C(=O)OR$^1$,
wherein R$^1$ is —H, C$_{5-12}$aryl-C$_{1-7}$alkyl, C$_{5-12}$aryl, C$_{3-12}$heterocyclyl, or C$_{1-7}$alkyl;
—OR$^2$ and —SR$^2$,
wherein R$^2$ is —H, C$_{5-12}$aryl-C$_{1-7}$alkyl, C$_{5-12}$aryl, C$_{3-12}$heterocyclyl, or C$_{1-7}$alkyl;
—C(=O)NR$^3$R$^4$,
wherein each of R$^3$ and R$^4$ is independently —H; or C$_{5-12}$aryl-C$_{1-7}$alkyl, C$_{5-12}$aryl, C$_{3-12}$heterocyclyl, or C$_{1-7}$alkyl; or R$^3$ and R$^4$ taken together with the nitrogen atom to which they are attached form a ring having from 3 to 7 ring atoms;
—NR$^5$R$^6$,
wherein each of R$^5$ and R$^6$ is independently —H; or C$_{5-12}$aryl-C$_{1-7}$alkyl, C$_{5-12}$aryl, C$_{3-12}$heterocyclyl, or C$_{1-7}$alkyl; or R$^5$ and R$^6$ taken together with the nitrogen atom to which they are attached form a ring having from 3 to 7 ring atoms;
—NR$^7$C(=O)R$^8$,
wherein:
R$^7$ is —H or C$_{1-3}$alkyl;
R$^8$ is C$_{5-12}$aryl-C$_{1-7}$alkyl, C$_{5-12}$aryl, C$_{3-12}$heterocyclyl, or C$_{1-7}$alkyl;
—S(=O)R$^9$ or —S(=O)$_2$R$^9$,
wherein R$^9$ is C$_{1-7}$alkyl, C$_{5-12}$aryl, or C$_{5-12}$aryl-C$_{1-7}$alkyl;
—F, —Cl, —Br, or —I;
—CN;
and additionally R$^{P1}$ and R$^{P2}$ taken together may be —CH=CH—CH=CH—;
wherein each C$_{1-5}$alkyl, C$_{2-5}$alkenyl, C$_{2-5}$alkynyl, C$_{3-6}$cycloalkyl, C$_{3-6}$cycloalkenyl, C$_{5-12}$aryl-C$_{1-7}$alkyl, C$_{5-12}$aryl, C$_{3-12}$heterocyclyl, and C$_{1-7}$alkyl is independently unsubstituted or substituted;
L is independently:
a linker group formed by a chain of 2, 3, or 4 linker moieties;
each linker moiety is independently —CH$_2$—, —NR$^N$—, —C(=X)—, or —S(=O)$_2$—;
exactly one linker moiety is —NR$^N$—, or:
exactly two linker moieties are —NR$^N$—;
exactly one linker moiety is —C(=X)—, and no linker moiety is —S(=O)$_2$—; or:
exactly one linker moiety is —S(=O)$_2$—, and no linker moiety is —C(=X)—;
no two adjacent linker moieties are —NR$^N$—;
X is independently =O or =S;
each R$^N$ is independently —H, saturated aliphatic C$_{1-3}$alkyl, or aliphatic C$_{2-3}$alkenyl;
A is independently:
C$_{6-14}$carboaryl,
C$_{5-14}$heteroaryl,
C$_{3-12}$carbocyclic,
C$_{3-12}$heterocyclic;
and is independently unsubstituted or substituted;
and pharmaceutically acceptable salts thereof.
2. A compound according to claim 1, wherein Y is independently —CH=.
3. A compound according to claim 1, wherein Y is independently —N=.
4. A compound according to claim 2, wherein J is independently —O—.
5. A compound according to claim 2, wherein J is independently —NR$^{N1}$—.
6. A compound according to claim 5, wherein Q is —O—.
7. A compound according to claim 5, wherein Q is —S—.
8. A compound according to claim 6, wherein the group A-L is independently selected from:
A—NR$^N$—C(=O)NR$^N$—,
A—NR$^N$—C(=S)NR$^N$—,
A—CH$_2$—NR$^N$—C(=O)NR$^N$—,
A—NR$^N$—C(=O)—,
A—C(=O)—NR$^N$—,
A—CH$_2$—C(=O)—NR$^N$—,
A—NR$^N$—CH$_2$—C(=O)—NR$^N$—, A—CH$_2$—NR$^N$—C(=O)—,
A—NR$^N$—S(=O)$_2$—NR$^N$—,
A—NR$^N$—S(=O)$_2$-,
A—S(=O)$_2$—NR$^N$—,
A—CH$_2$—NR$^N$—(=O)$_2$—NR$^N$—, and
A—CH$_2$—NR$^N$—S(=O)$_2$;
wherein each R$^N$ is independently —H or —Me.

9. A compound according to claim 6, wherein the group A-L is independently selected from:
A—NR$^N$—C(=O)NR$^N$—,
A—CH$_2$—NR$^N$—C(=O)—NR$^N$—, and
A—NR$^N$—C(=O)—NR$^N$—CH$_2$—;
wherein each R$^N$ is independently —H or —Me.

10. A compound according to claim 6, wherein the group A-L is independently A—NR$^N$—C(=O)—NR$^N$—, wherein each R$^N$ is independently —H or —Me.

11. A compound according to claim 6, wherein the group A-L is independently A—NH—C(=O)—NH—.

12. A compound according to claim 8:
wherein R$^{N1}$ is independently —H or a group selected from:
aliphatic saturated C$_{1-3}$alkyl, and
aliphatic C$_{2-3}$alkenyl,
and is independently unsubstituted or substituted; and
wherein R$^{N2}$ is independently —H or a group selected from:
aliphatic saturated C$_{1-3}$alkyl, and
aliphatic C$_{2-3}$alkenyl,
and is independently unsubstituted or substituted.

13. A compound according to claim 8, wherein:
R$^{N1}$ is independently —H or —Me; and
R$^{N2}$ is independently —H or —Me.

14. A compound according to claim 10, wherein:
R$^{N1}$ is independently —H or —Me; and
R$^{N2}$ is independently —H or —Me.

15. A compound according to claim 8, wherein:
R$^{N1}$ is independently —H; and
R$^{N2}$ is independently —H.

16. A compound according to claim 10, wherein:
R$^{N1}$ is independently —H; and
R$^{N2}$ is independently —H.

17. A compound according to claim 13, wherein each of R$^{P1}$, R$^{P2}$, R$^{P3}$, and R$^{P4}$ is independently —H or a group selected from:
aliphatic saturated C$_{1-3}$alkyl,
aliphatic C$_{2-3}$alkenyl,
aliphatic saturated C$_{1-5}$haloalkyl,
—S(=O)R$^9$ and —S(=O)$_2$R$^9$, wherein R$^9$ is aliphatic saturated C$_{1-3}$alkyl;
—F, —Cl,
—SR$^2$, wherein R$^2$ is aliphatic saturated C$_{1-3}$alkyl, and
—OR$^2$, wherein R$^2$ is aliphatic saturated C$_{1-3}$alkyl.

18. A compound according to claim 14, wherein each of R$^{P1}$, R$^{P2}$, R$^{P3}$ and R$^{P4}$ is independently —H or a group selected from:
aliphatic saturated C$_{1-3}$alkyl,
aliphatic C$_{2-3}$alkenyl,
aliphatic saturated C$_{1-5}$haloalkyl,
—S(=O)R$^9$ and —S(=O)$_2$R$^9$, wherein R$^9$ is aliphatic saturated C$_{1-3}$alkyl;
—F, —Cl,
—SR$^2$, wherein R$^2$ is aliphatic saturated C$_{1-3}$alkyl, and
—OR$^2$, wherein R$^2$ is aliphatic saturated C$_{1-3}$alkyl.

19. A compound according to claim 13, wherein each of R$^{P1}$, R$^{P2}$, R$^{P3}$, and R$^{P4}$ is independently —H, —Me, —S(=O)Me, —S(=O)$_2$Me, —F, —Cl, or —SMe.

20. A compound according to claim 14, wherein each of R$^{P1}$, R$^{P2}$, R$^{P3}$, and R$^{P4}$ is independently —H, —Me, —S(=O)Me, —S(=O)$_2$Me, —F, —Cl, or —SMe.

21. A compound according to claim 13, wherein each of R$^{P1}$, R$^{P2}$, R$^{P3}$, and R$^{P4}$ is independently —H.

22. A compound according to claim 14, wherein each of R$^{P1}$, R$^{P2}$, R$^{P3}$, and R$^{P4}$ is independently —H.

23. A compound according to claim 13, wherein:
R$^{P1}$ and R$^{P2}$ taken together are —CH=CH—CH=CH—; and
each of R$^{P3}$ and R$^{P4}$ is independently —H.

24. A compound according to claim 14, wherein:
R$^{P1}$ and R$^{P2}$ taken together are —CH=CH—CH=CH—; and
each of R$^{P3}$ and R$^{P4}$ is independently —H.

25. A compound according to claim 19, wherein A is independently C$_{6-14}$-carboaryl or C$_{5-14}$heteroaryl, and is independently unsubstituted or substituted.

26. A compound according to claim 19, wherein A is independently derived from: benzene, pyridine, thiadiazole, thiazole, pyrazole; and is independently unsubstituted or substituted.

27. A compound according to claim 19, wherein A is independently phenyl or pyrazolyl, and is independently unsubstituted or substituted.

28. A compound according to claim 20, wherein A is independently phenyl or pyrazolyl, and is independently unsubstituted or substituted.

29. A compound according to claim 26, wherein substituents on A, if present, are independently selected from: carboxylic acid; ester; amido; thioamido; acyl; halo; cyano; nitro; hydroxy; ether; thiol; thioether; acyloxy; carbamate; amino; acylamino; thioacylamino; aminoacylamino; aminothioacylamino;
sulfonamino; sulfonyl; sulfonate; sulfonamido; C$_{5-20}$aryl-C$_{1-7}$alkyl; C$_{5-20}$aryl;
C$_{3-20}$heterocyclyl; C$_{1-7}$alkyl; C$_{1-7}$haloalkyl; oxo; imino; hydroxyimino; and phosphate.

30. A compound according to claim 27, wherein substituents on A, if present, are independently selected from: carboxylic acid; ester; amido; thioamido; acyl; halo; cyano; nitro; hydroxy; ether; thiol; thioether; acyloxy; carbamate; amino; acylamino; thioacylamino; aminoacylamino; aminothioacylamino; sulfonamino; sulfonyl; sulfonate; sulfonamido; C$_{5-20}$aryl-C$_{1-7}$alkyl; C$_{5-20}$aryl;
C$_{3-20}$heterocyclyl; C$_{1-7}$alkyl; C$_{1-7}$haloalkyl; oxo; imino; hydroxyimino; and phosphate.

31. A compound according to claim 28, wherein substituents on A, if present, are independently selected from: carboxylic acid; ester; amido; thioamido; acyl; halo; cyano; nitro; hydroxy; ether; thiol; thioether; acyloxy; carbamate; amino; acylamino; thioacylamino; aminoacylamino; aminothioacylamino; sulfonamino; sulfonyl; sulfonate; sulfonamido; C$_{5-20}$aryl-C$_{1-7}$alkyl; C$_{5-20}$aryl;
C$_{3-20}$heterocyclyl; C$_{1-7}$alkyl; C$_{1-7}$haloalkyl; oxo; imino; hydroxyimino; and phosphate.

32. A compound having the following formula:

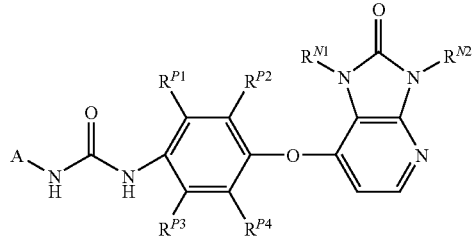

or a pharmaceutically acceptable salt thereof;
wherein:
each of $R^{P1}$, $R^{P2}$, $R^{P3}$ and $R^{P4}$ is independently —H, —Me, —F, —Cl, or —SMe;
$R^{N1}$ is independently —H or —Me;
$R^{N2}$ is independently —H or —Me; and
A is independently phenyl or pyrazolyl, and is independently unsubstituted or substituted.

33. A compound having the following formula:

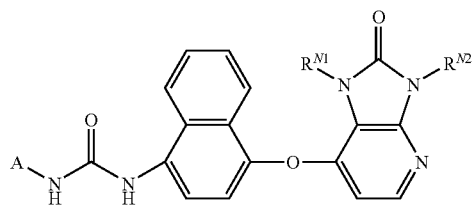

or a pharmaceutically acceptable salt thereof;
wherein:
$R^{N1}$ is independently —H or —Me;
$R^{N2}$ is independently —H or —Me; and;
A is independently phenyl or pyrazolyl, and is independently unsubstituted or substituted.

34. A composition comprising a compound according to claim 1 and a pharmaceutically acceptable carrier or diluent.

35. A composition comprising a compound according to claim 19 and a pharmaceutically acceptable carrier or diluent.

36. A composition comprising a compound according to claim 28 and a pharmaceutically acceptable carrier or diluent.

37. A composition comprising a compound according to claim 32 and a pharmaceutically acceptable carrier or diluent.

38. A composition comprising a compound according to claim 33 and a pharmaceutically acceptable carrier or diluent.

39. A compound selected from the following compounds and pharmaceutically acceptable salts thereof:

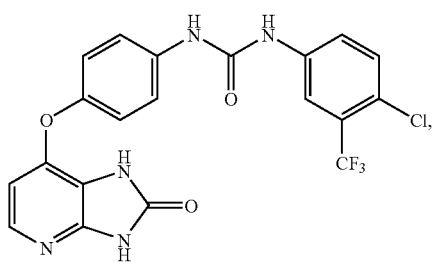

-continued

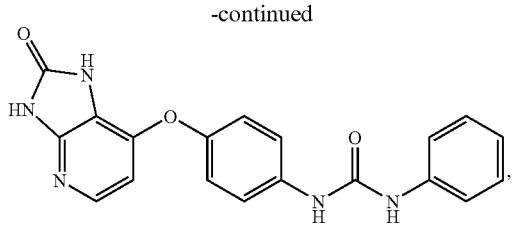

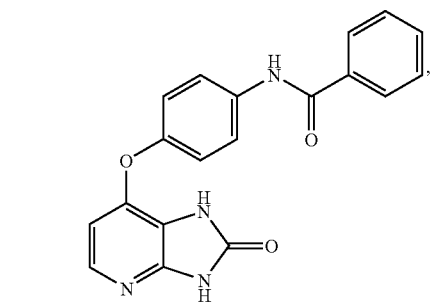

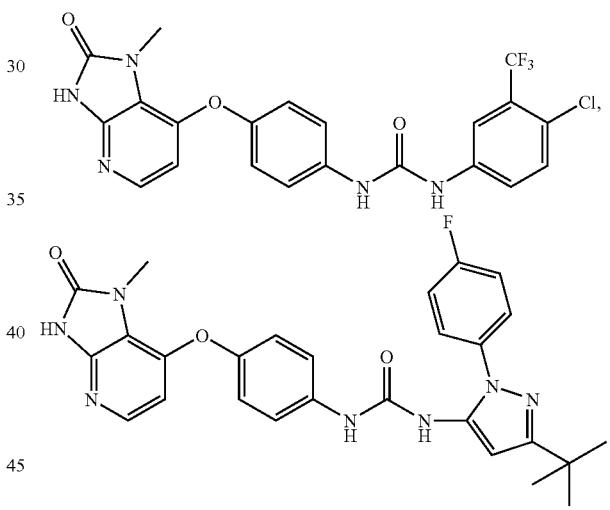

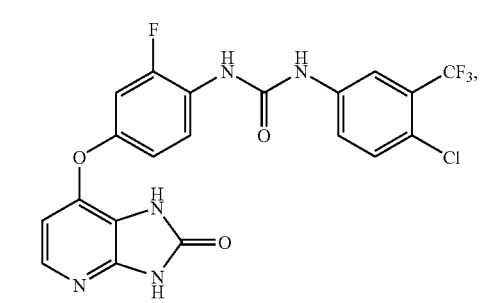

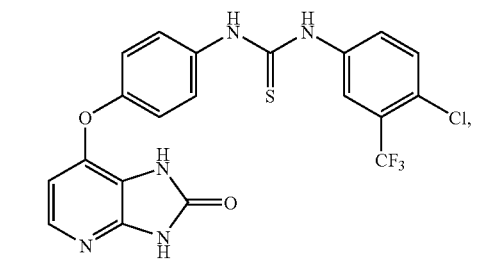

-continued
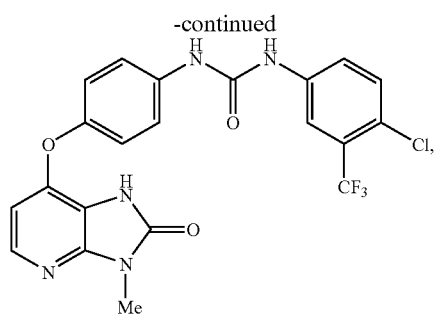
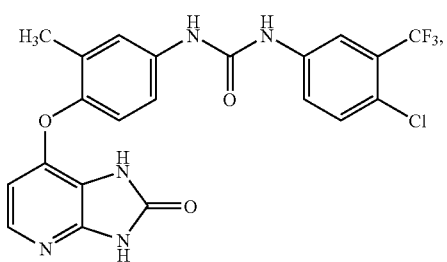
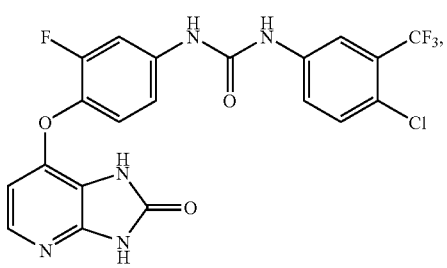
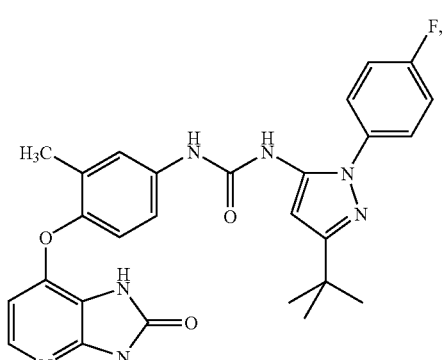
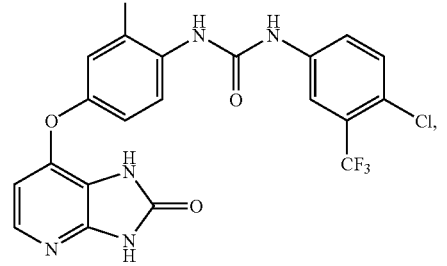
-continued
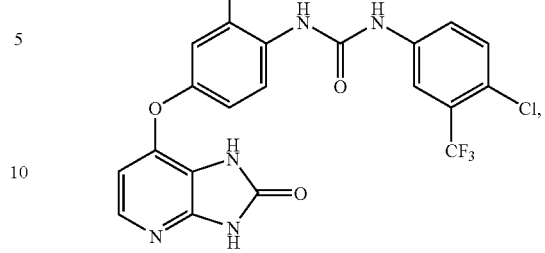
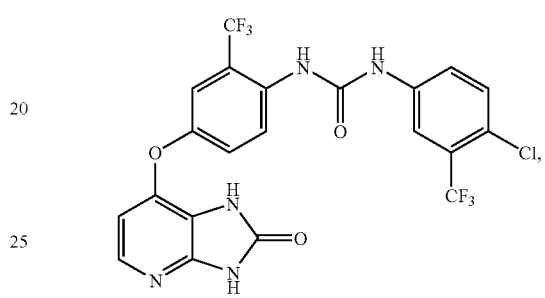
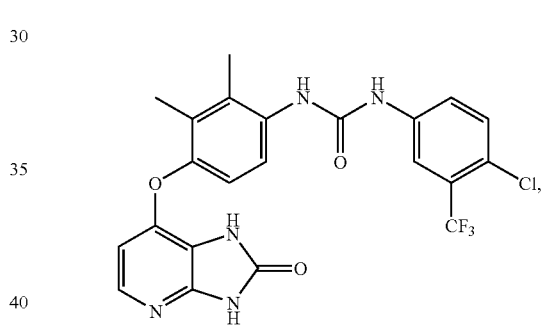
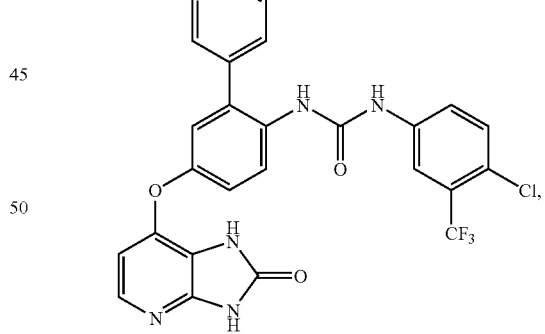
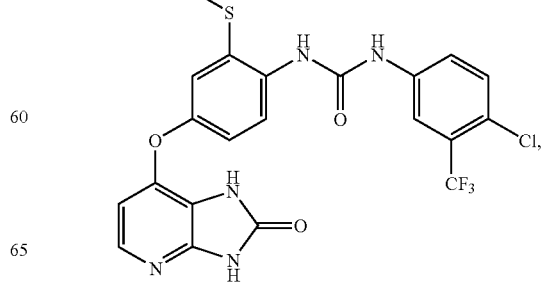

-continued
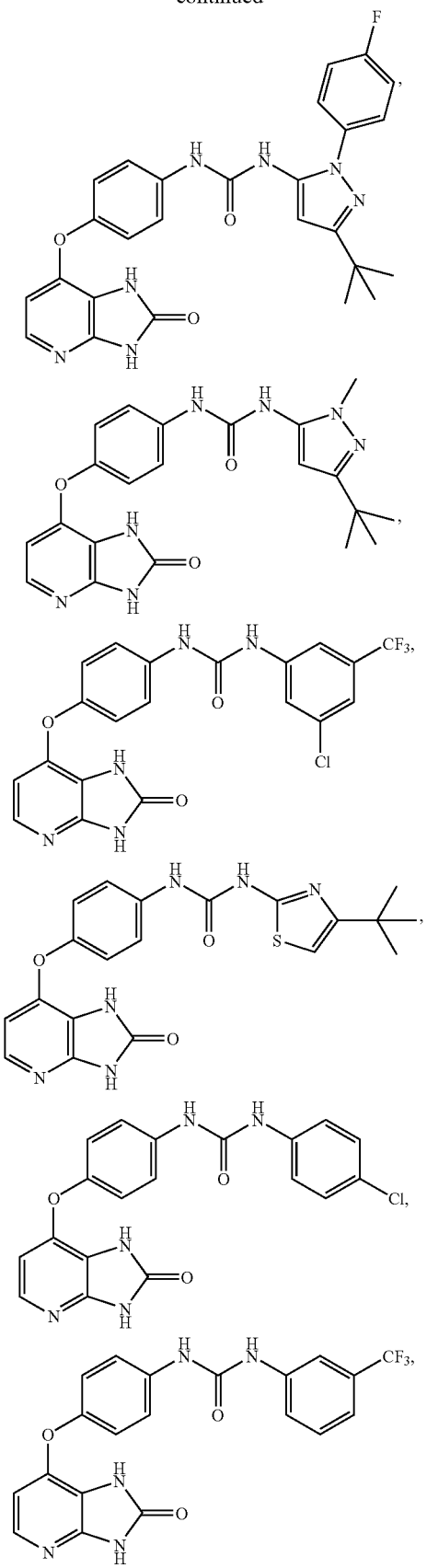
-continued
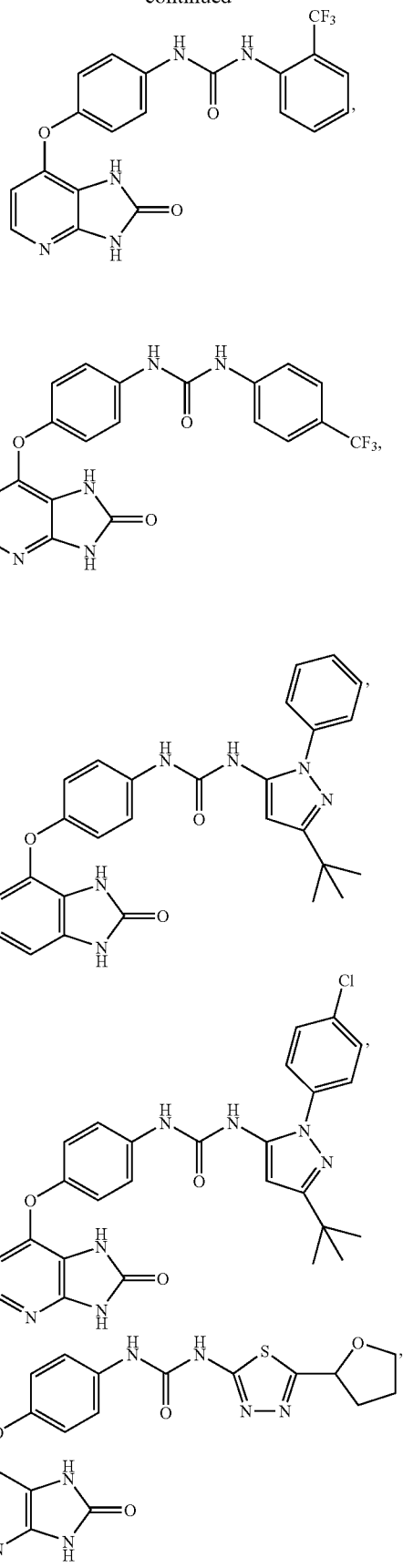

-continued
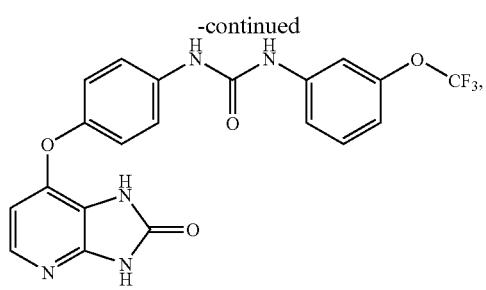
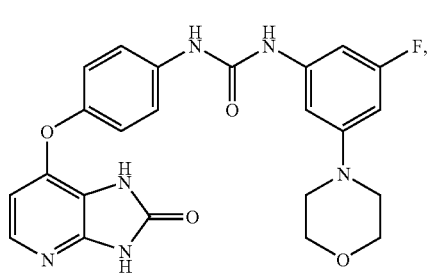
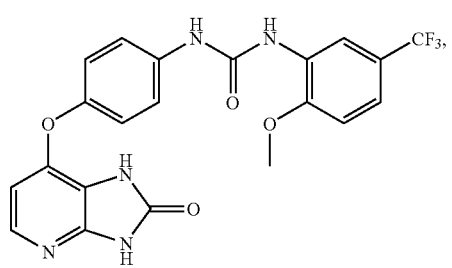
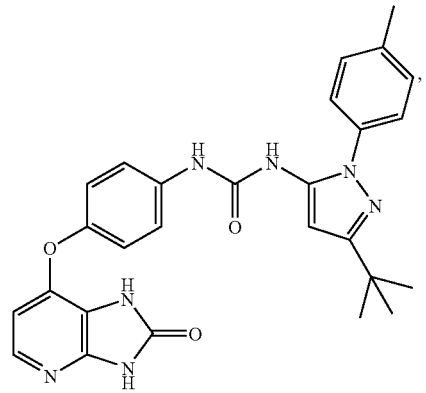
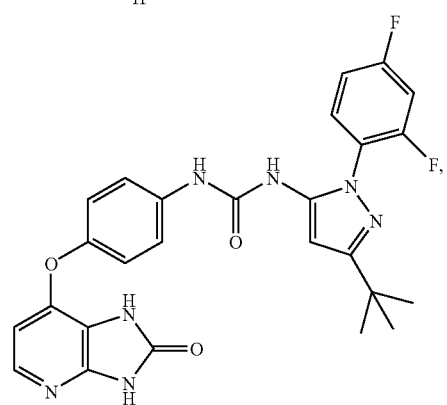
-continued
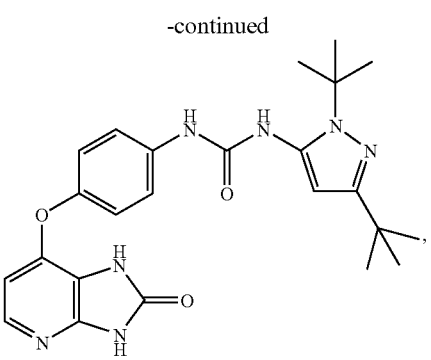
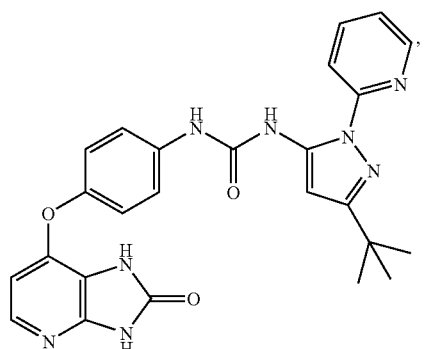
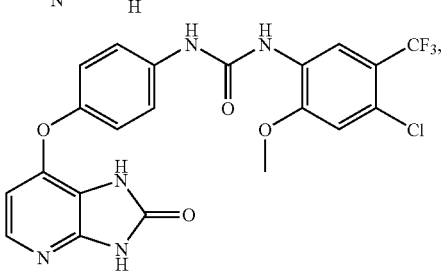
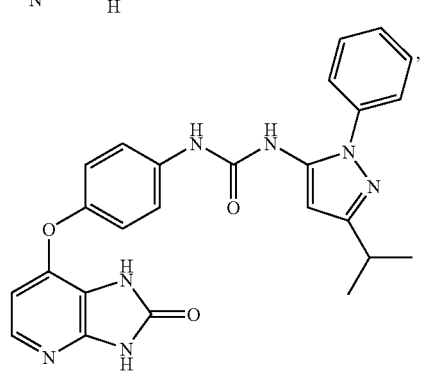
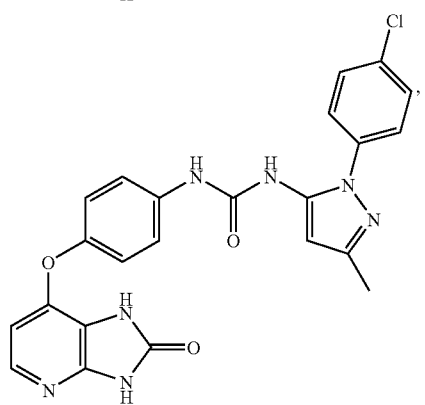

-continued
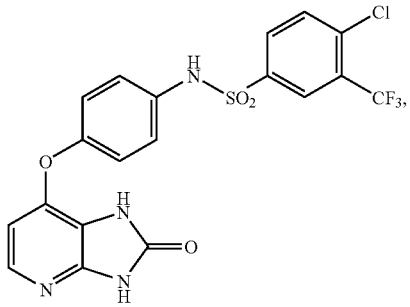
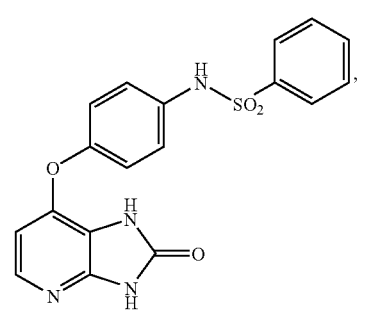
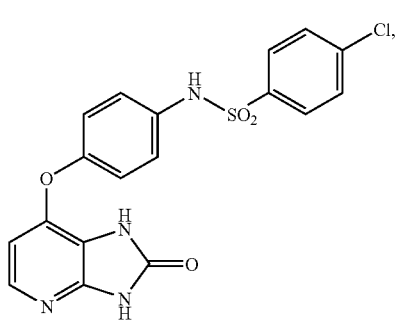
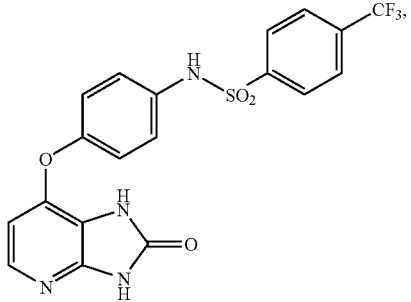
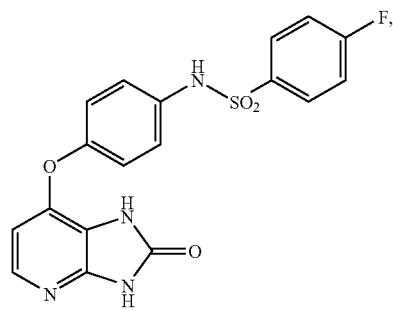
-continued
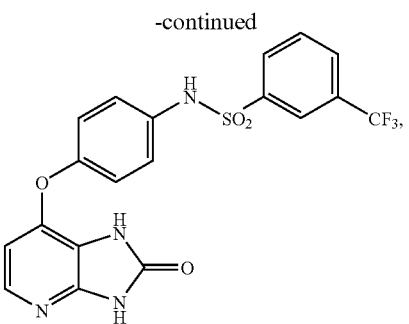
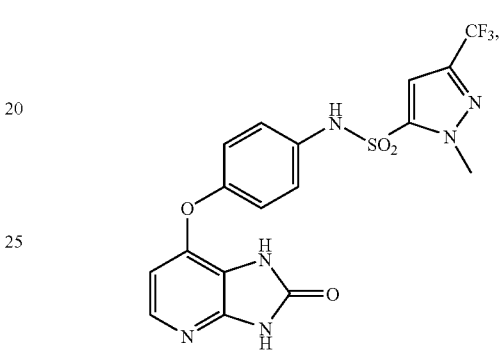
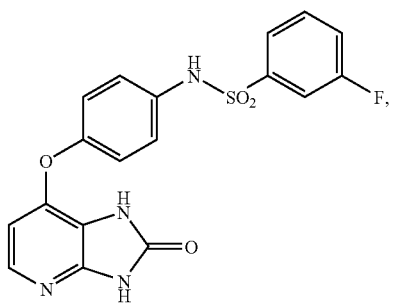
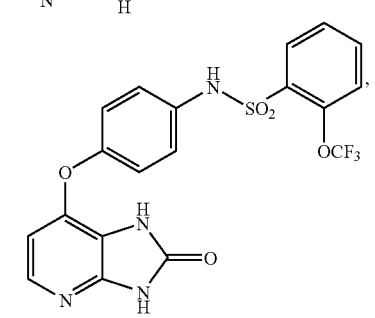
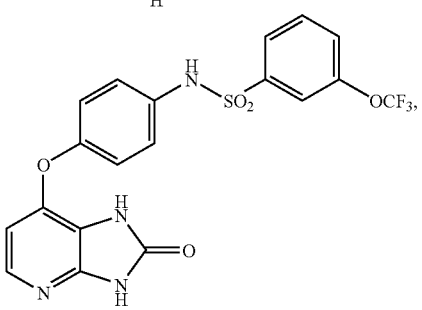

-continued
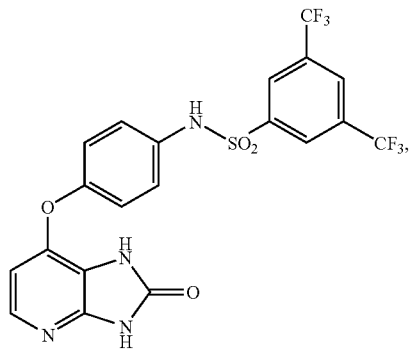
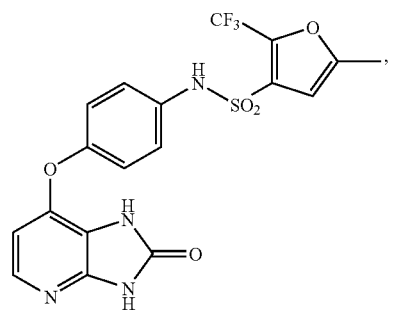
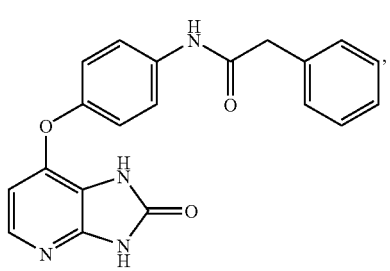
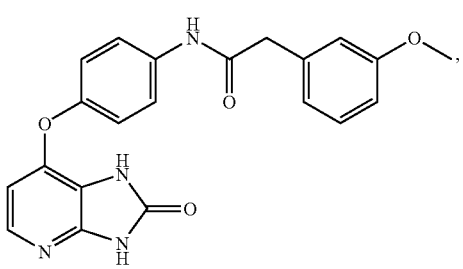
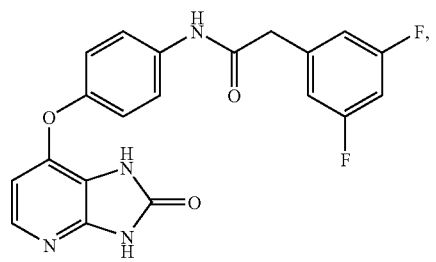
-continued
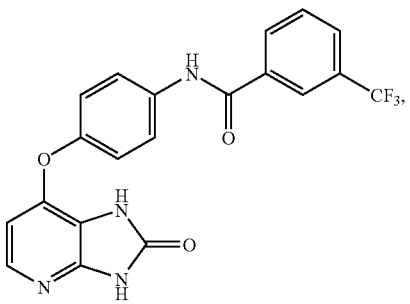
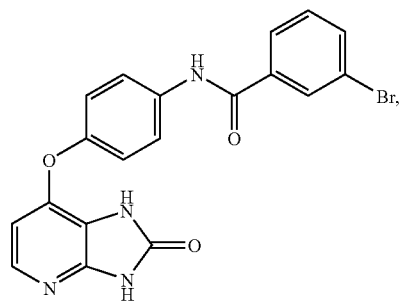
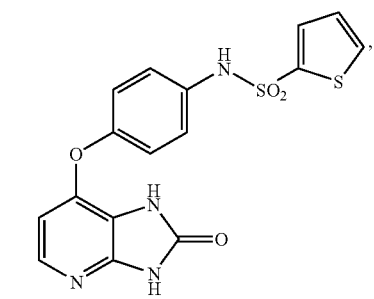
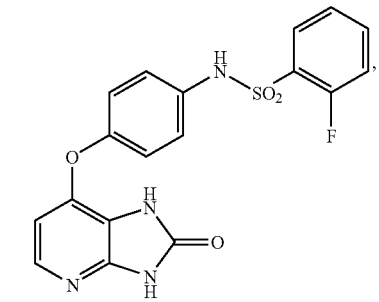
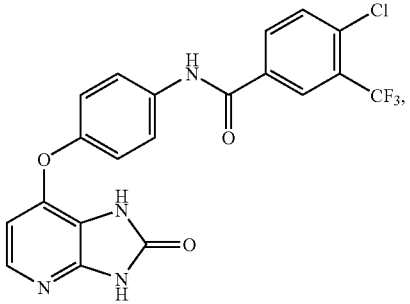

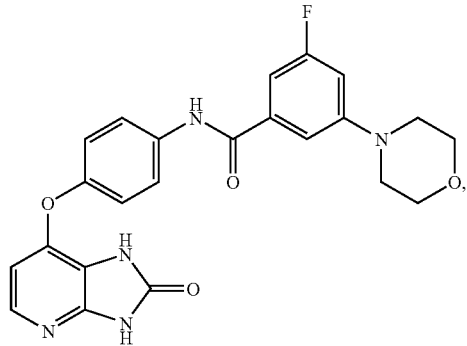

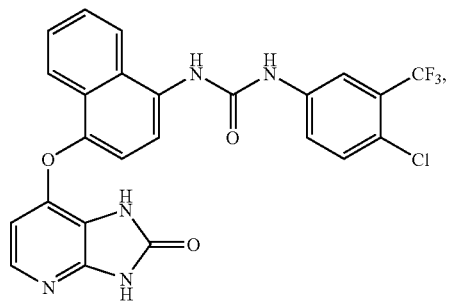

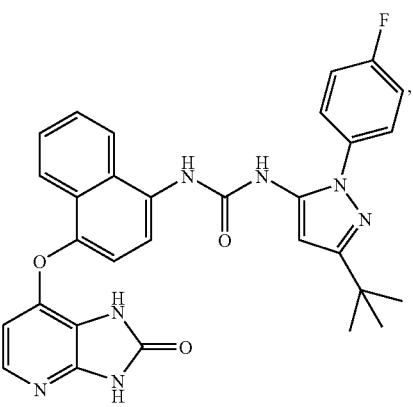

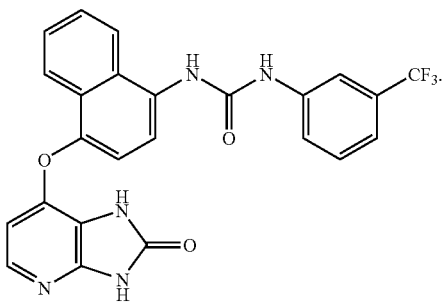

40. A composition comprising a compound according to claim 39 and a pharmaceutically acceptable carrier or diluent.

41. A compound according to claim 32, wherein A is substituted pyrazolyl, and has the following formula:

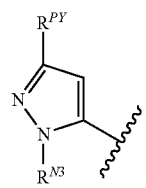

wherein:

$R^{PY}$ is independently saturated $C_{1-7}$alkyl; and $R^{N3}$ is independently phenyl, and is independently unsubstituted or substituted with one or more substituents selected from —F, —Cl, —Br, —I, —Me, and —CF$_3$.

42. A compound according to claim 32, wherein A is substituted pyrazolyl, and has the following formula:

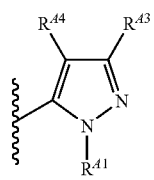

wherein $R^{A4}$ is H; $R^{A3}$ is —tBu, and $R^{A1}$ is —Ph or —Ph—Me.

43. A compound according to claim 33, wherein A is substituted pyrazolyl, and has the following formula:

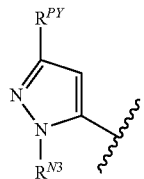

wherein:
  $R^{PY}$ is independently saturated $C_{1-7}$alkyl; and
  $R^{N3}$ is independently phenyl, and is independently unsubstituted or substituted with one or more substituents selected from —F, —Cl, —Br, —I, —Me, and —CF$_3$.

44. A compound according to claim 33, wherein A is substituted pyrazolyl, and has the following formula:

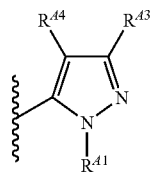

wherein $R^{A4}$ is H; $R^{A3}$ is —tBu, and $R^{A1}$ is —Ph or —Ph—Me.

* * * * *